US011027046B2

United States Patent
Stevenson et al.

(10) Patent No.: US 11,027,046 B2
(45) Date of Patent: Jun. 8, 2021

(54) TEXTILE PRODUCTS HAVING SELECTIVELY APPLIED SEALANT OR COATING AND METHOD OF MANUFACTURE

(71) Applicant: Hothouse Medical Limited, Strathclyde (GB)

(72) Inventors: David Granville Stevenson, Strathclyde (GB); Timothy Rawden Ashton, Strathclyde (GB); Brian McMurray, Pinebluff, NC (US); Chadd Clark, Greenville, SC (US); Lindsey Calcutt, Greenville, SC (US); Kayla Wilson, Seneca, SC (US); Josh Davidson, Greenville, SC (US)

(73) Assignee: Hothouse Medical Limited, Strathclyde (GB)

( * ) Notice: Subject to any disclaimer, the term of this patent is extended or adjusted under 35 U.S.C. 154(b) by 105 days.

(21) Appl. No.: 16/407,041

(22) Filed: May 8, 2019

(65) Prior Publication Data

US 2019/0307924 A1 Oct. 10, 2019

Related U.S. Application Data

(63) Continuation-in-part of application No. 16/273,320, filed on Feb. 12, 2019, now Pat. No. 10,926,003, (Continued)

(30) Foreign Application Priority Data

Oct. 31, 2017 (GB) .................................... 1717885

(51) Int. Cl.
*A61F 2/06* (2013.01)
*A61L 27/50* (2006.01)
(Continued)

(52) U.S. Cl.
CPC ............. *A61L 27/507* (2013.01); *A61L 27/34* (2013.01); *A61L 27/48* (2013.01); *A61L 27/502* (2013.01);
(Continued)

(58) Field of Classification Search
CPC ........ A61F 2/06; A61F 2002/077; A61F 2/07; A61L 2420/00–08; A61L 27/28;
(Continued)

(56) References Cited

U.S. PATENT DOCUMENTS 4,459,252 A   7/1984   MacGregor
4,657,544 A   4/1987   Pinchuk
(Continued)

FOREIGN PATENT DOCUMENTS

JP      2009-11804 A    1/2009
WO   WO 2006/038031 A2   7/1997
(Continued)

OTHER PUBLICATIONS

King et al., Can. Textile J. 108(4):24-30 (1991) (Year: 1991).*
(Continued)

*Primary Examiner* — Brian A Dukert
*Assistant Examiner* — Rebecca Lynee Zimmerman
(74) *Attorney, Agent, or Firm* — Hoffmann & Baron, LLP

(57) ABSTRACT

A substantially fluid impermeable textile graft may be produced by selective application of a substantially water-soluble material or masking agent, and optionally selective removal of excess substantially water-soluble material, followed by the application of a substantially water-insoluble sealant. The inner surface of the graft includes a coating of the substantially water-soluble material thereon. The outer surface includes a coating of the substantially water-insoluble sealant disposed thereon. The tubular wall having the coating of the substantially water-insoluble sealant is, (Continued)

after curing thereof, substantially impermeable to liquid. The substantially water-soluble material is removed from the graft after the application of the substantially water-insoluble sealant.

50 Claims, 19 Drawing Sheets

Related U.S. Application Data which is a continuation of application No. PCT/GB2018/053161, filed on Oct. 31, 2018.

(51) Int. Cl.

| | | |
|---|---|---|
| *A61L 27/34* | (2006.01) | |
| *A61L 27/48* | (2006.01) | |
| *A61L 27/52* | (2006.01) | |
| *A61L 31/10* | (2006.01) | |
| *A61L 31/12* | (2006.01) | |
| *A61L 31/14* | (2006.01) | |
| *A61L 27/56* | (2006.01) | |
| *A61F 2/07* | (2013.01) | |

(52) U.S. Cl.
CPC .............. *A61L 27/52* (2013.01); *A61L 27/56* (2013.01); *A61L 31/10* (2013.01); *A61L 31/129* (2013.01); *A61L 31/146* (2013.01); *A61F 2/07* (2013.01); *A61L 2420/08* (2013.01)

(58) Field of Classification Search
CPC ........ A61L 27/507; A61L 27/34; A61L 27/48; A61L 27/502; A61L 27/52; A61L 31/10; A61L 31/129; A61L 31/146; A61L 27/56; A61L 2420/08; B05D 1/32–327; B05B 12/20–29; B05B 12/26; B32B 5/28; B81C 2201/0198
See application file for complete search history.

(56) References Cited

U.S. PATENT DOCUMENTS

| | | |
|---|---|---|
| 4,718,907 A | 1/1988 | Karwoski et al. |
| 4,743,252 A | 5/1988 | Martin, Jr. et al. |
| 4,743,258 A | 5/1988 | Ikada et al. |
| 5,163,951 A | 11/1992 | Pinchuk et al. |
| 5,246,452 A | 9/1993 | Sinnott |
| 5,298,276 A | 3/1994 | Jayaraman |
| 5,383,927 A | 1/1995 | De Goicoechea et al. |
| 5,840,240 A | 11/1998 | Stenoien et al. |
| 5,851,229 A | 12/1998 | Lentz et al. |
| 5,851,230 A | 12/1998 | Weadock et al. |
| 5,866,217 A | 2/1999 | Stenoien et al. |
| 6,939,377 B2 | 9/2005 | Jayaraman et al. |
| 7,022,135 B2 | 4/2006 | Zilla et al. |
| 7,211,108 B2 | 5/2007 | Furst et al. |
| 7,297,159 B2 | 11/2007 | Hossainy et al. |
| 7,329,531 B2 | 2/2008 | Keenan |
| 8,414,910 B2 | 4/2013 | Wang |
| 2002/0187288 A1 | 12/2002 | Lim et al. |
| 2003/0055494 A1 | 3/2003 | Bezuidenhout et al. |
| 2003/0149471 A1 | 8/2003 | Briana et al. |
| 2003/0149474 A1 | 8/2003 | Becker |
| 2004/0024448 A1 | 2/2004 | Chang et al. |
| 2004/0182511 A1 | 9/2004 | Rakos et al. |
| 2004/0215337 A1 | 10/2004 | Hasin et al. |
| 2007/0043428 A1* | 2/2007 | Jennings .................. A61L 31/16 623/1.15 |
| 2009/0012607 A1 | 1/2009 | Kim et al. |
| 2009/0041823 A1 | 2/2009 | Larena-Avellanenda et al. |
| 2015/0044408 A1 | 2/2015 | Caballero et al. |
| 2016/0302911 A1 | 10/2016 | Soletti |

FOREIGN PATENT DOCUMENTS

| | | |
|---|---|---|
| WO | WO 2008/030939 A2 | 3/2001 |
| WO | WO 03/066118 A1 | 8/2003 |
| WO | WO 2010/086863 A2 | 8/2010 |
| WO | WO 2013/110720 A1 | 8/2013 |
| WO | WO 2014/025506 A1 | 2/2014 |

OTHER PUBLICATIONS

PCT Search Report and Written Opinion for PCT/IB 2020/000350 dated Sep. 8, 2020.
King, Martin w., "Designing Fabrics for Blood Vessel Replacement", Canadian Textile Journal, May 1991, pp. 24-30.
Teodorescu,Mirela et al., "Poly(vinylpyrrolidone)—A Versatile Polymer for Biomedical and Beyond Medical Applications", PolymerPlastics Technology and Engineering54: pp. 923-943, 2015.
Office Action dated Oct. 20, 2020 for Japanese Application No. 2020-543414.

* cited by examiner

TEXTILE PRODUCTS HAVING SELECTIVELY APPLIED SEALANT OR COATING AND METHOD OF MANUFACTURE

CROSS-REFERENCE TO RELATED APPLICATIONS

This application is a Continuation-In-Part of U.S. patent application Ser. No. 16/273,320, filed Feb. 12, 2019, which is a Continuation of International Application No. PCT/GB2018/053161, filed Oct. 31, 2018, which designated the United States of America, and which embodiments claim the benefit of Great Britain Application No. GB 1717885.6, filed Oct. 31, 2017, the contents of all of which are incorporated by reference herein.

FIELD OF THE INVENTION

This invention relates to textile products, such as a vascular or endovascular prostheses having a selectively applied sealing layer or coating and particularly but not exclusively, a method of manufacturing the textile products, such as prostheses, a kit of parts for manufacturing the textile products, such as prostheses, a vascular system including the prosthesis, a method of implanting the prosthesis and a method of implanting the vascular system.

BACKGROUND TO THE INVENTION

Vascular prostheses, or grafts, are used extensively in surgical procedures, such as in treating abdominal and thoracic vascular disease. Vascular grafts are typically required to be sealed prior to implantation, in order to prevent blood from leaking from the vascular graft after implant. Known techniques for sealing vascular grafts include the use of biodegradable (or bioresorbable or bioabsorbable) animal-derived materials such as bovine gelatine, bovine albumin or bovine collagen to seal the graft. Other techniques for sealing vascular grafts use synthetic materials, some of which are not able to biodegrade when implanted in a human or animal body.

It is desirable for the sealed graft, once implanted in a human or an animal body, to allow the ingrowth of tissue on the inner surface of the vascular graft and to ensure that the ingrowing tissue adheres to the inner surface of the vascular graft. However, conventional techniques for sealing vascular grafts often suffer from the ingress of the sealant into the inner surface of the vascular graft. The presence of sealing material has an adverse effect on the growth of tissue on the inner surface of the graft. Furthermore, the presence of sealing material on the inner surface of the graft also contributes to poor adhesion between the ingrowing tissue and the vascular graft, which can lead to reduced vascular performance of the vascular graft. It is therefore desirable to provide a vascular graft which does not hinder the ingrowth of tissue and which allows the ingrowing tissue layer to adhere to the inner surface.

In an attempt to better enable growth and adhesion of tissue on the inner surface of the graft, biodegradable animal-derived materials such as those noted above can be used to seal the graft. When such a graft is implanted, it is desirable for the sealant material to degrade once the ingrowing tissue layer is sufficiently mature. However, conventional methods of sealing vascular grafts do not exhibit consistent and predictable degradation times. This has considerable implications on the performance of some vascular grafts. For example, if the sealant material degrades before the ingrowing tissue layer has developed into a pseudointima (an example of a tissue layer on the inner surface of a vascular graft), blood will leak from the vascular graft. If the sealant material degrades too slowly, the ingrowing tissue will suffer from poor adhesion to the inner surface of the graft (because the inner surface of the graft is still coated in sealing material), and is likely to delaminate from the vascular graft. Haemorrhagic dissection could then occur in the pseudointima. There is therefore a need to provide a method of sealing vascular grafts that enables predictable growth and adhesion of tissue to the inner surface of the vascular graft.

A further issue with existing vascular grafts is that some animal-derived sealants of the type typically used are thought to increase the risk of bovine spongiform encephalopathy (BSE) transmission. This risk is usually mitigated by extensive supply chain regulation requirements, which are onerous and burdensome. It is desirable to provide a vascular graft which has less burdensome regulatory requirements, such that new materials and designs can be brought to use in a shorter time and in a more cost-effective way.

Furthermore, animal-derived sealants are incompatible with an array of processing techniques, which limits the options available to vascular graft designers. Vascular grafts sealed using animal-derived sealants are also typically required to be transported, or packaged, with control over the temperature and humidity to obviate deterioration of the sealant material. Therefore, it would also be desirable to provide a vascular graft which has less stringent transport and packaging requirements.

Furthermore, elastomeric coatings may change the flexibility of the fabric and, when fashioned into medical products such as vascular grafts and the like, may have a deleterious effect on the handling characteristic which are very important to surgeons. Thus, it would be desirable to provide a vascular graft which has sufficient sealing due to an elastomeric coating on the external surface and which is substantially free of the same coating material on the opposing side, e.g., luminal side, and also has flexibility and handling characteristics acceptable to surgeons.

SUMMARY OF THE INVENTION

The masking agent may be a water-soluble polymer layer, a water-soluble polymer, a water-soluble material, a water-soluble coating and/or a water-soluble layer.

The sealant may be a water-insoluble material, a water-insoluble sealant, a water-insoluble coating, and/or a water-insoluble layer.

For purposes of this invention, the water-soluble layer and the water-insoluble layer are applied to textile fabrics, medical device fabrics, implantable medical device textiles and various configurations of medical and non-medical textiles.

It is an object of the present invention to provide a vascular prosthesis and/or a method of manufacturing a vascular prosthesis, the inner surface of which better allows the ingrowth of biological tissue. One aspect of the present invention is to provide an implantable textile, such as a vascular prosthesis, and/or a method of manufacturing an implantable textile, such as a vascular prosthesis, the inner surface of which better allows the ingrowth of biological tissue. It is a further aspect of the present invention to provide an implantable textile, such as a vascular prosthesis, and/or a method of manufacturing an implantable textile, such as a vascular prosthesis, the inner surface of which is substantially devoid of sealing material. Another aspect of the present invention is to provide a vascular prosthesis and/or a method of manufacturing a vascular prosthesis, which better facilitates ingrowing tissue to adhere to the inner surface of the vascular prosthesis. It is a further aspect of the present invention to provide a vascular prosthesis and/or a method of manufacturing a vascular prosthesis, which better allows for predictable growth and adhesion of tissue to the inner surface of the vascular prosthesis. It is still a further aspect of the invention to provide a vascular prosthesis which strikes a balance between too much and too little masking agent. Too little masking agent will allow the sealant to migrate through the graft wall. Too much masking agent on the outside interferes with sealant adhesion and thus affects the ability to reach the permeability that is require in a vascular prosthesis. There must be sufficient masking agent to prevent sealant penetration balanced with the amount of masking agent that ends up on the outer graft surface. It is also an aspect of the invention to achieve a balance between the amount of sealant coverage and sealant adhesion required to attain adequate sealing and too much sealant such that it destroys the flexibility and handling characteristics of the prosthesis.

It is also a further aspect of the present invention to provide a kit of parts for manufacturing a vascular prosthesis. It is a further aspect of the present invention to provide a vascular system which allows, for example, synthetic assistive heart components to be connected to blood vessels and the heart.

It is a further aspect of the present invention to mitigate or at least obviate at least some of the issues in the prior art. Further aspects and embodiments of the present invention will be apparent from a reading of the present document.

According to a first aspect of the invention there is provided a method of manufacturing a vascular prosthesis, the method comprising the steps of:
(i) providing a conduit comprising a wall, the wall of the conduit comprising an inner surface and an outer surface, at least a section of the conduit being porous;
(ii) adding a masking agent to at least a part of the porous section of the conduit; and
(iii) adding a sealant to at least a part of the porous section of the conduit, the sealant being configured to mitigate movement of fluid through the wall of the conduit;
wherein the masking agent is configured to mitigate presence of the sealant on the inner surface of the conduit.

The vascular or endovascular prosthesis of the present invention is not limited to a prosthesis comprising a conduit or tubular portion. The vascular or endovascular prosthesis of the present invention may be or may comprise a non-conduit or non-tubular shaped structure or portion. Thus, the wall of the vascular or endovascular prosthesis being subjected to the masking agent and the sealant is not limited to a conduit wall. Thus, a substrate may be a non-conduit shaped structure or portion. Further, medical textile products are within the scope of the present invention.

The sealant may form a sealing layer on at least a part of the outer surface of the wall of the conduit.

The sealant may form a sealing layer on substantially all of the outer surface of the wall of the conduit.

The masking agent may form a masking agent layer on at least a part of the inner surface of the wall of the conduit.

The masking agent may form a masking agent layer on substantially all of the inner surface of the wall of the conduit.

Substantially all of the conduit may be porous.

The method may comprise one or more masking agent removal steps, the, or each, masking agent removal step comprising the step of removing at least a part of the masking agent from the conduit.

The method may comprise the step of removing at least a part of the masking agent from at least a part of the outer surface of the wall of the conduit prior to the step of adding the sealant to the porous section of the conduit.

The method may comprise the step of removing at least a part of the masking agent from the inner surface of the wall of the conduit subsequent to the step of adding the sealant to at least a part of the porous section of the conduit.

The method may comprise the step of removing substantially all of the masking agent from the conduit subsequent to the step of adding the sealant to at least a part of the porous section of the conduit.

At least one of the masking agent removal steps may be carried out at a temperature of between approximately 15° C. and approximately 140° C.

At least one of the masking agent removal steps may comprise the step of removing at least a part of the masking agent by applying a solvent thereto.

The solvent may comprise water.

The conduit may be at least one of: agitated, rotated, spun, and shaken, or the like, during at least one of the masking agent removal steps.

At least one of the masking agent removal steps may be carried out by etching, plasma etching, ablating and/or abrading the masking agent.

The inner surface of the wall of the conduit may be configured to promote the growth of biological tissue thereon.

The masking agent may comprise a polymer.

The masking agent may comprise a water-soluble polymer.

The masking agent may comprise at least one of: polyvinylpyrrolidone, glycerol, methyl cellulose, poly(ethylene glycol) and poly(ethylene glycol) hydrogel. The masking agent may comprise at least one of: polyvinylpyrrolidone (PVP), glycerol, methyl cellulose, poly(ethylene glycol) (PEG), polyethylene oxide (PEO), and poly(ethylene glycol) hydrogel. The masking agent may also include other biological hydrophilic polymers as described herein.

The masking agent may be biocompatible.

The masking agent may form a biocompatible masking agent layer when added to the conduit.

The masking agent may be added to at least a part of the porous section of the conduit from a masking agent solution. As used herein porous refers to being permeable to the passage of liquids such as blood under normal physiological conditions in a human patient.

The masking agent solution may be a polymer solution.

The step of adding the masking agent to at least a part of the porous section of the conduit may be performed by spraying the masking agent solution onto at least a part of the porous section of the conduit.

The masking agent solution may be added to the conduit by spraying the masking agent onto at least a part of the inner surface of the wall of the conduit.

The step of adding the masking agent to at least a part of the porous section of the conduit may be performed by immersing at least a part of the porous section of the conduit in the masking agent solution.

Substantially all of the conduit may be immersed in the masking agent solution.

The masking agent solution may comprise between approximately 5% weight/volume (w/v) of polymer in solution and approximately 30% w/v of polymer in solution.

The method may be carried out such that the step of adding the sealant to at least a part of the porous section of the conduit does not result in the removal of the masking agent from the porous section of the conduit.

The masking agent may be configured to biodegrade when the vascular prosthesis is implanted inside the human or animal body.

The conduit may be a woven fibrous polymer conduit.

The sealant may comprise a polymer.

The sealant may be a water-insoluble polymer.

The sealant may form a sealing layer when added to the conduit, the sealing layer being a polymer layer.

The sealant may comprise at least one of: silicone, room temperature vulcanising silicone, thermoplastic polyurethane, aliphatic polycarbonate, one or more thermoplastic elastomers, and polycarbonate.

The sealant may be added to the conduit from a sealant solution.

The sealant solution may be a polymer solution.

The sealant solution may comprise an organic solvent.

The sealant solution may comprise at least one of heptane and xylene.

The sealant may be added to at least a part of the porous section of the conduit by brushing and/or spraying the sealant thereon.

The sealant may be configured to mitigate movement of blood through the wall of the conduit.

The weight ratio of the sealant to the masking agent may be from about 0.1:1 to about 100:1. The weight ratio of the sealant to the masking agent may be from about 0.1:1 to about 71:1. The weight ratio of the sealant to the masking agent may be from about 0.1:1 to about 31:1.

The method may comprise the further step of sterilising the vascular prosthesis. The method may comprise the further step of sterilising the vascular prosthesis and/or medical device containing the textile substrate of the present invention.

The vascular prosthesis may be sterilised by way of at least one of: a gamma sterilisation process, an electron beam sterilisation process, and an ethylene oxide sterilisation process.

The conduit may be moveable between a contracted state and an extended state. The conduit may comprise a plurality of crimps. The conduit may comprise a plurality of crimps to provide, for example, flexibility for extending and contracting the conduit or prosthesis.

The step of adding the masking agent to at least a part of the porous section of the conduit may be carried out, at least in part, while the conduit is in the contracted state, in the extended state, and/or when moved between the contracted state and the extended state.

The step of adding the sealant to at least a part of the porous section of the conduit may be carried out, at least in part, while the conduit is in the contracted state, in the extended state, and/or when moved between the contracted state and the extended state.

The method may comprise one or more steps of weighing the conduit and/or measuring the length of the conduit, to determine, at least in part, the amount of masking agent, and/or or the amount of sealant, to add to at least a part of the porous section of the conduit.

The step of adding the masking agent to at least a part of the porous section of the conduit may comprise the step of providing gas to the conduit.

The gas may be directed towards the outer surface of the wall of the conduit.

The gas may be air.

The method may comprise the step of adding a support member to the conduit.

The support member may be added to the outer surface of the wall of the conduit.

The support member may be wrapped around the outer surface of the wall of the conduit.

The conduit may comprise a plurality of crimps, and the support member may be arranged to nest between the plurality of crimps.

The step of adding the support member to the conduit may be carried out prior to the step of adding the sealant to the conduit.

The step of adding the sealant to the conduit may be used, at least in part, to attach the support member to the conduit.

The support member may be a flexible, polymer member.

The method may comprise one or more steps of selectively adding sealant to one or more sections of the conduit, such that the conduit comprises at least two sections comprising substantially different amounts of sealant thereon.

The vascular prosthesis may be reversibly sealable. The masking agent may be selectively removable from the conduit. The masking agent may be added to, and subsequently removed from, the conduit. The sealant may be selectively removable from the conduit. The sealant may be added to, and subsequently removed from, the conduit. The masking agent and the sealant may be selectively removable from the conduit. The masking agent and the sealant may be added to, and subsequently removed from, the conduit.

The method may comprise one or more steps of adding the sealant to the conduit. The conduit may be configured to have variable flexibility throughout its length. The method may comprise the step of decreasing the flexibility of one or more sections of the conduit by adding sealant thereto. The method may comprise the step of selectively adding sealant to one or more sections of the conduit, such that the conduit comprises at least two sections comprising substantially different amounts of sealant thereon. The method may comprise one or more steps of selectively adding sealant to one or more sections of the conduit. The one or more steps of selectively adding sealant to one or more sections of the conduit may include adding sealant onto sealant that is present on the conduit. In this arrangement, different sections of the conduit may be configured to have different degrees of flexibility.

The vascular prosthesis may be configurable to be implantable inside the human or animal body. The vascular prosthesis may be configurable to be implantable or deliverable inside the human or animal body. The vascular prosthesis may be configured to be implantable inside the human or animal body. The vascular prosthesis may be configured to be implantable or deliverable inside the human or animal body.

The vascular prosthesis may be biocompatible. The term biocompatible used herein is in reference to materials which are compatible with implantation in the human or animal body, that is materials which can be implanted in the human or animal body without being harmful or toxic to surrounding tissue. The vascular prosthesis may be made from biocompatible materials. The vascular prosthesis may be made from substantially entirely biocompatible materials.

The vascular prosthesis may be a vascular graft. The vascular prosthesis may be configured to be flexible. The vascular prosthesis may be flexible.

The vascular prosthesis may have an inlet and an outlet. The vascular prosthesis may be configurable to allow fluid to flow from the inlet of the vascular prosthesis to the outlet of the vascular prosthesis. The vascular prosthesis may be configured to obviate fluid leaking therefrom. The vascular prosthesis may be configured to allow fluid to flow from the inlet of the vascular prosthesis to the outlet of the vascular prosthesis, and to prevent fluid from leaking from the vascular prosthesis. The step of adding the sealing layer to the porous section may configure the vascular prosthesis to obviate fluid leaking therefrom. The fluid may be a liquid. The fluid may be blood. It will be understood that the vascular prosthesis may be configured to obviate and/or prevent fluid leaking therefrom insofar as it is configured to obviate and/or prevent fluid from passing through the wall of the conduit of the vascular prosthesis.

The step of adding the sealant to at least a part of the porous section of the conduit may convert the conduit to a vascular prosthesis.

The vascular prosthesis may be made substantially entirely from polymeric materials.

The vascular prosthesis may be configured to obviate the leaking of blood therefrom at a blood pressure of up to approximately 300 mmHg (40 kPa), optionally up to approximately 200 mmHg (26.7 kPa).

The conduit may be made from a polymer material. The conduit may be a polymer conduit. The conduit may be made from one or more polymers. The conduit may be a woven conduit. The conduit may be a knitted conduit. The conduit may be made from woven fibres. The conduit may be a woven, polymer, fibrous conduit. The conduit may comprise polyester. The conduit may comprise polytetrafluoroethylene (PTFE). The conduit may comprise polyethylene terephthalate (PET). The conduit may comprise polyurethane (PU).

The method may comprise the step of applying heat to the conduit. The method may comprise the step of altering the shape of the conduit by applying heat to the conduit.

The conduit may be substantially cylindrically shaped. The conduit may be substantially tube shaped. The conduit may have a diameter of up to approximately 44 mm, optionally between approximately 8 mm and approximately 32 mm. The conduit may have a substantially uniform cross section throughout.

The conduit may comprise one or more crimps. The method may comprise the step of adding one or more crimps to the conduit. The method may comprise the step of mounting the conduit on a frame member. The method may comprise the step of affixing the conduit to a frame member. The frame member may be configurable to allow the conduit to move from the contracted state to the extended state. The frame member may be configurable to allow the conduit to move from the extended state to the contracted state. In the contracted state, the conduit may comprise between approximately 7 crimps per cm of length of the conduit and approximately 10 crimps per cm of length of the conduit. In the extended state, the conduit may comprise between approximately 4 crimps per cm of length of the conduit and approximately 6 crimps per cm of length of the conduit.

The conduit may comprise a twill-weave section. The conduit may be a twill-weave conduit. The conduit may be a 1/1 twill-weave. The conduit may comprise a plain-weave section. The conduit may be a plain-weave conduit. The weft yarn pick-rate of the conduit may be between approximately 25 ppcm and approximately 50 ppcm, optionally between approximately 36 ppcm and approximately 45 ppcm. Useful yarns may include multifilament yarns.

The conduit or medical textile is not limited to a woven textile. Other textile constructions, such as knitted textiles, braided textiles, fabric webs, fabric felts, filament spun textiles, and the like, can be used. Such textile or fabric constructions may be used with the methods, coatings, and/or masking agents of the present invention in both medical applications (including vascular and non-vascular applications) and non-medical applications.

In general, useful yarn materials include, but are not limited to, polyesters, polypropylenes, polyethylenes, polyurethanes, polytetrafluoroethylenes, and combinations thereof. The yarns may be of the monofilament, multifilament, or spun type. Multifilament yarns may contain from about 8 filaments to about 96 fiber filaments, desirably from about 20 filaments to about 40 filaments, more desirably from about 25 filaments to about 30 filaments. The yarns may have a linear density from about 18 denier (about 20 decitex) to about 140 denier (about 154 decitex), more desirably from about 30 denier (about 33 decitex) to about 60 denier (about 67 decitex), more desirably from about 40 denier (about 44 decitex) to about 45 denier (50 decitex). The yarns may be flat, twisted, and/or textured, and may have high, low or moderate shrinkage and/or bulk and crimp properties. Twisted yarns include S-twisted yarns and Z-twisted yarns. The number of twists per inch may vary from about 2 twists per inch (about 0.8 twists per cm) to about 15 twists per inch (about 6 twists per cm), more desirably from about 5 twists per inch (about 2 twists per cm) to about 12 twists per inch (about 5 twists per cm). Desirably, the yarns are single ply yarns or multi-ply yarns. Multi-ply yarns may contain from about 2 yarns per ply or bundle to about 4 yarns per ply or bundle.

The textile graft of the present invention may be woven from yarns using any known weave pattern, including simple plain weaves, basket weaves, twill weaves, velour weaves and the like. Weave patterns include warp yarns running along the longitudinal length of the woven product and weft also known as fill yarns running around the width or circumference of the woven product. The warp and the fill yarns are at approximately 90 degrees to one another with fabric flowing from the machine in the warp direction. The weave pattern may have from about 80 to about 325 warp yarns per inch (about 30 to about 128 warp yarns per cm) and about 80 to about 200 fill or weft yarns per inch (about 30 to about 80 fill yarns per cm). The wall thickness may be any conventional useful thickness, for example about 0.04 mm to about 1 mm.

Knitting involves the interlooping or stitching of yarn into vertical columns (wales) and horizontal rows (courses) of loops to form the knitted fabric structure. In warp knitting, the loops are formed along the textile length, i.e., in the wale or warp direction of the textile. Non-limiting stitch counts may include about 20 to about 60 wales per inch per layer (about 8 to about 25 wales per cm per layer) and 30 to 80 courses per inch per layer (about 12 to about 32 courses per cm per layer). Non-limiting overall number of stitches may vary from about 600 to about 5,000 stitches per square inch (about 100 to about 900 stitches per square centimeter). Useful knitting patterns include, but are not limited to, locknit knits (also referred to as tricot or jersey knits), reverse locknit knits, sharkskin knits, queenscord knits, atlas knits, velour knits, and the like. The wall thickness may be any conventional useful thickness, for example about 0.1 mm to about 1.5 mm.

The conduit may comprise one or more inlets. The conduit may comprise one or more outlets. The conduit may be a Y-shaped conduit. The conduit may be a T-shaped conduit. The conduit may be one or more of a cylindrical, tubular, Y-shaped, T-shaped, and multi-channel conduit. The conduit may have a bulbous shape or a portion having a bulbous shape. Such a bulbous shape may have, but is not limited to, a Valsalva aortic root profile. The present invention, however, is not limited to the conduit-shaped textiles. Other shaped textiles, such as planar or shaped sheets or tapes, may be used with the present invention.

The conduit may be a porous conduit. The conduit may be a porous conduit, for example having a water permeability of greater than 0.16 ml/min/cm$^2$ at 120 mm Hg pressure.

The inner surface of the wall of the conduit may be configured to promote biological tissue growth thereon. The inner surface of the wall of the conduit may be configured to allow biological tissue to grow thereon. The inner surface of the wall of the conduit may be configured to promote the growth of biological tissue thereon, at least in part by being substantially devoid of the sealant. The inner surface of the wall of the conduit may be configured to promote the growth of pseudointima. The inner surface of the wall of the conduit may be configured to allow the growth of pseudointima to occur thereon. The inner surface of the wall of the conduit may be configured to promote the adhesion of biological tissue thereto. The inner surface of the wall of the conduit may be configured to allow biological tissue to adhere thereto. The inner surface of the wall of the conduit may be configured to promote the adhesion of platelets thereto.

The inner surface of the wall of the conduit may be fibrous. The inner surface of the wall of the conduit may comprise woven fibres. The inner surface of the wall of the conduit may comprise a braided section. The inner surface of the wall of the conduit may be a substantially braided surface.

The masking agent may form a sacrificial layer. The masking agent may form a masking layer. The masking agent may form a sacrificial masking layer on at least a part of the conduit. The masking agent may be reversibly applicable to the conduit.

The masking layer may be an oleophobic layer.

The masking agent may be added to at least a part of the conduit. The masking agent may be added to substantially all of the conduit. The masking agent may be added to substantially all of the porous section of the conduit. The masking agent may be added to the inner surface of the wall of the conduit.

The method may comprise the further step of removing at least part of the masking agent from the conduit. The method may comprise one or more masking agent removal steps. The masking agent may be removed from the conduit by applying a masking agent remover to the masking agent.

The method may comprise a first masking agent removal step carried out prior to the step of adding the sealant to at least a part of the porous section. The method may comprise a second masking agent removal step carried out subsequent to the step of adding the sealant to at least a part of the porous section of the conduit. The method may comprise a first masking agent removal step carried out prior to the step of adding the sealant to at least a part of the porous section, and a second masking agent removal step carried out subsequent to the step of adding the sealant to at least a part of the porous section of the conduit.

The method may comprise the step of removing at least a part of the masking agent from the outer surface of the wall of the conduit. The method may comprise the step of removing at least part of the masking agent from the outer surface of the wall of the conduit, prior to the addition of the sealant. The method may comprise the step of removing at least a part of the masking agent from the outer surface of the wall of the conduit, such that at least a part of the outer surface of the wall of the conduit is devoid of the masking agent. In this arrangement, the sealant may be added to at least a part of the outer surface of the wall of the conduit.

The step of removing at least part of the masking agent from the outer surface of the wall of the conduit may be carried out by etching, plasma etching, abrading, and/or ablating.

The step of removing at least a part of the masking agent may comprise the step of applying a solvent to the masking agent. The solvent may be water.

The method may comprise the step of removing substantially all of the masking agent from the conduit. The step of removing substantially all of the masking agent from the conduit may be carried out after the step of adding the sealant to at least a part of the porous section of the conduit. The step of removing substantially all of the masking agent, when performed after the addition of the sealant to at least a part of the porous section of the conduit, may be carried out such that it does not result in the removal of the sealant from the conduit.

The step of removing substantially all of the masking agent may comprise the step of applying a solvent to the masking agent. The solvent may be water.

The step of removing at least a part of the masking agent may be carried out at a temperature of between approximately 15° C. and approximately 140° C., optionally between approximately 15° C. and approximately 95° C., optionally between approximately 35° C. and approximately 45° C., optionally approximately 40° C. The step of removing at least a part of the masking agent may be carried out for between approximately 40 minutes and approximately 300 minutes, optionally between approximately 40 minutes and approximately 60 minutes, optionally between approximately 45 minutes and approximately 55 minutes, optionally for approximately 51 minutes.

The step of removing at least a part of the masking agent may be carried out by applying gas to the conduit. The step of removing at least a part of the masking agent may be carried out by applying steam to the conduit. The step of removing at least a part of the masking agent may be carried out in an autoclave.

The method may comprise the step of agitating the conduit. The step of agitating the conduit may be carried out during any of the other steps of the method. The step of removing at least part of the masking agent may be carried out while agitating the conduit in a solution comprising a solvent. The solvent may be water.

When applied to the conduit, the masking agent may form a masking agent layer. The masking agent layer may be a polymer layer. The masking agent may be applied to the conduit using a masking agent solution. The method may comprise the step of applying the masking agent solution to the conduit. The method may comprise the further step of removing solvent from the masking agent solution.

The masking agent solution may comprise a solvent. The masking agent solution may comprise a polar solvent. The masking agent solution may comprise water.

The step of removing solvent from the masking agent solution may be carried out by evaporating solvent therefrom. The method may comprise the further step of evaporating solvent from the masking agent solution at a temperature of between approximately 15° C. and approximately 80° C., optionally between approximately 50° C. and approximately 80° C.

The masking agent may be added to the conduit by immersing the conduit in the masking agent. The masking agent may be added to the conduit by immersing the conduit in the masking agent solution. The masking agent may be added to the conduit by immersing the conduit in the masking agent solution while agitating the conduit. The masking agent may be added to the conduit by immersing the conduit in the masking agent, or in the masking agent solution, for up to approximately 1 minute. The masking agent may be added to the conduit by immersing the conduit in the masking agent, or in the masking agent solution, for up to approximately 1 minute while agitating the conduit.

The masking agent may be added to the conduit by applying a masking agent solution to the inner surface of the wall of the conduit. The masking agent may be added to the conduit by applying a masking agent solution to the outer surface of the wall of the conduit.

The masking agent may be added to the conduit by immersing the conduit in the masking agent, by dipping the conduit in the masking agent, by spray coating the masking agent onto the conduit, and/or by brushing the masking agent onto the conduit.

The masking agent solution may be added to the conduit by spraying the masking agent onto at least a part of the porous section of the conduit.

The masking agent may comprise polyvinylpyrrolidone (PVP). The masking agent may comprise PVP having a molecular weight of between approximately 6,000 g/mol and approximately 15,000 g/mol, optionally between approximately 8,000 g/mol and approximately 12,000 g/mol, optionally approximately 10,000 g/mol. The masking agent may comprise glycerol. The masking agent may comprise PVP and glycerol.

The masking agent may be water-soluble.

The masking agent solution may comprise PVP and water. The masking agent solution may comprise PVP, glycerol and water.

The masking agent may comprise between approximately 3% w/v and approximately 30% w/v of polymer in solution, optionally between approximately 5% w/v and approximately 30% w/v of polymer in solution, optionally between approximately 5% w/v and approximately 20% w/v of polymer in solution, optionally between approximately 5% w/v and approximately 10% w/v of polymer in solution, optionally between approximately 5% w/v and approximately 7% w/v of polymer in solution, optionally approximately 7% w/v of polymer in solution, optionally approximately 6% w/v of polymer in solution, optionally approximately 5% w/v of polymer in solution, optionally approximately 4% w/v of polymer in solution, optionally approximately 3% w/v of polymer in solution. The masking agent may comprise between approximately 3% w/v and approximately 80% w/v of polymer in solution.

The masking agent solution may comprise between approximately 3% w/v of PVP in solution and approximately 30% w/v of PVP in solution, optionally between approximately 5% w/v and approximately 30% w/v of PVP in solution, optionally between approximately 5% w/v and approximately 20% w/v of PVP in solution, optionally between approximately 5% w/v and approximately 10% w/v of PVP in solution, optionally approximately 7% w/v of PVP in solution, optionally approximately 6% w/v of PVP in solution, optionally approximately 5% w/v of PVP in solution, optionally approximately 4% w/v of PVP in solution, optionally approximately 3% w/v of PVP in solution.

The masking agent solution may comprise approximately 1% w/v of glycerol in solution. The masking agent solution may comprise approximately 6% w/v of PVP in solution, and approximately 1% w/v of glycerol in solution. The ratio of glycerol to masking agent in the masking agent solution may be between approximately 1% and approximately 100%. The ratio of glycerol to masking agent in the masking agent solution may be between approximately 1% and approximately 30%, optionally between approximately 1.5% and approximately 30%, optionally between approximately 5% and approximately 30%, optionally between approximately 1% and approximately 20%, optionally between approximately 1% and approximately 15%, and optionally between approximately 1% and approximately 10%.

The masking agent may comprise methyl cellulose. The masking agent may comprise poly(ethylene glycol) (PEG). The masking agent may comprise PEG hydrogel.

The masking agent may be made from a biocompatible material, or from biocompatible materials. Applying the masking agent to the conduit may form a biocompatible layer.

The terms biodegrade, biodegradable, bioabsorbable and bioresorbable are used herein to refer to materials which degrade over time when implanted in the human or animal body.

The masking agent may comprise a bioresorbable, or a biodegradable material. The masking agent may be biodegradable. The masking agent may be configured to biodegrade when implanted inside a human or animal body. The masking agent may be configured to bioresorb when implanted inside a human or animal body. The masking agent may be a biodegradable polymer. The masking agent may comprise a biodegradable polymer. The masking agent may be configurable to be biodegradable.

During the step of adding the masking agent to at least a part of the porous section of the conduit, the conduit may be moved from the contracted state to the extended state. During the step of adding the masking agent to at least a part of the porous section of the conduit, the conduit may be moved from the extended state to the contracted state. The step of adding the masking agent to at least a part of the porous section of the conduit may be carried out while the conduit is moved between the contracted state and the extended state. The step of adding the masking agent to at least a part of the porous section of the conduit may be carried out while the conduit is in the contracted state. The step of adding the masking agent to at least a part of the porous section of the conduit may be carried out while the conduit is in the extended state. One or more of the steps of the method may be carried out while the conduit is moved between the contracted state and the extended state.

The step of moving the conduit between the contracted state and the extended state may elongate the conduit by a factor of up to approximately 100%. The step of moving the conduit between the contracted state and the extended state may elongate the conduit by a factor of between approximately 45% and approximately 55%. The step of moving the conduit between the contracted state and the extended state may elongate the conduit by a factor of approximately 50%. In the contracted state, the length of the conduit may be reduced from its fully extended length by a factor of between approximately 20% and approximately 80%, optionally between approximately 20% and approximately 40%, optionally between approximately 40% and approximately 60%. In the extended state, the length of the conduit may be reduced from its fully extended length by a factor of between approximately 20% and approximately 80%, optionally between approximately 20% and approximately 40%, optionally between approximately 40% and approximately 60%.

The step of adding the masking agent to at least a part of the porous section of the conduit may include providing gas to the conduit. The gas may be configured to flow towards the outer surface of the wall of the conduit. In this arrangement, the step of adding the masking agent to the conduit results in the masking agent being formed preferentially on the inner surface of the wall of the conduit. In this arrangement, the outer surface of the wall of the conduit may remain substantially devoid of the masking agent. The gas may be air.

The sealant may be configured to substantially block the porous section of the conduit, such that the flow of fluid through the porous section of the conduit is mitigated. The sealant may be configured to prevent, or obviate, movement of fluid through the wall of the conduit. The fluid may be blood.

The sealant may be added to at least a part of the outer surface of the wall of the conduit. The sealant may be added to substantially all of the outer surface of the wall of the conduit.

The method may be carried out such that the step of adding the sealant to at least a part of the porous section of the conduit does not result in the removal of the masking agent. In this arrangement, the sealant and the masking agent are compatible with each other. That is, the sealant and the masking agent can be in contact with each other without either the sealant or the masking agent being damaged or, when applied to the conduit, from being removed therefrom.

The sealant may be biocompatible. The sealant may be made from a biocompatible material, or from biocompatible materials. The sealant may form a sealing layer. The sealing layer may be a biocompatible layer. The sealant may form a biocompatible layer.

The sealant may be a polymer. The sealing layer may be a polymer layer. The sealant may comprise polyurethane. The sealant may comprise thermoplastic polyurethane (TPU). The sealant may comprise silicone. The sealant may comprise polyurethane and silicone. The sealant may comprise TPU and silicone. The sealant may comprise aliphatic polycarbonate. The sealant may comprise polyurethane and aliphatic polycarbonate. The sealant may comprise TPU and aliphatic polycarbonate. The sealant may comprise room temperature vulcanising (RTV) silicone. The sealant may comprise RTV silicone elastomer. The sealant may comprise polycarbonate. The sealant may comprise one or more thermoplastic elastomers.

The sealant solution may comprise polyurethane. The sealant solution may comprise TPU. The sealant solution may comprise silicone. The sealant solution may comprise polyurethane and silicone. The sealant solution may comprise TPU and silicone. The sealant solution may comprise aliphatic polycarbonate. The sealant solution may comprise polyurethane and aliphatic polycarbonate. The sealant solution may comprise TPU and aliphatic polycarbonate. The sealant solution may comprise RTV silicone. The sealant solution may comprise RTV silicone elastomer. The sealant solution may comprise polycarbonate. The sealant solution may comprise one or more thermoplastic elastomers.

The organic solvent may be an aprotic solvent. The organic solvent may be a non-polar solvent. The sealant solution may comprise heptane. The sealant solution may comprise xylene. The sealant solution may comprise silicone and heptane. The sealant solution may comprise silicone and xylene. The sealant solution may comprise RTV silicone elastomer and heptane. The sealant solution may comprise RTV silicone elastomer and xylene. The sealant solution may comprise polyurethane and heptane. The sealant solution may comprise polyurethane and xylene. The sealant solution may comprise polycarbonate and heptane. The sealant solution may comprise polycarbonate and xylene.

The sealant solution may comprise a polar solvent. The sealant solution may comprise dimethylacetamide (DMAC). The sealant solution may comprise tetrahydrofuran (THF). The sealant solution may comprise TPU and DMAC. The sealant solution may comprise thermoplastic polyurethane and THF.

The sealant may be configurable to mitigate against environmental stress cracking. The sealant, when applied to the conduit may be configured to mitigate against environmental stress cracking.

The method may comprise the step of removing solvent from the sealant. The method may comprise the step of removing solvent from the sealant solution. The step of removing solvent may be carried out by evaporating solvent from the sealant. The step of removing solvent may be carried out by evaporating solvent from the sealant solution.

The sealant may be added to the conduit by brushing the sealant onto the conduit. The sealant may be added to the conduit by spray-coating the sealant onto the conduit. The sealant may be added to the conduit by dipping the conduit in the sealant. The sealant may be added to the conduit by casting the sealant onto the conduit. The sealant may be added to the conduit by immersing the conduit in the sealant. The sealant may be added by vapour deposition. The sealant may be added by chemical vapour deposition. The sealant may be added by electrostatic spinning and/or filament spinning. The sealant may be added to the conduit by wiping the sealant onto the conduit. The sealant may be added to the conduit while the conduit is rotated about its longitudinal axis. The sealant may be added to the conduit while the conduit is rotated about its longitudinal axis at up to approximately 2,000 rpm, optionally between 700 rpm and 2,000 rpm, optionally between approximately 40 rpm and approximately 80 rpm, optionally at approximately 60 rpm.

Prior to applying the masking agent and the sealant, the surface of the textile, medical textile or medical device (e.g. prosthesis) may be surface treated with an elastomer. The elastomer may be the same elastomer as the sealant or it may be a different elastomer. Such surface treatment is designed to be a very light application of the elastomer to ensure that no elastomer penetrates through the wall of the textile fabric. Such surface treatment may be applied by light surface spraying, selective area coating or application of thin elastomeric fibers prior to their cure. For example, spots of elastomer may be placed along the length and radius. The purpose of surface treating is to ensure that the sealant will have a place to adhere in the event that excess masking agent unintentionally interferes with the sealant. The surface treatment will repel the masking agent, thus providing an attachment/adhesion site for the sealant.

The surface treatment may also be used to alter the properties of the textile to, for example, promote adhesion of the sealing agent thereat. This may involve surface activation for altering chemical adhesion properties on the textile for enhanced securement of the sealant thereat. Further, the hydrophilicity and/or hydrophobicity of portions of the textile may also be modified for enhanced attraction and/or repulsion of the masking agent(s) and/or sealants. Non-limiting techniques may include, but are not limited to, the use of plasma generation, including low pressure or vacuum generation, atmospheric pressure generation, elevated pressure generation, including for example, glow discharge generation, corona discharge generation, dielectric-barrier discharge generation, and the like. Further, ultraviolet irradiation and laser treatments may be used. Such preconditioning before applying the masking agent and/or the sealant may promote sealant attachment via physical and/or chemical modification of the textile substrate. Further, the textile patterns themselves may be modified to include greater extents of floating yarns to provide a raised yarn or velour surface to the textile where such raised yarns will provide greater access points for sealant securement to the graft.

During the step of adding the sealant to the conduit, the conduit may be moved from the contracted state to the extended state. During the step of adding the sealant to the conduit, the conduit may be moved from the extended state to the contracted state. During the step of adding the sealant to the conduit, the conduit may be moved between the contracted state and the extended state.

The step of adding the sealant to the conduit may be carried out, at least in part, when the conduit is in the contracted state. The step of adding the sealant to the conduit may be carried out, at least in part, when the conduit is in the extended state. The step of adding the sealant to the conduit may be carried out, at least in part, when the conduit is moved between the contracted state and the extended state.

The step of moving the conduit between the contracted state and the extended state may elongate the conduit by up to approximately 100%. The step of moving the conduit between the contracted state and the extended state may elongate the conduit by between approximately 45% and approximately 55%. In the contracted state, the length of the conduit may be reduced from its fully extended length by a factor of between approximately 20% and approximately 80%, optionally between approximately 20% and approximately 40%, optionally between approximately 40% and approximately 60%. In the extended state, the length of the conduit may be reduced from its fully extended length by a factor of between approximately 20% and approximately 80%, optionally between approximately 20% and approximately 40%, optionally between approximately 40% and approximately 60%.

The sealant, once added to the conduit, may comprise between approximately 4 mg per $cm^2$ and 19 mg per $cm^2$ of silicone, optionally approximately 8 mg per $cm^2$.

The method may comprise the further step of drying the vascular prosthesis. The further step of drying the vascular prosthesis may be carried out at a temperature of between approximately 15° C. to approximately 45° C. The further step of drying the vascular prosthesis may be carried out after the step of removing at least part of the masking agent from the conduit. The further step of drying the vascular prosthesis may be carried out after the step of adding the sealant to the conduit. The drying step may be configured to, at least in part, remove residual solvent, water, or the like, from the vascular prosthesis.

The further step of drying the vascular prosthesis may comprise the step of providing gas to the vascular prosthesis. The gas may be air.

The method may comprise multiple drying steps.

The, or each, drying step may be carried out at a temperature of between approximately 15° C. to approximately 45° C.

The method may comprise the step of weighing the conduit. The step of weighing the conduit may be carried out prior to the step of adding the masking agent to the conduit. The step of weighing the conduit may be carried out prior to the step of adding the sealant to the conduit. The step of weighing the conduit may be used to determine, at least in part, the amount of masking agent to be applied to the conduit. The step of weighing the conduit may be used to determine, at least in part, the amount of sealant to be applied to the conduit.

The method may comprise the step of measuring the length of the conduit. The measurement of the length of the conduit may be used, at least in part, to determine the amount of masking agent to be added to the conduit. The measurement of the length of the conduit may be used, at least in part, to determine the amount of sealant to be added to the conduit.

The weight of the conduit, and the length of the conduit, may be used, at least in part, to determine the amount of masking agent to be added to the conduit. The weight of the conduit, and the length of the conduit, may be used, at least in part, to determine the amount of sealant to be added to the conduit.

The support member may be added to the wall of the conduit. The support member may be added to the inner surface of the wall of the conduit. The support member may be added to the inner surface and the outer surface of the wall of the conduit. The sealant may be configured to attach the support member to the conduit. In this arrangement, the support member is added to the conduit and the sealant is then added to the conduit in order to seal the conduit, and to attach the support member to the conduit.

The support member may be a cable, wire or the like. The support member may comprise at least one of a polymer material, a metal material, a shape memory alloy, and a superelastic alloy. The support member may comprise at least one of: polyethylene terephthalate, polytetrafluoroethylene, polyurethane, polycarbonate, silicone, stainless steel, titanium, nickel, and nickel titanium (Nitinol). The support member may be a flexible member. The support member may be capable of being wrapped around the conduit. The support member may be arranged to nest between the crimps of the conduit. The support member may be a flexible, polymer wire. The support member may be a metallic or polymeric member, such as a shape memory metallic or polymeric member. The support member may be disposed at an inner portion of the conduit, at an outer portion of the conduit, within the textile wall of the conduit, and combinations thereof. The support member may be secured to the conduit by the sealant, for example the sealant may encapsulate the support member or the support member may be embedded in the sealant. In some embodiments, the support member may be secured to the conduit by other means, such as suturing, adhesive bonding, etc. The support member may be arranged longitudinally, radially or a combination thereof, about the conduit.

The support member may be biocompatible.

The vascular prosthesis may be connectable to one or more further prosthesis, or prostheses. The inlet of the vascular prosthesis may be connectable to an outlet of a further prosthesis. The outlet of the vascular prosthesis may be connectable to an inlet of a further prosthesis. The vascular prosthesis may be connectable to one or more heart valves, or synthetic heart valves. The vascular prosthesis may be connectable to a cardiac assist device, a ventricular assist device, a left ventricular assist device, and/or a right ventricular assist device, a biological heart valve, or the like. The further prosthesis may be a biological heart valve.

The vascular prosthesis may be connectable to one or more blood vessels. The vascular prosthesis may be connectable to one or more blood vessels by way of suture(s).

The vascular prosthesis may be locatable between a first end and a second end of a severed, or diseased, blood vessel. The inlet of the vascular prosthesis may be connectable to the first end of the severed, or diseased, blood vessel. The outlet of the vascular prosthesis may be connectable to the second end of the severed, or diseased blood vessel.

The method may comprise the step of sterilising the vascular prosthesis. The step of sterilising the vascular prosthesis may be carried out by way of a gamma sterilisation process. The further step of sterilising the vascular prosthesis may be carried out by way of an electron beam sterilisation process. The further step of sterilising the vascular prosthesis may be carried out by way of ethylene oxide sterilisation. The method may comprise one or more sterilisation steps. The vascular prosthesis may be configured to be capable of being sterilised, such that the vascular prosthesis is not damaged or structurally altered by being sterilised. The step of sterilising the vascular prosthesis may configure the vascular prosthesis to be suitable for implantation in the human or animal body.

According to a second aspect of the invention there is provided a vascular prosthesis comprising:

a conduit comprising a wall, the wall of the conduit comprising an inner surface and an outer surface, at least a section of the conduit being porous;

wherein at least a part of the porous section comprises a sealant configured to mitigate movement of fluid through the wall of the conduit; and wherein the inner surface of the wall of the conduit is substantially devoid of the sealant.

The sealant may form a sealing layer on at least a part of the outer surface of the wall of the conduit.

The sealant may form a sealing layer on substantially all of the outer surface of the wall of the conduit.

Substantially all of the conduit may be porous.

The inner surface of the wall of the conduit may be configured to promote the ingrowth of biological tissue thereon.

The conduit may be a woven fibrous polymer conduit.

The sealant may form a sealing layer, the sealing layer being a polymer layer.

The sealant may comprise at least one of: silicone, room temperature vulcanising silicone, thermoplastic polyurethane, aliphatic polycarbonate, one or more thermoplastic elastomers, and polycarbonate.

The sealant may be configured to mitigate movement of blood through the wall of the conduit.

The vascular prosthesis may be sterilised.

The vascular prosthesis may be sterilised by way of at least one of the following: a gamma sterilisation process, an ethylene oxide sterilisation process, and an electron beam sterilisation process.

The conduit may be moveable between a contracted state and an extended state.

The conduit may comprise a support member.

The support member may be located substantially adjacent to the outer surface of the wall of the conduit.

The support member may be wrapped around the outer surface of the wall of the conduit.

The conduit may comprise a plurality of crimps, the support member being arranged to nest between the plurality of crimps.

The sealant may be arranged to, at least in part, attach the support member to the conduit.

The support member may be a flexible, polymer member.

The conduit may be configured to have at least two sections having substantially different amounts of sealant thereon.

Embodiments of the second aspect of the invention may include one or more features of the first aspect of the invention or its embodiments. Similarly, embodiments of the first aspect of the invention may include one or more features of the second aspect of the invention or its embodiments.

According to a third aspect of the present invention there is provided a kit of parts for manufacturing a vascular prosthesis, the kit of parts comprising:

(i) a conduit comprising a wall, the wall of the conduit comprising an inner surface and an outer surface, at least a section of the conduit being porous;

(ii) a masking agent; and (iii) a sealant;

when applied to at least a part of the porous section of the conduit, the masking agent being configured to mitigate presence of the sealant on the inner surface of the conduit; and when applied to at least a part of the porous section of the conduit, the sealant being configured to mitigate movement of fluid through the wall of the conduit.

Addition of the sealant to at least a part of the porous section of the conduit may form a sealing layer on at least a part of the outer surface of the wall of the conduit.

Addition of the masking agent to at least a part of the porous section of the conduit may form a masking agent layer on at least part of the inner surface of the wall of the conduit.

Substantially all of the conduit may be porous.

The kit of parts may comprise a masking agent remover, the masking agent remover being operable to remove applied masking agent from the conduit.

The masking agent remover may comprise a solvent.

The solvent may comprise water.

The masking agent remover may be operable to remove applied masking agent from the conduit at a temperature of between approximately 15° C. and approximately 140° C.

The kit of parts may comprise an abrading tool, the abrading tool being operable to remove applied masking agent from the conduit.

The inner surface of the wall of the conduit may be configured to promote the ingrowth of biological tissue thereon.

The masking agent may comprise a polymer.

The masking agent may comprise a water-soluble polymer.

The masking agent applied to the conduit may form a masking agent layer, the masking agent layer being a polymer layer.

The masking agent may comprise at least one of: polyvinylpyrrolidone, glycerol, methyl cellulose, and poly(ethylene glycol) hydrogel. The masking agent may comprise at least one of: polyvinylpyrrolidone, glycerol, methyl cellulose, polyethylene oxide, and poly(ethylene glycol) hydrogel, as well as biological products as further described herein such as collagen and gelatine.

The masking agent may be biocompatible.

Masking agent applied to the conduit may form a biocompatible masking agent layer.

The kit of parts may comprise a masking agent solution, the masking agent solution being operable to apply masking agent to the conduit.

The masking agent solution may be a polymer solution.

The conduit may be immersible in the masking agent solution.

The masking agent solution may comprise between approximately 5% w/v of polymer in solution and approximately 30% w/v of polymer in solution.

When the masking agent and the sealant are applied to the conduit, the sealant may be configured such that addition of the sealant to the conduit does not result in the removal of the applied masking agent from the conduit.

The masking agent may be configured to biodegrade when implanted inside the human or animal body.

The conduit may be a woven fibrous polymer conduit.

The sealant may comprise a polymer, optionally a water-insoluble polymer.

The sealant, when applied to the conduit, may form a sealing layer, the sealing layer being a polymer layer.

The sealant may comprise at least one of: silicone, room temperature vulcanising silicone, thermoplastic polyurethane, aliphatic polycarbonate, one or more thermoplastic elastomers, and polycarbonate.

The kit of parts may comprise a sealant solution operable to apply sealant to the conduit.

The sealant solution may be a polymer solution.

The sealant solution may comprise an organic solvent.

The sealant solution may comprise at least one of heptane and xylene.

The kit of parts may comprise a sealant applicator operable to apply sealant to the conduit, and/or a masking agent applicator operable to apply masking agent to the conduit.

The sealant applicator may be an apparatus for spray coating the sealant, and/or a brush, or the like.

The masking agent applicator may be a brush, an apparatus for spray-coating the masking agent, an apparatus for dipping or immersing the conduit in the masking agent, and/or an apparatus for wiping the masking agent onto the conduit.

The sealant, when applied to at least a part of the porous section of the conduit, may be configured to mitigate movement of blood through the wall of the conduit.

The conduit may be moveable between a contracted state and an extended state.

The kit of parts may comprise a further prosthesis.

The further prosthesis may be at least one of: a biological heart valve, a synthetic heart valve, a cardiac assist device, and a ventricular assist device, or the like.

The kit of parts may comprise a weighing device and/or a device for measuring the length of the conduit.

The kit of parts may comprise a gas flow apparatus operable to provide gas flow to the conduit.

The gas may be air.

Embodiments of the third aspect of the invention may include one or more features of the first and/or second aspects of the invention and/or their embodiments. Similarly, embodiments of the first and/or second aspects of the invention may include one or more features of the third aspect of the invention and/or its embodiments.

According to a fourth aspect of the present invention, there is provided a method of manufacturing a vascular prosthesis according to the second aspect of the present invention.

Embodiments of the fourth aspect of the invention may include one or more features of the first, second and/or third aspects of the invention and/or their embodiments. Similarly, embodiments of the first, second and/or third aspects of the invention may include one or more features of the fourth aspect of the invention and/or its embodiments.

According to a fifth aspect of the present invention, there is provided a vascular prosthesis manufactured using the method of the first aspect of the present invention.

Embodiments of the fifth aspect of the invention may include one or more features of the first, second, third and/or fourth aspects of the invention and/or their embodiments. Similarly, embodiments of the first, second, third and/or fourth aspects of the invention may include one or more features of the fifth aspect of the invention and/or its embodiments.

According to a sixth aspect of the present invention, there is provided a vascular system, the vascular system comprising:
a vascular prosthesis manufactured according to the first aspect of the invention; and
a further prosthesis;
wherein the vascular prosthesis is connected to the further prosthesis, such that fluid can flow between the vascular prosthesis and the further prosthesis.

The further prosthesis may be at least one of: a biological heart valve, a synthetic heart valve, a cardiac assist device, and a ventricular assist device, or the like.

The further prosthesis may be a left ventricular assist device, a right ventricular assist device, and/or a synthetic heart valve, or the like.

Embodiments of the sixth aspect of the invention may include one or more features of the first, second, third, fourth and/or fifth aspects of the invention and/or their embodiments. Similarly, embodiments of the first, second, third, fourth, and/or fifth aspects of the invention may include one or more features of the sixth aspect of the invention and/or its embodiments.

According to a seventh aspect of the present invention, there is provided a vascular system, the vascular system comprising:
a vascular prosthesis according to the second aspect of the invention; and
a further prosthesis;
wherein the vascular prosthesis is connected to the further prosthesis, such that fluid can flow between the vascular prosthesis and the further prosthesis.

The further prosthesis may be at least one of: a biological heart valve, a synthetic heart valve, a cardiac assist device, and a ventricular assist device, or the like.

The further prosthesis may be a left ventricular assist device, a right ventricular assist device, and/or a synthetic heart valve, or the like.

Embodiments of the seventh aspect of the invention may include one or more features of the first, second, third, fourth, fifth and/or sixth aspects of the invention and/or their embodiments. Similarly, embodiments of the first, second, third, fourth, fifth and/or sixth aspects of the invention may include one or more features of the seventh aspect of the invention and/or its embodiments.

According to an eighth aspect of the invention there is provided a method of implanting a vascular prosthesis, the method comprising the steps of:
providing a vascular prosthesis manufactured according to the first aspect of the invention;
connecting an inlet of the vascular prosthesis to a first blood vessel; and
connecting an outlet of the vascular prosthesis to a second blood vessel;
such that blood can flow between the first and second blood vessels through the vascular prosthesis.

The first and second blood vessels may be formed from a blood vessel which is diseased, or has been severed, bisected, or the like.

Embodiments of the eighth aspect of the invention may include one or more features of the first, second, third, fourth, fifth, sixth and/or seventh aspects of the invention and/or their embodiments. Similarly, embodiments of the first, second, third, fourth, fifth, sixth and/or seventh aspects of the invention may include one or more features of the eighth aspect of the invention and/or its embodiments.

According to a ninth aspect of the present invention, there is provided a method of implanting a vascular prosthesis, the method comprising the steps of:

providing a vascular prosthesis according to the second aspect of the invention;

connecting the vascular prosthesis to a first blood vessel; and connecting the vascular prosthesis to a second blood vessel;

such that blood can flow between the first and second blood vessels through the vascular prosthesis.

The first and second blood vessels may be formed from a blood vessel which is diseased, or has been severed, bisected, or the like.

Embodiments of the ninth aspect of the invention may include one or more features of the first, second, third, fourth, fifth, sixth, seventh and/or eighth aspects of the invention and/or their embodiments. Similarly, embodiments of the first, second, third, fourth, fifth, sixth, seventh and/or eighth aspects of the invention may include one or more features of the ninth aspect of the invention and/or its embodiments.

According to a tenth aspect of the invention there is provided a method of implanting a vascular system, the method comprising the steps of:

providing a vascular system, the vascular system comprising:

a vascular prosthesis manufactured according to the first aspect of the invention; and a further prosthesis;

wherein the vascular prosthesis is connectable to the further prosthesis;

connecting the vascular prosthesis to the further prosthesis, such that blood can flow therebetween;

connecting an end of a blood vessel to the vascular prosthesis; and connecting the further prosthesis to the heart;

such that blood can flow between the blood vessel and the heart through the vascular system.

The further prosthesis may be a heart valve, a cardiac assist device, and/or a ventricular assist device, or the like. The further prosthesis may be a left ventricular assist device, a right ventricular assist device, and/or a synthetic heart valve, or the like.

Embodiments of the tenth aspect of the invention may include one or more features of the first, second, third, fourth, fifth, sixth, seventh, eighth and/or ninth aspects of the invention and/or their embodiments. Similarly, embodiments of the first, second, third, fourth, fifth, sixth, seventh, eighth and/or ninth aspects of the invention may include one or more features of the tenth aspect of the invention and/or its embodiments.

According to an eleventh aspect of the invention there is provided a method of implanting a vascular system, the method comprising the steps of:

providing a vascular system, the vascular system comprising:

a vascular prosthesis according to the second aspect of the invention; and a further prosthesis;

wherein the vascular prosthesis is connectable to the further prosthesis;

connecting the vascular prosthesis to the further prosthesis, such that blood can flow therebetween;

connecting an end of a blood vessel to the vascular prosthesis; and connecting the further prosthesis to the heart;

such that blood can flow between the blood vessel and the heart through the vascular system.

The further prosthesis may be at least one of: a biological heart valve, a synthetic heart valve, a cardiac assist device, and a ventricular assist device, or the like.

The further prosthesis may be a left ventricular assist device, a right ventricular assist device, and/or a synthetic heart valve, or the like.

Embodiments of the eleventh aspect of the invention may include one or more features of the first, second, third, fourth, fifth, sixth, seventh, eighth, ninth and/or tenth aspects of the invention and/or their embodiments. Similarly, embodiments of the first, second, third, fourth, fifth, sixth, seventh, eighth, ninth and/or tenth aspects of the invention may include one or more features of the eleventh aspect of the invention and/or its embodiments.

According to a twelfth aspect of the invention there is provided a method of manufacturing a vascular prosthesis, the method comprising the steps of:

(i) providing a conduit comprising a wall, the wall of the conduit comprising an inner surface and an outer surface, at least a section of the conduit being porous; and (ii) adding a masking agent to at least a part of the porous section;

wherein the masking agent is configured to mitigate movement of fluid through the wall of the conduit.

Embodiments of the twelfth aspect of the invention may include one or more features of the first, second, third, fourth, fifth, sixth, seventh, eighth, ninth, tenth and/or eleventh aspects of the invention and/or their embodiments. Similarly, embodiments of the first, second, third, fourth, fifth, sixth, seventh, eighth, ninth, tenth and/or eleventh aspects of the invention may include one or more features of the twelfth aspect of the invention and/or its embodiments.

According to a thirteenth aspect of the invention there is provided a vascular prosthesis comprising:

a conduit comprising a wall, the wall of the conduit comprising an inner surface and an outer surface, at least a section of the conduit being porous;

wherein at least a part of the porous section comprises a masking agent configured to mitigate movement of fluid through the wall of the conduit.

Embodiments of the thirteenth aspect of the invention may include one or more features of the first, second, third, fourth, fifth, sixth, seventh, eighth, ninth, tenth, eleventh and/or twelfth aspects of the invention and/or their embodiments. Similarly, embodiments of the first, second, third, fourth, fifth, sixth, seventh, eighth, ninth, tenth, eleventh and/or twelfth aspects of the invention may include one or more features of the thirteenth aspect of the invention and/or its embodiments.

In another aspect or embodiment, a method of manufacturing a tubular graft may comprise the steps of: providing a textile comprising a tubular wall disposed between a first open end and an opposed second open end, an inner surface and an opposed outer surface defining an interior wall portion therein between, the tubular wall comprising a textile construction of one or more filaments or yarns, the textile construction by itself being permeable to liquid; applying a substantially water-soluble material to at least a portion of the tubular wall; and applying a substantially water-insoluble synthetic sealant to at least a part of the outer surface of the tubular wall, the substantially water-insoluble synthetic sealant being configured to mitigate movement of fluid through the wall of the conduit; wherein the water-soluble material is configured to mitigate penetration of the sealant to the inner surface of the conduit.

The step of applying the water-soluble material to at least a portion of the tubular wall may further comprise applying the water-soluble material to at least a portion of the inner surface and a portion of the interior portion of the tubular wall. The step of applying the water-soluble material to at least a portion of the tubular wall may further comprise applying the water-soluble material to at least a portion of the outer surface of the tubular wall.

The water-soluble material may be a solution of the water-soluble material and a solvent. The solvent may be selected form the group consisting of water, lower alcohols, and combinations thereof. The solvent may be at least partially removed prior to applying the substantially water-insoluble synthetic sealant.

The method may further comprise removal of at least a portion of the water-soluble material by dissolution, abrading, peeling, degrading, and combinations thereof.

The water-soluble material may be selected from the group consisting of polyvinylpyrrolidone, glycerol, methyl cellulose, poly(ethylene glycol), poly(ethylene glycol) hydrogel, polyethylene oxide, collagen, albumin, gelatin, and combinations thereof. The water-soluble material may have a molecular weight from about 400 to about 1,000,000. The water-soluble material may include plasticizers, such as but not limited to poly(ethylene glycol), polyethylene oxide, and the like.

The substantially water-insoluble synthetic sealant may be an elastomeric material selected from the group consisting of moisture curing, light curing, thermo-curing, platinum catalysed, anaerobic curing materials or a combination of these curing mechanisms. The elastomeric material may be selected from the group consisting of silicones, polyurethanes, polycarbonates, thermoplastic elastomers, and combinations thereof.

The one of more of the substantially water-soluble coating or the substantially water-insoluble coating may further comprise a component selected from the group consisting of a colorant, a therapeutic agent, a dye, and a fluorescent indicator.

The water-soluble material may comprise polyvinylpyrrolidone having a molecular weight of between approximately 6,000 g/mol and approximately 15,000 g/mol.

The applying the water-soluble material may form layer on substantially all of the inner surface of the tubular wall.

The method may further comprise curing the substantially water-insoluble synthetic sealant.

The method may further comprise curing the substantially water-insoluble synthetic sealant; and thereafter removing at least a portion of the water-soluble material. The method may further comprise removing substantially all of the water-soluble material from the inner surface of the tubular wall.

The method may further comprise: removing at least a part of the water-soluble material from at least a part of the outer surface of the tubular wall prior to the applying the substantially water-insoluble synthetic sealant.

The removing of at least the portion of the water-soluble material may be carried out at a temperature of between approximately 15° C. and approximately 140° C.

The removing at least the portion of the water-soluble material may further comprise the step of applying a solvent thereto. The solvent may comprise water, lower alcohols, and combinations thereof.

The tubular textile may be agitated, rotated, spun, and shaken, or the like, during the removal of the water-soluble material.

The removal of the water-soluble material may comprises dissolving, etching, plasma etching, ablating, abrading and combinations thereof of the water-soluble material.

The step of applying the water-soluble material may further comprise spraying the water-soluble material, brushing the water-soluble material, immersing at least a portion of the tubular wall into a solution of the water-soluble material, and combinations thereof.

The substantially water-insoluble synthetic sealant may be a polymer solution. The polymer solution may comprise an organic solvent. The organic solvent may comprise at least one of heptane and xylene.

The substantially water-insoluble synthetic sealant may be applied by brushing, spraying, roller coating the substantially water-insoluble synthetic sealant thereon.

The may further comprise one or more steps of selectively applying the substantially water-insoluble synthetic sealant to one or more portions of the tubular wall, such that the tubular wall comprises at least two sections having substantially different amounts of the substantially water-insoluble synthetic sealant thereon.

The tubular wall having the coating of the substantially water-insoluble synthetic sealant may be, after curing thereof, substantially impermeable to liquid. After curing of the substantially water-insoluble synthetic sealant, the tubular wall may have a water permeability of about 0.16 ml/min/cm$^2$ at 120 mm Hg pressure or less than 0.16 ml/min/cm$^2$ at 120 mm Hg pressure.

In another aspect or embodiment, a textile may comprise: a tubular wall disposed between a first open end and an opposed second open end and having an inner surface and an opposed outer surface, the tubular wall comprising a textile construction of one or more filaments or yarns, the textile construction by itself being permeable to liquid; wherein a portion of the inner surface comprises a coating of a substantially water-soluble material thereon; wherein the outer surface further comprises a coating of a substantially water-insoluble synthetic sealant disposed thereon; and wherein the tubular wall having the coating of the substantially water-insoluble synthetic sealant is, after curing thereof, substantially impermeable to liquid.

The water-soluble material may be selected from the group consisting of polyvinylpyrrolidone, glycerol, methyl cellulose, poly(ethylene glycol), poly(ethylene glycol) hydrogel, polyethylene oxide, and combinations thereof. The water-soluble material may have a molecular weight from about 400 to about 1,000,000.

The coating of the water-soluble material may comprise an oleophobic layer.

The water-soluble material may comprise polyvinylpyrrolidone having a molecular weight of between approximately 6,000 g/mol and approximately 15,000 g/mol.

The water-soluble material may comprise polyvinylpyrrolidone and glycerol.

The substantially water-insoluble synthetic sealant may be an elastomeric material selected from the group consisting of moisture curing, light curing, thermo-curing, platinum catalyzed, anaerobic curing materials or a combination of these curing mechanisms. The elastomeric material may be selected from the group consisting of silicones, polyurethanes, polycarbonates, thermoplastic elastomers, and combinations thereof.

One of more of the substantially water-soluble coating or the substantially water-insoluble coating may comprise a component selected from the group consisting of a colorant, a therapeutic agent, a dye, and a fluorescent indicator.

After curing of the substantially water-insoluble synthetic sealant, the tubular wall may have a water permeability of about 0.16 ml/min/cm$^2$ at 120 mm Hg pressure or less than 0.16 ml/min/cm$^2$ at 120 mm Hg pressure.

The textile construction may be selected from the group consisting of a weave of the one or more filaments or yarns, a knit of the one or more filaments or yarns, a braid of the one or more filaments or yarns, and a web of the one or more filaments or yarns.

The tubular wall may be a crimped wall having a series of peaks and valleys. The substantially water-insoluble synthetic sealant may be disposed at about 8 mg/cm$^2$ of area of the tubular wall or greater than 8 mg/cm$^2$ of area of the tubular wall.

The tubular wall may be a non-crimped wall being substantially free of peaks and valleys. The substantially water-insoluble synthetic sealant may be disposed at about 4 mg/cm$^2$ of area of the tubular wall or greater than 4 mg/cm$^2$ of area of the tubular wall.

The substantially water-insoluble synthetic sealant may be disposed at about 14 mg/cm$^2$ of area of the tubular wall or less than 14 mg/cm$^2$ of area of the tubular wall.

The textile may include one portion of the tubular wall has a first level of the substantially water-insoluble synthetic sealant to provide a first soft, flexible zone; and another portion of the tubular wall has a second level of the substantially water-insoluble synthetic sealant to provide a second zone stiffer than the first zone; where the second level the substantially water-insoluble synthetic sealant is greater than the first level of the substantially water-insoluble synthetic sealant.

Different zones may be created along the length of the device (e.g. prosthesis or graft) and engineered to accommodate a variety of applications and body architecture. For example, a particular need may exist for the device to be turned, curved or twisted in order to properly perform its function in the body, as well as to the physiology of the patient. Tortuous pathways are often present in the body and the medical devices of the present invention are able to accommodate for such areas. The present disclosure and all of its embodiments allow for the creation of such zones by the creation of one or more sealant layers on all of, or at portions of, the graft, and also by the incorporation of support members as described further herein, which as discussed may be adhered to or embedded in the sealant material. As discussed, the support members may be polymeric or metallic and may be in a variety of forms such as elongate members, coils, wraps, rings or a combination of such forms. An important feature of all embodiments of the invention is that the sealant material is capable of serving as a foundational layer for further coatings or for support members due to the excellent adherence of the base sealant layer to its graft substrate.

Additionally, the present invention and its various embodiments contemplates the tailoring of the sealant surface such that its coefficient of friction may be varied and desirably sufficiently low such that the sealant does not stick to itself and/or sufficiently low enough that when used in devices such as endovascular devices, has sufficient lubricity to facilitate delivery and deployment in the body. For example, the sealant surface desirably slides into delivery sheaths, slides across itself and does not stick to itself, to other portions of the device, other devices or the body. Such surface properties may be imparted by altering the sealant surface chemically or physically with lubricous groups or coatings to provide the desired coefficient of friction properties desired. Such surface properties may be in addition to the other properties the sealant possesses in the present invention.

At least a portion of the coating of the substantially water-insoluble synthetic sealant may engage at least a portion of the one or more filaments or yarns.

The textile structure may be an implantable medical device. The implantable medical device may be selected from the group consisting of surgical vascular grafts, and endovascular grafts, ventricular assist devices, artificial heart conduits, meshes, patches, hernia plugs, vascular wraps, heart valves, filters, and the like.

The textile structure may be a delivery medical device, such as a catheter.

In another embodiment, a textile structure may comprise: a fluid permeable polymeric textile layer having opposing first and second surfaces and a length; a cross-linkable water-insoluble synthetic elastomeric layer on the first textile surface configured to render the liquid permeable polymeric textile layer substantially impermeable to fluid when cured; a substantially dried water-soluble polymer layer on the second textile surface; wherein water-soluble polymer layer substantially inhibits migration of the water-insoluble synthetic elastomeric layer onto the second surface; and wherein the water-soluble polymer layer is substantially removable by exposure to water.

In another embodiment, a textile structure may comprise: a fluid permeable polymeric textile layer having opposing first and second surfaces and a length; a cross-linkable water-insoluble synthetic elastomeric layer on the first textile surface configured to render the liquid permeable polymeric textile layer substantially impermeable to fluid when cured; a substantially dried water-soluble polymer layer on the second textile surface; wherein water-soluble polymer layer substantially inhibits migration of the water-insoluble synthetic elastomeric layer onto the second surface; and wherein the water-soluble polymer layer is substantially removable by exposure to water. The weight ratio of the cross-linkable water-insoluble elastomeric polymer to the water-soluble polymer may be from about 0.1:1 to about 100:1, including from about 1:1 to about 20:1.

In another embodiment, a textile structure may comprise: a fluid permeable polymeric textile layer having opposing first and second surfaces and a length; a crosslinked water-insoluble elastomeric polymer layer on the first textile surface forming a substantially fluid impermeable barrier, wherein the crosslinked water-insoluble elastomeric layer is adhered to the first textile surface by elastomeric shrinkage; a water dissolvable polymer layer dried on the second textile surface; wherein the weight ratio of the crosslinked water-insoluble elastomeric polymer to the water dissolvable polymer may be from about 0.1:1 to about 100:1. The weight ratio of the crosslinked water-insoluble elastomeric polymer to the water dissolvable polymer may be from about 1:1 to about 20:1.

In another embodiment, a graft may comprise: a tubular wall disposed between a first open end and an opposed second open end and having an inner surface and an opposed outer surface, the tubular wall comprising a textile construction of one or more filaments or yarns; wherein the outer surface comprises a coating or layer of a substantially water-insoluble sealant disposed thereon; wherein the inner surface is substantially free of the substantially water-insoluble sealant; and wherein the tubular wall has a water permeability of about 0.16 ml/min/cm² at 120 mm Hg pressure or less than 0.16 ml/min/cm² at 120 mm Hg pressure. The textile construction may be selected from the group consisting of a weave of the one or more filaments or yarns, a knit of the one or more filaments or yarns, a braid of the one or more filaments or yarns, and a web of the one or more filaments or yarns.

The coating or layer may be disposed within an intermediate portion of the tubular wall between the inner surface and the opposed outer surface.

The tubular wall may be a crimped wall having a series of peaks and valleys. The substantially water-insoluble sealant may be disposed at about 8 mg/cm² of area of the tubular wall or greater than 8 mg/cm² of area of the tubular wall.

The tubular wall may be a non-crimped wall being substantially free of peaks and valleys. The substantially water-insoluble sealant may be disposed at about 4 mg/cm² of area of the tubular wall or greater than 4 mg/cm² of area of the tubular wall.

The substantially water-insoluble sealant may be disposed at about 14 mg/cm² of area of the tubular wall or less than 14 mg/cm² of area of the tubular wall.

The substantially water-insoluble sealant may be an elastomeric material selected from the group consisting of moisture curing, light curing, thermo-curing, platinum catalyzed, anaerobic curing materials or a combination of these curing mechanisms. The elastomeric material may be selected from the group consisting of silicones, polyurethanes, polycarbonates, thermoplastic elastomers, and combinations thereof.

One of more of the substantially water-soluble coating (masking agent coating or layer) or the substantially water-insoluble coating (sealant coating or layer) may comprise a component selected from the group consisting of a colorant, a therapeutic agent, a dye, and a fluorescent indicator.

The substantially water-insoluble sealant (sealant coating or layer) may be selected from the group consisting of silicone, room temperature vulcanizing silicone, thermoplastic polyurethane, aliphatic polycarbonate, one or more thermoplastic elastomers, polycarbonate, and combinations thereof.

The graft may include one portion of the tubular wall having a first amount of the substantially water-insoluble sealant (sealant coating or layer) to provide a first soft, flexible zone; and another portion of the tubular wall having a second amount of the substantially water-insoluble sealant (sealant coating or layer) to provide a second zone stiffer than the first zone; wherein the second amount of the substantially water-insoluble sealant (sealant coating or layer) is greater than the first amount of the substantially water-insoluble sealant (sealant coating or layer). The graft may include multiple regions having pluralities of soft, flexible zones and stiffer zones. The different zones may serve as foundations for building engineered structures onto a graft.

In another embodiment, an implantable or deliverable medical textile may comprise: a wall having a textile construction and having a first surface and an opposed second surface; wherein the second surface comprises a coating of a substantially water-insoluble sealant disposed thereon; wherein the first surface is substantially free of the substantially water-insoluble sealant; and wherein the wall has a water permeability of about 0.16 ml/min/cm² at 120 mm Hg pressure or less than 0.16 ml/min/cm² at 120 mm Hg pressure.

An assembly for producing an implantable or deliverable medical textile having a selectively applied water-insoluble sealant layer and/or a selectively applied water-soluble masking agent layer comprises a mandrel having a length, a hollow lumen disposed within a portion of the length, at least one open end, and a plurality of perforations through a wall of the mandrel; a reservoir in fluid communication with the open lumen of the mandrel; and a water-soluble polymer disposed within the reservoir. The assembly may further comprise a tubular graft securably disposed over a portion of the mandrel having the plurality of perforations. The assembly may further comprise a vacuum source in fluid communication with the hollow lumen of the mandrel, and a manifold configured to provide selective fluid communication between the hollow lumen of the mandrel and the reservoir and/or the vacuum source. The assembly may further comprise a source of pressurized and/or blown air which is in fluid communication with the hollow lumen of the mandrel.

Embodiments of the present invention, however, are not limited to vascular prostheses, and the methods, coatings and masking agents may suitably be used with other textile products, including medical and non-medical textile products, such as but not limited to clothing, geotextiles, transportation textiles, military and/or defense textiles, safety and/or protective textiles, sports and/or recreation textiles, and the like. Further, textile products are not limited to tubular conduits, but may be of any shape including, but not limited to for example, sheets, tapes, or even three dimensional shaped products.

In another aspect or embodiment of the present invention, a method for manufacturing a substantially impermeable textile graft comprises: providing a textile graft having a first surface and an opposed second surface; providing a water soluble masking agent comprising polyvinylpyrrolidone and glycerol without mixing or combining the polyvinylpyrrolidone and the glycerol with added water; applying the water soluble masking agent to a portion of the first surface of the textile graft; providing a water insoluble sealing agent; maintaining the second surface of the textile graft receptive for receiving the water insoluble sealing agent; and applying the water insoluble sealing agent to the second surface of the textile graft. The water soluble masking agent may consist essentially of polyvinylpyrrolidone and glycerol. The water soluble masking agent may comprise from about 25% w/w of the polyvinylpyrrolidone in the glycerol to about 75% w/w of the polyvinylpyrrolidone in glycerol, including from about 30% w/w of the polyvinylpyrrolidone in the glycerol to about 70% w/w of the polyvinylpyrrolidone in glycerol, including from about 40% w/w of the polyvinylpyrrolidone in the glycerol to about 60% w/w of the polyvinylpyrrolidone in glycerol, more desirably including from about 45% w/w of the polyvinylpyrrolidone in the glycerol to about 55% w/w of the polyvinylpyrrolidone in glycerol, in particular about 50% w/w of the polyvinylpyrrolidone in the glycerol. The water soluble masking agent may be flowable. The water soluble masking agent may be prepared by dissolving the polyvinylpyrrolidone in the glycerol. The polyvinylpyrrolidone may be dissolved into the glycerol with one or more of stirring and application of heat. The step of maintaining the second surface of the textile graft receptive for receiving the water insoluble sealing agent may comprise preventing egress of the water soluble masking agent from the first surface to the second surface. The step of preventing the egress of the water soluble masking agent from the first surface to the second surface may comprise substantially prohibiting wicking of the water soluble masking agent from the first surface to the second surface. The step of maintaining the second surface of the textile graft receptive for receiving the water insoluble sealing agent may comprise removal of the water soluble masking agent from the second surface. The step of removal of the water soluble masking agent from the second surface may comprise dissolving the water soluble masking agent from the second surface. The step of removal of the water soluble masking agent from the second surface may comprise ablating the water soluble masking agent from the second surface. The polyvinylpyrrolidone may have a molecular weight of from about 2,500 g/mol to about 55,000 g/mol, including from about 3,500 g/mol to about 50,000 g/mol, from about 5,000 g/mol to about 40,000 g/mol, from about 5,000 g/mol to about 30,000 g/mol, from about 5,000 g/mol to about 20,000 g/mol, and desirably from about 8,000 g/mol to about 10,000 g/mol. The water insoluble sealing agent may comprise a material selected from the group consisting of silicones, polyurethanes, polycarbonates, thermoplastic elastomers, and combinations thereof. The step of applying the water insoluble sealing agent to the second surface of the textile graft may comprise spraying water insoluble sealing agent onto the second surface of the textile graft. The spraying may be forced air spraying or ultrasonic assisted forced air spraying. The method may further comprise removing the water soluble masking agent after the step of applying the water insoluble sealing agent. The may further comprise curing the water insoluble sealing agent. After curing of the water insoluble sealing agent, the textile graft may be substantially impermeable to liquid. After curing of the water insoluble sealing agent, the textile graft may have a water permeability of about 0.16 ml/min/cm$^2$ at 120 mm Hg pressure or less than 0.16 ml/min/cm$^2$ at 120 mm Hg pressure. The textile graft may be a tubular textile graft. The water soluble masking agent may have a viscosity from about 2,000 centipoise at room temperature to about 100,000 centipoise at room temperature, including from about 50,000 centipoise at room temperature to about 100,000 centipoise at room temperature. A textile graft made by these methods.

In another aspect or embodiment, a method for manufacturing an substantially impermeable textile graft may comprise: providing a textile graft having a first surface and an opposed second surface; providing a water soluble masking agent selected from the group consisting of polyvinylpyrrolidone, glycerol, methyl cellulose, poly(ethylene glycol), poly(ethylene glycol) hydrogel, polyethylene oxide, and combinations thereof; applying the water soluble masking agent to a portion of the first surface of the textile graft, wherein a portion of the water insoluble sealing agent is optionally disposed on the second surface of the textile graft; ablating a portion of the water soluble masking agent from the second surface of the textile graft; providing a water insoluble sealing agent selected from the group consisting of silicones, polyurethanes, polycarbonates, thermoplastic elastomers, and combinations thereof; and applying the water insoluble sealing agent to the second surface of the textile graft. The step of ablating may further comprise providing a flow of solid particulates against the second surface of the textile graft. The solid particulates may be a material selected from the group consisting of sodium bicarbonate, sodium chloride, sugar, magnesium sulphate, potassium chloride, and combinations thereof. The solid particulates have an average particle size across there largest dimension from about 50 microns to about 300 microns. The solid particulates may have a Moh's hardness from about 1 to about 4. The solid particulates may be sprayed at a pressure from about 10 psig to about 50 psig. Solid particles remaining on the graft may be removed, if desired, by any suitable technique. For example, solid particles ma be removed by vacuuming, washing, such as solvent washing, including washing with n-heptane. Washing may also be performed in an ultrasonic solvent bath. The method may further comprise curing the water insoluble sealing agent. After curing of the water insoluble sealing agent, the textile graft may be substantially impermeable to liquid. After curing of the water insoluble sealing agent, the textile graft may have a water permeability of about 0.16 ml/min/cm$^2$ at 120 mm Hg pressure or less than 0.16 ml/min/cm$^2$ at 120 mm Hg pressure. The method may further comprise removing the water soluble masking agent after the step of applying the water insoluble sealing agent. The method may further comprise adding a dye to the water insoluble sealing agent. The method may further comprise adding a dye to the water soluble masking agent. A textile graft made by these methods.

The masking agent may be applied to the graft prior to the application of the sealant composition. The present invention, however, is not so limited. For example, the masking agent and the sealant composition may be applied concurrently or substantially concurrently. Moreover, the masking agent may be formulated to minimize its wicking potential among or between yarns. One non-limiting example to minimize wicking potential of the masking agent is to use a high viscous and/or high surface tension masking agent formulation, such as masking agent components in glycerol with the separate addition of water. As such a masking agent is viscous, it may be heated during application to a graft, in particular to the application to one surface, such as to an inner or luminal surface of the graft. The heat may be moderate as viscosity decreases with increasing temperature. The opposed surface of the graft may be subjected to cooling, such as application of cold or cool air. The lower temperature will increase the viscosity of the masking agent, thereby acting as a barrier against migration of the masking agent towards the outer or opposed surface. The application of the cooling medium may be done with concurrent or substantially concurrent application of the sealant agent to the outer or opposed surface, or may be done prior to the application of the sealant agent. One non-limiting method for the concurrent or substantially concurrent application of the masking agent and sealant formulation may be the use of spray nozzles, or the like, for applying the masking agent to the inner surface of the graft with one or more spray nozzles and applying the sealant agent to the outer surface of the graft with one or more different spray nozzles, or the like. Spraying may include ultrasonic spraying. This may be especially beneficial for spraying of viscous fluids. Moreover, the textile graft may be rotated while applying either masking agent and/or the sealant agent. Such controlled rotation prevents potential pooling, especially for the masking agent, and provides for uniformity of the applied masking agent and/or the sealant agent.

In another aspect or embodiment, a method of providing a sealant to a textile graft may comprise: providing a textile graft having a first surface and an opposed second surface and having a textile pattern of yarns inter-engaging yarns and interstices between or in the yarns; providing a water soluble masking agent selected from the group consisting of polyvinylpyrrolidone, glycerol, methyl cellulose, poly(ethylene glycol), poly(ethylene glycol) hydrogel, polyethylene oxide, and combinations thereof; applying the water soluble masking agent to at least a portion of the first surface of the textile graft, wherein a portion of the water soluble masking agent is further disposed at a plurality of the interstices; providing a water insoluble sealing agent selected from the group consisting of silicones, polyurethanes, polycarbonates, thermoplastic elastomers, and combinations thereof; and applying the water insoluble sealing agent to the second surface of the textile graft and over the portion of the water soluble masking agent being disposed at a plurality of the interstices; whereby the water insoluble sealing agent spreads over the water soluble masking agent to provide one or more of the following: a substantially homogenous layer of the water insoluble sealing agent; a substantially uniform and uninterrupted coating of the water insoluble sealing agent; a layer of water insoluble sealing agent having a substantially uniform weight per given area of application; a substantially liquid impermeable barrier to the underlying textile graft surface; a substantially lower force to extend a graft coated with the water insoluble sealing agent as compared to comparable grafts which have not used a masking agent; a substantially less amount of water insoluble sealing agent to provide a substantially liquid impermeable barrier to the underlying textile graft surface as compared to comparable grafts which have not used a masking agent; and combinations thereof. The method may further comprise removing the water soluble masking agent after the step of applying the water insoluble sealing agent. The method may further comprise curing the water insoluble sealing agent. After curing of the water insoluble sealing agent, the water insoluble sealing agent may be disposed over the interstices between and in the yarns. The textile graft may be substantially impermeable to liquid. After curing of the water insoluble sealing agent, the textile graft may have a water permeability of about 0.16 ml/min/cm$^2$ at 120 mm Hg pressure or less than 0.16 ml/min/cm$^2$ at 120 mm Hg pressure. A textile graft made by these methods.

In another aspect or embodiment, a method of sealing a textile graft may comprise: applying a coating of a substantially water soluble masking agent, having a viscosity of from about 2,000 centipoise at room temperature to about 100,000 centipoise at room temperature, to at least a portion of a luminal surface of the textile graft, wherein a portion of the water soluble masking agent is further disposed at a plurality of interstices in the graft; and applying a water insoluble sealing agent to an outer graft surface opposing the luminal surface of the graft; wherein the water soluble masking agent causes one or more of the following to occur: a substantially homogenous layer of the water insoluble sealing agent is formed; a substantially uniform and uninterrupted coating of the water insoluble sealing agent is formed; a layer of water insoluble sealing agent having a substantially uniform weight per given area of application; a substantially liquid impermeable barrier to the underlying textile graft surface; a substantially lower force to extend a graft coated with the water insoluble sealing agent as compared to comparable grafts which have not used a masking agent; a substantially less amount of water insoluble sealing agent to provide a substantially liquid impermeable barrier to the underlying textile graft surface as compared to comparable grafts which have not used a masking agent; and combinations thereof.

Embodiments of the various aspects of the invention as recited herein may include one or more features of other aspects of the invention and/or their embodiments.

BRIEF DESCRIPTION OF THE DRAWINGS

Embodiments of the invention will now be described, by way of example, with reference to the drawings, in which:

FIGS. 2a and 2b show a detailed view of an inner surface of a wall of the conduit of FIG. 1a;

FIG. 7 depicts the addition of a support member to the conduit shown depicted in FIG. 1a;

DETAILED DESCRIPTION OF THE INVENTION

As used herein the term "substantially" and its equivalents refer to being at least 70% of a stated value, desirably within at least 80% of a stated value, and more desirably within 90% or 95% of a stated value.

As used herein the terms "about" or "approximate" and their equivalents refer to being within (plus and/or minus) at least 20% of a stated value, desirably within at least 10% of a stated value, and more desirably within 5% of a stated value.

As used herein the terms "layer" and "coating" may be used interchangeably to refer to a deposition of material over, underneath, or within a substrate, such as a textile substrate.

As used herein masking agent shall refer to any suitable non-biological, e.g., synthetic, hydrophilic polymer and any suitable biological hydrophilic polymer. However, it should be understood that other masking agents may be used.

With reference to FIGS. 1a to 1d, four stages of manufacture of a vascular prosthesis 16 are illustrated. In each of the FIGS. 1a to 1d two perspective views of the conduit 10 and/or the vascular prosthesis 16 are provided. The left hand views show an inlet 10c being forwardly disposed in the views, and the right hand views show an outlet 10d being forwardly disposed in the views.

Figure 1A:
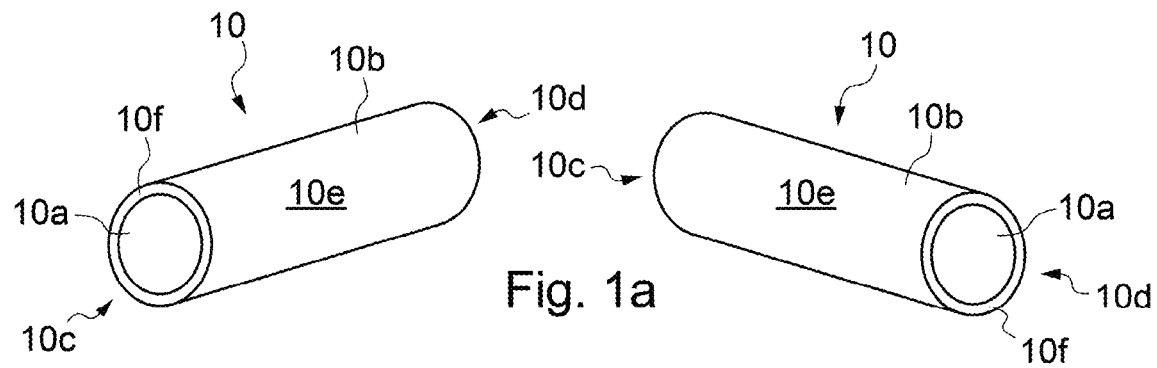
FIG. 1a depicts perspective views of a conduit from both inlet and outlet perspectives according to an embodiment of the invention.

FIG. 1a shows a conduit 10 which is suitable for implant in the human or animal body. The conduit 10 is a cylindrical conduit 10 and comprises a wall 10f. The wall 10f comprises an inner surface 10a and an outer surface 10b. The conduit 10 also comprises an inlet 10c and an outlet 10d. In the embodiment described here, substantially all of the conduit 10 is porous 10e. However, it should be understood that at least a section of the conduit 10 could be porous 10e. In this embodiment, the conduit 10 is a woven, fibrous polymer conduit 10. The woven nature of the conduit 10 leads to substantially all of the conduit 10 being porous 10e.

The conduit 10 comprises polyethylene terephthalate (PET). However, it should be understood that the conduit 10 could comprise other materials, such as polytetrafluoroethylene (PTFE). Other suitable polymers for medical textile applications may include, but are not limited to polyolefin, polyester, poly(ether amide), poly(ether ester), poly(ether urethane), poly(ester urethane), poly(ethylene-styrene/butylene-styrene), and other block copolymers.

In the embodiment illustrated and described here, the weft yarn pick-rate of the conduit 10 is approximately 45 ppcm. However, it should be understood that the weft yarn pick-rate of the conduit 10 could be between approximately 25 ppcm and approximately 50 ppcm.

The conduit 10 is moveable between a contracted state and an extended state.

FIG. 1a thus depicts an unprocessed conduit 10. In its unprocessed form, blood (an example of a fluid) can flow between the outer surface 10b of the wall 10f and the inner surface 10a of the wall 10f. That is, if fluid flows into the inlet 10c, the blood will leak through the porous section 10e of the conduit 10. The conduit 10 depicted in FIG. 1a must therefore be sealed prior to use as an implantable vascular prosthesis 16.

The conduit 10 depicted in FIG. 1a has been cut to a predetermined size. For example, the length of the conduit 10 may need to be altered depending on the size of vascular prosthesis 16 required. Furthermore, if the vascular prosthesis 16 is to be connected to at least one heart assist component (an example of a further prosthesis), this may also require a different size, or length of conduit 10 to be used. The conduit 10 is also weighed during this step of the manufacturing process.

In the embodiment illustrated here, the conduit 10 has a substantially uniform cross section throughout. However, it should be understood that the conduit 10 could have an irregular cross section throughout. For example, if the conduit 10 is to be connected between a further prosthesis, such as a heart valve, and an end of a severed blood vessel, the conduit 10 could have an irregular cross section throughout. As described in more detail below, in some embodiments the conduit 10 could be configured to have differing degrees of flexibility, either by selectively adding sealant 14 to different sections of the conduit 10, or in other ways.

As described above, it is desirable for the inner surface 10a of the wall 10f of the conduit 10 to remain free from, or substantially devoid of, the material used to seal the conduit 10. The reason for this is to ensure that the inner surface 10a of the wall 10f of the conduit 10, remains of a porous 10e, woven nature, to ensure that when the vascular prosthesis 16 is implanted in the human or animal body, biological tissue will grow into the inner surface 10a of the wall 10f of the conduit 10. This is important to ensure that ingrowing biological tissue forms a pseudointima (an example of an inner biological tissue layer within a vascular prosthesis). Furthermore, in addition to the promotion of biological tissue growth on the inner surface 10a of the wall 10f of the conduit 10, it is also advantageous if the biological tissue layer growing on the inner surface 10a of the wall 10f of the conduit 10 has good adhesion to the inner surface 10a. If the adhesion between the biological tissue layer and the inner surface 10a is insufficient, complications can arise such as haemorrhagic dissection.

Figure 1B:
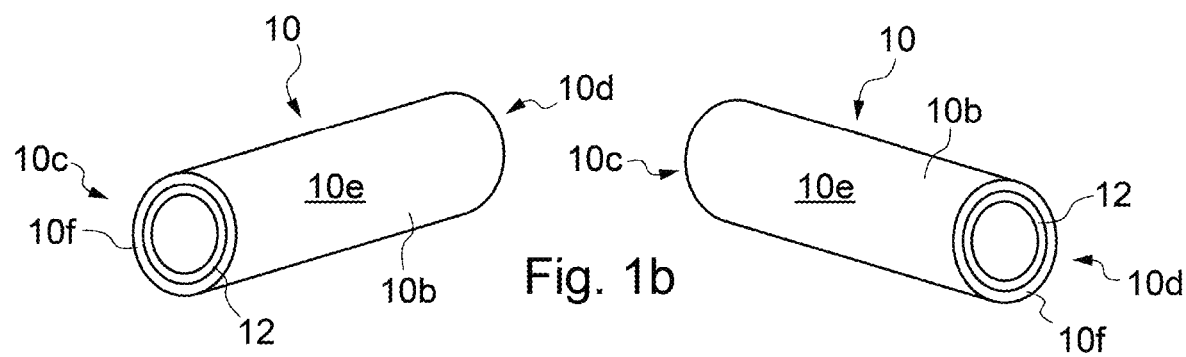
FIG. 1b depicts perspective views of the conduit of FIG. 1a after the addition of a masking agent.

FIG. 1b shows the conduit 10 after the addition of a masking agent 12. In this embodiment, the masking agent 12 forms a masking agent layer on the inner surface 10a of the wall 10f of the conduit 10. The masking agent layer is designed to protect the inner surface 10a of the conduit 10 during the manufacturing process illustrated and described herein. Specifically, the masking agent 12 is designed to mitigate presence of sealant 14 on the inner surface 10a of the wall 10f of the conduit 10.

Prior to the addition of the masking agent 12 to the conduit 10, the conduit 10 is weighed. The weight of the conduit 10 is then used, at least in part, to determine the amount of masking agent 12 to add to the conduit 10.

In this embodiment, the masking agent 12 is applied from a masking agent solution. The masking agent solution is a polymer solution. In the embodiment illustrated and described here, the polymer solution comprises approximately 7% w/v PVP (an example of a water-soluble polymer) in water (an example of a solvent). However, it should be understood that other polymers, such as glycerol, methyl cellulose and/or PEG could be used. Furthermore, it will be understood that the polymer solution could comprise between approximately 5% w/v PVP in solution and approximately 30% w/v PVP in solution. Moreover, the polymer solution could comprise between approximately 5% w/v polymer in solution and approximately 30% w/v polymer in solution. It should be understood that the masking agent 12 could comprise approximately 1% w/v of glycerol in solution. Without wishing to be bound by theory, it is thought that an advantage of adding glycerol to the masking agent 12 is that it mitigates cracking of the masking agent 12 when the masking agent 12 is added to the conduit 10.

In the embodiment described here, the masking agent 12 comprises PVP with a molecular weight of approximately 10,000 g/mol. However, it should be understood that the masking agent 12 could comprise PVP with a molecular weight of between approximately 6,000 g/mol and approximately 15,000 g/mol.

While in the embodiment described here the masking agent 12 comprises PVP, it should be understood that the masking agent 12 could comprise glycerol, methyl cellulose, PEG, PEO, and/or PEG hydrogel.

In the embodiment illustrated and described here, the masking agent 12 is biocompatible. However, it should be understood that, in some embodiments the masking agent 12 need not be biocompatible. For example, as described in more detail below, if substantially all of the masking agent 12 is to be removed from the conduit 10, then the masking agent 12 need not be biocompatible. In some embodiments, the masking agent 12 need not be removed, and in some embodiments only a part of the masking agent 12 is removed. In these arrangements, it is advantageous that the masking agent 12 is biocompatible, which allows the conduit 10 to be implanted in the human or animal body.

In this embodiment, the masking agent 12 is biodegradable. Therefore, any residual masking agent 12 present on the conduit 10 will biodegrade when the conduit 10 is implanted in the human or animal body. However, the masking agent 12 could be non-biodegradable. In this embodiment, substantially all of the masking agent 12 is removed from the conduit 10 prior to implantation, and therefore it is not necessary for the masking agent 12 to be biodegradable. In some embodiments, it may be advantageous for the masking agent 12 to be biodegradable.

With reference to FIG. 1b, the masking agent 12 is applied to the conduit 10 from a polymer solution. However, it will be appreciated that the masking agent 12 could be applied to the conduit 10 in other ways.

In this embodiment, the masking agent solution is applied to the conduit 10 by immersing the conduit 10 in the masking agent solution for approximately 1 minute, while agitating the conduit 10. However, it should be understood that the masking agent solution could be added to the conduit 10 in other ways, such as by dipping, spray coating, or by brushing. Furthermore, it should be understood that the masking agent 12 could be added to the conduit 10 without agitating the conduit 10. During the step of immersing the conduit 10 in the masking agent solution, the conduit 10 is moved between the contracted state and the extended state. However, it should be understood that the conduit 10 could be immersed in the masking agent solution while the conduit 10 is in the contracted state and/or the extended state.

In this embodiment, when the masking agent solution is added to the conduit 10, solvent is then evaporated from the masking agent solution. Solvent is therefore removed from the masking agent solution, and the masking agent 12 remains on the conduit 10.

In this embodiment, during the addition of the masking agent 12 to the conduit 10, a directed flow of air (an example of a gas) is provided to the conduit 10. The directed flow of air is directed towards the outer surface 10b of the wall 10f of the conduit 10, such that the masking agent 12 is preferentially formed on the inner surface 10a of the wall 10f of the conduit 10. It should be understood that while directed air flow is used here, other gases could be used.

In this embodiment, the masking agent 12 is formed, or added, substantially on the inner surface 10a of the wall 10f of the conduit 10. However, it should be understood that the masking agent 12 could be added to the outer surface 10b of the wall 10f of the conduit 10. The masking agent 12 is added to the porous section 10e of the conduit 10, although in other embodiments the masking agent 12 could be added to at least a part of the porous section 10e of the conduit 10. In this embodiment, the masking agent 12 forms a masking agent layer substantially on the inner surface 10a of the wall 10f of the conduit 10. However, it should be understood that the masking agent 12 could be added to other parts of the conduit 10, and that the masking agent 12 could form a masking agent layer on other parts of the conduit 10.

In the manufacturing process illustrated and described here, the residual masking agent 12 on the outer surface 10b of the wall 10f of the conduit 10 is removed prior to the addition of the sealant 14, in order to improve the adhesion between the sealant 14 (when applied to the conduit 10) and the outer surface 10b of the wall 10f of the conduit 10. In this embodiment, the residual masking agent 12 on the outer surface 10b is removed by ablating (an example of a first masking agent removal step). However, it should be understood that the masking agent 12 could be removed by applying a solvent, by heating, by etching, by plasma etching, by abrading, and/or by other techniques.

In the embodiment shown in FIG. 1b, the masking agent 12 is formed on substantially all of the inner surface 10a of the wall 10f of the conduit 10.

Figure 1C:
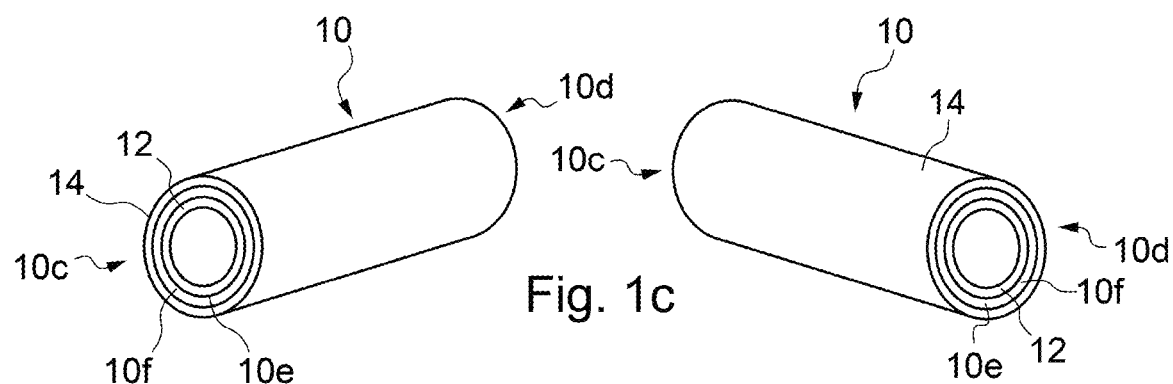
FIG. 1c depicts perspective views of the conduit of FIG. 1b after the addition of a sealant.

FIG. 1c shows the conduit 10 after the addition of the masking agent 12 and the sealant 14. In the embodiment described here, the sealant 14 is added to the conduit 10 from a sealant solution. In the embodiment described here, the sealant solution is a polymer solution comprising room temperature vulcanising silicone elastomer and xylene. However, it should be understood that the sealant solution could comprise at least one of polycarbonate, silicone, silicone elastomer, polyurethane, TPU, one or more thermoplastic elastomers, and/or aliphatic polycarbonate. It should also be understood that while the sealant 14 is added to the conduit 10 from a polymer solution comprising xylene, heptane could be used in place of xylene. Furthermore, in some embodiments the sealant solution may comprise a polar solvent, such as dimethylacetamide (DMAC) or tetrahydrofuran (THF).

When the sealant solution is applied to the conduit 10, solvent is evaporated from the sealant solution, which results in the formation of the sealant 14.

While in the embodiment illustrated and described here the sealant 14 is added to the conduit 10 from a sealant solution, it will be understood that the sealant 14 could be added to the conduit 10 in other ways and need not be added from a sealant solution.

The sealant 14 is added to the porous section 10e of the conduit 10. Therefore, in this embodiment, the sealant 14 is added to substantially all of the conduit 10, as in this embodiment the conduit 10 is entirely porous 10e. In other embodiments, the sealant 14 could be added to a part of the porous section 10e.

The presence of the masking agent 12 prevents the sealant 14 from adhering, or forming on, the inner surface 10a of the wall 10f of the conduit 10. The sealant 14 is applied to the conduit 10 by spraying the sealant 14 onto the outer section 10b of the conduit 10. However, it should be understood that other techniques for adding the sealant 14 to the conduit 10 could be used, such as brushing, wiping, immersing, dipping, vapour depositing, such as chemical vapour depositing, electrostatic spinning, and/or by casting.

In this embodiment, the sealant 14 is applied to the conduit 10, while the conduit 10 is in the extended state. However, it should be understood that the sealant 14 could be applied to the conduit 10 while the conduit 10 is in the contracted state or when the conduit 10 is moved between the contracted state and the extended state.

In this embodiment, the sealant 14 is added to the conduit 10 while the conduit 10 is rotated about its longitudinal axis at approximately 60 rpm. However, it should be understood that the conduit 10 could be rotated about its longitudinal axis at up to approximately 2,000 rpm.

In the embodiment described here, the sealant 14 comprises approximately 8 mg/cm$^2$ of silicone. However, it should be understood that the sealant could comprise between approximately 4 mg/cm$^2$ of silicone and approximately 19 mg/cm$^2$ of silicone.

Spraying and/or brushing the sealant 14 onto the outer surface 10b of the wall 10f of the conduit 10 is advantageous over some sealant application techniques because the sealant 14 is applied substantially only to the outer surface 10b of the conduit 10 and is not substantially applied to the inner surface 10a of the conduit 10. In this arrangement, the masking agent 12, and the addition of the sealant 14 to the conduit 10 by way of spraying, and/or brushing, the sealant 14 onto the conduit 10, mitigate presence of the sealant 14 on the inner surface 10a of the wall 10f of the conduit 10. However, it should be understood that other sealant 14 application techniques, such as wiping the sealant 14 onto the conduit 10, could be used.

In the embodiment illustrated and described here, it is advantageous if, when the sealant 14 is applied to the conduit 10, the masking agent 12 is not substantially covered, or blocked, by the sealant 14. The reason for this is that, if at least a part of the masking agent 12 is to be removed from the conduit 10, it is easier to remove the masking agent 12 if at least some of the masking agent 12 is exposed. For example, when removing at least a part of the masking agent 12 from the conduit 10 by applying a solvent, it is easier to do so if at least some of the masking agent 12 is exposed. In the embodiments described here, a significant amount of the masking agent 12 is exposed, and it is therefore relatively straightforward to use a variety of masking agent 12 removal techniques.

In this embodiment, the addition of the sealant 14 to the porous section 10e of the conduit 10 forms a sealing layer on the outer surface 10b of the wall 10f of the conduit 10. In this embodiment, the sealant 14 is biocompatible.

In this embodiment, the sealant 14, when applied to the conduit 10, is configured to mitigate against environmental stress cracking.

Figure 1D:
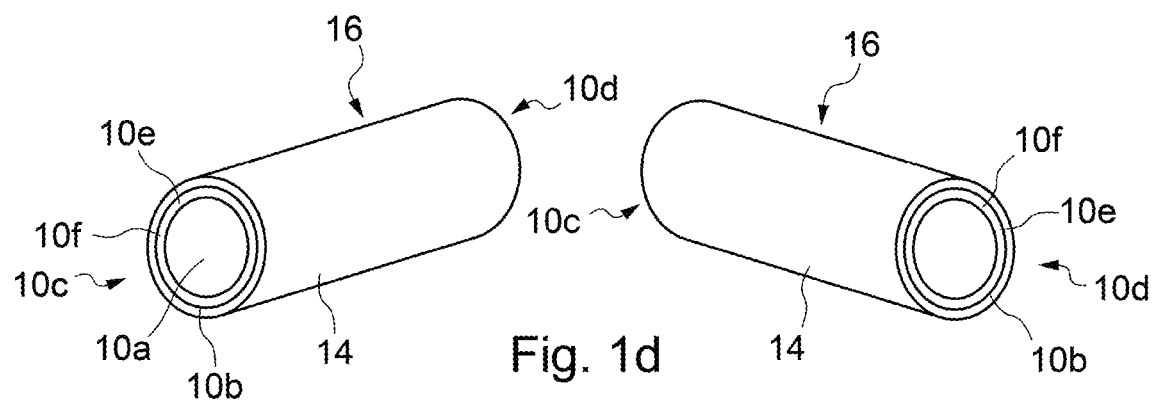
FIG. 1d depicts perspective views of the conduit of FIG. 1c after removal of substantially all of the masking agent.

FIG. 1d shows a vascular graft 16 (an example of a vascular prosthesis 16). In this embodiment, substantially all of the masking agent 12 has been removed from the conduit 10. The leaking of blood (an example of a fluid) through the wall 10f of the conduit 10 is now mitigated due to the addition of the sealant 14 to the conduit 10. Furthermore, the inner surface 10a of the wall 10f of the conduit 10 retains the porous, woven properties of the conduit 10, such that the inner surface 10a of the wall 10f of the conduit 10 allows for the ingrowth of biological tissue and also allows for biological tissue to have good adhesion thereto. The presence of the sealant 14 obviates the flow of blood through the wall 10f of the conduit 10, although it will be understood that blood can flow between the inlet 10c and the outlet 10d.

In the embodiment described here and shown in FIG. 1d, substantially all of the masking agent 12 has been removed from the conduit 10 by applying water to the conduit 10 at a temperature of approximately 95° C. (an example of a second masking agent removal step). In this second masking agent removal step, the masking agent 12 has been removed from the conduit 10 after the step of adding the sealant 14 to the conduit 10 has been carried out. In this process, water (an example of a solvent) has been used to remove substantially all of the masking agent 12 from the conduit 10. However, the masking agent 12 need not be removed substantially entirely from the conduit 10. Water need not be used as the solvent, as other solvents could be used to achieve the removal of the masking agent 12. It should be understood that the masking agent 12 could be removed from the conduit 10 in other ways, such as by etching, plasma etching, ablating, and/or abrading. While the masking agent 12 has been substantially removed from the conduit 10 at a temperature of approximately 95° C., it should be understood that the masking agent 12 could be removed from the conduit 10 at a temperature of between approximately 15° C. and approximately 140° C. In the embodiment described here, the step of removing the masking agent 12 from the conduit 10 is also used to cure the sealant 14 in a more efficient manner.

In the embodiment depicted in FIG. 1d, the masking agent removal step, carried out as described above, is carried out for approximately 51 minutes while the conduit 10 is agitated. Without wishing to be bound by theory, agitating the conduit 10 is thought to improve the efficiency of the masking agent 12 removal step. Whilst in this embodiment the masking agent removal step is carried out for approximately 51 minutes, it will be understood that the masking agent removal step could be carried out for between approximately 40 minutes and approximately 300 minutes. It will also be understood that multiple masking agent removal steps could be carried out.

In the embodiment illustrated and described here, the step of removing substantially all of the masking agent 12 from the conduit 10 does not result in the removal of the sealant 14 from the conduit 10.

As described in detail above, the manufacturing process comprises a first masking agent removal step, designed to improve the adhesion of the sealant 14 to the conduit 10, and a second masking agent removal step, designed primarily to remove the masking agent 12 from the inner surface 10a of the wall 10f of the conduit 10. However, it will be understood that multiple masking agent removal steps could be carried out. It should also be understood that for some embodiments of the invention it may not be necessary to carry out a masking agent removal step.

In the embodiment illustrated and described here, the vascular prosthesis 16 is reversibly sealable. That is, the sealant 14 could be removed from the conduit 10 and the sealant 14 could be applied to the conduit 10. For example, this could be necessary in the event of a manufacturing error. Similarly, the masking agent 12 may be added, and removed from, and subsequently added to the conduit 10. This could be necessary when carrying out more than one masking agent addition step.

In the embodiment illustrated and described here, the vascular prosthesis 16 can be sterilised by way of a gamma sterilisation process. However, it should be understood that the vascular prosthesis 16 could be sterilised by way of an electron beam sterilisation process. Another option for sterilising the vascular prosthesis 16 is to carry out ethylene oxide sterilisation. It will be appreciated that other sterilisation techniques could be applied to the vascular graft 16, either as an alternative to, or in addition to those described here.

The vascular prosthesis 16 depicted in FIG. 1d is configured to be implantable inside the human or animal body and is made from substantially entirely biocompatible materials. The vascular prosthesis 16 can be implanted in the human or animal body without being harmful or toxic to surrounding biological tissue.

The vascular prosthesis 16 illustrated in FIG. 1d is flexible, which allows the vascular prosthesis 16 to be manipulated by a medical practitioner in a more efficient way. In this embodiment, the addition of the sealant 14 to substantially all of the porous section 10e of the conduit 10 has converted the unprocessed conduit 10 to a vascular prosthesis 16.

Figure 2A:
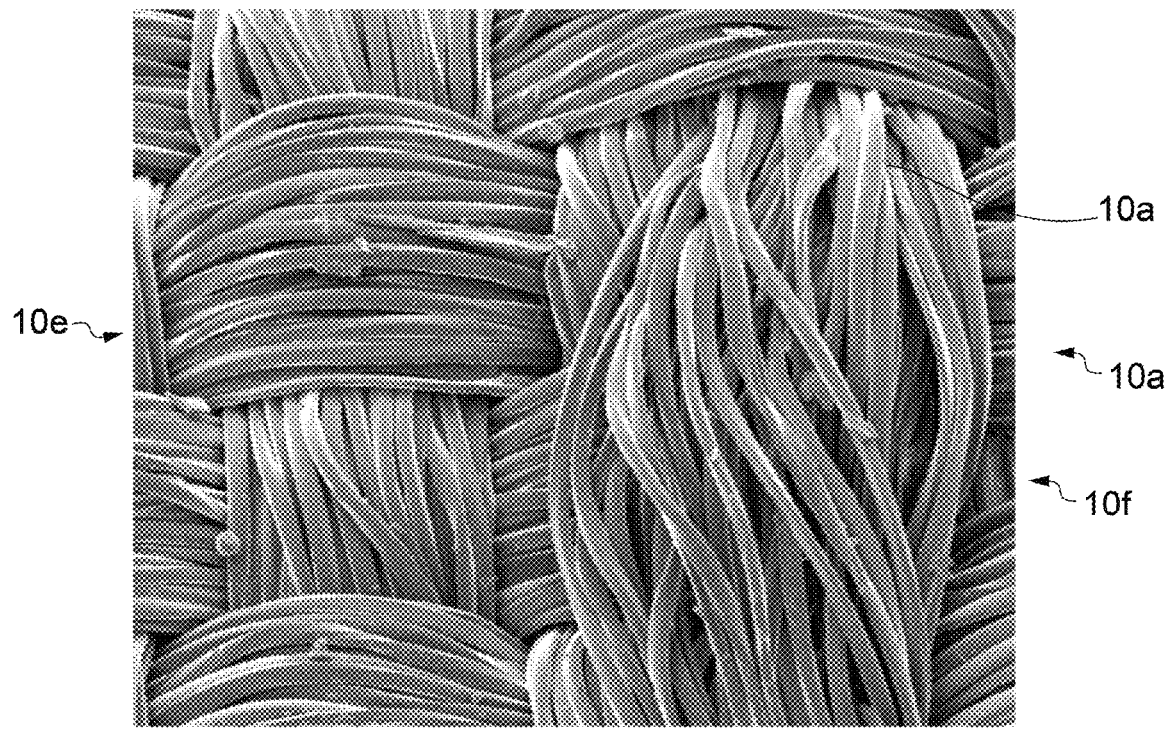
Figure 2B:
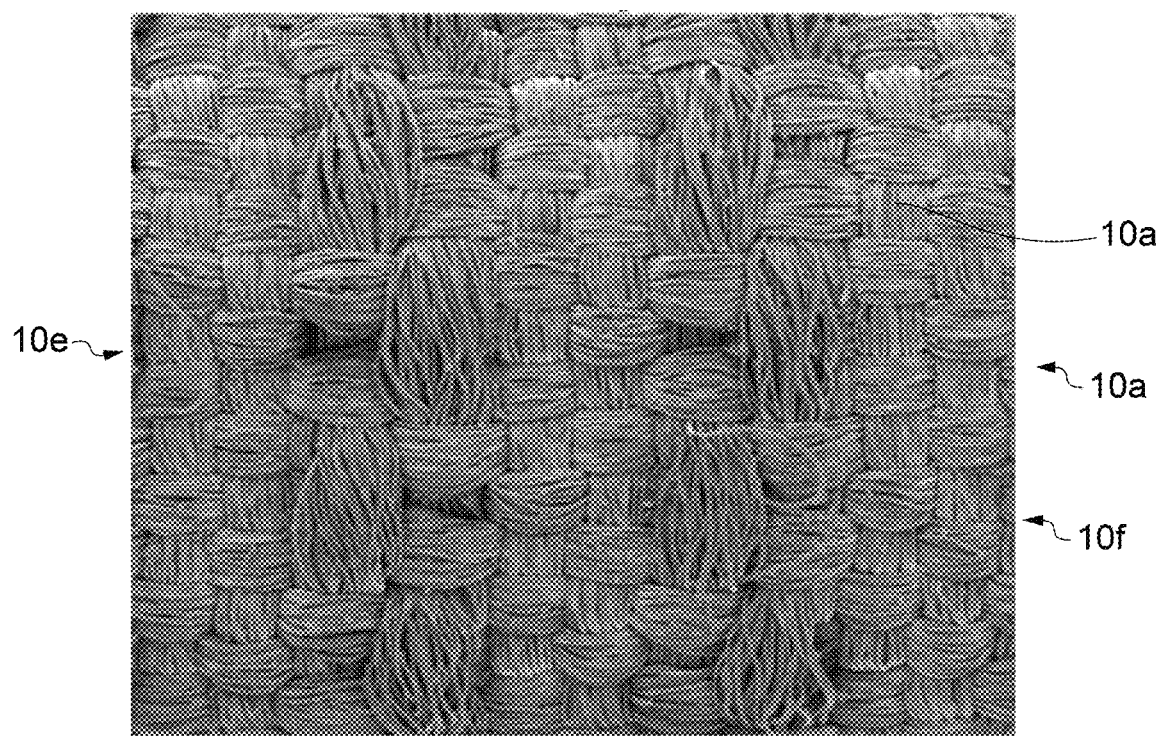

FIGS. 2a and 2b show the inner surface 10a of the wall 10f of the conduit 10 in more detail. FIGS. 2a and 2b show the porous nature of the conduit 10. The conduit 10 is a woven structure and, in this embodiment, is generally a 1/1 twill weave type. As described above, the unprocessed woven conduit 10 will allow blood to leak through the gaps in the fibres of the conduit 10, and it must therefore be sealed prior to implantation in the human or animal body.

The woven nature of the conduit 10 means that it is flexible. After applying the masking agent 12 and the sealing layer 14, the vascular graft 16 remains flexible, which helps to make the vascular graft 16 easier to manipulate and handle by, for example, a medical practitioner.

Figure 3A:
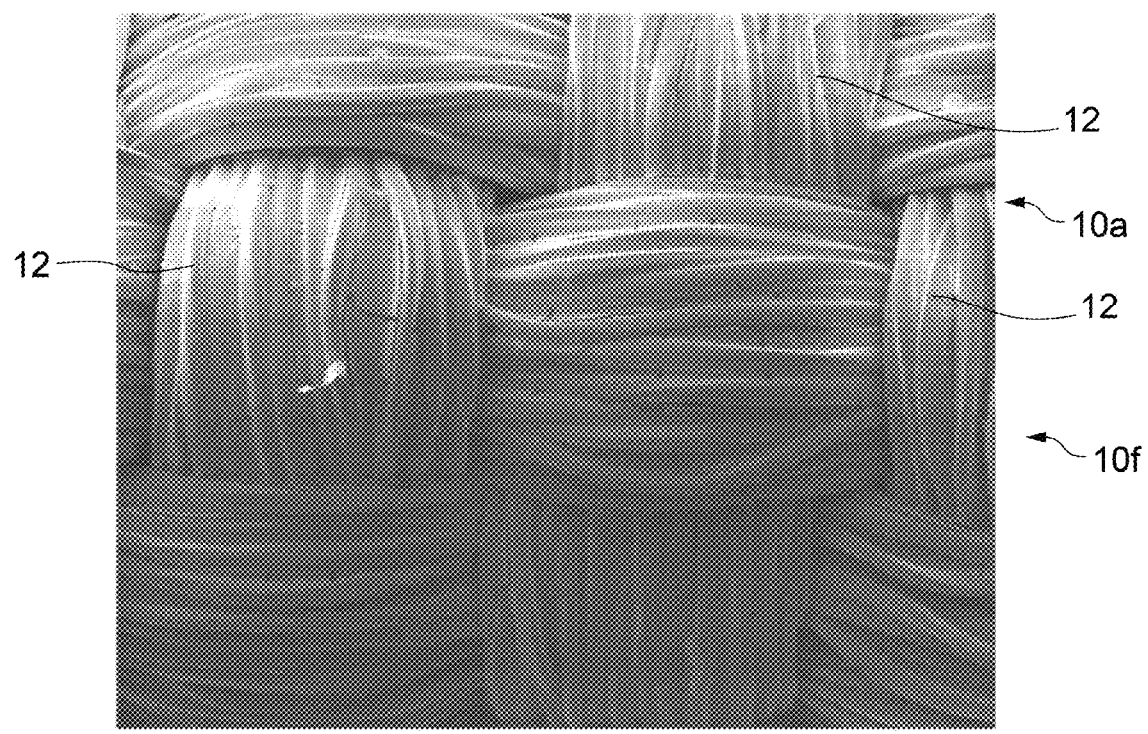
FIGS. 3a and 3b show a detailed view of the inner surface of the wall of the conduit of FIG. 1b after the addition of the masking agent.
Figure 3B:
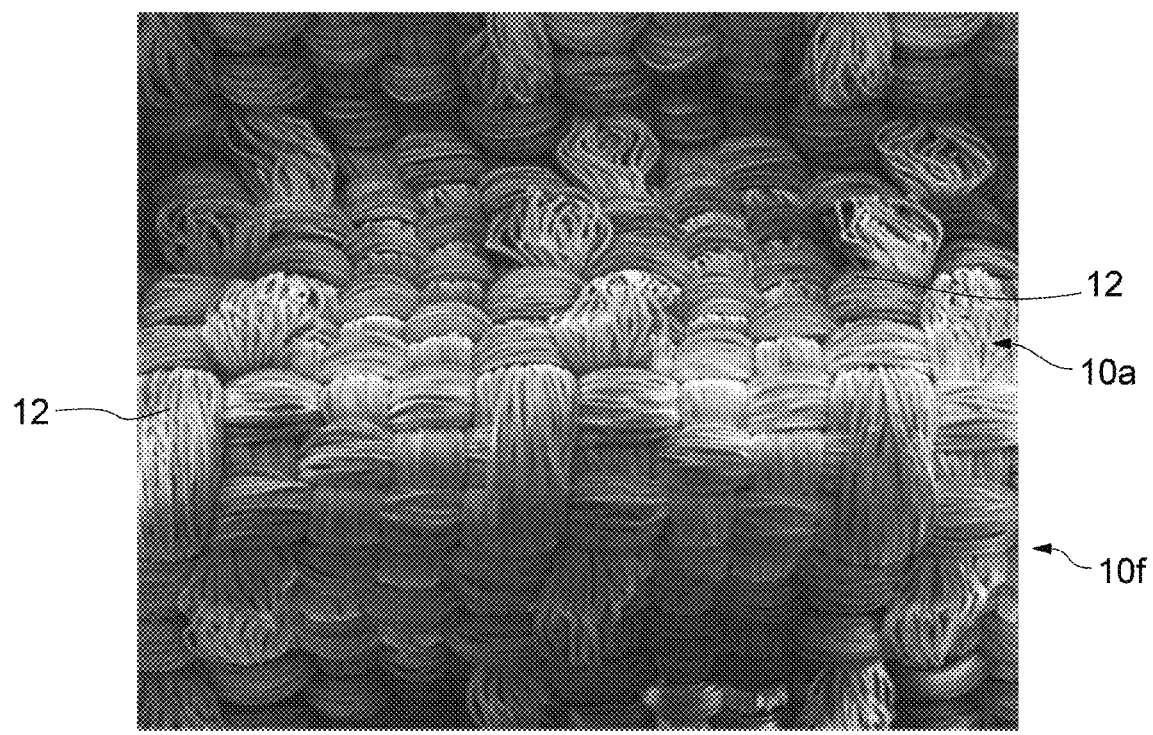

FIGS. 3a and 3b show a detailed view of the inner surface 10a of the wall 10f of the conduit 10 after the addition of the masking agent 12. In this embodiment, the masking agent 12 has been added to the conduit 10 from a polymer solution (an example of a masking agent solution) comprising approximately 5% w/v PVP in solution. In this embodiment, the conduit 10 has been immersed in the polymer solution. However, as described in more detail above, the masking agent 12 could be added to the conduit 10 in other ways and the polymer solution could comprise between approximately 5% w/v and approximately 30% w/v of polymer in solution. In the embodiment illustrated in FIGS. 3a and 3b, the conduit 10 has been immersed in the masking agent solution for approximately 1 minute. However, it should be appreciated that the conduit 10 could be immersed in the masking agent solution for other durations of time.

In the embodiment shown in FIGS. 3a and 3b, the masking agent 12 substantially blocks the porous section 10e of the conduit 10. When the sealant 14 is applied to the conduit 10, the masking agent 12 mitigates the presence of the sealant 14 on the inner surface 10a of the wall 10f of the conduit 10. In this embodiment, the masking agent 12 forms an oleophobic layer (an example of a masking layer). Without wishing to be bound by theory, it is thought that the oleophobic properties of the masking layer helps to mitigate the presence of the sealant 14 on the inner surface 10a of the wall 10f of the conduit 10. It should be understood that in some embodiments the masking agent 12 need not form an oleophobic layer.

Figure 4A:
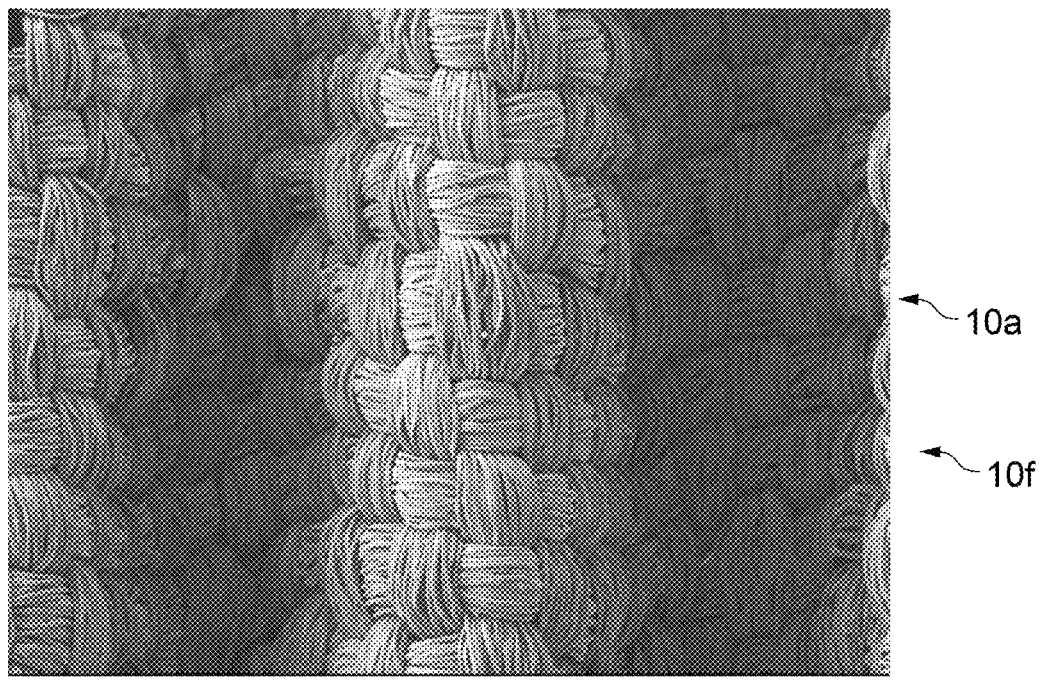
FIG. 4a shows a detailed view of the inner surface of the wall of the conduit of FIG. 1d.
Figure 4B:
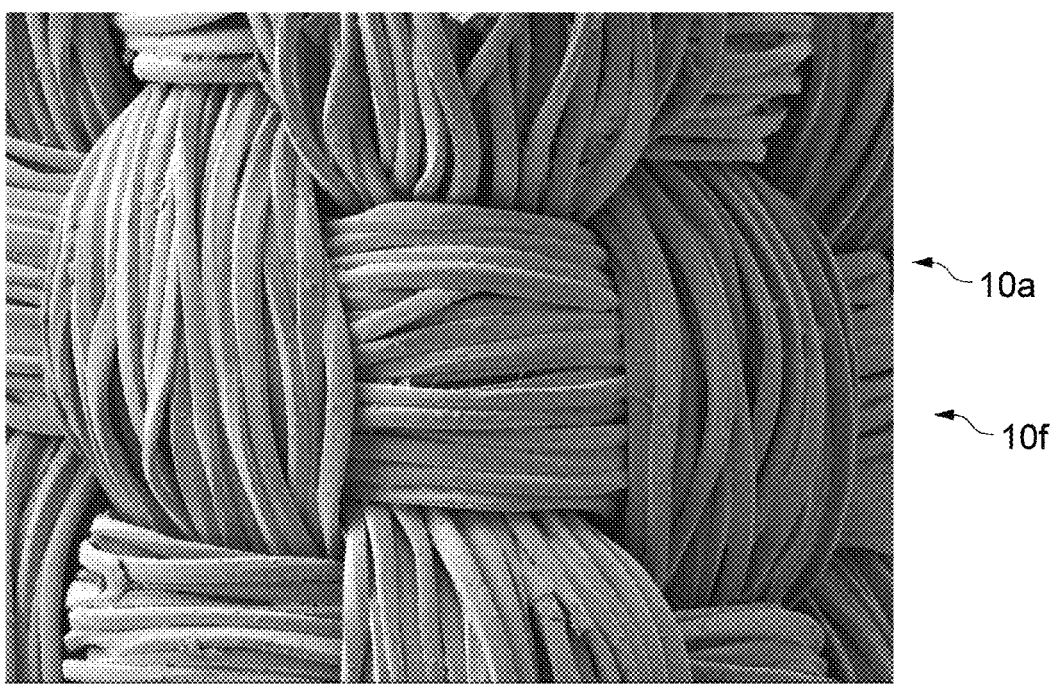
FIG. 4b shows a detailed view of the inner surface of the wall of the conduit of FIG. 1d.

FIGS. 4a and 4b show the inner surface 10a of the wall 10f of the conduit 10 after the sealant 14 has been added to the outer surface 10b of the wall 10f of the conduit 10. FIGS. 4a and 4b highlight the effectiveness of the masking agent 12 in mitigating the presence of sealant 14 on the inner surface 10a of the wall 10f of the conduit 10. In this embodiment, the masking agent 12 has been applied to the conduit 10 from a masking agent solution comprising approximately 7% w/v of PVP in solution. In the embodiment illustrated in FIGS. 4a to 5b, the sealant has been added to the outer surface 10b of the wall 10f of the conduit 10 by spray coating a sealant solution onto the outer surface 10b of the wall 10f of the conduit 10.

Figure 5A:
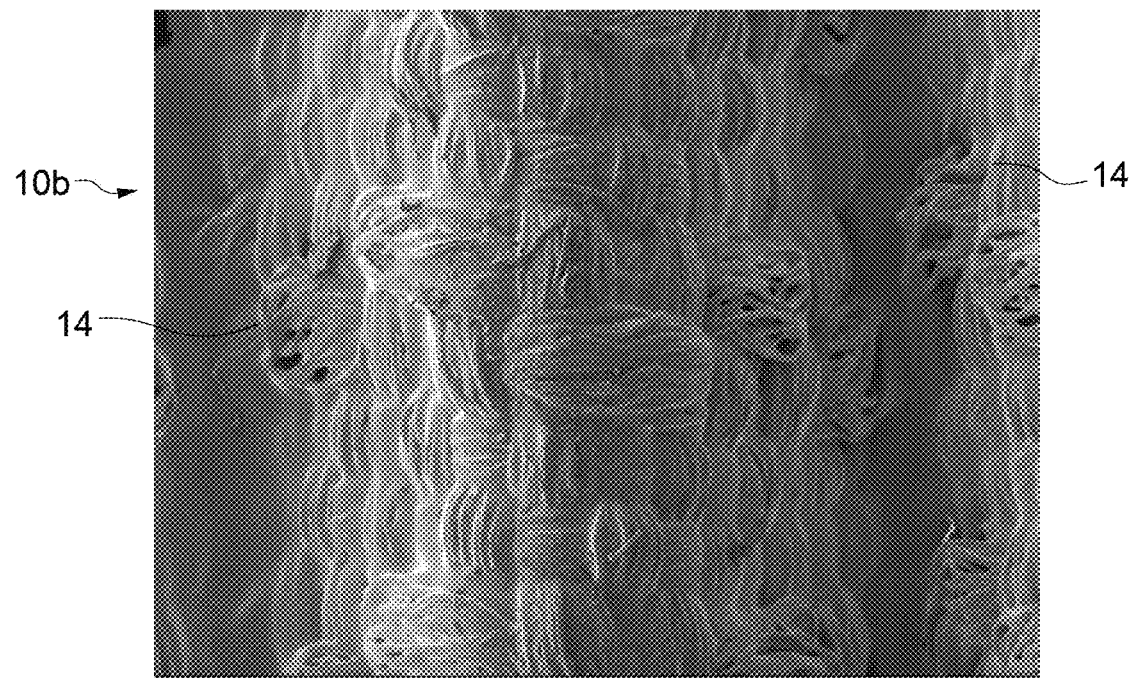
FIG. 5a shows a detailed view of the outer surface of the wall of the conduit of FIG. 1d.
Figure 5B:
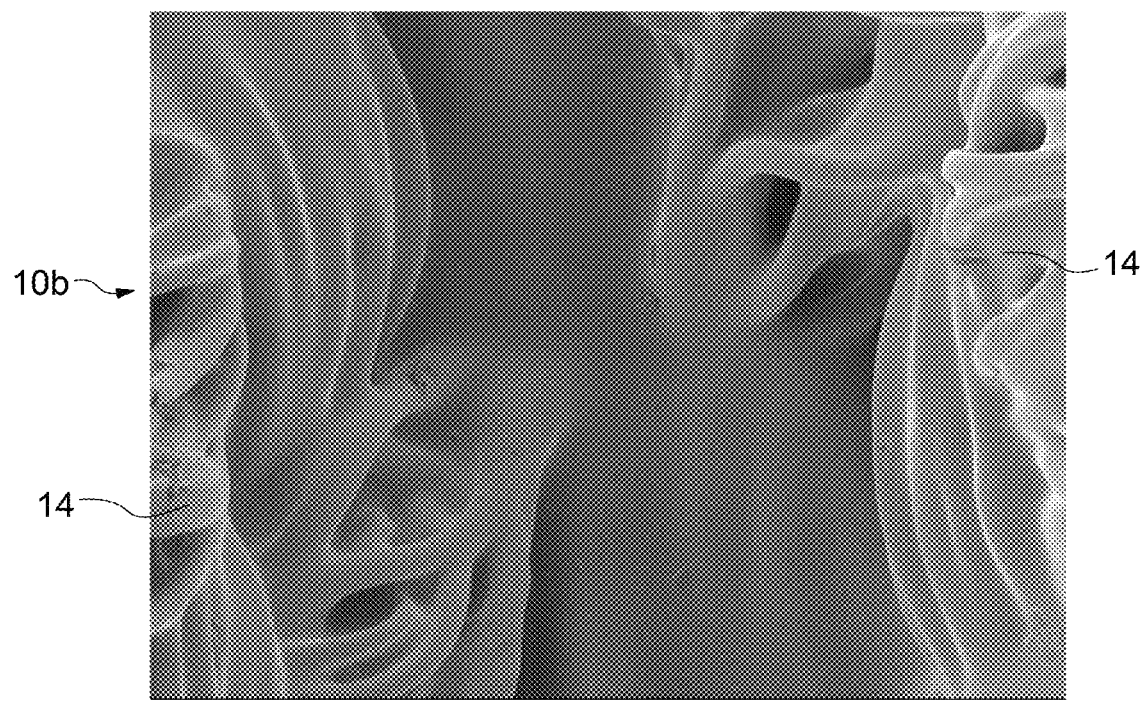
FIG. 5b shows a detailed view of the outer surface of the wall of the conduit of FIG. 1d.

FIGS. 5a and 5b show the presence of the sealant 14 on the outer surface 10b of the wall 10f of the conduit 10 of the embodiment shown in FIGS. 4a and 4b. In the embodiment shown in FIGS. 5a and 5b, the sealant solution comprises approximately 15% w/v of silicone in xylene.

FIGS. 4a and 4b, and FIGS. 5a and 5b, highlight the contrast between the inner surface 10a and the outer surface 10b of the wall 10f of the conduit 10 after the application of the sealant 14 to the conduit 10. The outer surface 10b of the conduit 10 is now substantially covered in the sealant 14, whereas the inner surface 10a of the wall 10f of the conduit 10 has retained the woven, porous properties of the conduit 10, because the inner surface 10a of the wall 10f of the conduit 10 is substantially devoid of the sealant 14. The masking agent 12 has mitigated the presence of the sealant 14 on the inner surface 10a of the wall 10f of the conduit 10. In this embodiment, the inner surface 10a of the wall 10f is configured to facilitate the growth of biological tissue thereon, and to allow for good adhesion between ingrowing biological tissue and the inner surface 10a. Presence of the sealant 14 on the inner surface 10a of the wall 10f of the conduit 10 could have an adverse impact on the ingrowth of biological tissue on the inner surface 10a of the wall 10f of the conduit 10, and on the adhesion between the biological tissue and the inner surface 10a of the wall 10f of the conduit 10.

Figure 6A:
FIG. 6a shows a detailed view of the outer surface of the wall of the conduit of FIG. 1d.

FIG. 6a shows a detailed view of the outer surface 10b of the wall 10f of the conduit 10 after the addition of the sealant 14. In this embodiment, the sealant 14 is configured to mitigate movement of fluid through the wall 10f of the conduit 10. The wall 10f of the conduit 10 is substantially blood impermeable (i.e., blood cannot pass or leak through the wall 10f at an appreciable rate) after the addition of the sealant 14.

Figure 6B:
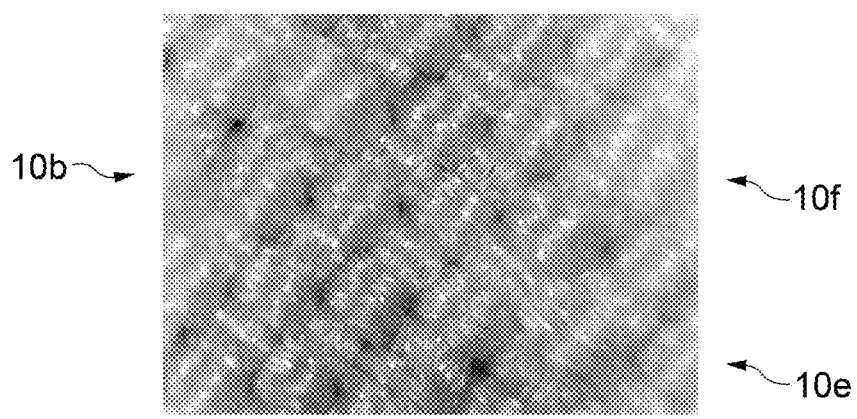
FIG. 6b shows a detailed view of the inner surface of the wall of the conduit of FIG. 1d.

FIG. 6b shows a detailed view of the inner surface 10a of the wall 10f of the conduit 10 after the addition of the sealant 14 to the conduit 10.

In the embodiment shown in FIGS. 6a and 6b, the masking agent 12 has been applied to the conduit 10 from a polymer solution comprising approximately 30% w/v PVP in solution, prior to the addition of the sealant 14. As described above, the masking agent 12 can be applied to the conduit 10 from a polymer solution comprising between approximately 5% w/v and approximately 30% w/v of polymer in solution.

One desirable feature for a sealed graft is that it may have sufficiently low levels of permeability to remain predominantly leak proof during the implant procedure. The applicable test method, as prescribed in ISO 7198, Whole Graft Permeability recommends testing using reverse osmosis (RO) filtered water at a test pressure of 120 mmHg. This parameter was based on a de facto standard established by the manufacturers of biologically sealed grafts (gelatin and collagen). A limit of 0.16 ml/min/cm$^2$ may be used to ensure that the graft meets and exceeds sealing capability of aforementioned grafts. Different applications, however, may have different permeability requirements, and such different permeability requirements are within the scope of the present invention.

Further embodiments were prepared according to the manufacturing process illustrated in FIGS. 1a to 6b and described above. The further embodiments are described in Table 1 below. The manufacturing process used to create the further embodiments listed in Table 1 is substantially the same as that illustrated and described in relation to FIGS. 1a to 6b, with the exception that different masking agents 12 and sealants 14 were used.

Commercial textile vascular grafts were used for the tests described hereinafter. Details for commercial graft samples are described below:

First Commercial Samples of Woven Graft Fabrics:
(a) Warp yarn: twisted, texturized, PET, 2 ply/44 denier per ply (or bundle)/27 filaments per ply or bundle.
(b) Weft yarn: twisted, texturized, PET, 2 ply/44 denier per ply (or bundle)/27 filaments per ply or bundle.
(c) Picks per cm, about 40 to 46.

Second Commercial Samples of Woven Graft Fabrics:
(a) Warp yarn: 80 Denier, 2 ply/40 denier per ply (or bundle)/27 filaments per ply (or bundle), PET, Spun Draw, texturized, 7.5 Twists per inch, Z twist.
(b) Weft yarn: 2 ply/40 Denier per ply (or bundle), 2 ply/40 denier per ply (or bundle)/27 filaments per ply or bundle, PET, TXT, S & Z Twist.
(c) Picks per inch, about 155.

The tests done below in Table 1 were performed on the first commercial samples of woven graft fabrics.

TABLE 1

| Masking Agent | | Sealant | | Sealant Coating Method | Sealant Coverage (mg/cm$^2$) | Leak Rate (ml/min/cm$^2$) | Leak Rate ≤0.16 ml/min/cm$^2$ |
|---|---|---|---|---|---|---|---|
| Polymer | Solvent | Polymer | Solvent | | | | |
| 7% w/v PVP | Water | 30% w/v Silicone | Xylene | Brush x 1 | 11.33 | 0.19 | No |
| 7% w/v PVP | Water | 30% w/v Silicone | Xylene | Brush x 1 | 8.30 | 0.19 | No |
| 4% w/v PVP | Water | TPU and Silicone | THF | Brush x 1 | 2.00 | 5.79 | No |
| 4% w/v PVP | Water | TPU and Silicone | THF | Brush x 2 | 3.70 | 0.46 | No |
| 30% w/v PVP | Water | 30% w/v Silicone | Xylene | Brush x 1 | 5.3 | 1.78 | No |
| 30% w/v PVP | Water | 30% w/v Silicone | Xylene | Brush x 1 | 5.2 | 3.49 | No |
| 30% w/v PVP | Water | 30% w/v Silicone | Xylene | Brush x 1 | 7.6 | >12.24 | No |
| 25% w/v PVP and 18% w/v Glycerol | Water | 30% w/v Silicone | Xylene | Brush x 1 | — | — | No |
| 7% w/v PVP | Water | 30% w/v Silicone | Xylene | Brush x 1 | 4.8 | 0 | Yes |
| 7% w/v PVP | Water | 30% w/v Silicone | Xylene | Brush x 2 | 8.9 | 0 | Yes |
| 7% w/v PVP | Water | 30% w/v Silicone | Xylene | Brush x 3 | 8.3 | 0 | Yes |
| 7% w/v PVP | Water | 30% w/v Silicone | Heptane | Brush x 1 | 7.6 | 0.69 | No |
| 7% w/v PVP | Water | 30% w/v Silicone | Heptane | Brush x 2 | 13.8 | 0.02 | Yes |
| 7% w/v PVP | Water | 30% w/v Silicone | Heptane | Brush x 3 | 18.6 | 0 | Yes |
| 7% w/v PVP | Water | 30% w/v Silicone | Xylene | Brush x 1 | 8.0 | 0.09 | Yes |
| 7% w/v PVP | Water | 30% w/v Silicone | Xylene | Brush x 2 | 11.5 | 0.14 | Yes |
| 7% w/v PVP | Water | 30% w/v Silicone | Xylene | Brush x 2 | 11.5 | 0.05 | Yes |
| 7% w/v PVP | Water | 30% w/v Silicone | Xylene | Brush x 3 | 15.6 | 0 | Yes |
| 7% w/v PVP | Water | 30% w/v Silicone | Xylene | Brush x 1 | 7.1 | 0.01 | Yes |
| 7% w/v PVP | Water | 30% w/v Silicone | Xylene | Brush x 2 | 9.7 | 0.03 | Yes |
| 7% w/v PVP | Water | 30% w/v Silicone | Xylene | Brush x 2 | 9.1 | 0.03 | Yes |
| 7% w/v PVP | Water | 30% w/v Silicone | Xylene | Brush x 3 | 12.6 | 0.02 | Yes |
| 7% w/v PVP | Water | 30% w/v Silicone | Xylene | Brush x 1 | 6.0 | 0.22 | No |
| 7% w/v PVP | Water | 30% w/v Silicone | Xylene | Brush x 2 | 14.3 | 0.03 | Yes |
| 7% w/v PVP | Water | 30% w/v Silicone | Xylene | Brush x 2 | 9.8 | 0.10 | Yes |
| 7% w/v PVP | Water | 30% w/v Silicone | Xylene | Brush x 3 | 13.8 | 0.06 | Yes |
| 12% w/v PVP | Water | 30% w/v Silicone | Xylene | Brush x 2 | 11.0 | 6.25 | No |
| 12% w/v PVP | Water | 30% w/v Silicone | Xylene | Brush x 2 | 11.3 | 1.81 | No |

TABLE 1-continued

| Masking Agent | | Sealant | | Sealant Coating Method | Sealant Coverage (mg/cm$^2$) | Leak Rate (ml/min/cm$^2$) | Leak Rate ≤0.16 ml/min/cm$^2$ |
|---|---|---|---|---|---|---|---|
| Polymer | Solvent | Polymer | Solvent | | | | |
| 7% w/v PVP | Water | 15% w/v Silicone | Xylene | Spray x 1 | 3.5 | 7.24 | No |
| 7% w/v PVP | Water | 15% w/v Silicone | Xylene | Spray x 2 | 5.6 | 0.07 | Yes |
| 7% w/v PVP | Water | 15% w/v Silicone | Xylene | Spray x 3 | 5.3 | 0.57 | No |
| 7% w/v PVP | Water | 15% w/v Silicone | Xylene | Spray x 1 | 6.7 | 5.11 | No |
| 7% w/v PVP | Water | 15% w/v Silicone | Xylene | Spray x 1 | 8.7 | 0.01 | Yes |
| 7% w/v PVP | Water | 15% w/v Silicone | Xylene | Spray x 1 | 6.4 | 0.02 | Yes |
| 7% w/v PVP | Water | 15% w/v Silicone | Xylene | Spray x 1 | 4 | 8.41 | No |
| 7% w/v PVP | Water | 15% w/v Silicone | Xylene | Spray x 1 | 6.3 | 8.99 | No |
| 7% w/v PVP | Water | 15% w/v Silicone | Xylene | Spray x 1 | 3.8 | 5.05 | No |
| 7% w/v PVP | Water | 15% w/v Silicone | Xylene | Spray x 1 | 8.1 | 1.17 | No |
| 7% w/v PVP | Water | 15% w/v Silicone | Xylene | Spray x 1 | 7.9 | 0.14 | Yes |
| 7% w/v PVP | Water | 15% w/v Silicone | Xylene | Spray x 1 | 8.2 | 5.94 | No |
| 7% w/v PVP | Water | 15% w/v Silicone | Xylene | Spray x 1 | 8.8 | 1.08 | No |
| 7% w/v PVP | Water | 15% w/v Silicone | Xylene | Spray x 1 | 11.4 | 0.01 | Yes |
| 7% w/v PVP | Water | 15% w/v Silicone | Xylene | Spray x 1 | 6.8 | 5.93 | No |
| 7% w/v PVP | Water | 15% w/v Silicone | Xylene | Spray x 1 | 7.4 | 0.16 | Yes |
| 7% w/v PVP | Water | 15% w/v Silicone | Xylene | Spray x 1 | 11.9 | 0 | Yes |
| 6% w/v PVP and 1% w/v Glycerol | Water | 15% w/v Silicone | Xylene | Spray x 1 | 7.8 | 0.04 | Yes |

A hobby spray gun was used for all spray application tests where sealants were sprayed onto graft samples. The spray distance from the graft samples was approximately 50 mm. Grafts were held horizontally on mandrel and rotated in a rotisserie. Spray rates were not measured but were controlled by a combination of the nozzle traverse rate (estimated at 2 seconds/cm), graft rotation speed (estimated between one and three revolutions per second) and overall spray volume rate. Craft bristle brushes were used for all brush application tests where sealants were brushed onto graft samples.

As indicated in Table 1, if the wall 10f has a Leak Rate ≤0.16 ml/min/cm$^2$ then the conduit 10 is considered suitable for implantation and is considered substantially impermeable. In some further embodiments, the masking agent 12 comprises glycerol. Without wishing to be bound by theory, the presence of glycerol in the masking agent 12 is thought to mitigate cracking of the masking agent 12 when applied to the conduit 10.

Masking agents described herein prevent sealants, such as the liquid silicone elastomer dispersion, from penetrating throughout the thickness of the graft wall and reaching the lumen or blood contacting surface of the graft. Sealants, such as silicone, are believed to adhere to graft fibres on the external surface of the graft through two mechanisms:
  a. Where graft fibres have had the mask agent ablated or otherwise free of the masking agents, the liquid silicone elastomer dispersion adheres to the surface of the graft fibres, such as PET fibres.
  b. Where surface fibres are individually sheathed by the masking agent, these fibres are encapsulated and a mechanical interlocking takes place rather than surface adhesion.

Silicone will adhere to the PET fibre surface where there is no masking agent, but will also encapsulate PET fibres which are sheathed in masking agent.

The masking agent is believed to act like a slurry when applied to a textile and can flow and cover gaps between the yarn bundles and also seep between the yarn fibers. It acts as a viscous mixture moving through the fabric and settling and collecting at areas of low energy. Rather than attaching to individual fibers it continues to move and pool until a masking agent drying process initiates and through the evaporation of its solvent, such as water, the masking agent then solidifies wherever it has gathered.

The elastomeric sealant (e.g., silicone) may not adequately attach to the textile surface where excessive concentrations of masking agent are present. If the masking agent is too viscous and has fully encapsulated an area of fabric and then dried, there may be no exposed yarn filaments for the silicone to mechanically encapsulate and lock onto. Without this mechanical encapsulation of the yarn by the silicone, then the adhesion may be poor and possibly non-existent once the masking agent is removed.

While the masking agent may appear to thinly coat the individual filaments as it moves or washes through the textile, the concentrations remaining in these washed through areas after drying are not sufficient to prevent subsequent encapsulation and adhesion of the silicone adhesive to the yarn bundles.

Any synthetic hydrophilic polymer and any biological hydrophilic polymer, e.g., gelatin, partially hydrolysed collagen, dextran, hyaluronic acid, alginates and starches (e.g., hydroxyethyl starch) and chitosan may be used as masking agents. Pluronic F127 PEG, which is soluble in cold water but insoluble in warm water, may also be used as a masking agent. Desirably, masking agents derived from animal products may are removed prior to vascular applications. As such, the masking agents, including animal derived masking agents, if any, are removed from the final product, such grafts may suitable be used in vascular applications. Furthermore, as the masking agents are removed from the textile graft prior to any applications with a patient, including vascular applications, the masking agents need not be biocompatible.

Desirably, the masking agent is highly soluble in water. It can be any polymer which can swell in a liquid which has a Hildebrand Solubility Parameter (Delta SI units) of 24 or higher.

Masking agents useful with the present invention may have molecular weights from about 400 or 1,000 to about 1,000,000. Desirably, the molecular weight may vary from about 3,000 to about 30,000, and more desirably from about 6,000 to about 15,000

One useful sealant may be a dispersion of silicone in a nonpolar 'solvent' or carrier medium. Useful cross linking is through acetoxy 'room temp vulcanisation' chemistry but two part platinum cure chemistry could also be used as well as ultraviolet (UV) curing.

For samples employing a polymer supplied as a dispersion, for example NuSil MED 6605 and Med 6606, discrete amounts of polymer dispersion were decanted by weight into individual pots for either direct coating onto the graft or further addition of solvent, by weight.

All silicone dispersions used were acetoxy curing. Curing schedules are recommended at 72 hours, however due to the extremely thin cross section/large surface area of the graft, full cures have been observed apparent within 24 hours. Subsequent washing of the device in water may speed up the curing and ensure full cross linking. These times are, however, non-limiting, and other cure times and conditions may suitably be used.

The preferred polymers for coating, in order to achieve a soft and flexible graft with handling characteristics similar to that of a gelatin sealed graft, are those with very low Shore hardness values. The preferred silicone elastomers, MED 6605 and MED 6605 have Durometer Type A values of 25 and 20 respectively. Both of these grades can provide grafts with suitable flexibility and handling characteristics, when thin coatings are applied. As multiple coatings are applied, stiffness may increase and flexibility may reduce.

Harder grades can be used as an alternative to thicker coatings in order to create stiffer grafts if required.

Alternative coatings, such as TPU-Silicones (Advansource Chronosil 75A or Aor-Tech Elast-Eon E5-130) can be used however, these have Durometer Hardness of 75 A and 77 A respectively, therefore may create grafts which may be stiffer, if desired, than current gelatin sealed grafts. Such stiffer grafts may have some benefits for specific applications, however, may not meet expectations for conventional surgeon handling.

Additional useful sealant materials include, but are not limited to:

(a) Applied Silicone Corporation, PN 40021, Implant grade high strength RTV Silicone Elastomer Dispersion in Xylene. This material is suitable for use in fabricating high strength, elastic membranes of any shape and thickness using processes such as dipping, casting, spraying or brushing. After evaporating the solvent, the silicone is room temperature vulcanized (RTV) by exposure to ambient air. The key features of this material are high strength, low durometer, (Shore A 24) and is supported by ISO 10993 testing and compendium to support regulatory submissions.

(b) AdvanSource Biomaterials Corporation, ChronoFlex AR, polycarbonate based thermoplastic urethanes. These materials may be used for moulding, casting and dip-coating and are fully synthesized in liquid providing high strength & elongation while maintaining the inherent polycarbonate advantage of long-term permanent durability and resistance to environmental stress cracking (ESC). Additionally, they may be electrospun or used in water emulsion processes. Examples of specific useful materials include, but are not limited to, ChronoFlex C80A 5% and ChronoFlex AR 23%.

Suitable sealants are low durometer elastomers (desirably less than or equal to about 40 A durometer or shore hardness 40 A, more desirably less than or equal to about 30 A durometer or shore hardness 30 A, even more desirably less than or equal to about 20 A durometer or shore harness 20 A) and have good biostability.

One parameter which may be considered in the choice of sealant is the stiffness or elastic modulus. Usually with elastomers the modulus is not linear thus at each elongation the stress (or force) is measured. A material with lower stress @ % strain will provide less resistance to extension and will therefore feel more flexible and closer to matching the handling of a gelatin sealed graft.

Preferred materials are low stress silicone rubbers, such as NuSil MED 6605 and MED 6606, with Stress @ Strain values <180 @ 200%.

Useful Polyurethane and Silicone-polyurethane grades, include, but are not limited to:

TABLE 2

| Material | Manufacturer | Grade | Stress (psi) at % elongation |
| --- | --- | --- | --- |
| Silicone Rubber | NuSil | MED 6606 | 50 @ 100% |
| Silicone Rubber | NuSil | MED 6605 | 160 @ 300% |
| Silicone Rubber | Applied Silicone | Dispersion PN 40021 | 170 @ 300% |
| TPU-Silicone | Advansource | ChronoSil adjusted | 570 @ 200% |
| TPU-silicone | Biomerics | Quadrasil Elast-EON E5-130 | 725 @ 200% |
| TPU-aliphatic polycarbonate | Advansource | Chronoflex AL 75A | 800 @ 200% |
| TPU-10% silicone | Advansource | ChronoSil 75A 10% Si | 834 @ 200% |

The present invention is not limited to the use of silicone as the polymeric sealant. Other useful coating materials for both medical and non-medical textiles may include, for example, polytetrafluoroethylene, polyethylene, poly(hydroxyethly methacrylate), poly(vinyl alcohol), polycaprolactone, poly(D, L-lactic acid), poly(L-lactic acid), poly (lactide-co-glycolide), poly(hydroxybutyrate), poly (hydroxybutyrate-co-valerate), polydioxanone, polyorthoester, polyanhydride, poly(glycolic acid), poly (glycolic acid-cotrimethylene carbonate), polyphosphoester, polyphosphoester urethane, poly(amino acids), cyanoacrylates, poly(trimethylene carbonate), poly(iminocarbonate), copoly(ether-esters), polyalkylene oxalates, polyphosphazenes, polyiminocarbonates, aliphatic polycarbonate, polyethylene oxide, polyethylene gylcol, poly(propylene oxide), polyacrylamide, polyacrylic acid (30-60% solution), polymethacrylic acid, poly(N-vinyl-2-pyrollidone), polyurethane, poly(aminoacid), cellulosic polymer (e.g. sodium carboxymethyl cellulose, hydroxyethyl cellulose), collagen, carrageenan, alginate, starch, dextrin, gelatin, poly(lactide), poly(glycolide), polydioxanone, polycaprolactone, polyhydroxybutyrate, poly(phospazazene), poly(phosphate ester), poly(lactide-co-glycolide), poly(glycolide-co-trimethylene carbonate), poly(glycolide-co-caprolactone), polyanhydride, polyamide, polyesters, polyether, polyketone, polyether elastomer, parylene, polyether amide elastomers, polyacrylate-based elastomer, polyethylene, polypropylene, and/or and derivatives thereof. Other useful coating materials, in particular for but not limited to non-medical textiles, may include natural rubbers, natural gums, acrylic polymers, polybutadienes, styrene-butadiene copolymers or rubbers, butadiene-acrylonitrile copolymers, polyisobutylenes, isoprene-isobutylene copolymers, polysulfide rubbers, chloroprene rubbers (neoprene), chlorosulfonated polyethylene, fluorinated polymers, vinyl resins, and the like. Further, coating materials may include metallic materials and powdered materials.

Figure 7:
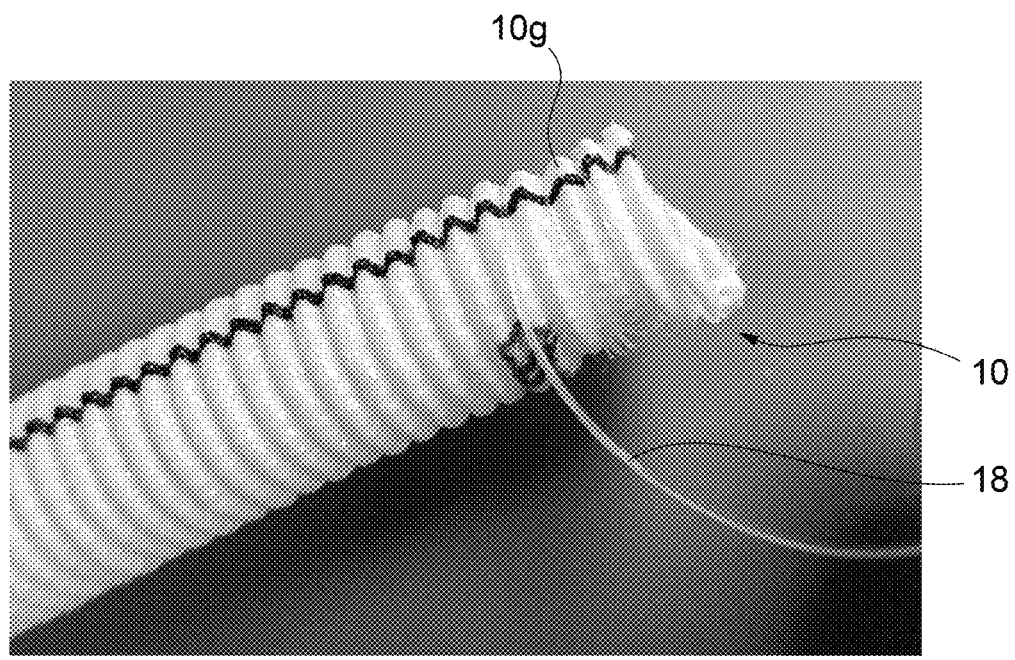

FIG. 7 depicts a further embodiment of the conduit 10. As best shown in FIG. 7, the conduit 10 comprises a number of crimps 10g. In this embodiment, a support member 18 is added to the outer surface 10b, of the wall 10f of the conduit 10. In particular, the support member 18 is added by multiple stages of sealant application. For example, the sealant may be added to the outer surface of the conduit 10 as described above, then the support member 18 may be disposed over the sealed graft, followed by applying another stage of sealant application, which after drying and/or curing will aid in the securement of the support member 18 to the conduit 10. However, it should be understood that the support member 18 could be added to the conduit 10 in other ways. The step of adding the support member 18 to the outer surface 10b of the wall 10f of the conduit 10 is carried out prior to the step of adding the sealant 14 to the conduit 10. The sealant 14 is configured to attach the support member 18 to the conduit 10. In this embodiment, the support member 18 is added to the conduit 10 and the sealant 14 is then added to the conduit 10 in order to seal the conduit 10, and to attach the support member 18 to the conduit 10. Moreover, it should be understood that it is within the scope of the present invention to have multiple applications of masking agent and/or sealant either after or prior to drying and/or curing the prior application.

The support member 18 is a flexible, polymer wire, which in this embodiment is wrapped around the outer surface 10b of the wall 10f of the conduit 10 and is arranged to nest between the crimps 10g of the conduit 10. One of the advantages of adding the support member 18 to the conduit 10, as illustrated and described here, is that the conduit 10 is made more robust while retaining much of its flexible characteristics. As stated above, the conduit 10 is able to be manipulated by a medical practitioner in a more efficient way because the conduit 10 is flexible.

In the embodiment illustrated in FIG. 7, the support member 18 is made from polyethylene terephthalate (PET). However, it is understood that the support member 18 could comprise at least one of: a polymer material, a metal material, a shape memory alloy, and a superelastic alloy. In some embodiments, the support member 18 could comprise at least one of: polyethylene terephthalate, polytetrafluoroethylene, polyurethane, polycarbonate, silicone, stainless steel, titanium, nickel, and nickel titanium (Nitinol).

Figure 8:
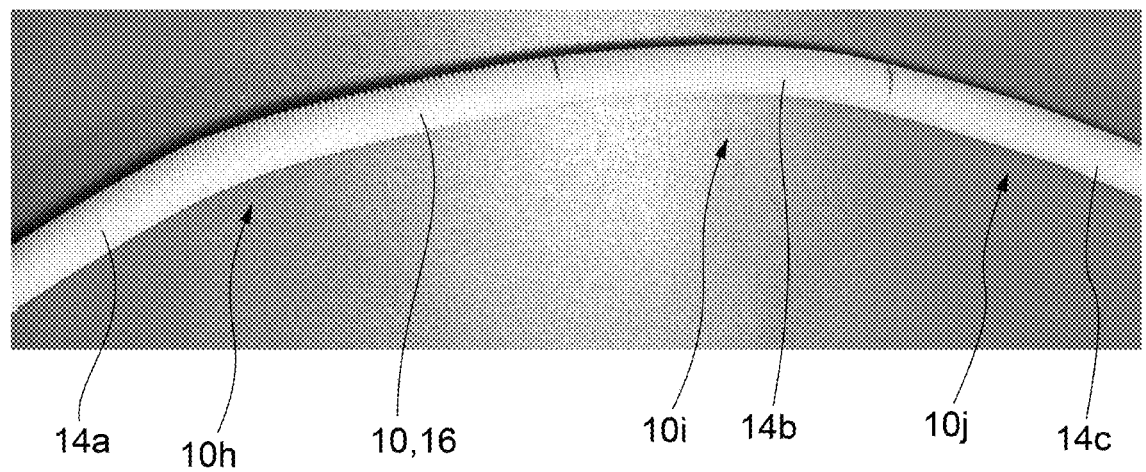
FIG. 8 depicts an alternative embodiment of a conduit manufactured according to the process of FIGS. 1a to 1d.

FIG. 8 shows an alternative embodiment of a conduit 10 manufactured according to the process illustrated in FIGS. 1a to 1d. The conduit 10 depicted in FIG. 8 has been manufactured in the same way as that depicted in FIG. 1d, with the following differences. The conduit 10 has three sections 10h, 10i, 10j. Sealant 14a, 14b and 14c has been selectively added to the sections 10h, 10i, 10j, such that each section 10h, 10i, 10j, has a different amount of sealant 14a, 14b, 14c, present thereon. In this embodiment, each of the sections 10h, 10i, 10j have a substantially different degree of flexibility. The first section 10h has a higher degree of flexibility than the second section 10i. Similarly, the second section 10i has a higher degree of flexibility than the third section 10j. As shown in FIG. 8, the crimps 10g of the first section 10h are more visible than in the second section 10i and third section 10j, because the second and third sections 10i, 10j, have a higher amount of sealant added thereto, which causes the crimps 10g in these sections 10i, 10j, to be less pronounced. In applications where a further prosthesis is connected to an end of the vascular prosthesis 16, the end of the third section 10j is more suited for connection to the further prosthesis.

An example of how the vascular graft 16 may be used will now be provided.

The vascular graft 16 described in FIGS. 1a to 6b, which may be thought of as a sealed, processed conduit 10, is capable of being implanted in the human or animal body over the long term. This is because the vascular graft 16 is biocompatible, that is it will not illicit a foreign body response in the human or animal body, and it is not toxic to surrounding biological tissue.

The masking agent 12 is configured to biodegrade in the body. Therefore, any residual masking agent 12 present on the conduit 10 will biodegrade in the body. However, as described in more detail above, the masking agent 12 need not be biodegradable, as in some embodiments the masking agent 12 will be removed substantially entirely from the conduit 10. In other embodiments, the masking agent 12 need not be removed from the conduit 10.

The vascular graft 16 can be used to bypass a region, or a section of a blood vessel. For example, if a medical practitioner identifies a blocked, a diseased region or partially blocked region of a blood vessel, they may decide to bypass that region by using the vascular graft 16. In this example, the inlet 10c of the vascular graft 16 may be attached to one point of the blood vessel, and the outlet 10d of the vascular graft 16 may be attached to another point of the blood vessel. In another example, the blood vessel could be diseased, or have been severed or bisected in order to connect the vascular graft 16 to two ends of the severed blood vessel. Because the vascular graft 16 is sealed, blood may flow through the vascular graft 16 in order to bypass the blocked, diseased, or partially blocked region of the blood vessel, and the leaking of blood through the walls 10f of the conduit 10 is mitigated by the presence of the sealant 14.

Once the vascular graft 16 is in place, biological tissue will grow into the inner section 10a of the vascular graft 16 in order to form a pseudointima. Over time, the psuedointima will form, adhering to the inner section 10a of the vascular graft 16. During this time, the vascular graft 16 prevents leakage of blood through the wall 10f and acts as a scaffold for the ingrowing biological tissue.

The vascular graft 16 may also be used to connect a further prosthesis, such as a heart assist device, a biological heart valve or a synthetic heart valve, to a blood vessel. For example, the inlet 10c of the vascular graft 16 may be connected to an outlet of a synthetic heart valve, and the outlet 10c1 of the vascular graft 16 may be connected to an end of a blood vessel. The advantage of this use of the vascular graft 16 is that a heart assist component can be used with a wide variety of shapes and sizes of blood vessels, as the vascular graft 16 can be provided in a range of sizes. The medical practitioner is then able to select which particular vascular graft 16 will interface well with the synthetic heart valve and the blood vessel. This avoids the need for a range of different configurations of heart assist device to be used, as a standard part can be used and customised by adding different types and sizes of vascular graft 16. It will be appreciated that, depending on the nature of the heart assist device, multiple vascular grafts 16 could be used with the heart assist device.

While the embodiments illustrated and described here show a cylindrical conduit 10 with an inlet 10c and an outlet 10d, other shapes of conduit 10 could be used. For example, a Y shaped, T-shaped, or a multi-channel conduit 10 could be used.

Figure 9A:
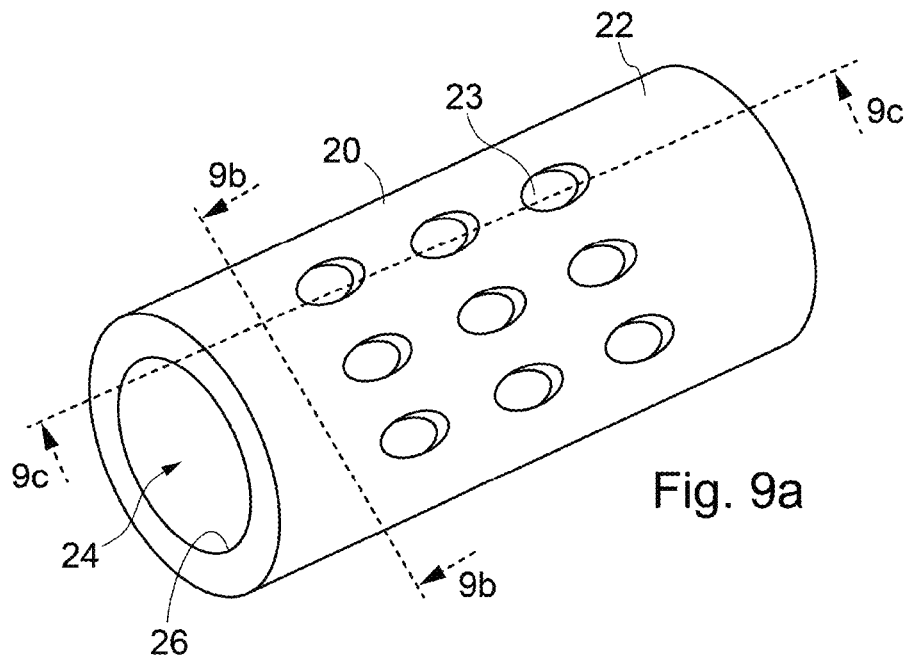
FIG. 9a is a perspective view of a hollow and perforated mandrel for use with the present invention.
Figure 9B:
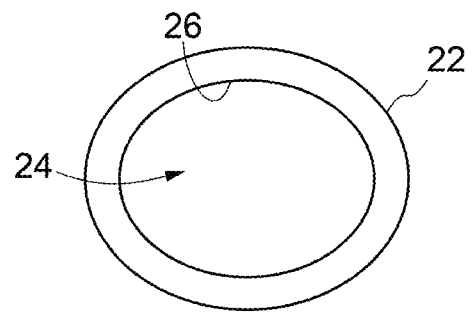
FIG. 9b is a cross-section view of the mandrel of FIG. 9a taken along the 9b-9b axis showing a hollow lumen passageway through the mandrel.
Figure 9C:
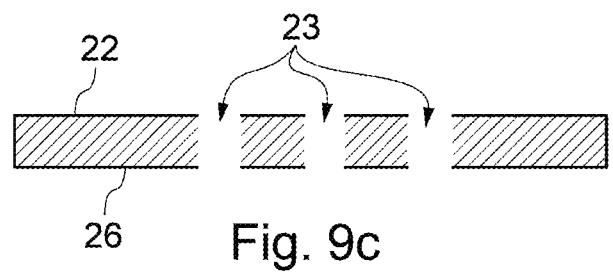
FIG. 9c is a partial cutaway view of the wall of the mandrel of FIG. 9a taken along the 9c-9c axis showing perforations or holes through the mandrel wall.

FIG. 9a is a perspective view of a perforated mandrel 20 useful with the systems and/or kits of the present invention for processing textile substrates in accordance with the present invention. As depicted in FIGS. 9a and 9b, the mandrel 20 may be a hollow mandrel having an open lumen 24. One or both ends 25, 27 of the mandrel 20 may be open ends. Alternatively, one or both ends 25, 27 of the mandrel 20 may be closed ends (not shown). As depicted in FIGS. 9a and 9c, perforations or holes 23 may be disposed within the tubular wall of the mandrel 20.

The mandrel 20 may be used for a variety of purposes. For example, the mandrel 20 could be used to deliver the masking agent or the water-soluble material to a tubular textile, such as a graft. In such a use, a tubular textile (not shown) may be disposed over the outer surface 22 of the mandrel 20. The masking agent or the water-soluble material may be delivered into the open lumen 24 of the mandrel 20, for example into the open lumen 24 via an open end 25. The opposed end 27 may be closed or open, such as in the case of a circulating system for the fluid masking agent or water-soluble material. The fluid masking agent or water-soluble material would flow through the perforations or holes 23 and onto and into the graft (not shown) disposed over the mandrel 20.

The mandrel 20 may have a controlled amount of fluid masking agent or water-soluble material within the lumen 24 to control the amount of fluid masking agent or water-soluble material exposed to the graft (not shown). The fluid masking agent or water-soluble material contained within the mandrel 20 may be forced onto the graft through the use of a pressure differential (higher pressure within the lumen 24 than outside the lumen 24) or through rotational forces when the mandrel 20 is disposed on or within a rotating or spinning device.

A mandrel not having the perforations 20 (not shown) may be used to dispose a layer of fluid masking agent or water-soluble material over the outer surface of the mandrel. The masking layer may be viscous enough or partially cured to remain on the mandrel until a graft is disposed over the mandrel. The masking layer may then be releasably disposed over the inner surface of the graft.

The mandrel 20 may also be used for control of fluid migration. For example, the pressure within the lumen 24 may be lower than the pressure outside of the lumen 24. Such a negative pressure or vacuum may be used to migrate the masking agent or water-soluble material away from the outer surface of a graft (not shown).

The mandrel 20 may also be used for drying the fluid masking agent or water-soluble material. A warm gas, such as air, may be introduced into the lumen 24, flow through the perforations or holes 23, and dry the fluid masking agent or water-soluble material. Alternatively, a heat source may be disposed outside of the mandrel 20, and the flow of heat, such as heated air, may be controlled through the application of a negative pressure at the lumen 24.

A mandrel, either the same or different, may be used throughout different applications and techniques described herein, such as, but not limited to, masking agent application and/or dispersion, masking agent drying, sealant application and/or dispersion, sealant drying and/or curing, textile washing, and the like. A tubular textile may be substantially disposed over a mandrel or only a portion of the tubular textile may be disposed over a mandrel. For example, one end of a tubular textile may be supported by a mandrel and the other end of the tubular textile may be supported by a different mandrel, and the like.

The substantially water-insoluble sealant may also be applied to the graft while the graft is on a solid or non-perforated mandrel or on a perforated mandrel 20. The substantially water-insoluble sealant may be applied to the graft by any suitable means, such as by brushing, spraying, roller coating, spinning the substantially water-insoluble sealant thereon.

Furthermore, if desired the substantially water-insoluble sealant may be cured with the graft disposed over a mandrel.

Further, other materials, such as colorants, therapeutic agents, dyes, fluorescent indicators, and the like may be applied to the graft.

Therapeutic agents may include, but are not limited to: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promoters (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; agents which interfere with endogenous or vasoactive mechanisms; and combinations thereof.

Masking Agent Drying and Uniformity Tests

Tests were performed to determine how long it took for a standard woven graft immersed in PVP to dry at different concentrations, and if PVP dried in a homogeneous fashion throughout the textile. A series of tests at different concentrations of PVP were done to determine if the concentration made a difference on the drying nature of the substance.

The tests used 15%, 10% & 5% PVP solution profiles. First, a 15% solution of PVP was made with 15 g of PVP and 100 mL of water. This was agitated until PVP was fully dissolved into solution. Graft samples were prepared by cutting approximately 50 mm of a commercial tubular graft. The graft samples were, if necessary, dried and were weighed. Graft samples were then soaked in the 15% PVP solution. The wet grafts were weighed to provide initial weights. The samples were placed vertically near a running fan. The graft samples were weighed at 5-minute intervals until there was a constant weight being displayed. The graft samples were cut into 4 labelled pieces. Each quarter piece was weighed. The quarter pieces were then washed, dried, re-weighed when fully dry. The lengths of the dry-washed graft were measured.

Next, 50 mL of water was added to the 15% PVP solution in order to make a 10% PVP solution. The above textile processing steps were repeated for the 10% PVP solution.

Next 150 mL of water was added to the 10% PVP solution to make a 5% PVP solution. The above textile processing steps were repeated for the 5% PVP solution.

Results: 15% PVP Profile

TABLE 3

| Time (min) | Weight (g) |
|---|---|
| Dry | 1.709 |
| 0 | 4.817 |
| 5 | 4.229 |
| 10 | 3.81 |
| 15 | 3.399 |
| 20 | 3.056 |
| 25 | 2.775 |
| 30 | 2.543 |
| 35 | 2.36 |
| 40 | 2.235 |
| 45 | 2.152 |
| 50 | 2.122 |
| 55 | 2.117 |
| 60 | 2.113 |
| 65 | 2.113 |

| Length measured | Length (mm) |
|---|---|
| Initial | 51 |
| Final | 52 |

| Quarter | With PVP | Without PVP | wt % PVP in piece |
|---|---|---|---|
| 1 | 0.507 | 0.418 | 17.6 |
| 2 | 0.519 | 0.421 | 18.9 |
| 3 | 0.569 | 0.461 | 19.0 |
| 4 | 0.516 | 0.427 | 17.2 |
| Total | 2.111 | 1.727 | 18.2 |
| Total expected | 2.113 | 1.709 | |

Table 3 showed that the 15% PVP coated graft took over an hour to dry fully in ambient air, it also showed that there was a slight increase in the length of the graft after being coated, washed and dried. After drying, the samples averaged 18.2 weight percent PVP. Further, the distribution of PVP among the samples was substantially consistent. Graft samples or pieces 2 and 3 had slightly higher PVP levels. These pieces had a seam of the graft on them, so it appeared that the seam was probably absorbing more PVP. Thus, about 15 to about 21 weight percent PVP was deposited onto the graft when immersed in the 15% PVP solution.

Results: 10% PVP Profile

TABLE 4

| Time (min) | Weight (g) |
|---|---|
| Dry | 1.699 |
| 0 | 4.891 |
| 5 | 4.292 |
| 10 | 3.881 |
| 15 | 3.491 |
| 20 | 3.159 |
| 25 | 2.849 |
| 30 | 2.580 |
| 35 | 2.124 |
| 40 | 2.040 |
| 45 | 2.000 |
| 50 | 1.994 |
| 55 | 1.994 |

| Length measured | Length (mm) |
|---|---|
| Initial | 48 |
| Final | 51 |

| Quarter | With PVP | Without PVP | wt % PVP in piece |
|---|---|---|---|
| 1 | 0.543 | 0.469 | 13.6 |
| 2 | 0.598 | 0.51 | 14.7 |
| 3 | 0.394 | 0.334 | 15.2 |
| 4 | 0.459 | 0.394 | 14.2 |
| Total | 1.994 | 1.707 | 14.4 |
| Total expected | 1.994 | 1.699 | |

Table 4 showed that the 10% PVP covered graft took just under an hour to dry completely, and that the 10% PVP solution covering, washing and drying had also caused a slight increase in the length of the graft. The slightly higher weight % of PVP in pieces 2 and 3 also suggested that the seam of the graft absorbed more of the PVP than the rest of the graft. After drying, the samples averaged 14.4 weight percent PVP. Thus, about 10 to about 18 weight percent PVP was deposited onto the graft when immersed in the 10% PVP solution.

Results: 5% PVP Profile

TABLE 5

| Time (min) | Weight (g) |
|---|---|
| Dry | 1.514 |
| 0 | 3.197 |
| 5 | 2.735 |
| 10 | 2.385 |
| 15 | 2.070 |
| 20 | 1.820 |
| 25 | 1.650 |
| 30 | 1.590 |
| 35 | 1.588 |
| 40 | 1.588 |

| Length measured | Length (mm) |
|---|---|
| Initial | 47 |
| Final | 47 |

TABLE 5-continued

| Quarter | With PVP | Without PVP | wt % PVP in piece |
|---|---|---|---|
| 1 | 0.357 | 0.348 | 2.5 |
| 2 | 0.423 | 0.406 | 4.0 |
| 3 | 0.432 | 0.412 | 4.6 |
| 4 | 0.371 | 0.354 | 4.6 |
| Total | 1.583 | 1.52 | 4.0 |
| Total expected | 1.588 | 1.514 | |

Table 5 showed that the 5% PVP covered graft took the least time to dry completely, and that its length did not seem to alter after coating, washing and drying, the PVP did to a minor degree to 'sink' to the bottom of this graft. Thus, about 2 to about 8 weight percent PVP was deposited onto the graft when immersed in the 5% PVP solution.

Conclusions

The 15% PVP covered graft took the most time to dry by approximately 25 minutes. In terms of drying evenly anyone of these concentrations was acceptable.

Various drying techniques are suitable for use with the present invention. For example, textile grafts and/or textile substrates may be dried at room temperature to remove the solvent(s) from the deposited masking agent solution and/or from the sealant solution. Forced air, such as use of a fan or fans or other sources of air movement and/or sources of pressurized air, may be used to facilitate drying. The forced air, if any, may be applied at any suitable angle or combination of angles. The air may or may not flow into the interior lumen of the graft. For example, forced air may be directed towards outer surface of a tubular graft, either perpendicularly, substantially perpendicularly, at an acute angle, and/or at an obtuse angle. Moreover, forced air may be directed towards the interior lumen of the tubular graft, such as towards one open end of the tubular graft, or even from within the interior lumen of the tubular graft. The direction of air flow and the amount of extend of the air flow may be varied to control drying times and even to control resultant physical properties of the graft. Forced air flow may also be useful in aiding migration of the masking agent towards the interior portions of the graft and away from exterior portions of the graft. In other words the masking agent desirably retracts when drying. This would aid in the securement of the sealant material at the exterior portions of the textile graft while also aiding in the blocking of sealant migration towards the interior portions of the graft. The present invention, however, is not limited to the use of air as a drying medium, and other suitable media, including gaseous media, may be used. Further, the present invention is not limited to room temperature drying, and elevated drying temperatures above room temperature may suitably be used.

Moreover, a fluid, such as water, including heated water, may be used with the present invention as described below. The use of heated water aids in the removal of the water-soluble masking agent from the textile product. Further, the use of heated water may also aid in curing of the sealant or sealing agent.

Furthermore, drying and/or curing the sealant material may also be controlled using forced air or other medium, ambient forced air or other medium, heated forced air or other medium, non-forced ambient air or other medium, non-forced heated air or other medium, and the like. Not only may curing times of the sealant material be controlled, but also, to some extent, the properties of the sealant layer may be controlled. The sealant material may be selected, dried or cured, and or selectively deposited, such that the sealant material, as is cures, shrinks about the textile substrate, e.g., the outer surface of the textile graft.

Masking Agent Removal Tests

Different washing methods for the grafts were performed to determine which method would extract the highest levels of PVP and if the chosen method has any effect on the length and crimp of the graft.

Two wash processes were considered, an Ultrawave ultrasonic bath and a domestic washing machine.

Procedures

Part 1: No Sealant Coating

This trial was first done on 6 grafts that were not coated with silicone in order to establish if 100% of the PVP could be removed with the chosen washing methods.

Grafts were prepared by cutting approximately 6×60 mm lengths of commercial woven grafts. All 6 grafts were measured, weighed, and labelled with notches cut into the side. A 15% PVP solution was made with 15 g of PVP and 100 mL of water. All 6 samples were submerged in the 15% PVP in solution. All 6 samples were dried vertically near a running fan. All dried samples were weighed.

An ultrasonic bath was set to 40 degrees Celsius. Samples 1, 2, and 3 were submerged into the ultrasonic bath. Samples 1-3 were left in the ultrasonic bath for 15 minutes. These samples were removed from the ultrasonic bath and were dried vertically near a fan. The dried 1-3 samples were weighed and their lengths were measured and recorded.

Samples 4, 5, and 6 were placed in a washing bag and then into a washing machine. The washing machine was set to a 40 degrees Celsius, 800 RPM, 51 minute wool wash setting. Samples 4-6 were removed from the washing machine and were allowed to dry. Samples 4-6 were weighed and their lengths were recorded.

Part 2: Silicone in Heptane Sprayed Sealant Coating

Samples 1-3 were re-washed, dried, measured and weighed. Samples 1-3 were then submerged in the 15% PVP solution. All 6 samples were dried vertically near a running fan. The dried samples were weighed.

All 6 samples were stretched out and sprayed with silicone in heptane coating. The 6 samples were then allowed to return to their relaxed states under a fume hood and were allowed to dry. An ultrasonic water bath was set to 40 degrees Celsius. Once dry, samples 1-3 were submerged in the ultrasonic bath for 15 minutes. These samples were removed from the bath and were dried vertically near a fan. The dried samples 1-3 were weighed, and their lengths were measured and recorded.

Once dry, samples 4-6 were placed in a washing bag and then into a washing machine. The washing machine was set to a 40 degree Celsius, 800 RPM, 51 minute wool wash setting. The samples were removed from the washing machine and were allowed to dry. Once dry, the samples 4-6 were weighed, and their lengths were measured and recorded.

Results

TABLE 6

No Sealant Coating

| Measurement | Ultrasonic Bath at 40 Degrees | | | Washing Machine Wool Setting | | |
|---|---|---|---|---|---|---|
| | Sample 1 | Sample 2 | Sample 3 | Sample 4 | Sample 5 | Sample 6 |
| Initial Weight (g) | 2.747 | 3.177 | 2.456 | 2.641 | 2.772 | 2.846 |
| Dried PVP weight (g) | 3.508 | 4.048 | 3.179 | 3.445 | 3.568 | 3.658 |
| Washed Weight (g) | 2.779 | 3.212 | 2.467 | 2.641 | 2.772 | 2.847 |
| PVP left (g) | 0.032 | 0.035 | 0.011 | 0.000 | 0.000 | 0.001 |
| Initial Length (mm) | 62.5 | 61 | 57 | 57 | 56 | 63.5 |
| Final Length (mm) | 62.5 | 62 | 57 | 57 | 56 | 63.5 |

The majority of the samples that were put in the washing machine were cleared of PVP while the samples that were put in the ultrasonic bath all still had some minor PVP on them after washing.

TABLE 7

Silicone in Heptane Sprayed Sealant Coating

| Measurement | Ultrasonic Bath at 40 Degrees | | | Washing Machine Wool Setting | | |
|---|---|---|---|---|---|---|
| | Sample 1 | Sample 2 | Sample 3 | Sample 4 | Sample 5 | Sample 6 |
| Initial Weight (g) | 2.747 | 3.177 | 2.456 | 2.641 | 2.772 | 2.847 |
| Dried PVP weight (g) | 3.510 | 3.911 | 3.123 | 3.389 | 3.538 | 3.57 |
| Dried PVP + Coating weight (g) | 3.737 | 4.08 | 3.323 | 3.583 | 3.843 | 3.825 |
| Washed Weight (g) | 2.779 | 3.212 | 2.467 | 2.641 | 2.772 | 2.847 |
| Silicone applied (g) | 0.227 | 0.169 | 0.200 | 0.194 | 0.305 | 0.255 |
| PVP + silicone left on graft (g) | 0.252 | 0.186 | 0.214 | 0.206 | 0.312 | 0.266 |
| PVP left (g) | 0.025 | 0.017 | 0.014 | 0.012 | 0.007 | 0.011 |
| Initial Length (mm) | 62.5 | 61 | 57 | 57 | 56 | 63.5 |
| Length after coating (mm) | 81 | 79 | 73 | 79 | 79 | 79 |
| Final Length (mm) | 70 | 66 | 62 | 61 | 64 | 65 |
| Ratio of PVP Applied to Silicone Applied, wt./wt. | 3.4 | 4.3 | 3.3 | 3.9 | 2.5 | 2.8 |
| Ratio of Silicone Applied to PVP Applied, wt./wt. | 0.29 | 0.23 | 0.30 | 0.26 | 0.40 | 0.36 |
| Percent PVP Removed, wt. % | 96.7 | 97.7 | 97.9 | 98.4 | 99.1 | 98.5 |

Although there was some PVP left on the grafts that went in the washing machine, there is significantly less PVP left on them as opposed to the grafts washed in the ultrasonic bath. In all cases, greater than about 90 weight percent of the PVP was removed. Indeed, in all cases greater than about 95 weight percent of the PVP was removed.

In Table 7, the weight ratio of PVP to silicone applied varied from about 2.5:1.0 to about 4.3:1.0. Conversely, the weight ratio of silicone to PVP applied varied from about 0.40:1.0 to about 0.23:1.0.

Further, ratios are described in Table 11 below.

The ratios described in Tables 7 and 11 are non-limiting.

The weight ratio of PVP (or other masking agents) to silicone (or other sealant agents) may vary from about 10:1 wt. PVP (or other masking agents)/wt. silicone (or other sealant agents) to about 0.01:1 wt. PVP (or other masking agents)/wt. silicone (or other sealant agents), desirably from about 1:1 wt. PVP (or other masking agents)/wt. silicone (or other sealant agents) to about 0.05:1 wt. PVP (or other masking agents)/wt. silicone (or other sealant agents), more desirably from about 0.5:1 wt. PVP (or other masking agents)/wt. silicone (or other sealant agents) to about 0.1:1 wt. PVP/wt. silicone.

Conversely, the weight ratio of silicone (or other sealant agents) to PVP (or other masking agents) may vary from about 0.1:1.0 wt. silicone (or other sealant agents)/wt. PVP (or other masking agents) to about 100:1 wt. silicone (or other sealant agents)/wt. PVP (or other masking agents, desirably from about 1:1 wt. silicone (or other sealant agents)/wt. PVP (or other masking agents to about 20:1 wt. silicone (or other sealant agents)/wt. PVP (or other masking agents, more desirably from about 2:1 wt. silicone (or other sealant agents)/wt. PVP (or other masking agents to about 10:1 wt. silicone (or other sealant agents)/wt. PVP (or other masking agents.

Mask and Dye Tests

Materials

Fabric—Diameter 22 mm, flat tube twill weave and Diameter 10 mm. Crimped twill weave.

Silicone—NuSil Med16-6606 (Temporary implant grade).

Solvent—n-Heptane, 50:50 with silicone dispersion.

Dye—Easy Composites Royal blue pigment for RTV silicone, mixed to approx. 10% of silicone solid content.

Sample Description

For Flat 22 mm fabric samples, the following masking agent formulations were used:

71 A—Bare Fabric
71 B—6% PVP
71 C—6% PVP+1.5% Glycerol (by volume of Mask solution)
71 D—6% PVP+1.5% Glycerol+4% PVP (Total 10% PVP)

The #71B-D flat fabric samples were immersed into the PVP solution and then removed. All #71 samples were mounted on suspended mandrels (Post masking, Pre-coating).

For Crimped Diameter 10 mm fabric samples, the following masking agent formulations were used:

70 A—Bare Fabric
70 B—6% PVP
70 C—6% PVP+1.5% Glycerol (by volume of Mask solution)
70 D—6% PVP+1.5% Glycerol+4% PVP (Total 10% PVP)

The #70B-D crimped fabric samples were immersed into the PVP solution and then removed. All #70 samples were mounted on suspended mandrels (Post masking, Pre-coating).

Masking Agent Preparation

Masking agents were prepared using the same method as described above, with the additional steps to add glycerol for samples B and C (both #70 and #71) and then additional PVP for samples D (both #70 and #71).

Measured the target weight of PVP into plastic beaker on scale balance. A 100 ml masking agent solution was prepared therefore target mass of 4 g PVP required (4% concentration). Measured the target volume of de-ionised water into a 100 ml plastic measuring cylinder. A 100 ml Mask solution to be prepared therefore target volume of 96 ml required. Added de-ionised water into the PVP in plastic beaker. Placed magnetic stirrer in the water and place the beaker on the magnetic stirrer. Turned the magnetic stirrer on at a speed of 350-450 RPM, ensuring the stirrer is centred in the beaker. The stirring was done at room temperature. Stirring was continued until there was no visible PVP solute, or for a minimum of at least 2 minutes. After stirring the masking agent solution was removed from stirrer and used for graft preparation, samples B.

Additional steps were used for samples C, i.e. added glycerol. Returned the plastic beaker to scale balance, tared, and added required quantity of glycerol to the mask agent solution. The target glycerol content was 1.5% by volume of masking agent solution. This corresponded to a target weight of 1.5 g. (Note this corresponded to 25% Glycerol to PVP). Set beaker on stirrer and stirred for at least 2 minutes. This masking agent solution used for samples C.

Additional steps were used for samples D, i.e., additional PVP. Returned the plastic beaker to scale balance, tared, and added the required quantity of PVP to the masking agent solution. The target PVP content was 10% by volume of Mask solution. This corresponded to an additional 4 g PVP added. (Note this effectively reduced the glycerol to PVP ratio from 25% to 15%). This masking agent solution was used for samples D.

Sealant Preparation

The silicone sealant dispersion as-supplied had a 30% solid content, the dispersion was diluted by an additional 100% of solvent. This reduced the solid content to 15%. Additionally, a blue dye was added to the silicone dispersion to provide a visual indication of the coverage and depth of penetration of silicone into the fabric structure.

In particular, 20 ml of silicone dispersion was measured out from its container, in the as-supplied state, and placed into a plastic beaker. An additional 20 ml of n-Heptane solvent was added. The mixture was beaked and was set on scales, tared, and drops of dye were added using dropper. The recommended dye concentration range was 0.3% to 5%, depending of section thickness, therefore a target of 5% was set in order to provide a strong blue colour for visualization. A deviation from this target was due to a calculation of the solid content being at 30% rather than 15%, therefore the actual concentration of dye to silicone was 10% rather than 5%.

Sample Preparation

The individual samples were prepared with masking agent formulations according to the following table.

TABLE 8

|  | No Mask | 6% PVP | 6% PVP + Glycerol (@25% of PVP) | 10% PVP + Glycerol (@15% of PVP) |
| --- | --- | --- | --- | --- |
| Flat Fabric | 71A | 71B | 71C | 71D |
| Crimped Fabric | 70A | 70B | 70C | 70D |

Samples B-D were immersed in the mask agent solution, as per the above table. The samples were assembled onto mandrel such that each fabric was held at diameter by sized end bungs, but remained unsupported on the inner surface. The inner surface of each fabric was not in contact with the mandrel to avoid affecting mask performance, location and concentrations.

Dispersion drop assessment was undertaken as described below.

Each sample was fully coated with at least 2 coats of silicone dispersion. The intention was to ensure sufficient silicone was present on the outer surface to effect a suitable coverage without concerns for lack of silicone during visual evaluations. Brush coating was done onto a rotating graft on rotisserie at approximately one revolution per second. Grafts were left overnight for solvent evaporation. Grafts were left to fully cure for recommended 72 hrs before being removed from mandrel for washing. The grafts were then placed in a delicate bag and put on 95° C. Tumble Machine Wash cycle for approximately 2 hours 30 mins.

Samples were masked, coated, washed and cut opened flat.

Dispersion Drop Assessment

Prior to full coating, a single drop of polymer dispersion was applied to each sample, and video recorded in order to visually assess if there were noticeable differences in the behaviour of the dispersion on the masked fabric.

Sample A—No Mask. Slow spread of the single drop of polymer dispersion across fabric. Appeared to be soaking into and through fabric Sample B—6% PVP Mask. Rapid spread of the single drop of polymer dispersion across fabric. Appeared to spread more readily than soaking into and through fabric Sample C—6% PVP+1.5% Glycerol Mask. First drop of the single drop of polymer dispersion had rapid spread across fabric. The second drop of the single drop of polymer dispersion was inconclusive, possibly due to sagging fabric holding the pool.

Sample D—10% PVP+1.5% Glycerol Mask. Inconclusive—possibly due to sagging fabric holding the pool Dispersion Drop Assessment across face of the graft:

Sample A—No Mask. Slower spread of the single drop of polymer dispersion across fabric. Appeared to soak into fabric.

Sample B—6% PVP Mask. Rapid spread of the single drop of polymer dispersion across fabric. Coverage was more uneven with pooling of dispersion in valleys.

Sample C—6% PVP+1.5% Glycerol Mask. Fabric clearly resisted dispersion soaking in.

Sample D—10% PVP+1.5% Glycerol Mask. Fabric clearly resisted dispersion soaking in.

In summary, this Dispersion Droplet Assessment showed that even the lower concentration of masking agent, (Samples B, 6% PVP), appeared to initiate a significantly different response when compared to a non-masked fabric.

A "pooling" effect was seen on the flat fabrics, samples 71C, 71D, was most likely a result of the excess dispersion being unable to run off the fabric or through the fabric. This effect was perhaps also evident in the crimped fabric, particularly Samples 70B, 70D, where there was pooling of the dispersion in the valleys, highlighted by the darker colour, unlike the non-masked sample 70A, which appears far more uniform in colour/coverage.

Assessment of Sealant Coverage and Penetration

Following the wash cycle to remove the masking agent the grafts were cut lengthways to provide visualization of inner and outer surfaces. Each graft was visualized under optical microscopy on: (a) the outer surface—to confirm presence and uniformity of sealant coating; (b) the inner surface—to confirm presence or ingress of blue silicone, either through the fabric or between the yarn filaments; and (c) sectional view—to assess the level of penetration through the yarn bundles.

Results

Both samples without mask appeared to have permitted the dyed blue silicone dispersion into the yarn bundles and penetrate to the inner surface while the application of the mask appears to have prevented this ingress on all samples.

TABLE 9

| | Mask Applied | Penetration of Polymer to Inner Surface |
|---|---|---|
| Flat Fabric Samples | | |
| 71A | None | Yes |
| 71B | 6% PVP | No |
| 71C | 6% PVP + Glycerol | No |
| 71D | 10% PVP + Glycerol | No |
| Crimped Fabric Samples | | |
| 70A | None | Yes |
| 70B | 6% PVP | No |
| 70C | 6% PVP + Glycerol | No |
| 70D | 10% PVP + Glycerol | No |

Figure 10A:
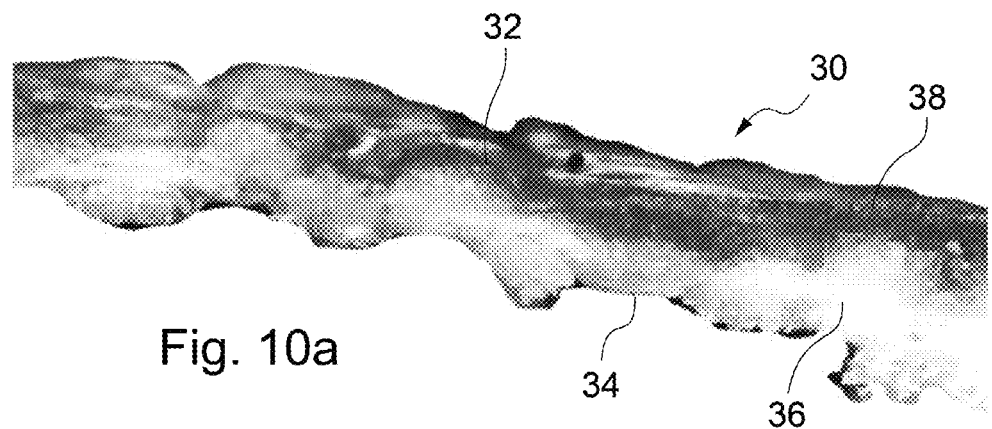
FIG. 10a is a photograph of a cross-section of a textile graft of the present invention showing sealing layer or coating on outer surface portions of the textile graft and showing the inner surface portions of the textile graft being substantially free of any sealing layer or coating.
Figure 10B:
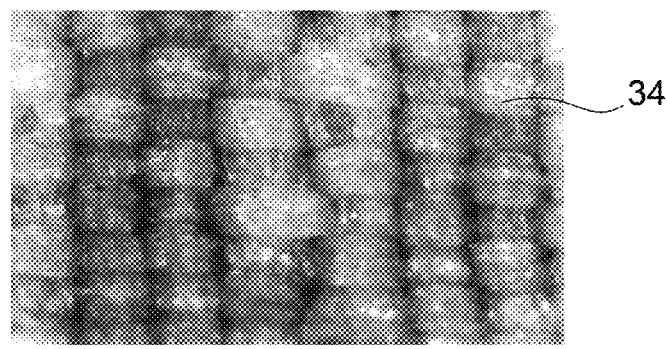
FIG. 10b is a photograph of a portion of the inner surface of the textile graft of FIG. 10a showing the inner surface portion of the textile graft being substantially free of any sealing layer or coating.
Figure 10C:
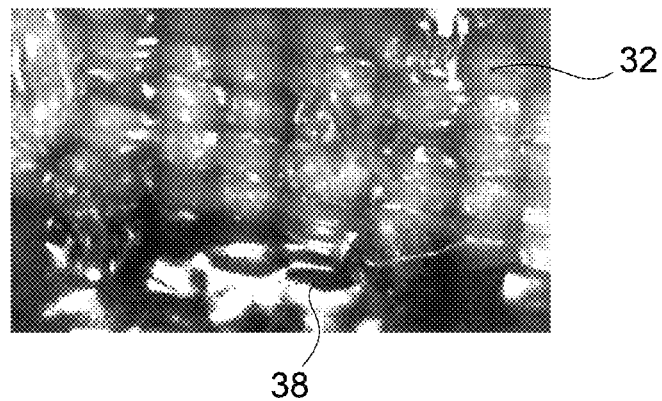
FIG. 10c is a photograph of a portion of the outer surface of the textile graft of FIG. 10a showing the outer surface portion of the textile graft being substantially covered with the sealing layer or coating.

Photographs of crimped fabric sample 70D are provided in FIGS. 10a-10c. FIG. 10a is a photograph of a portion of the cross-section of the tubular wall of the crimped fabric sample 70D. As shown in FIGS. 10a-10c, the fabric sample or textile graft 30 includes an outer textile surface 32, an opposed inner textile surface 34, and a textile wall 36 disposed therein between. As shown in FIGS. 10a and 10c, a sealing layer or coating 38 is disposed over the outer surface 32. Moreover, as shown in FIG. 10a, the sealing layer or coating 38 extends into a portion of the textile wall. As shown in FIGS. 10a and 10b, the inner surface 34 is substantially, including completely, free of the sealing layer or coating 38.

Figure 11:
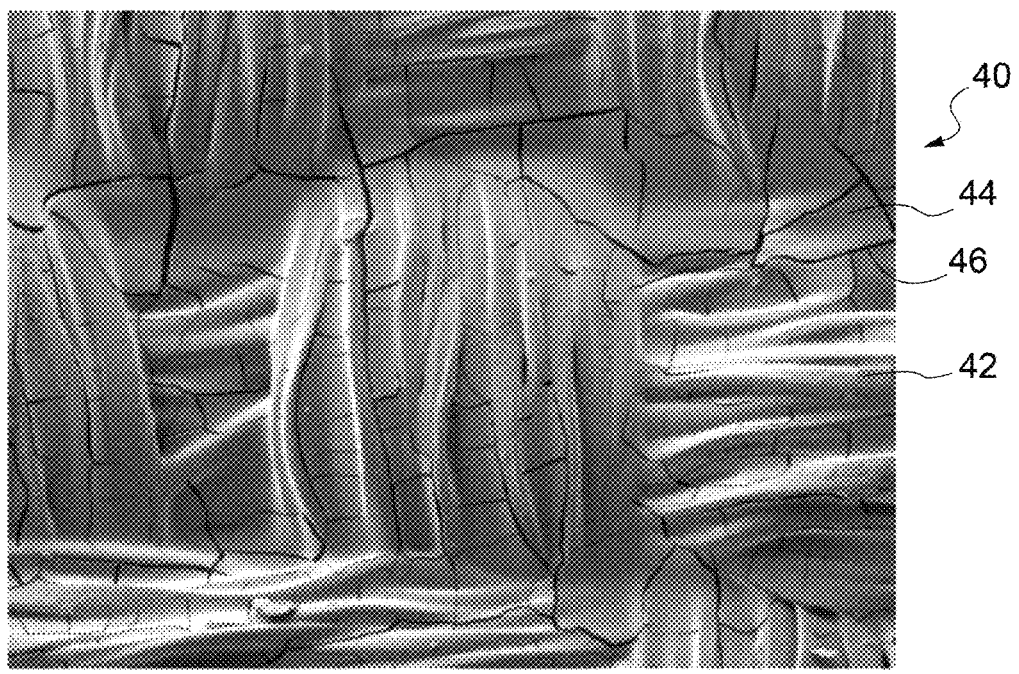
FIG. 11 is a photograph of a dried 40% PVP masking agent concentration applied to a graft sample.

FIG. 11 shows a microphotograph or scanning electron microscope (SEM) photograph of a dried 40% PVP masking agent concentration applied to a graft sample 40. The dried masking agent slurry 44 gathered and encapsulated the yarn structure 42 and had cracks 46. It is evident that the silicone sealant would not be able to effect any permanent adhesion or encapsulation onto this surface fully encapsulated by the masking agent.

The masking agent solution may encapsulate whole yarn bundles and individual yarn fibers, depending on the concentration of the masking agent solution. The higher concentrated masking agent solution (i.e. >30% w/w PVP, >20% w/w of PVP glycerol in water) seems to be too thick to flow into the yarn bundles and coat individual fibers, as seen in FIG. 11. Additionally, high concentrations of masking solution dries as a thick, brittle mask layer, in which many samples develop micro cracks 46 throughout the masking layer 44, as seen in FIG. 11. If the masking agent solution concentration is low (<10% w/w PVP, with or without glycerol in water), the masking agent may encapsulate the yarn bundle and individual fibers, however, a limitation of using a low concentration of masking agent solution may be lack of complete, consistent coverage around each yarn bundle and/or fiber. If this is the case, portions of the fiber are exposed for a surface for potential sealant attachment. Some results show, using low concentrations of masking agent solution, the sealant encapsulates and traps the masking layer; therefore, the masking is not fully washed out of the final product. The key of an appropriate masking solution that works is to have a controlled application process of a targeted concentration for each application as set forth by the present invention.

The overall mechanism of masking agent may include two main concepts, depending on the size of the void or gap: (1) a physical effect for macro pathways (i.e. voids between yarn bundles) and (2) chemical effect for micro pathways (i.e. voids between fibers and voids in micro cracks within the masking layer).

(1) Physical Effect: Filling macro pathways is based on the physical ability for the masking agent solution to penetrate and flow into large voids between the yarn bundles. When the yarn bundles are completely encapsulated with a masking agent layer, the masking agent layer fills the voids between each yarn bundle and blocks entry into the yarn bundle. In turn, the sealant would not be able to penetrate within the macro pathways between each yarn or micro pathways between each fiber due to the presence of masking to fill these voids.

(2) Chemical Effect: For micro pathways throughout the textile, whether micro pathways refer to micro cracks within the masking layer, micro voids between the yarn bundles or micro voids between individual fibers, the chemical mechanism of the masking solution's repulsion effect or ability to repel away from the sealant causes the sealant not to fill the micro voids. The repelling mechanism occurs when the oleophobic sealant tries to come into contact or close proximity with the highly hydrophilic masking layer. This is proven using solution solubility theory and solubility parameters developed by Joel H. Hildebrand. SI Hildebrand values (∂[SI]) demonstrate the masking solution and sealant solubility parameters indicating the solvency behavior of their specific solvents when they come into contact with one another. As noted in the Handbook of Solubility Parameters, CRC Press, 1983, the solvents in the masking solution (water and glycerol) are on the hydrophilic end of the solubility parameter range, whereas the solvent of the sealant (Heptane) is on the opposite end of the solubility parameter range. The ∂[SI] of water is 48.0, ∂[SI] of glycerol is 36.2, and ∂[SI] n-Heptane is 15.3.

Thus, the masking agents of the present invention hinder undesirable migration of the sealant through, physical (e.g., blocking) and repulsion mechanisms. Thus, it may be desirable to use a sealant(s) whose solvent(s) has a solubility parameter of less than about 20 ∂[SI], for example from about 10 ∂[SI] to about 20 ∂[SI] and a masking agent solution(s) whose solvent(s) has a solubility parameter of greater than about 30 ∂[SI], for example from about 30 ∂[SI] to about 50 ∂[SI].

Conclusions

The use of blue dye in the silicone dispersion provided an excellent visual assessment of silicone penetration into the fabric. Both samples coated without prior mask application demonstrated substantial ingress of blue silicone sealant through the fabric to the inner surface. All three masking agent formulations appeared to substantially prevent ingress of silicone to the inner surface.

Silicone Sealing Tests for Commercial Vascular Grafts

The following equipment and materials were used to test sealing commercial grafts according to the present invention.

8 mm crimped polyester fabric commercial graft
14 mm crimped polyester fabric commercial graft
Polyvinylpyrrolidone (PVP) Powder
NuSil MED-6606 RTV Silicone
N-Heptane
Royal Blue Pigment
De-ionised water
Magnetic Stirrer
Coating Variable Ranges The following values were used for the testing of the inventive sealing techniques of the present invention.

PVP concentration in de-ionised water was varied on a weight basis at 1%, 2%, 4%, 6%, 8%, 10%, 15%, 20%, 25%, and 30%.

Glycerol and silicone dispersion concentration was tested at PVP concentrations of 4%, 8%, 15%, and 30%. Glycerol concentrations were used on PVP concentrations of 5%, 15%, and 30%. These concentrations were percentage of glycerol to PVP.

The variations of PVP, glycerol, and silicone tested were as follows:

TABLE 10

| Sample | PVP Concentration (%) | | | | | | | | | | Glycerol Concentration (% of PVP) | | | Silicone Concentration (%) | |
|---|---|---|---|---|---|---|---|---|---|---|---|---|---|---|---|
| | 1 | 2 | 4 | 6 | 8 | 10 | 15 | 20 | 25 | 30 | 5 | 15 | 30 | 15 | 30 |
| 1 | X | | | | | | | | | | | | | X | |
| 2 | | X | | | | | | | | | | | | X | |
| 3 | | | X | | | | | | | | | | | X | |
| *4 | | | | X | | | | | | | | | | X | |
| 5 | | | | | X | | | | | | | | | X | |
| 6 | | | | | | X | | | | | | | | X | |
| *7 | | | | | | | X | | | | | | | X | |
| 8 | | | | | | | | X | | | | | | X | |
| 9 | | | | | | | | | X | | | | | X | |
| *10 | | | | | | | | | | X | | | | X | |
| *11 | | | X | | | | | | | | | X | | X | |
| 12 | | | X | | | | | | | | | | X | X | |
| 13 | | | | | X | | | | | | | X | | X | |
| 14 | | | | | X | | | | | | | | X | X | |
| 15 | | | | | | | X | | | | | X | | X | |
| *16 | | | | | | | X | | | | | | X | X | |
| 17 | | | | | | | | | | X | X | | | X | |
| 18 | | | | | | | | | | X | | | X | X | |
| *19 | | | X | | | | | | | | | X | | | X |
| 20 | | | X | | | | | | | | | X | | | X |
| 21 | | | | | X | | | | | | | X | | | X |
| 22 | | | | | X | | | | | | | X | | | X |
| 23 | | | | | | | X | | | | | X | | | X |
| 24 | | | | | | | X | | | | | X | | | X |
| 25 | | | | | | | | | | | X | X | | X | |
| *26 | | | | | | | | | | | X | X | | | X |

*Denotes samples to be applied to both types of grafts, i.e., First and Second graft samples.

Sample Preparation

Each sample was made from of a section of the commercial grafts. The grafts were first cut to length by first fully stretching the graft to remove the crimps, and then a section of 180 mm length was cut with a single edge razor blade. Each sample was weighed.

Mask Preparation

A measured amount of de-ionised water was placed into a 100 ml plastic beaker. A magnetic stirrer was placed into the de-ionised water. While stirring, PVP and glycerol (if any) were added. Stirring continued until there was no solute visible.

Masking Agent Application

The graft samples were coated by immersing the graft samples within the mask solution and agitating the graft by gloved hands, so the samples were fully coated inside and out.

Once the grafts were fully coated, excess mask solution, if any, was removed. Next, each graft was attached to a mandrel by using cable ties. One end of the graft was secured to the mandrel by a cable tie, then the graft was extended to 60% of its overall extended length (108 mm), and the other end of the graft was secured to the mandrel by another cable tie. The mandrel was then placed horizontally on a rotating mount and allowed to air dry. Once dry, the masked grafts were weighed.

Sealant Preparation

The silicone dispersion was supplied as a 30% solid content. Additional amounts of n-Heptane were added to reduce that solid content to 22.5% then 15. A blue dye was added to the silicone dispersion.

Sealant Application

The mandrel with the graft mounted was be placed on the rotary motor to slowly spin the graft. The sealant was applied with a paint brush starting at one end and working to the other end. This was repeated until there was an excess of sealant dispersion on the graft. Once the targeted level of silicone was applied onto the graft, the graft was transferred to a rotating mount and allowed to air dry. Once dry, the sealed graft was weighed.

Masking Agent Removal

Once the grafts were fully dried, the masking agents were removed. This was done by washing the grafts in a washing machine on a 90° C. wash (with no detergent). This caused the PVP to dissolve in the water and thus be removed from the graft. The 90° C. temperature also aided in complete curing of the silicone. When the wash was complete, the grafts were hung up to air dry. After drying, the finished grafts were weighed.

Silicone Adherence

A good coating adhesion can also be demonstrated if the graft coating maintains its integrity in a high pressurised state. Pressure can be used as a measure over all sizes of grafts because most of the overall hoop stress is borne by the stiffer fabric material of the graft. Furthermore, most of the forces acting on the silicone coating for delaminating it happen in the gaps between bundles of fibres as the weave structure does not change for different diameters of graft, then this area and consequently the force acting on that area will be consistent. Therefore, irrespective of the size of graft the same pressure will produce the same force to delaminate the silicone coating.

To ensure the position of the bundles within the fabric are as uniform as possible over all diameters, the fabric was crimp removed so the graft is in its fully extended shape. In accomplishing this, the pressure applied was above the pressure that it takes to fully extend the graft. Since this pressure will be different for each size of graft, the graft that needs the highest pressure to fully extend itself (i.e., the one of smallest diameter) will be used as a worst-case scenario. Once this worst-case pressure is determined, a factor of safety (FOS) is applied and it is this FOS corrected pressure that is used as a minimum requirement for all grafts. If the graft can be pressurised to this FOS corrected pressure with no visual signs of the coating delaminating (bubbles forming), then it can be deduced that the coating has sufficient and acceptable adhesion/integrity.

One method of testing for delamination is as follows:
Connect the graft to a pressure rig, ensuring one end is plugged;
Slowly apply pressure to the graft;
Stop at 120 mmHg (clinical pressure) and look for signs of delamination (bubbles);
Measure the leak rate and record it in $mm/cm^2/min$;
Increase the pressure in increments up to the FOS corrected figure is reached;
If any signs of delamination are visible at any point stop the test, mark as failed;
Hold at the FOS corrected pressure for 1 min; and
If no signs of delamination are present, mark graft as pass.
The following pressure tests were conducted:
The grafts were pressurised with water to observe if there were any signs of the silicone losing its bond from the graft. The pressure was to be increased slowly to a maximum pressure of 600 mmHg. The adherence was noted as follows:
0—Silicone is well adhered to graft and showing no signs of failure;
1—Graft reached the maximum pressure, but the leak rate has visibly increased;
2—Silicone coating has started to fail, showing jets of water coming from the graft; and
3—Silicone coating has failed, and a bubble has appeared on the surface.

Penetration Depth

The effectiveness of the mask was determined by how far the silicone wicked through the fabric. Desirably, the silicone will sit on the outside surface of the graft and not unduly penetrate the graft structure. If the masking agent was not effective, then the silicone was visible within the fabrics and on the inside edge. To visualise this, the grafts were cut lengthways and a cross section was examined under high magnification.

The degree of penetration was noted as follows;
0—Silicone only visible on the outer surface of the graft;
1—Silicone is visible between fibres of the graft but only up to 50% of the thickness;
2—Silicone is visible penetrating to the inside surface; and
3—Silicone visible everywhere, the entire graft structure is blue.

Test Results Summaries

TABLE 11

WEIGHT SUMMARIES

| | | Weight of Graft Segment | | | | | |
|---|---|---|---|---|---|---|---|
| Sample Name | Initial (g) | After Masking and Drying (g) | After Sealant and Curing (g) | After Washing and Drying (g) | Amount of Masking Agent Applied (g) | Amount of Sealant Applied (g) | Ratio of Sealant to Masking Agent (g/g) |
| 1 | 0.703 | 0.714 | 1.496 | 1.485 | 0.011 | 0.782 | 71.1 |
| 2 | 0.714 | 0.739 | 1.484 | 1.46 | 0.025 | 0.745 | 29.8 |
| 3 | 0.741 | 0.779 | 1.436 | 1.392 | 0.038 | 0.657 | 17.3 |
| 4 | 0.673 | 0.721 | 1.239 | 1.182 | 0.048 | 0.518 | 10.8 |
| A4 | 1.089 | 1.159 | 2.31 | 2.229 | 0.07 | 1.151 | 16.4 |
| 5 | 0.689 | 0.778 | 1.199 | 1.1 | 0.089 | 0.421 | 4.7 |
| 6 | 0.698 | 0.778 | 1.216 | 1.129 | 0.08 | 0.438 | 5.5 |
| 7 | 0.694 | 0.813 | 1.454 | 1.319 | 0.119 | 0.641 | 5.4 |
| A7 | 1.026 | 1.198 | 2.047 | 1.86 | 0.172 | 0.849 | 4.9 |
| 8 | 0.695 | 0.864 | 1.492 | 1.31 | 0.169 | 0.628 | 3.7 |
| 9 | 0.688 | 0.939 | 1.541 | 1.276 | 0.251 | 0.602 | 2.4 |
| 10 | 0.663 | 0.969 | 1.537 | 1.207 | 0.306 | 0.568 | 1.9 |
| 11 | 0.739 | 0.778 | 1.382 | 1.339 | 0.039 | 0.604 | 15.5 |
| A11 | 1.08 | 1.119 | 2.086 | 2.041 | 0.039 | 0.967 | 24.8 |
| 12 | 0.658 | 0.712 | 1.262 | 1.201 | 0.054 | 0.55 | 10.2 |
| 13 | 0.717 | 0.83 | 1.486 | 1.368 | 0.113 | 0.656 | 5.8 |
| 14 | 0.719 | 0.816 | 1.463 | 1.357 | 0.097 | 0.647 | 3.7 |
| 15 | 0.717 | 0.853 | 1.513 | 1.367 | 0.136 | 0.66 | 4.9 |
| 16 | 0.701 | 0.888 | 1.502 | 1.298 | 0.187 | 0.614 | 3.3 |
| A16 | 0.896 | 1.103 | 1.731 | 1.503 | 0.207 | 0.628 | 3.0 |
| 17 | 0.738 | 1.067 | 1.879 | 1.531 | 0.329 | 0.812 | 2.5 |
| 18 | 0.719 | 1.183 | 1.881 | 1.395 | 0.464 | 0.698 | 1.5 |
| 19 | 0.705 | 0.754 | 1.502 | 1.446 | 0.049 | 0.748 | 15.3 |
| A19 | 0.878 | 0.924 | 1.682 | 1.632 | 0.046 | 0.758 | 16.5 |
| 20 | 0.717 | 0.759 | 2.063 | 2.016 | 0.042 | 1.304 | 31.0 |
| 21 | 0.709 | 0.809 | 1.46 | 1.355 | 0.1 | 0.651 | 6.5 |
| 22 | 0.741 | 0.844 | 2.121 | 2.007 | 0.103 | 1.277 | 12.4 |
| 23 | 0.715 | 0.855 | 1.487 | 1.333 | 0.14 | 0.632 | 4.5 |
| 24 | 0.688 | 0.867 | 2.03 | 1.846 | 0.179 | 1.163 | 6.5 |
| 25 | 0.711 | 1.057 | 1.818 | 1.451 | 0.346 | 0.761 | 2.2 |
| 26 | 0.699 | 1.038 | 2.464 | 2.115 | 0.339 | 1.426 | 4.2 |
| A26 | 1.356 | 2.058 | 4.448 | 3.689 | 0.702 | 2.39 | 3.4 |

The ratio of sealant to masking agent on a gram to gram or weight dry basis varied from about 1:1 to about 70:1. Useful ratios also include ratios of sealant to masking agent from about 2:1 to about 20:1, including from about 2:1 to about 10:1, on a dry weight basis. These ratios, however are non-limiting. The weight ratio of silicone (or other sealant agents) to PVP (or other masking agents) may vary from about 0.1:1.0 wt. silicone (or other sealant agents)/wt. PVP (or other masking agents) to about 100:1 wt. silicon (or other sealant agents)/wt. PVP (or other masking agents, desirably from about 1:1 wt. silicone (or other sealant agents)/wt. PVP (or other masking agents to about 20:1 wt. silicone (or other sealant agents)/wt. PVP (or other masking agents, more desirably from about 2:1 wt. silicone (or other sealant agents)/wt. PVP (or other masking agents to about 10:1 wt. silicone (or other sealant agents)/wt. PVP (or other masking agents.

TABLE 12

PENETRATION TEST RESULTS

| Sample Number | PVP % | Glycerol as % of PVP | Penetration Grading Scale 0-3 | Comment |
|---|---|---|---|---|
| 1 | 1 | 0 | 3 | |
| 2 | 2 | 0 | 3 | |
| 3 | 4 | 0 | 2 | |
| 4 | 6 | 0 | 2 | |
| A4 | 6 | 0 | 2 | |
| 5 | 8 | 0 | 2 | |
| 6 | 10 | 0 | 1 | |
| 7 | 15 | 0 | 2 | |
| A7 | 15 | 0 | 2 | |
| 8 | 20 | 0 | 2 | |
| 9 | 25 | 0 | 0 | Delaminated |
| 10 | 30 | 0 | 0 | Delaminated |
| A10 | 30 | 0 | | Not Made |
| 11 | 4 | 5 | 2 | |
| A11 | 4 | 5 | 2 | |
| 12 | 4 | 30 | 2 | |
| 13 | 8 | 5 | 2 | |
| 14 | 8 | 30 | 2 | |
| 15 | 15 | 5 | 1 | |
| 16 | 15 | 30 | 0 | |
| A16 | 15 | 30 | 1 | |
| 17 | 30 | 5 | 0 | Delaminated |
| 18 | 30 | 30 | 0 | Delaminated |
| 19 | 4 | 15 | 2 | |
| A19 | 4 | 15 | 2 | |
| 20 | 4 | 15 | 2 | |
| 21 | 8 | 15 | 2 | |

TABLE 12-continued

PENETRATION TEST RESULTS

| Sample Number | PVP % | Glycerol as % of PVP | Penetration Grading Scale 0-3 | Comment |
|---|---|---|---|---|
| 22 | 8 | 15 | 1 | |
| 23 | 15 | 15 | 1 | |
| 24 | 15 | 15 | 1 | |
| 25 | 30 | 15 | 0 | Delaminated |
| 26 | 30 | 15 | 0 | Delaminated |
| A26 | 30 | 15 | 0 | Delaminated |

The results, which are tabulated in order of PVP masking agent concentrations, showed a clear correlation between higher levels of PVP and reduced penetration of the silicone sealant into the inner lumen of the graft samples.

In general, PVP mask concentration of 10% or greater prevented the bulk penetration of silicone to more than 50% into the fabric thickness. In some samples, they were small "fingers" or "slivers" of silicone evident between the yarn bundles at the interstices created by warp and weft yarn bundles. Such interstitial silicone represented a very small percentage of the overall inner surface area of the fabric.

Adhesion Test Results

TABLE 13

| Sample Number | PVP (g) | Glycerol as % of PVP | Measured Leakage (ml/min) @120 mmHg Result 1 | Measured Leakage (ml/min) @600 mmHg Result 3 | Adhesion grading Scale 0-3 |
|---|---|---|---|---|---|
| 1 | 1 | 0 | 0 | 0 | 0 |
| 2 | 2 | 0 | 0 | 0 | 0 |
| 3 | 4 | 0 | 0 | 0 | 0 |
| 4 | 6 | 0 | 0 | 4 | 0 |
| A4 | 6 | 0 | 33 | | 3 |
| 5 | 8 | 0 | 19 | | 1 |
| 6 | 10 | 0 | 40 | | 1 |
| 7 | 15 | 0 | 4 | 14 | 0 |
| A7 | 15 | 0 | 31 | | 1 |
| 8 | 20 | 0 | 12 | 46 | 1 |
| 9 | 25 | 0 | Delaminated | | 3 |
| 10 | 30 | 0 | >500 | | 3 |
| A10 | 30 | 0 | | | |
| 11 | 4 | 5 | 0 | 1 | 0 |
| A11 | 4 | 5 | 0 | 5 | 0 |
| 12 | 4 | 30 | 0 | 0 | 0 |
| 13 | 8 | 5 | 9 | 86 | 2 |
| 14 | 8 | 30 | 1 | 22 | 1 |
| 15 | 15 | 5 | 3 | 22 | 1 |
| 16 | 15 | 30 | 1.5 | | 1 |
| A16 | 15 | 30 | 34 | 190 | 1 |
| 17 | 30 | 5 | >1000 | | 3 |
| 18 | 30 | 30 | >1001 | | 3 |
| 19 | 4 | 15 | 0 | 0 | 0 |
| A19 | 4 | 15 | 4 | 27 | 0 |
| 20 | 4 | 15 | 0 | 0 | 0 |
| 21 | 8 | 15 | 0.5 | 5 | 0 |
| 22 | 8 | 15 | 0 | | 3 |
| 23 | 15 | 15 | 1.5 | 11 | 0 |
| 24 | 15 | 15 | 0 | | 3 |
| 25 | 30 | 15 | Delaminated | | 3 |
| 26 | 30 | 15 | Delaminated | | 3 |
| A26 | 30 | 15 | Delaminated | | 3 |

The above results, which are tabulated in order of PVP masking agent concentrations, show a clear correlation between higher levels of PVP and reduced adhesion of the silicone sealant to the fabric. Two mechanisms by which silicone penetrated into the inner surface of the fabric were observed, i.e., either through the yarn bundle fibers or by passing between the gaps in the yarn bundles. The lower concentrations of mask agent (>4% PVP) appeared to inhibit the flow of polymer through the yarn fibers, however it was not in all cases sufficient to substantially prevent the ingress of small "fingers" or "slivers" of silicone polymer between the gaps in the bundles, i.e., interstitial spaces between proximately juxtaposed yarns within the textile pattern. It appeared that slightly larger concentrations of mask agent (>15%) was required to completely block the passage of silicone polymer through between the gaps in the fiber bundles.

Assessment of Handling

The handling characteristics of grafts are the result of a series of complex interactions between the fabric structure, the graft diameter, the crimp pitch and form, the thickness profile of the polymer sealant and the amount of penetration of the sealant into the yarn bundles.

The below assessment parameters, although subjective, aim to consider all of the following: bend radius at kink formation, flexibility, hoop stiffness (ability to remain fully open) and stretching.

A grading score (1-4) was used to assess handling characteristics;
 1—Graft judged more flexible than reference sample.
 2—Graft judged comparable to reference sample.
 3—Graft judged to be stiffer than reference sample but with useable characteristics.
 4—Graft judged too stiff for comparable use.

The reference sample was considered to have excellent overall handling and at least comparable to currently commercially available gelatin sealed grafts.

Polymer Sealant Coverage

The amount of polymer sealant coverage on each sample was reported in $mg/cm^2$ and was calculated by dividing the overall mass of polymer applied to each individual graft by the surface area of the graft. Previous crimped prototypes have demonstrated both effective sealing and suitable handling characteristics with polymer coverages of at least about 8 $mg/cm^2$ ranging up to about 14 $mg/cm^2$. Coverage levels above 14 $mg/cm^2$ increased the overall stiffness of the handling characteristics beyond that of a standard gelatin sealed graft, however increase stiffness and therefore increased amount of polymer coverage may be advantageous for some graft applications.

Tensile Extension Force

Samples were mounted between jaws of Lloyd Tensile Test machine with jaws spacing of 80 mm. The machine was zeroed and the jaws extended by 20% (16 mm) and the maximum measured force was recorded.

The results recorded are tabulated below, ranked in order from low to high for force-to-extend by 20%.

These results demonstrated a strong correlation between handling assessment and force-to-extend, with lower extension forces corresponding to improved handling characteristics.

A review of the polymer coverage values indicated that coverage levels of up to 40 $mg/cm^2$ might be considered in order to achieve comparable handling characteristics to the reference sample (grading 2), as indicated by graft sample #15.

All grafts which demonstrated delamination of the polymer sealant during pressurized adhesion tests are by a note (1) highlighted in italics. This list indicates that poor adhesion can result in low Extension Forces and improved handling characteristics. This result supports the theory that acceptable handling characteristics rely on lower levels of penetration of sealant into the yarn bundles.

TABLE 14

| Sample No. | Dia, mm | Extended Length, mm | Surface Area, cm² | Polymer Coverage, mg/cm² | Handling Assessment Grading, 1 to 4 | Force to Extend by 20% (N) |
|---|---|---|---|---|---|---|
| 18 (1) | 8 | 130 | 32.7 | 43 | 1 | 0.29986 |
| 10 (1) | 8 | 125 | 31.4 | 38 | 1 | 0.37938 |
| 5 | 8 | 120 | 30.1 | 36 | 1 | 0.4067 |
| 25 (1) | 8 | 130 | 32.7 | 44 | 1 | 0.41064 |
| 6 | 8 | 135 | 33.9 | 33 | 2 | 0.48247 |
| 16 | 8 | 130 | 32.7 | 40 | 2 | 0.48938 |
| 17 (1) | 8 | 140 | 35.2 | 44 | 1 | 0.52805 |
| 8 | 8 | 130 | 32.7 | 40 | 2 | 0.53074 |
| 7 | 8 | 132 | 33.2 | 40 | 2 | 0.54057 |
| 9 (1) | 8 | 125 | 31.4 | 41 | 1 | 0.57061 |
| 13 | 8 | 140 | 35.2 | 39 | 2 | 0.58817 |
| 4 | 8 | 125 | 31.4 | 38 | 2 | 0.60156 |
| 12 | 8 | 135 | 33.9 | 35 | 3 | 0.69369 |
| 15 | 8 | 135 | 33.9 | 40 | 2 | 0.71933 |
| 14 | 8 | 130 | 32.7 | 42 | 3 | 0.76625 |
| 3 | 8 | 135 | 33.9 | 41 | 3 | 0.78701 |
| 11 | 8 | 130 | 32.7 | 41 | 3 | 0.90773 |
| 1 | 8 | 135 | 33.9 | 44 | 3 | 1.0072 |
| 19 | 8 | 135 | 33.9 | 43 | 3 | 1.0302 |
| 23 | 8 | 140 | 35.2 | 38 | 3 | 1.0372 |
| 2 | 8 | 140 | 35.2 | 41 | 3 | 1.1116 |
| 21 | 8 | 125 | 31.4 | 43 | 3 | 1.1234 |
| 26 (1) | 8 | 134 | 33.7 | 63 | 4 | 1.1571 |
| 22 | 8 | 125 | 31.4 | 64 | 4 | 1.8936 |
| 24 (1) | 8 | 111 | 27.9 | 66 | 4 | 2.1711 |
| 20 | 8 | 115 | 28.9 | 70 | 4 | 3.0235 |
| 64B | 10 | 620 | 194.7 | 12.1 | Reference Sample | |

Note:
(1) demonstrated delamination of the polymer sealant during pressurized adhesion tests Conclusions Acceptable handling characteristics were achieved with lower levels of penetration of sealant into the yarn bundles. The use of the masking agents to limit the amount of polymer penetration into textile fabric can be utilized for improved handling characteristics. Polymer coverage levels of up to 40 mg/cm² were demonstrated to achieve comparable handling characteristics to the reference sample as assessed by surgeon users.

Photographs of select samples from Tables 10-14 are reproduced in FIGS. 12-19. Description of these figures follow.

Figure 12:
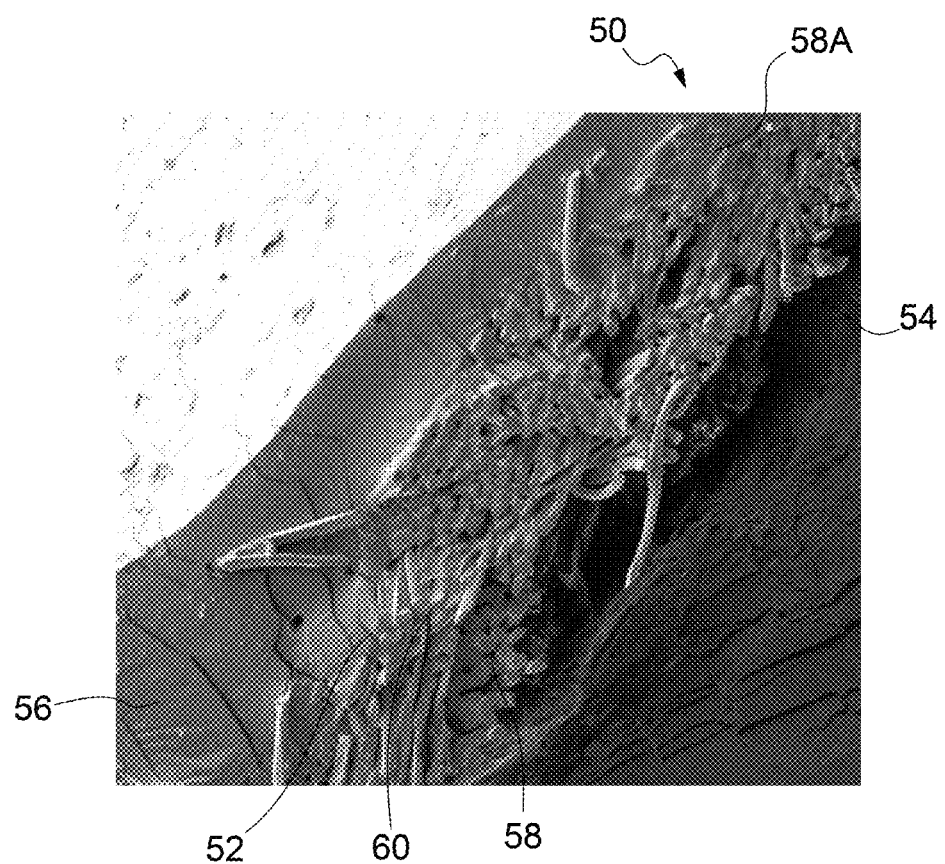
FIG. 12 is a scanning electron microscope (SEM) photograph of a cross-sectional section of textile sample 2, which is described below in conjunction with Tables 10-14.
Figure 13:
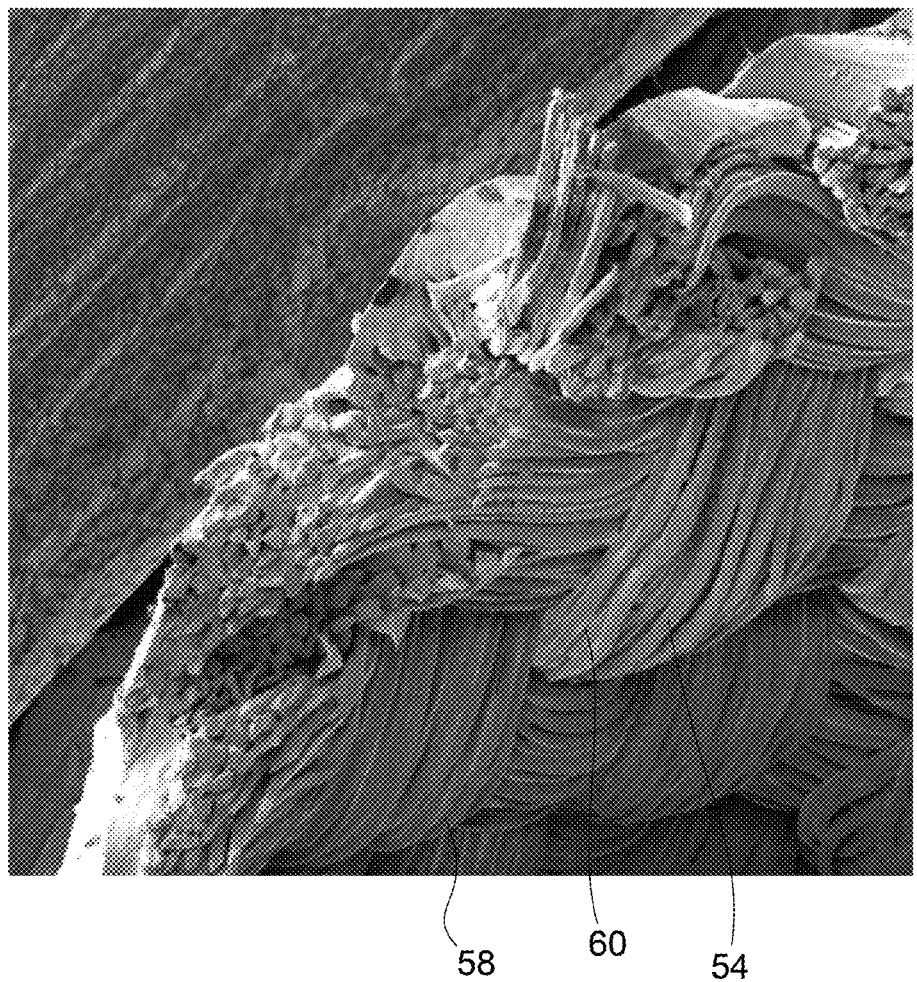
FIG. 13 is a SEM photograph of an inner surface of textile sample 2, which is described below in conjunction with Tables 10-14.

FIGS. 12 and 13 are SEM photographs of sample 2 from the above-described Tables. Sample 2 had the following characteristics:
  Masking Solution: 2% PVP, 0% Glycerol in water;
  Silicone Dispersant: 15% Silicone in heptane;
  Silicone Coverage: 41 mg/cm²;
  Silicone Penetration Grading: 3 (Silicone visible);
  Silicone Adherence Grading: 0 (Silicone is well adhered to graft and showing no signs of failure);
  Measured Leakage at 120 mmHg: 0 ml/min;
  Measured Leakage at 600 mmHg: 0 ml/min;
  Handling Assessment: 3 (Graft judged to be stiffer than Reference but with useable characteristics); and
  Tensile Force to Extend Graft by 20%: 1.112 N.

FIG. 12 is a SEM photograph of a cross-section of the textile 50 of Sample 2. The outer surface 52 of the textile 50 was fully coated with silicone sealant 56. Fiber bundles 58A were fully encapsulated by the silicone sealant 56. The silicone sealant was disposed throughout the cross-section of the fiber bundle or the multi-filament yarn 58. As depicted in FIG. 13, the inner textile surface 54 also had noticeable amounts of silicone sealant 60 at the fiber bundles 58.

Figure 14:
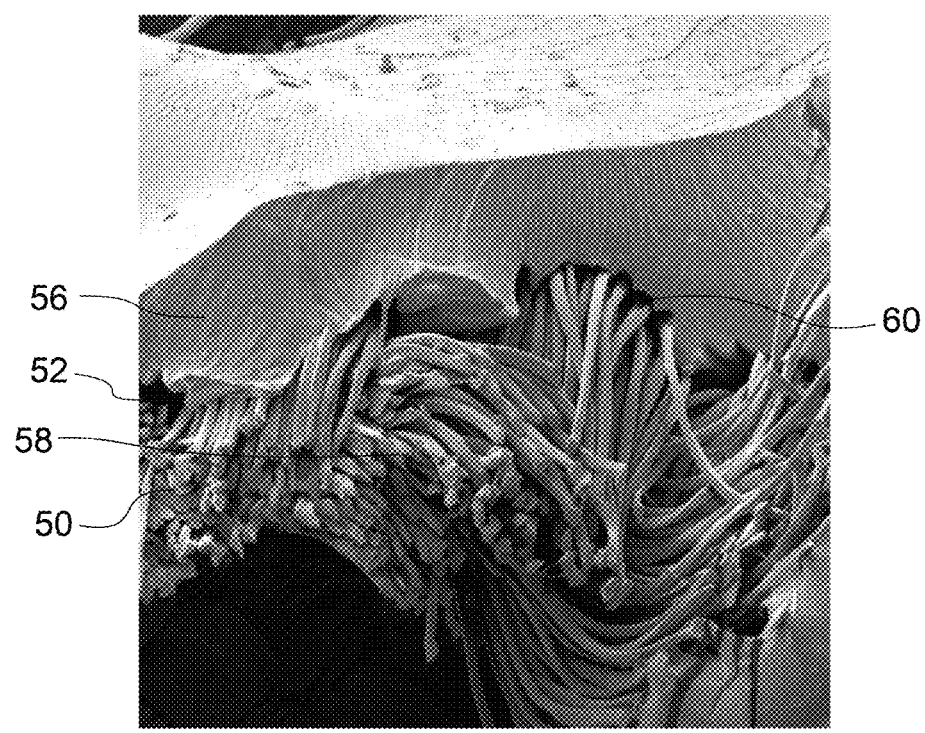
FIG. 14 is a SEM photograph of a cross-sectional section of textile sample 9, which is described below in conjunction with Tables 10-14.
Figure 15:
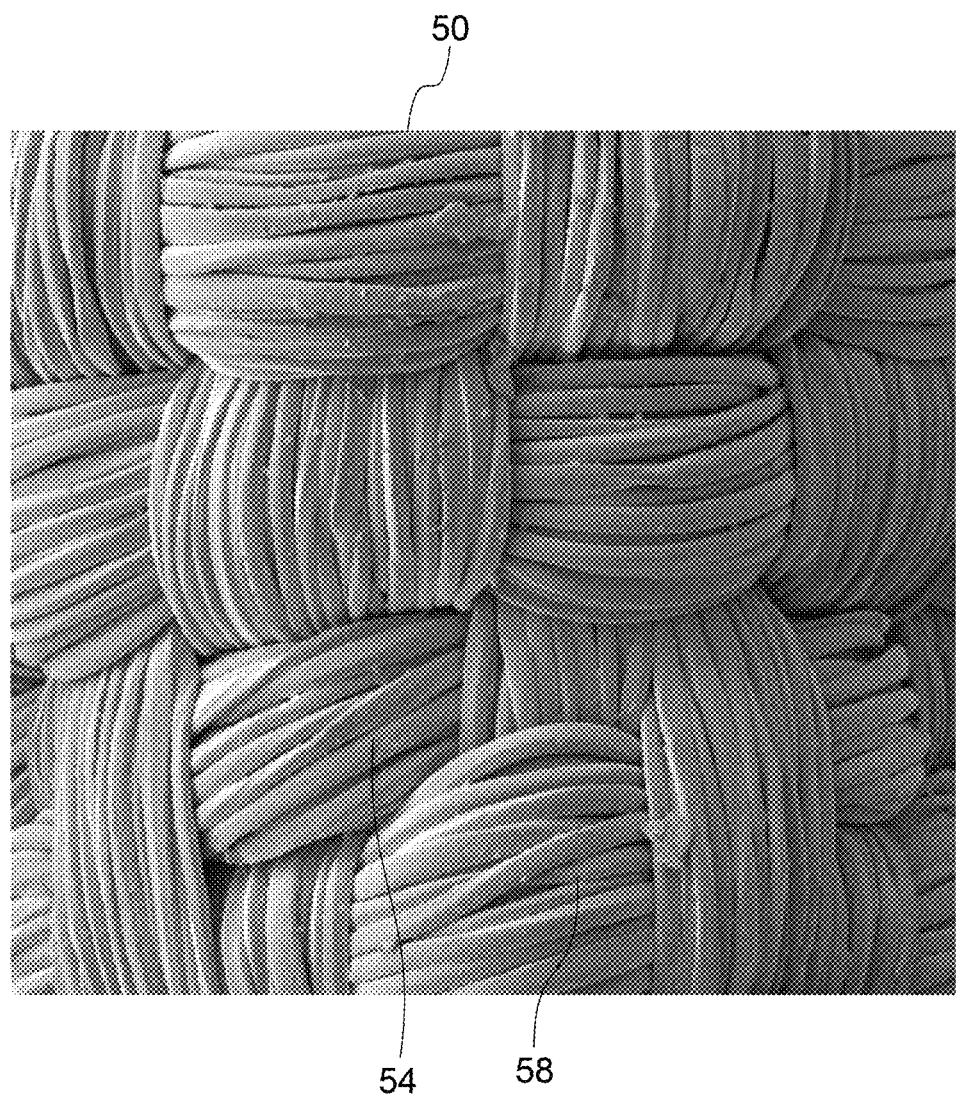
FIG. 15 is a SEM photograph of an inner surface of textile sample 9, which is described below in conjunction with Tables 10-14.

FIGS. 14 and 15 are photographs of sample 9 from the above-described Tables. Sample 9 had the following characteristics:
  Masking Solution: 25% PVP, 0% Glycerol in water;
  Silicone Dispersant: 15% Silicone in heptane;
  Silicone Coverage: 41 mg/cm²;
  Silicone Penetration Grading: 0 (Silicone only visible on the outer surface of the graft);
  Silicone Adherence Grading: 3 (Delaminated, Silicone coating has failed, and a bubble has appeared on the surface);
  Measured Leakage at 120 mmHg: Delaminated;
  Measured Leakage at 600 mmHg: Delaminated;
  Handling Assessment: 1 (Graft judged more flexible than Reference Sample); and
  Tensile Force to Extend Graft by 20%: 0.571 N.

FIG. 14 is a photograph of a cross-section of the textile 50 of Sample 9. The outer surface 52 of the textile 50 was fully coated with silicone sealant 56. Individual textile bundles 58 were general free of silicone sealant penetration. There was, however, delamination of the silicone sealant 56 from the textile fibers at the outer surface as noted by delamination spaces. As depicted in FIG. 15, the inner textile surface 54 and all fiber bundles 58 thereat were free of any noticeable amounts of silicone sealant 60.

Figure 16:
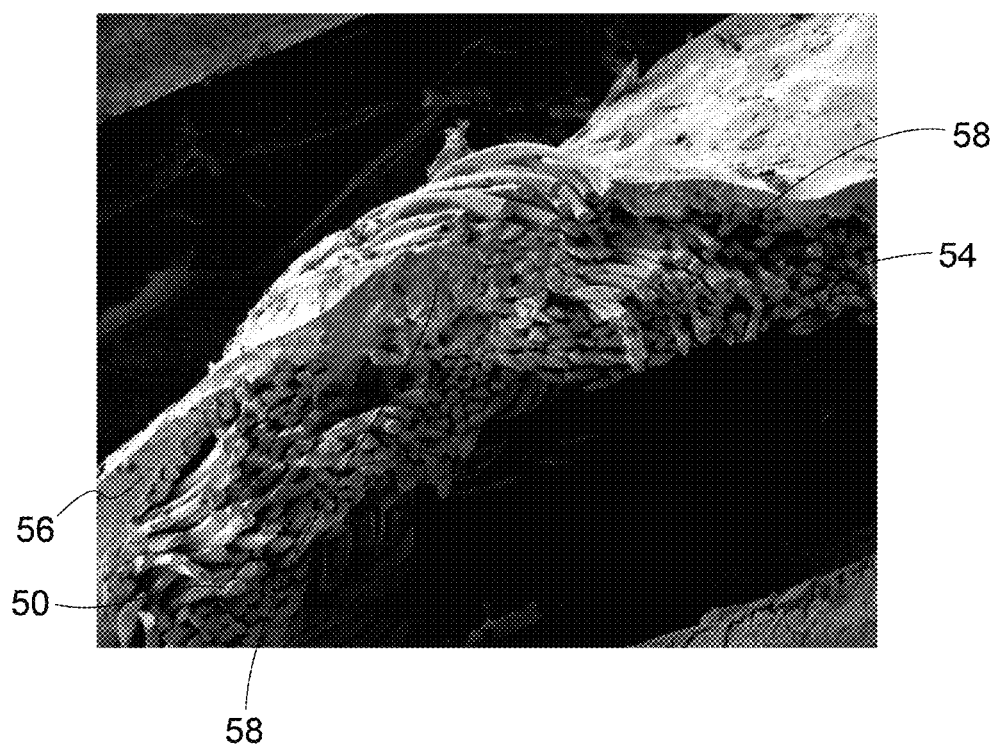
FIGS. 16-18 are SEM photographs of cross-sectional sections of textile sample 7, which is described below in conjunction with Tables 10-14.
Figure 17:
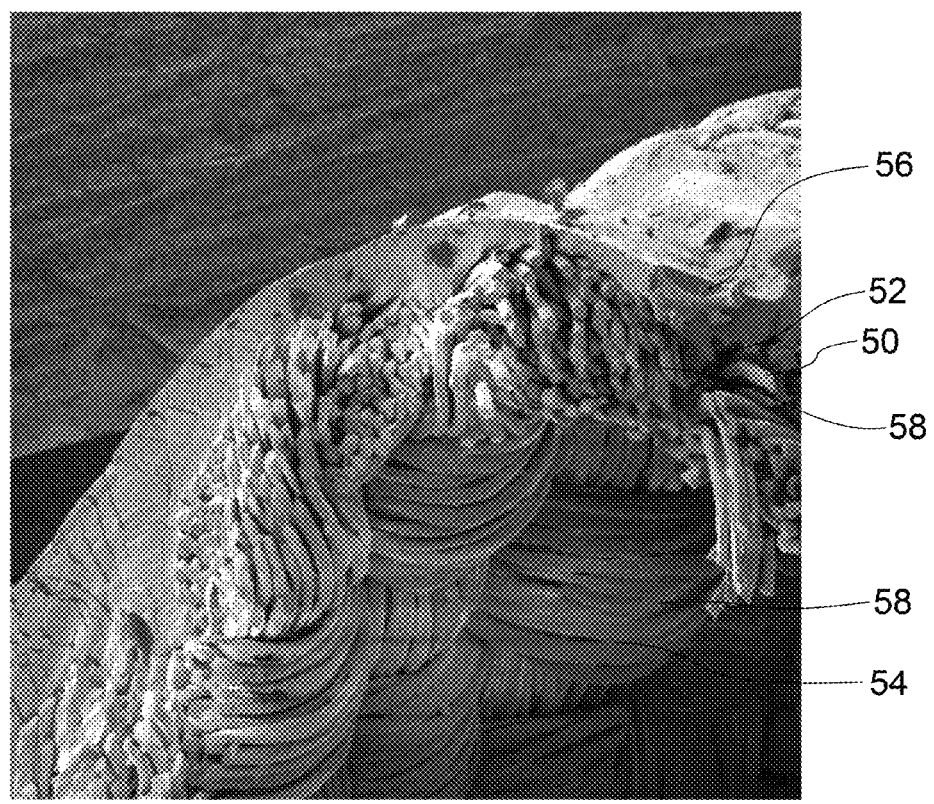
Figure 18:
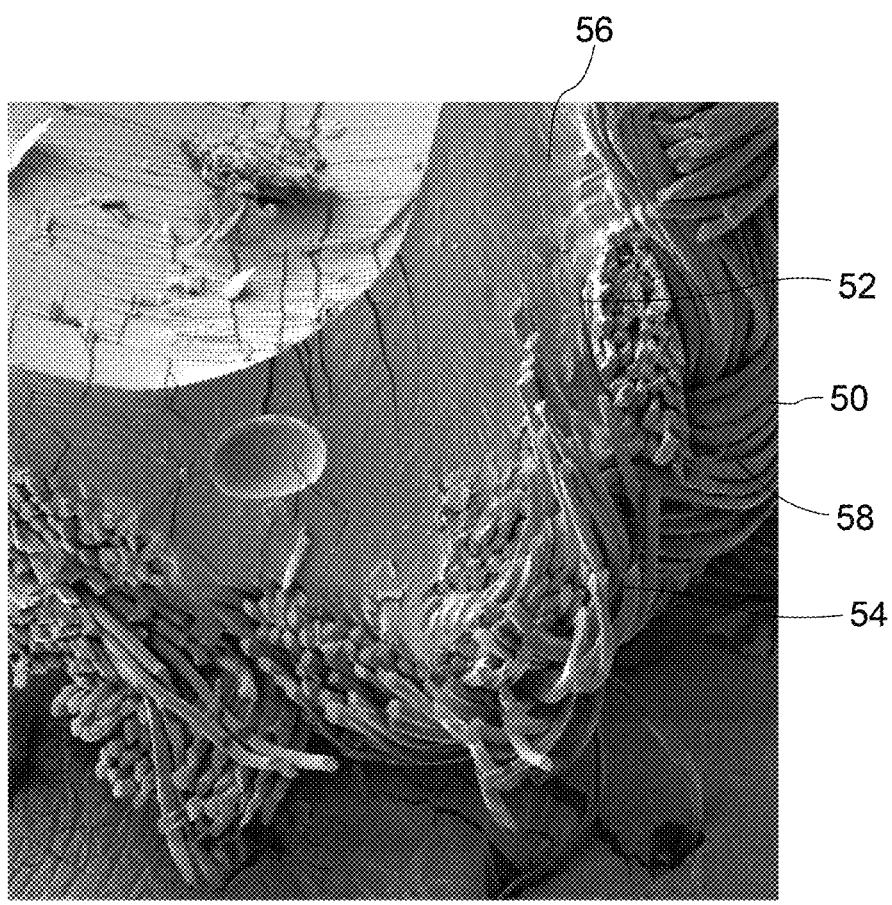

FIGS. 16-18 are SEM photographs of sample 7 from the above-described Tables. Sample 7 had the following characteristics:
  Masking Solution: 15% PVP, 0% Glycerol in water;
  Silicone Dispersant: 15% Silicone in heptane;
  Silicone Coverage: 40 mg/cm²;
  Silicone Penetration Grading: 2 (Silicone is visible penetrating to the inside surface);
  Silicone Adherence Grading: 0 (Silicone is well adhered to graft and showing no signs of failure);
  Measured Leakage at 120 mmHg: 4 ml/min;
  Measured Leakage at 600 mmHg: 14 ml/min;
  Handling Assessment: 2 (Graft judged comparable to Reference Sample 64B); and
  Tensile Force to Extend Graft by 20%: 0.541 N.

FIG. 16 shows an SEM photograph of a cross-section of the textile 50 of Sample 7. As shown in FIG. 16, the textile fiber bundles 58 on the outer textile surface 52 were penetrated and encapsulated with silicone sealant 56. The textile fiber bundles 58 at the inner textile surface 54 were free from silicone sealant 60 penetration. As shown in FIGS. 17 and 18, the silicone sealant 56 penetrated and encapsulated the textile fiber bundles 58 at the outer textile surface. The fiber bundles 58 at the inner textile surface 54 were free from silicone sealant 56.

Figure 19:
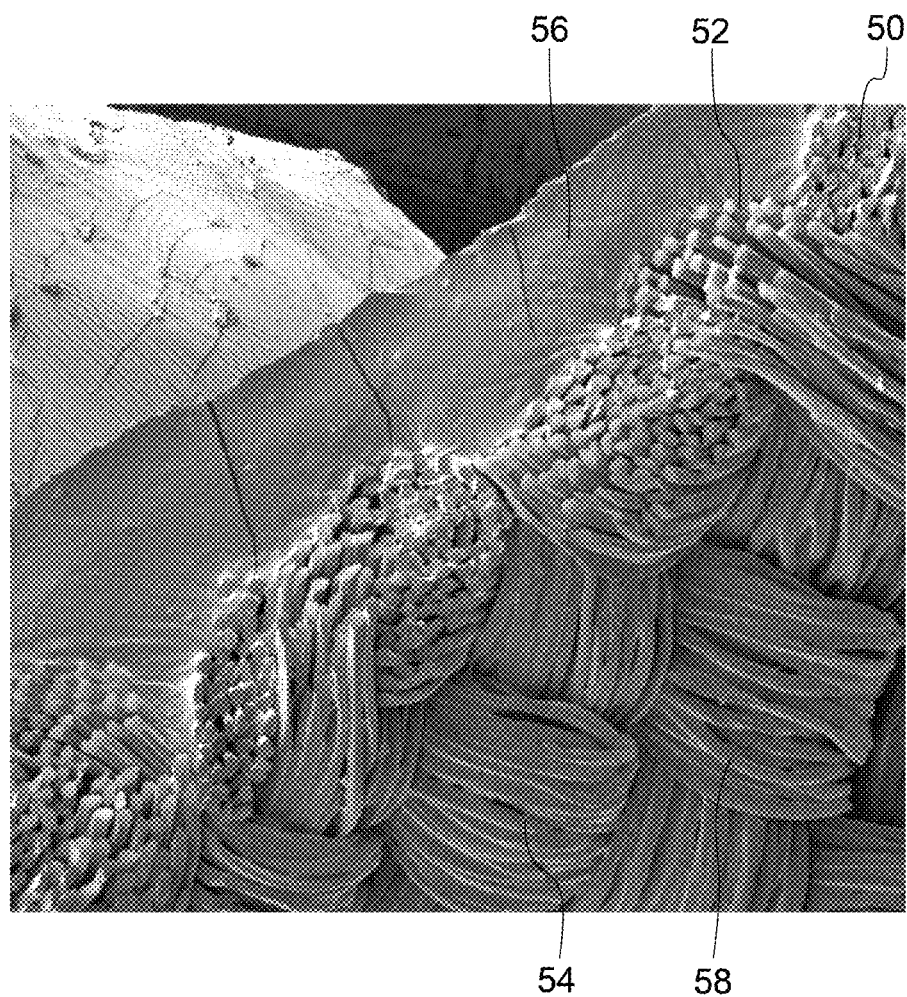
FIG. 19 is a SEM photograph of a cross-sectional section of textile sample 15, which is described below in conjunction with Tables 10-14.

FIG. 19 is an SEM photograph of sample 15 from the above-described Tables. Sample 15 had the following characteristics:
  Masking Solution: 15% PVP, 5% Glycerol in water;
  Silicone Dispersant: 15% Silicone in heptane;
  Silicone Coverage: 40 mg/cm²;
  Silicone Penetration Grading: 2 (Silicone is visible penetrating to the inside surface);
  Silicone Adherence Grading: 1 (Graft reached the maximum pressure, but the leak rate has visibly increased);
  Measured Leakage at 120 mmHg: 3 ml/min;
  Measured Leakage at 600 mmHg: 22 ml/min;

Handling Assessment: 2 (Graft judged comparable to Reference Sample 64B); and

Tensile Force to Extend Graft by 20%: 0.719 N.

FIG. 19 is a SEM photograph of a cross-section of the textile 50 of Sample 15. The silicone sealant 56 encapsulated the outer fibers of the fiber bundles 58 at the outer textile surface 2. The fiber bundles 58 at the inner textile 54 were free from penetration of the silicone sealant 56. Dyed silicone sealant (not shown) was visible ay the inner surface 54.

Glycerol Hydration of Masking Agents

The use of glycerol within different masking agent formulations has been demonstrated on multiple formulations with the aim of hydrating or plasticizing the (PVP) masking agent and improving its ability to cover and fill the yarn structure and prevent the sealant dispersion from ingress to the inner surface.

Masking Agent Sample Preparation

Masking agents were prepared using following method:

A target weight of PVP (MW 10,000) was introduced in a plastic beaker on a scale balance. A 100 ml masking agent solution was prepared at a target mass of 10 g PVP (10% concentration). The target volume of de-ionised water was introduced into a 100 ml plastic measuring cylinder. A target volume of 90 ml was required. The de-ionised water was added into the PVP in plastic beaker. A magnetic stirrer rod was placed in the water, and the beaker was placed on the magnetic stirrer. The magnetic stirrer was turned on at a speed of 350-450 RPM, the stirrer was centered in the beaker. The stirring was done at room temperature. Stirring continued until there was no visible PVP solute, but for at least 2 minutes. After stirring the masking agent solution, it can be removed from stirrer and used for control sample preparation.

Additional steps were used for subsequent samples with added glycerol. The plastic beaker was returned to scale balance, tared, and the required quantity of glycerol was added to the masking agent solution. The target glycerol content was calculated as a percentage by mass of the PVP. The target weight of Glycerol added at each stage was 1 g, corresponding to cumulative weights of 1, 2, 3, 4, 5, 6, 7, 8, 9 and 10 g. Each beaker was stirred for at least 2 minutes after each added quantity of Glycerol.

A summary of the samples prepared are shown below.

TABLE 15

| Sample Ref. | Volume of water | PVP Weight | PVP % w/v | Glycerol Weight | Glycerol as % of PVP |
|---|---|---|---|---|---|
| Control | 90 ml | 10 g | 10% | 0 | 0 |
| A) 10% Glycerol | 90 ml | 10 g | 9.9% | 1 g | 10% |
| B) 20% Glycerol | 90 ml | 10 g | 9.8% | 2 g | 20% |
| C) 30% Glycerol | 90 ml | 10 g | 9.7% | 3 g | 30% |
| D) 40% Glycerol | 90 ml | 10 g | 9.6% | 4 g | 40% |
| E) 50% Glycerol | 90 ml | 10 g | 9.5% | 5 g | 50% |
| F) 60% Glycerol | 90 ml | 10 g | 9.4% | 6 g | 60% |
| G) 70% Glycerol | 90 ml | 10 g | 9.3% | 7 g | 70% |
| H) 80% Glycerol | 90 ml | 10 g | 9.3% | 8 g | 80% |
| I) 90% Glycerol | 90 ml | 10 g | 9.2% | 9 g | 90% |
| J) 100% Glycerol | 90 ml | 10 g | 9% | 10 g | 100% |

Dispersion Drop Castings

Three individual drops of each masking agent formulation were cast onto a dark coloured sheet to allow visual observation during the drying process. The drying was accelerated by using a desk fan at room temperature Assessments of the masking agents after drying were as follows:

TABLE 16

| Sample Ref. | Assessment after 12 hours | Assessment after 96 hours |
|---|---|---|
| Control | Looked white, Dry to touch | Dry, Brittle |
| A) 10% Glycerol | Looked hydrated, Dry to touch | Looked hydrated, Dry to touch |
| B) 20% Glycerol | Hydrated, Soft, Tacky to touch | Hydrated, Soft, Tacky to touch |
| C) 30% Glycerol | Very Sticky to touch | Sticky to touch |
| D) 40% Glycerol | Sticky, still wet | Sticky, still wet |
| E) 50% Glycerol | Wet to touch | Wet to touch |
| F) 60% Glycerol | Wet to touch | Wet to touch |
| G) 70% Glycerol | Wet to touch | Wet to touch |
| H) 80% Glycerol | Wet to touch | Wet to touch |
| I) 90% Glycerol | Wet to touch | Wet to touch |
| J) 100% Glycerol | Wet to touch | Wet to touch |

Conclusions

The control masking agent formulation (e.g., PVP-only) dried out fully within a few hours and became brittle. Use of this PVP-only masking agent may result in a stiff graft structure once mask is applied and dried. The use of 10% glycerol helped to hydrate the PVP masking agent solution, and appeared dry after 12 hours. A masking agent solution consisting of 20% glycerol retains some hydration at 12 hours and is soft/deformable to touch. A range of between about 1% and about 30% glycerol to PVP, by weight, provides appropriate ranges for use with the present invention.

Moreover, the present invention is not limited to vascular prostheses in conduit-type shapes. The methods, coatings, and masking agents of the present invention may suitably be used with other textile products, including medical and non-medical (e.g., non-implantable) textile products. Other medical products may include ventricular assist devices, artificial heart conduits, medical sheets, patches, meshes, and the like. Non-medical textiles may include, but are not limited to, clothing, geotextiles, transportation textiles, military and/or defense textiles, safety and/or protective textiles, sports and/or recreation textiles, and the like. Further, textile products are not limited to tubular conduits, but may be of any shape including, but not limited to for example, sheets and/or tapes (e.g., two-dimensional products), or even three-dimensional shaped products other than conduit-shaped products.

Useful polymeric materials and/or for fibers for non-medical or non-implantable textiles may include, but are not limited to, polyethylene terephthalate (PET), polytetrafluoroethylene (PTFE), expanded polytetrafluoroethylene (ePFTE), polyolefins, polyesters, poly(ether amides), poly (ether esters), poly(ether urethanes), poly(ester urethanes), poly(ethylene-styrene/butylene-styrenes), and other block copolymers. Useful animal fibers for the non-medical or non-implantable textiles of the present invention may include, but are not limited to, wool, alpaca, angora, mohair, llama, cashmere, and silk. Useful natural fibers may include, but are not limited to, linen, cotton bamboo, hemp, corn, nettle, soy fiber, and the like.

The masking agents and/or the sealants may be applied by brushing, spray-coating, dipping or immersing, and the like. The present invention, however is not limited to such techniques, and other techniques, such as chemical deposition, vapor deposition, chemical vapor deposition, physical vapor deposition, printing and the like, may suitably be used.

These techniques are generally suitable for medical textiles. However, for large commercial scale textile production, including non-medical textiles, other techniques may also be used. For example, coating and/or masking materials for textile sheets or substrates may be applied by squeegee type coating, roller coating, knife coating, nip coating, dip coating, cast coating, chemical deposition, vapor deposition, and the like. Moreover, printing techniques, such as roller printing, stencil printing, screen printing, inkjet printing, lithographic printing, 3D printing, and the like may be used with the present invention for applying the masking agents and/or the sealing agents. Furthermore, mechanical devices may be employed to control the depth of penetration of the masking agent and/or sealing agent into the wall of the textile substrate of graft. For example, with a tubular graft an expandable balloon may be to control the depth of penetration of the masking agent into the graft wall.

Selective Mask Agent Removal Techniques:

If desired, masking agent may be selectively removed, either in total or partially, from portions and/or surfaces of textile material of the present invention. One technique for selectively removing the masking agent is through the use of a particulate solid flowing against a portion or a surface of the textile. The particulate solid may ablate the masking agent to remove it from the portion and/or surface of the textile. Such flow of a particular solid is typically performed with a flow media, such as air, but other flow media, including gasses, vapors, or liquids, may be used.

Desirably, the particulate solid has physical properties that will not unduly harm or adversely affect the textile graft or substrate of the present invention. One useful particulate solid is sodium bicarbonate. Other useful particulate solids include, but are not limited to, sodium chloride, sugar, magnesium sulphate, potassium chloride, calcium carbonate (including calcite), and talc. Sodium bicarbonate has a Moh's hardness of about 2.5. Other materials having a Moh's hardness from about 1 to about 5 may be used, more desirably a Moh's hardness from about 3 to about 4 may be used.

When the particulate solid is being used to remove the water soluble masking agent of the present invention, it may be desirable to use a water soluble particulate solid, such a sodium bicarbonate. Use of a water soluble particulate solid may be useful in the removal of the solid particulate from the textile after ablation, for example by washing or spraying with water and/or a solvent, either before or after the application of the sealing agent or sealant. Any suitable organic or inorganic solvent may be used to wash or spray the textile.

The particulate solid may have any useful particle size. In general, the larger the particle size or the coarser the material may offer greater ablating potentials. Useful particle sizes may vary from an average particle size from about 10 microns to about 1,000 microns, including from about 50 microns to about 350 microns, in particular an average particle size from about 100 microns to about 300 microns. Average particle sizes from about 250 microns to about 300 microns have been used to ablate masking agents from textiles substrates of the present invention. Such average particle sizes may be on a weight basis or a volume basis depending upon the test method for measuring particle size.

Preferably the particulate solid or ablating material should have a crystalline structure and geometry with a particle size of greater than about 10 microns. A wide variety of substances could be used to abrade the mask. Any granular material which is capable of being pressure blasted when entrained in a pressurised flow of gas may be used. The granular material may have a hardness which exceeds that of the masking agent. Preferably the blasting material should be water soluble and non toxic. Examples of particularly useful materials include, but are not limited to, sodium bicarbonate, sodium chloride, sugar, magnesium sulphate, potassium chloride, and combinations thereof.

Force of the ablating materials striking a surface also effects the ablating of the masking agent. Higher ablating pressures offer greater masking agent removal potentials, but may present higher potentials for damage of the textile pattern or yarns within the textile patterns. Desirably, solid particulates for ablating the textile substrates of the present invention are sprayed at a pressure from about 10 pounds per square inch force (psig) (or about 70 kilopascal gauge or kPa gauge) to about 50 psig (or about 340 kPa gauge). Useful spraying pressures include from about 20 psig (or about 140 kPa gauge) to about 50 psig (or about 340 kPa gauge), more desirably from about 20 psig (or about 140 kPa gauge) to about 30 psig (or about 210 kPa gauge).

High ablating pressures, such as substantially greater than 50 psig (or 340 kPa gauge) may create multiple fibre breakages on the outer surface of the textile graft. While it may not be desirable to overly weaken the textile graft, textile grafts are typically over-engineered and are much stronger than required, so some yarn surface damage may be tolerates. Indeed, such broken outer yarn filaments, if present, may create a texturized effect on the outer surface of the coated graft, which may improve, for example, the general handling of the graft and adhesion of the sealant coating.

The present invention, however, is not limited to the use of solid particulate matter for ablating the masking agent from textile substrates, and other techniques may suitably be used. For example, a brush, such as a bristle brush, may be used to selectively remove masking agent.

Details of selective masking agent removal are further described below in Table 17.

TABLE 17

| Abrading Technique | Soda Blasting | Static Brushing | Rotating Bristle Brushing |
|---|---|---|---|
| Methods | Sodium bicarbonate (Ecostrip) with an average particle size of 285 microns was sprayed at 20-50 psig (140-340 kPa gauge) onto a rotating graft. | A hand held, bristle brush (0.5 mm bristle diameter, 15 mm bristle length) was held static against a rotating graft. | A counter rotating brush (0.4 mm bristle diameter, 30 mm bristle length) was brushed alongside the rotating graft. |

TABLE 17-continued

| Abrading Technique | Soda Blasting | Static Brushing | Rotating Bristle Brushing |
|---|---|---|---|
| Graft Samples | (A) PET woven graft, crimped, straight (10 mm ID) with 35% PVP + 15% Glycerol Mask (B) PET woven graft, crimped, straight (14 mm ID) with 20% PVP + 15% Glycerol Mask | (A) PET woven graft, crimped, straight (14 mm ID) with 20% PVP + 15% Glycerol Mask | (A) PET woven graft, crimped, straight (14 mm ID) with 20% PVP + 15% Glycerol Mask |

Conclusions

Soda blasting (sodium bicarbonate) abrading methods for removing masking off the outer surface worked well, while leaving the inner masking agent surface intact. Soda blasting is compatible with complex textile or graft geometry, including being particularly suitable for use on a crimped graft. Some non-limiting parameters in soda or particulate blasting are grain particle size and blast pressure. The use of soda or particulate blasting to improve adhesion levels of the silicone to PET yarn has been demonstrated. A crimped graft using a 20% PVP mask may, under certain conditions show delamination, however, this graft had improved levels of silicone adhesion when ablated with sodium bicarbonate under the same conditions. Graft inner surfaces appeared fully intact after blast abrasion. The sealing agent or sealant, however, is not limited to the use of silicone, and other sealing agent or sealant formulations may include, but not limited to, silicone, room temperature vulcanizing silicone, thermoplastic polyurethane, aliphatic polycarbonate, one or more thermoplastic elastomers, polycarbonate, and combinations thereof with or without solvent; and the masking agent, however, is not limited to the use of polyvinylpyrrolidone, and masking agent formulations may include, but not limited to, polyvinylpyrrolidone glycerol, methyl cellulose, poly(ethylene glycol), polyethylene oxide, poly(ethylene glycol) hydrogel, and combinations thereof with or without water or other solvent.

Bristle brushing showed some disruption to the outer mask surface. Static bristle brush and rotating bristle brush abrading methods with rotating graft may have a disadvantage with respect to controlling the level of force applied to the graft. For crimped grafts, larger brush contact surfaces may tend to focus the brushing action at the graft peaks, leaving valleys with limited abrasion.

Further details of the sodium bicarbonate abrasion tests are described below in Table 18.

TABLE 18

PVP Mask Concentration

| Soda Blast Pressure (psig) | 20% PVP + 15% Glycerol | 50% PVP (No Glycerol) | Broken Yarns Identified (Yes/No) | Yarn Damage Ranking (0-3)* |
|---|---|---|---|---|
| 20 |  | X | No | 0 |
| 25 | X |  | No | 0 |
| 30 |  | X | Yes | 1 |
| 35 | X |  | Yes | 1 |
| 40 |  | X | Yes | 2 |
| 45 | X |  | Yes | 2 |
| 50 | X |  | Yes | 3 |

*Yarn Damage Ranking
0 - No broken yarns identified
1 - Localized single yarn breakages,
2 - Localized multiple yarn breakages
3 - Broken yarn filaments over majority of surface.

The utility of abrading the outer surface layer of masking agent to control masking coverage on a graft's exterior has been demonstrated. Such abrading may be used in preparation for subsequent coating and to increase silicone adhesion to PET graft. Ablating and other removal techniques allow for heavier application of masking agents, thereby providing greater assurance levels that the inner surface of the graft is free, including substantially free and completely free, of any silicone ingress during the application thereof. Abrading methods tested included soda blasting, static brushing, and rotating bristle brushing, but other techniques may be used. The ablation techniques may be used with any suitable masking agent, such as polyvinylpyrrolidone glycerol, methyl cellulose, poly(ethylene glycol), polyethylene oxide, poly(ethylene glycol) hydrogel, and combinations thereof with or without water or other solvent, and with any suitable The sealing agent or sealant, such as silicone, room temperature vulcanizing silicone, thermoplastic polyurethane, aliphatic polycarbonate, one or more thermoplastic elastomers, polycarbonate, and combinations thereof with or without solvent.

Sealant or Silicone Application by Spraying Using Forced Air:

Target silicone coverage on the PET woven grafts for these examples was 14 mg/cm$^2$. The dispersion mass of silicone based on the target coverage was calculated and loaded into an application syringe. Each sample graft was sprayed using a one-way pass (right to left) method with approximately 45 second delay between each spray pass to allow initial flash-off of excess solvent from the sealant composition. For silicone spraying, spray pressure was 11 pounds per square inch (psig) (or about 76 kPa gauge), traverse speed was 20 mm per second, and rotation speed of graft was typically from about 100 revolutions—per-minute or RPM to about 150 RPM. Higher rotations speeds, for example 300 RPM, were also tested. The spray passes were repeated until sealant volume in the syringe was used or applied.

PET Graft Sample Descriptions:
Graft Samples:
(A) Samples #111-119: Straight woven PET crimped graft (14 mm ID),
(B) Samples #120-121: Valsalva PET graft (22×20 mm ID)

Masking Agent Composition:
Mask Formulation: 12% PVP with 15% Glycerol (as % of PVP) (Sample #114 dyed blue).

The masking agent solution was applied via immersion dipping of above graft samples 111 to 120 with rigorous manual manipulation. Excess masking was removed via manual squeezing between fingers for the straight grafts and between a roller press for the Valsalva grafts.

Sealant Agent Composition:
MED6-6606 (NuSil) silicone dispersion in heptane, 15% solid content, was used. Samples Nos. 111 and 115 further contained blue dye.

Spray Results:
Results of applying an even silicone coating across the length of the graft using forced air spraying are described below in Table 19.

Silicone coated sample #111 demonstrated no leakage at 120 mmHg, but had bubble delamination at the peaks of the crimps and along the graft seam at 250 mmHg. Silicone coated sample #112 demonstrated heavy beading from peaks at 120 mmHg and no delamination at 600 mmHg. Silicone coated sample #114 demonstrated beading from peaks at 120 mmHg and no delamination at 600 mmHg. Silicone coated sample #116 demonstrated bubble delamination along both graft seams at 120 mmHg and expanded bubble delamination along the seams at pressures >120 mmHg. Silicone coated sample #117 and #118 demonstrated heavy beading and leakage at the peaks of the crimps during leak testing at 120 mmHg. Silicone coated sample #119 demonstrated initial delamination at graft seams then quickly migrated to cover the full circumference of the graft during leak testing at 120 mmHg. Silicone coated Valsalva samples #120 and #121 demonstrated heavy beading and leakage at the peaks of the crimps during leak testing at 120 mmHg. Bubble delamination on the Valsalva graft occurred near the transition of the bulge and the crimped body of the graft.

TABLE 19

| | | Position of Sample | | | | | | | |
|---|---|---|---|---|---|---|---|---|---|
| | | 6 | 5 | 4 | 3 | 2 | 1 | Average | SD |
| #111 | Length (mm) | 71 | 68.5 | 67.5 | 68.5 | 68.5 | 57 | | |
| | Weight (g) | 0.77 | 0.733 | 0.717 | 0.716 | 0.717 | 0.632 | | |
| | Weight/Length (mg/mm) | 10.85 | 10.70 | 10.62 | 10.45 | 10.47 | 11.09 | 10.70 | 0.22 |
| #112 | Length (mm) | 71.5 | 71.5 | 71.5 | 71.5 | 72.5 | 73 | | |
| | Weight (g) | 0.784 | 0.772 | 0.77 | 0.777 | 0.779 | 0.775 | | |
| | Weight/Length (mg/mm) | 10.97 | 10.80 | 10.77 | 10.87 | 10.74 | 10.62 | 10.79 | 0.11 |
| #113 | Length (mm) | 73.7 | 71.5 | 70.7 | 72.7 | 71.5 | 72.5 | | |
| | Weight (g) | 0.778 | 0.759 | 0.78 | 0.815 | 0.799 | 0.826 | | |
| | Weight/Length (mg/mm) | 10.56 | 10.62 | 11.03 | 11.21 | 11.17 | 11.39 | 11.00 | 0.31 |

Note:
SD is an abbreviation for standard deviation

Silicone Coated PET Graft Leak Tests (ISO 7198—Whole Graft Leak Testing) are described below in Table 20.

TABLE 20

| Sample # | Silicone Coverage (mg/cm$^2$) | Permeability (ml/min/cm$^2$) | Comments on Leakage at 120 mmHg | Delamination at 600 mmHg |
|---|---|---|---|---|
| # 111 | 10.3 | 0.00 | Near water tight | Yes |
| # 112 | 10.5 | 0.04 | Heavy Beading from Peaks | No |
| # 113 | 10.5 | 0.06 | Heavy Beading from Peaks | No |
| # 114 | 10.9 | 0.02 | Beading | No |
| # 116 | 14.2 | 0.01 | Bubble delamination at seams | Yes |
| # 117 | 14.0 | 0.49 | Heavy Beading from Peaks | No |
| # 118 | 14.2 | 0.02 | Beading at Peaks | Yes |
| # 119 | 15.3 | n/a | Full Delamination | n/a |
| # 120 | 13.4 | 0.58 | Heavy Beading from Peaks & Delamination at Bulge | n/a |
| # 121 | 12.1 | 0.34 | Delamination at Bulge | n/a |

Observations and Conclusions:
Spray coating methods using forced air provided a consistent and an even coverage of silicone deposition throughout the length of the woven PET crimped graft.

For Samples #111-114, spray parameters had a 25% dispersion loss during the spraying process, where actual silicone coverage (10.5 mg/cm$^2$) was less than targeted coverage (14 mg/cm$^2$). This dispersion loss is believed to be due to the forced air flow from the fume hood. It may be beneficial to shield the graft and nozzle from the high extraction flow to reduce direct dispersion loss during spraying. This dispersion loss was accounted for during preparation of Samples #116-121. For Samples #116-121, actual silicone coverage was between 12.1 and 15.3 mg/cm$^2$. These results show that the process has a reasonably good level of control and repeatability.

Average water permeability of silicone sprayed grafts was 0.03 ml/min/cm$^2$. All silicone coated graft samples demonstrated water beading from the crimped graft peaks during the leak testing at 120 mmHg. Under these test conditions, 12% masking agent concentration may be too high to permit full and reliable adhesion of the silicone to the graft without potential delamination.

During pressure leak testing, the weakest attachment strength of silicone to the textile or fabric appeared consistently to be at the seams of the woven PET graft. Samples #111, 116, and 118 demonstrated a bubble delamination on opposing graft seams. These observations suggest that the masking coverage may be affected by the localized variation in the weave structure on the seams of the graft. While not being bound by any particular theory, it is proposed this is due to the locally tight weave structure of the graft seam which presumably retains a higher mask concentration and/or offers a less texturized surface for the silicone attachment.

As used herein a seam may refer to a discontinuity or a controlled change in a textile pattern along a portion of a textile graft, such as for example an edge of a flat woven tubular graft. The seam may be caused by a change in yarn density. The change in yarn density may be influenced by adding or dropping yarn ends during weaving or the like. The change in yarn density may also be influenced by changing relative spacing of the yarns within the textile pattern.

For the Valsalva samples #120 and 121, the predominant area for delamination was on the Valsalva bulge adjacent to the transition to the crimped body. Although only hypothesis and not being bound by such hypothesis, it is believed that the masking agent wiping process employed was less effective at removing excess masking agent from this localized area, as the non-crimped bulge passed through the rollers and transitioned to the crimped body. The process to remove excess masking may therefore, if desired, be modified to accommodate any transitions between graft structure, e.g. crimped to non-crimped or additional branches, etc. For example, selective application of masking agent may be used where such portions of the graft may have lower level of applied masking agent as compared to the other portions of the graft. Alternately, or in addition to, selective removal of excess agent may be applied, including selective removal at just desired portion of the graft.

Thus, the spraying of the textiles of the present invention with the use of forced air has been demonstrated as an effective method of controllably adding sealant or sealing agent. Any suitable agent or sealant, such as, but not limited to, silicone, room temperature vulcanizing silicone, thermoplastic polyurethane, aliphatic polycarbonate, one or more thermoplastic elastomers, polycarbonate, and combinations thereof with or without solvent may be used.

Silicone Spraying Trials Using Ultrasonic Application Techniques:

The spraying silicone using ultrasonic on the exterior surface of a woven PET graft was investigated. Woven PET straight grafts were spray coated using a target silicone coverage. The ability for the sprayer to apply an even silicone coating across the length of the graft using ultrasonic techniques was investigated. The silicone coated grafts were tested for leakage.

Spray Equipment and Methods:

Automatic spraying system that utilized ultrasonic nozzles to atomize solutions to spray coat various substrates was used. Three benchtop models of the system included: (1) 400 (400×400 mm stage), (2) prism 500 (500×500 mm stage), and (3) prism 800 (800×800 mm stage). Listed below were the variables for the spraying experiments.

1. Silicone MED6-6606 (NuSil) Percent Solids Concentration:
    a. Original Percent Solids: 30%.
    b. Diluted Percent Solids: 24% (4:1 MED6-6606: Additional Heptane).
    c. 2 mL of MED51-4900-7 COLOR MASTER BATCH FOR LIQUID SILICONE ELASTOMERS was added to approximately 90 mL of diluted solution.

2. Head Type—Frequency of ultrasonics: ILDS Ultrasonic head from Ultrasonic Systems, Inc., Haverhill, Mass., USA.

3. Flow Rate—Syringe pump driven: 2.1 mL/min.

4. Head speed: 7-21 mm/sec.

5. Head Height: 10-20 mm.

6. Air Direction Pressure: 10-15 psig (or about 70-105 kPa gauge).

7. PM: 500.

8. Stroke Length: 110 mm.

9. #of Passes: 4-16 (Dependent of flowrate, and amount needed to deposit).

10. Time (Dependent on number of passes and head speed).

Methods:

For samples 64, non-crimped PET grafts (about 14 mm ID) were cut into about 8 to 10 cm segments. Each segment was loaded onto the spindle mandrel and secured with tape. The recipes with parameters listed below in the test matrix were completed for each sample.

For samples 45, crimped PET grafts (about 14 mm ID) were stretched out to 28 cm and cut into 4 equal parts, approximately 110 mm total when fully stretched. Each sample was placed on the spindle mandrel and coated with the below parameter listed in the test matrix above. Each sample was evaluated for its ability to seal according to ISO 7198: Whole graft permeability.

Results:

TABLE 21

PET Graft Sample Silicone Spray Coating Parameters

| Sample Number | Flow Rate | Head Speed | Head Height | Air Dir Press | RPM | # Passes | Time Top | Oven Temp |
|---|---|---|---|---|---|---|---|---|
| 64-7A | 2.1 | 21 | 20 | 10 | 500 | 12 | 0:01:07 | RT |
| 64-7B | 2.1 | 21 | 20 | 10 | 500 | 12 | 0:01:07 | RT |
| 64-7C | 2.1 | 21 | 20 | 10 | 500 | 8 | 0:00:45 | RT |
| 64-11A | 2.1 | 21 | 20 | 10 | 500 | 8 | 0:00:45 | RT |
| 64-11B | 2.1 | 21 | 10 | 10 | 500 | 8 | 0:00:45 | RT |
| 64-11-C | 2.1 | 21 | 10 | 15 | 500 | 8 | 0:00:44 | RT |
| 64-12A | 2.1 | 21 | 10 | 15 | 500 | 12 | 0:01:07 | RT |
| 64-12B | 2.1 | 10.5 | 10 | 15 | 500 | 12 | 0:02:10 | RT |
| 64-12-C | 2.1 | 10.5 | 10 | 15 | 500 | 6 | 0:01:05 | RT |
| 64-8A | 2.1 | 21 | 20 | 10 | 500 | 8 | 0:00:45 | 55 |
| 64-8B | 2.1 | 21 | 20 | 10 | 500 | 4 | 0:00:22 | RT |
| 64-8C | 2.1 | 21 | 20 | 10 | 500 | 4 | 0:00:22 | 55 |
| 45-17A | 2.1 | 21 | 20 | 10 | 500 | 12 | 0:01:07 | RT |
| 45-17B | 2.1 | 21 | 20 | 10 | 500 | 8 | 0:00:44 | RT |
| 45-17C | 2.1 | 21 | 20 | 10 | 500 | 16 | 0:01:29 | RT |
| 45-17D | 2.1 | 21 | 10 | 10 | 500 | 12 | 0:01:07 | RT |
| 45-18A | 2.1 | 21 | 10 | 10 | 500 | 8 | 0:00:45 | RT |
| 45-18B | 2.1 | 21 | 10 | 10 | 500 | 16 | 0:01:29 | RT |
| 45-18C | 2.1 | 21 | 20 | 10 | 500 | 4 | 0:00:22 | RT |
| 45-18D | 2.1 | 14 | 20 | 10 | 500 | 8 | 0:01:05 | RT |
| 45-21A | 2.1 | 7 | 20 | 10 | 500 | 4 | 0:01:04 | RT |
| 45-21B | 2.1 | 10.5 | 20 | 10 | 500 | 12 | 0:02:10 | RT |
| 45-21C | 2.1 | 21 | 20 | 10 | 500 | 8 | 0:00:45 | RT |
| 45-21D | 2.1 | 21 | 20 | 10 | 500 | 16 | 0:01:29 | RT |
| 45-14 | 2.1 | 21 | 20 | 10 | 500 | 15 | 0:03:13 | RT |

Note:
"RT" is room temperature

TABLE 22

Digital Measuring Microscope Cross-Sectional Penetration Depth Chart

| Graft Number | Coating Amount Target | Si Thickness - Fabric Surface (μm) | Fabric Thick (μm) | Penetration Depth (μm) | Penetration Depth (%) |
|---|---|---|---|---|---|
| 45-17C | 10.8 mg/cm² | 10 | 192 | 0 | |
| | | 231 | 146 | 0 | |
| | | 233 | 199 | 0 | |
| | | 150 | 252 | 78 | 31% |
| 45-18D | 8 mg/cm² | 45 | 95 | 0 | 0% |
| | | 13 | 108 | 0 | 0% |
| | | 65 | 130 | 0 | 0% |
| | | 20 | 171.65 | 60.112 | 35% |
| | | 24 | 164 | 62 | 38% |
| | | 39 | 60 | 0 | 0% |
| | | 13 | 169 | 69 | 41% |
| | | 38 | 184 | 57 | 31% |
| | | 37 | 73 | 0 | 0% |
| 45-21B | 16 mg/cm² | 85 | | | |
| | | 127.3 | | | |
| | | 170 | | | |
| | | 146 | | | |
| | | | 214.1 | 54.1 | 25% |
| | | 190 | 38.7 | 20% | |
| 64-11A | 5.4 mg/cm² | 24 | 166 | 51.5 | 31% |
| | | 0 | 194 | 101 | 52% |
| | | 97.8 | | | |
| | | 29 | | | |
| 64-12B | 16 mg/cm² | 110 | | 0 | |
| | | 130 | 130 | 0 | |
| | | 151 | 173 | 0 | |
| | | 160 | 166 | 95 | 57% |
| | | 125 | 131 | 0 | |
| 64-12C | 8 mg/cm² | 63 | 220 | 0 | |
| | | 42 | 164 | 0 | |
| | | 91 | 60 | 0 | |
| | | 10 | 226 | 0 | |
| | | 29 | 189 | 75 | 40% |
| | | 93 | 85 | 0 | |
| | | 16 | 190 | 118 | 62% |
| 91145 sample 14 | Unknown | 23 | 123 | 45 | 37% |
| | | 45 | 207 | 0 | |
| | | 32 | 159 | 0 | |
| | | 0 | 174 | 75 | 43% |
| | | 28 | 96 | 0 | |
| | | 65 | 109 | 0 | |
| | | 11 | 96 | 0 | |
| | | 18 | 182 | 63 | 35% |
| Noanix | Unknown | No Coating Visible | | | |

TABLE 23

Permeability and Delamination Testing
(ISO 7198 - Whole Graft Leak Test)
Pressure (psig) 2.4
Ran for 30 secs

| Number | Coat (mg/cm^2) | Crimp/Straight | Leak? | Amount leaked (mL) | Delamination |
|---|---|---|---|---|---|
| 45-18C | 2.7 | Crimp | Yes | 440 | No |
| 45-17B | 5.4 | Crimp | Yes | 256 | No |
| 45-21A | 8 | Crimp | Yes | ~15 | No |
| 45-17C | 10.8 | Crimp | | | No |
| 45-21B | 16 | Crimp | | | No |
| 64-8B | 2.7 | Straight | Yes | 467 | No |
| 64-11A | 5.4 | Straight | Yes | 470 | No |
| 64-12C | 8 | Straight | No | 0 | No |
| 64-12B | 16 | Straight | No | 0 | No |

Observations and Conclusions:

Spray coating using Ultrasonic and force air shaping with a spinning substrate on 14 mm inner diameter non-crimped and crimped woven PET grafts provided an even coverage when assessed visually, a 24% solids silicone content was used with Ultrasonic. No masking agent was used before silicone was applied.

Using ultrasonic spraying methods, silicone coverage levels are directly correlated to speed of head, ultrasonic frequency, rotational speed of graft, height of spray nozzle away from substrate, and flow rate of dispersion.

Leak testing demonstrated that silicone did not delaminate, however, grafts did see varying levels of permeability based on the amount and thickness of silicone applied. Blue dye aids in cross-sectional imaging and penetration depth. The depth varies depending on the large intestacies of the base fabric. PVP masking agent does affect penetration depth.

Masking Agent Deposition Examples

Various Masking Agent compositions, application methods, drying methods and washing methods on PET graft material were explored. Testing included Polyvinylpyrrolidone (PVP) in water, PVP/Glycerol in water, and PVP in Glycerol as masking agents.

Methods:

Masking Solution A (PVP/Glycerol in Water) Preparation:
PVP Masking solutions found in Table 1 and 2 were created. Each solution was made by mixing water and PVP in a small collection container, then adding glycerol, if any, and dye.

TABLE 24

Solution Concentrations for Round 1 of Masking Agent Deposition Testing

| Sample No. | Total Solution Mass (g) | Mass of Water (g) | Glycerol Mass (g) | | | | | PVP Mass (g) | | | | |
|---|---|---|---|---|---|---|---|---|---|---|---|---|
| | | | 0% | 10% | 25% | 40% | 50% | 5% | 10% | 25% | 40% | 50% |
| 1 | 30 | 28.5 | 0.0 | | | | | 1.5 | | | | |
| 2 | 30 | 27.0 | 0.0 | | | | | | 3.0 | | | |
| 3 | 30 | 22.5 | 0.0 | | | | | | | 7.5 | | |
| 4 | 30 | 18.0 | 0.0 | | | | | | | | 12.0 | |
| 5 | 30 | 15.0 | 0.0 | | | | | | | | | 15.0 |
| 6 | 30 | 25.5 | | 3.0 | | | | 1.5 | | | | |
| 7 | 30 | 24.0 | | 3.0 | | | | | 3.0 | | | |
| 8 | 30 | 19.5 | | 3.0 | | | | | | 7.5 | | |
| 9 | 30 | 15.0 | | 3.0 | | | | | | | 12.0 | |
| 10 | 30 | 12.0 | | 3.0 | | | | | | | | 15.0 |

TABLE 24-continued

Solution Concentrations for Round 1 of Masking Agent Deposition Testing

| | | | Mass (g) | | | | | | | | | |
|---|---|---|---|---|---|---|---|---|---|---|---|---|
| Sample No. | Total Solution Mass (g) | Mass of Water (g) | Glycerol Mass (g) | | | | | PVP Mass (g) | | | | |
| | | | 0% | 10% | 25% | 40% | 50% | 5% | 10% | 25% | 40% | 50% |
| 11 | 30 | 21.0 | | 7.5 | | | | 1.5 | | | | |
| 12 | 30 | 19.5 | | 7.5 | | | | | 3.0 | | | |
| 13 | 30 | 15.0 | | 7.5 | | | | | | 7.5 | | |
| 14 | 30 | 10.5 | | 7.5 | | | | | | | 12.0 | |
| 15 | 30 | 7.5 | | 7.5 | | | | | | | | 15.0 |
| 16 | 30 | 16.5 | | | 12.0 | | | 1.5 | | | | |
| 17 | 30 | 15.0 | | | 12.0 | | | | 3.0 | | | |
| 18 | 30 | 10.5 | | | 12.0 | | | | | 7.5 | | |
| 19 | 30 | 6.0 | | | 12.0 | | | | | | 12.0 | |
| 20 | 30 | 3.0 | | | 12.0 | | | | | | | 15.0 |
| 21 | 30 | 13.5 | | | | | 15.0 | 1.5 | | | | |
| 22 | 30 | 12.0 | | | | | 15.0 | | 3.0 | | | |
| 23 | 30 | 7.5 | | | | | 15.0 | | | 7.5 | | |
| 24 | 30 | 3.0 | | | | | 15.0 | | | | 12.0 | |
| 25 | 30 | 0.0 | | | | | 15.0 | | | | | 15.0 |

TABLE 25

Application Methods for Round 1 of Masking Agent Deposition Testing

| | Sample # (refer to Test Matrix) Application Method | | | | |
|---|---|---|---|---|---|
| Sample No. | 1A | 1B | 1C | 1D | 2 |
| 1 | 1 | 6 | 11 | 16 | 21 |
| 2 | 2 | 7 | 12 | 17 | 22 |
| 3 | 3 | 8 | 13 | 18 | 23 |
| 4 | 4 | 9 | 14 | 19 | 24 |
| 5 | 5 | 10 | 15 | 20 | 25 |
| 6 | 26 | 31 | 36 | 10 | 46 |
| 7 | 27 | 32 | 37 | 42 | 47 |
| 8 | 28 | 33 | 38 | 43 | 48 |
| 9 | 29 | 34 | 39 | 44 | 49 |
| 10 | 30 | 35 | 40 | 45 | 50 |
| 11 | 51 | 56 | 61 | 66 | 71 |
| 12 | 52 | 57 | 62 | 67 | 72 |
| 13 | 53 | 58 | 63 | 68 | 73 |
| 14 | 54 | 59 | 64 | 69 | 74 |
| 15 | 55 | 60 | 65 | 70 | 75 |
| 16 | 76 | 81 | 86 | 91 | 96 |
| 17 | 77 | 82 | 87 | 92 | 97 |
| 18 | 78 | 83 | 88 | 93 | 98 |
| 19 | 79 | 84 | 89 | 94 | 99 |
| 20 | 80 | 85 | 90 | 95 | 100 |
| 21 | 101 | 106 | 111 | 116 | 121 |
| 22 | 102 | 107 | 112 | 117 | 122 |
| 23 | 103 | 108 | 113 | 118 | 123 |
| 24 | 104 | 109 | 114 | 119 | 124 |
| 25 | 105 | 110 | 115 | 120 | 125 |

TABLE 26

Solution Concentrations for Round 2 of Masking Agent Deposition Testing

| | | | Mass (g) | | | | | | |
|---|---|---|---|---|---|---|---|---|---|
| Sample No. | Total Solution Mass (g) | Mass of Water (g) | Glycerol Mass (g) | | | | PVP Mass (g) | | |
| | | | 0% | 2% | 6% | 8% | 10% | 15% | 20% |
| 1 | 20 | 18.0 | 0.0 | | | | 2.0 | | |
| 2 | 20 | 17.0 | 0.0 | | | | | 3.0 | |
| 3 | 20 | 16.0 | 0.0 | | | | | | 4.0 |
| 4 | 20 | 17.6 | | 0.4 | | | 2.0 | | |
| 5 | 20 | 16.6 | | 0.4 | | | | 3.0 | |
| 6 | 20 | 15.6 | | 0.4 | | | | | 4.0 |
| 7 | 20 | 16.8 | | | 1.2 | | 2.0 | | |
| 8 | 20 | 15.8 | | | 1.2 | | | 3.0 | |
| 9 | 20 | 14.8 | | | 1.2 | | | | 4.0 |
| 10 | 20 | 16.4 | | | | 1.6 | 2.0 | | |
| 11 | 20 | 15.4 | | | | 1.6 | | 3.0 | |
| 12 | 20 | 14.4 | | | | 1.6 | | | 4.0 |

TABLE 27

Application Methods for Round 2 of Masking Agent Deposition Testing

| | Sample # (refer to Test Matrix) Application Method | | | | |
|---|---|---|---|---|---|
| Sample No. | 1A | 1B | 1C | 1D | 2 |
| 1 | 1 | 2 | 3 | 4 | 5 |
| 2 | 6 | 7 | 8 | 9 | 10 |
| 3 | 11 | 12 | 13 | 14 | 15 |
| 4 | 16 | 17 | 18 | 19 | 20 |
| 5 | 21 | 22 | 23 | 24 | 25 |
| 6 | 26 | 27 | 28 | 29 | 30 |
| 7 | 31 | 32 | 33 | 34 | 35 |
| 8 | 36 | 37 | 38 | 39 | 40 |
| 9 | 41 | 42 | 43 | 44 | 45 |
| 10 | 46 | 47 | 48 | 49 | 50 |
| 11 | 51 | 52 | 53 | 54 | 55 |
| 12 | 56 | 57 | 58 | 59 | 60 |

Masking Solution B (PVP in Glycerol) Preparation:

Four PVP solutions for deposition were created: (1) 25% w/w PVP in water, (2) 50% w/w PVP in water, (3) 25% w/w PVP in glycerol and (4) 50% w/w PVP in glycerol. Each solution was made by mixing PVP with glycerol in a small collection container and heated for 10 minutes.

Masking Application Methods:

For each Masking solution A and B, the following five application methods were used to deposit the masking solution onto a petri dish or straight onto a PET sample.

Application Method 1A: Coated the petri dish with 0.5 mL of solution and laid woven PET coupon sample on top of the spread solution. The sample was air dried.

Application Method 1B: Coated the petri dish with 0.5 mL of solution and laid woven PET coupon sample on top of spread solution. Place deposition weight on top of the sample. The sample was air dried.

Application Method 1C: Coated the petri dish with 4 mL of solution and allowed the solution to air dry on the bottom of the dish.

Application Method 1D: Coated petri dish with 4 mL of solution and placed in 50° C. oven to dry. Checked sample after 30 minutes in the oven and made visual observations. If all water appears to have evaporated, sample was removed from oven and make observations described below. If water had not evaporated, continued to check samples every 15 minutes until samples were dry and can be removed from the oven. When removed, proceed with observations described below.

Application Method 2: Placed the woven PET coupon sample in the petri dish and used transfer pipet to coat the sample with 0.5 mL of solution. Dropped the solution in an evenly distributed manner to the top face of the sample. The sample was air dried.

Application Method 3: Immersion of woven PET crimped graft in the Mask solution.

Masking Drying Techniques:

Used heat during the drying process to assess the influence of the masking agent during the drying process. Investigated the influence of (1) ambient air flow with rotation after Mask application method 3, (2) heat using an oven after Mask application method 1D, (3) irradiated heat using heated internal mandrel after Mask application method 3, (4) forced hot air 33 mm away from the sample after Mask application method 3, and (5) hot air flow through the inner diameter of the PET graft sample after Mask application method 3.

Masking agent drying techniques of forced hot air on exterior (A), heated internal mandrel (B), and hot air flow through the inner diameter of the PET graft sample.

Masking Agent Observations:

After deposition of Masking solution, the samples were allowed to dry. Round 1 samples were dried for 90 hours, and Round 2 samples were dried for 21 hours. After drying, results were documented based on the following parameters:

1. Visual Inspection:
Noted any visual abnormalities in the deposition or dissemination of the solution on the test sample. Took photograph of each dried sample from the top and bottom of each dried sample to note the drying pattern and wicking penetration of each sample.

2. Brittleness/Stiffness:
Manually manipulated each sample to test its brittleness. Rated the brittleness on a 0-5 scale where 0 is indistinguishable and 5 is glazed icing. Used 18 g blunt tip needle to puncture sample and make observations on whether the sample is sticky, tacky, or brittle.

3. Drying Time:
Note the time allowed for the sample to dry and/or time points at which observations were made on the sample.

Results:

PVP/Glycerol in Water Mask:

PVP concentration 10% and 15% produced the most "fabric like" samples. PVP concentration >25% were too hard and brittle without having glycerol present. Glycerol concentrations of 0% and 6% produced the most "fabric like" samples. Glycerol concentration >10% tended not to dry.

Generally, an even material distribution and 100% penetration for method 1 (pipetting masking agent solution onto the woven PET coupon sample) and method 2 (placing the woven PET coupon sample on top of the masking agent solution) was obtained; therefore, no major differences between the two methods were observed. Added weight or force on a coupon sample laying on top of the masking agent solution created a drying pattern gradient, where less masking agent concentrated in the center of the PET sample (PET sample under the weight), and less or no masking agent present around the edges of PET sample, where there was no added weight.

There was no major difference in visual inspection, brittleness, or drying time for PVP in water masking agent solutions deposited with heat when compared to samples of the same concentration with no heat.

PVP in Glycerol Mask:

Solutions of PVP in glycerol (no water) may be used as a masking agent. Concentrations of 50% w/w PVP fully dissolves in glycerol with heat and stirring. An even masking agent distribution and controlled wick of masking agent was observed for 25% w/w and 50% w/w PVP in glycerol solution. The PVP/glycerol masking agent solution tends to perform like a heavy syrup or molasses during wicking. The PVP/glycerol masking agent solution may have a viscosity from about 2,000 to about 100,000 centipoise at room temperature, more desirably a viscosity from about 50,000 to about 100,000 centipoise at room temperature. Viscosity ranges of from about 5,000 to about 100,000 centipoise at room temperature; from about 10,000 to about 100,000 centipoise at room temperature; from about 15,000 to about 100,000 centipoise at room temperature; from about 20,000 to about 100,000 centipoise at room temperature; from about 25,000 to about 100,000 centipoise at room temperature; from about 30,000 to about 100,000 centipoise at room temperature; from about 35,000 to about 100,000 centipoise at room temperature; from about 40,000 to about 100,000 centipoise at room temperature; from about 50,000 to about 100,000 centipoise at room temperature; from about 55,000 to about 100,000 centipoise at room temperature; from about 60,000 to about 100,000 centipoise at room temperature; from about 65,000 to about 100,000 centipoise at room temperature; from about 70,000 to about 100,000 centipoise at room temperature; from about 75,000 to about 100,000 centipoise at room temperature; from about 80,000 to about 100,000 centipoise at room temperature; from about 70,000 to about 90,000 centipoise at room temperature; are also useful. Masking agent solutions of 12% and 20% PVP in water had viscosities of less than about 20 centipoise at room temperature. Glycerol was tested to have a viscosity of about 210 centipoise at room temperature. A 50% PVP in glycerol has a viscosity of greater than 80,000 centipoise at room temperature. Surface tension (pendant drop method) was measured at about 70 mN/m for water, about 65 mN/m for glycerol, 64 mN/m for 20% PVP in water; and about 68 mN/m for 12% PVP in water. These tests were all done within about twenty minutes. The PVP in glycerol samples were so viscous that results could not be measured within the normal twenty minute time period. The use or application of the PVP/glycerol masking agent solution has the advantage of controlling or minimizing wicking of the agent solution through the textile fibers, thereby possibly minimizing or eliminating the need for selective removal of the PVP/glycerol masking agent solution from undesired portion of the textile graft.

Mask Drying Techniques:

masking agent are desirably but not necessarily open to ambient air during drying. The drying techniques are not limited to PVP or polyvinylpyrrolidone, and the drying techniques may be used on any suitable masking agent formulations, such as but not limited to, polyvinylpyrrolidone glycerol, methyl cellulose, poly(ethylene glycol), polyethylene oxide, poly(ethylene glycol) hydrogel, and combinations thereof with or without water or other solvent.

Additional Observations of Mask on Woven PET crimped grafts were as follows:

TABLE 28

Fabric & Mask Weights For Drying Trials

| | Sample No. | | | | | | |
|---|---|---|---|---|---|---|---|
| | #109 A | #109 B | #109 C | #109 D | #109 A2 | #110 | #114 |
| Fabric | PET | PET | PET | PET | PET | PET | PET |
| Extended length (cm) | 24.5 | 25 | 25 | 24.7 | 24.7 | 23.5 | 34.5 |
| Surface Area (cmsq) | 169 | 173 | 173 | 171 | 171 | 162 | 152 |
| Mass fabric (mg) | 2311 | 2370 | 2363 | 2292 | 2309 | 2320 | 2124 |
| Drying Method | Flow Cabinet | Flow Cabinet | Hot Air Dryer | Heated Mandrel | Hot Internal air | Hot Internal air | Hot Internal air |
| Mass, Wet mask (mg) | 5553 | 5729 | 5417 | 5501 | 5529 | 5110 | |
| Mass, Dry mask (mg) | 2760 | 2817 | 2788 | 2706 | 2757 | 2720 | 2403 |
| Mass Mask added (mg) | 449 | 447 | 425 | 414 | 448 | 400 | 279 |
| Mass Mask/Fabric SA (mg/cmsq) | 2.65 | 2.59 | 2.46 | 2.43 | 2.63 | 2.46 | 1.84 |
| % Wt gain | 19.4% | 18.9% | 18.0% | 18.1% | 19.4% | 17.2% | 13.1% |
| Mass (post washing) (mg) | 2307 | | | | | | |

Masking agent coverage on woven PET crimped grafts varied based on masking agent drying techniques. Ambient air dried samples (#109A and 109B) looked identical and had a uniform blue color. Hot air dried sample (#109C) appeared significantly darker blue than all other samples, although it had a paler 'watermarked' area adjacent to the hairdryer fan and was additionally slightly bowed, presumably due to the air force from the fan. Heated manual sample (#109D) was very uniformly colored in the region directly adjacent to the heated mandrel. The crimp had also extended out in length in this region. In the zone above the heated mandrel the color was not as uniform and more closely resembled samples #109A & #109B. Also, in this zone, the crimps had not elongated in length, suggesting a differential in the drying sequence between the area directly heated and cooler area above.

Heat via oven did not appear to improve or hinder masking drying quality or decrease time of drying on woven PET coupon samples. However, heat increased PVP dissolvability in water and glycerol. Temperature and time are considerations for PVP and glycerol combinations with and without added water. Increased temperatures and/or increased rates of temperature increases may effect the final masking formulation. If heated too fast or too high, milky solutions may appear. Further, care should be taken not to "burn" the glycerol. Moderate temperatures and slow temperature increases are preferred. Heating conditions, including temperature, time and rate, should be selected so as not to degrade the masking agent components to a point where the function of the components are adversely effected. Some degradation, however, for example discoloration, may be acceptable or even desirable. For masking agent drying, a lid or cover over the masking agent coated woven PET coupon sample increased drying time. Woven PET samples with Ambient Dried Masking Agent With Rotation: Samples #109A and #109B demonstrated exterior graft body a uniform color, seam appears slightly darker blue, and color of inner surface appears identical to outer surface.

Hot Air Dried Mask on Exterior Surface of PET Graft: Sample #109C demonstrate exterior graft body a darker blue color compared to other samples and the color of inner surface appears a lighter blue compared to the outer surface.

Heated Mandrel Drying of Masking Agent From Interior Surface of PET Graft: Sample #109D demonstrated a uniformed exterior graft body color with inner and outer surfaces showing uniform depth of color.

Hot Air Flow Drying of Masking Agent Through Interior Surface of PET Graft: Sample #110 demonstrated a uniformed exterior color between the peaks and valleys of the crimped graft with a paler blue top surface compared to its bottom surface of the graft.

Visual assessment results of the inner and outer surface of each graft sample after masking agent are described below.

TABLE 29

| Sample # | Fabric | Masking Agent Drying Method | Outer and Inner Surface Different Colour Intensity Y/N | Overall Uniformity of Mask Coverage | Uniformity between Peak/Valley of Crimp |
|---|---|---|---|---|---|
| #109 A | PET | Ambient | N | Y | N |
| #109 B | PET | Ambient | N | Y | N |
| #109 C | PET | Hot Air External | Y | Y | N |
| #109 D | PET | Hot Mandrel | N | Y | Y |

TABLE 29-continued

| Sample # | Fabric | Masking Agent Drying Method | Outer and Inner Surface Different Colour Intensity Y/N | Overall Uniformity of Mask Coverage | Uniformity between Peak/Valley of Crimp |
|---|---|---|---|---|---|
| #109 A2 | PET | Hot Air Internal | Y | Y | N |
| #110 | PET | Hot Air Internal | Y | N | Y |
| #114 | PET | Hot Air Internal | Y | Y | N |

These results indicated that hot airflow around the outer graft surface may promote conglomeration of the masking agent on the outer surface (#109 C) and hot airflow through the internal lumen may promote conglomeration of masking agent on the inner surface (#109A2, #110, #114).

There was notable overall uniformity on graft sample #109A2 on both outside and inside surfaces, however this graft showed some variation between peaks and valleys of the crimps.

Graft sample #110, however, demonstrated some variation between the top and bottom faces, yet both faces showed considerable uniformity between peaks and valleys of the crimps.

For graft sample #109A2 (A) and #110 (B) after masking agent drying, there were inconsistencies between the funnelling of heated air through the inside of grafts #109A2, #110, #114 and this may have resulted in significant variation in the resultant airflow acting on the inner surface.

Mask Washing Process:

A blue water-soluble dye was added to the masking agent solution used for all samples in order to provide a visual indication of both location of masking agent and concentration of masking agent on the dried graft. Sample #109 A was applied with masking agent in an identical manner to #109 B and then subjected to a 90C 'Cotton Wash' to assess the viability of removal of the blue dye from the woven PET graft. It was unclear if the dye stained only the PVP Mask or if it can permanently stain the PET yarn and therefore dye cannot be fully removed during the wash cycle.

The mass of the graft was measured at each stage with the graft mass, post-wash returning to 2307 mg vs 2311 mg pre-mask application. This indicated that all PVP mask had been removed by the wash process, however after washing and drying #109A appeared to have a very pale blue color, as compared below alongside a fresh graft sample. The presence of this blue tone suggests that traces of blue dye can stain the PET graft permanently and is therefore may not be a good tool by itself for assessing or confirming the presence of PVP masking agent in the finished sealed graft post-washing.

Observations and Conclusions:

For PVP/Glycerol in water masks: Masking agent concentrations were most "fabric like" with PVP concentration <25% w/w (most preferred 10-15% w/w) and glycerol concentrations <10% w/w (most preferred 0-6% w/w). Glycerol concentrations >10% w/w did not completely dry. PVP concentrations >25% w/w (at low glycerol concentrations) seemed hard and brittle. Heat increased the ability for PVP to dissolve in water.

For PVP in glycerol (no water) masks: PVP/glycerol may be used as a masking agent without any added water. Concentrations of 50% w/w PVP were fully dissolved in glycerol with heat and stirring. An even masking agent distribution during application and controlled wicking of making agent was observed while using 50% w/w PVP in glycerol. The PVP/glycerol masking agent solution tended to perform like molasses during wicking, whereas the PVP/glycerol/water masking agent solution tended to perform like water during wicking. Excess masking agent on the outside of the graft can be removed or washed off with water.

PVP/Glycerol without added water may contain trace amounts of moisture from exposure, for example, from atmospheric conditions. As used herein PVP/Glycerol without added water may be substantially free of water, for example less than 0.5 weight percent water, more desirably less than 0.1 weight percent water, including less that 0.01 weight percent water. For PVP/Glycerol formulations with purposely added water, it is believed that the added water may wick to some degree through the fibers of the yarn. Having PVP/Glycerol without added water does not present such a wicking problem.

Masking agent solutions of PEG in Water were also prepared. In particular, nine PEG solutions for deposition were created as follows: (1) 10% w/w PEG (MW 600) in water, (2) 25% w/w PEG (MW 600) in water, (3) 50% w/w PEG (MW 600) in water, (4) 10% w/w PEG (MW 4000) in water, (5) 25% w/w PEG (MW 4000) in water, (6) 50% w/w PEG (MW 4000) in water, (7) 10% w/w PEG (MW 8000) in water, (8) 25% w/w PEG (MW 8000) in water and (9) 50% w/w PEG (MW 8000) in water. Each solution was made by mixing PEG with water in a small collection container. The PEG masking samples tested at 10% w/w concentration did not dry completely. PEG (MW 600) masking samples remained liquid at all concentrations tested. PEG (MW 4000, MW 8000) masking samples were almost completely solid at 50%. PEG masking samples at 50% w/w concentration did not completely dissolve. PEG (MW 600, 4000, and 8000) dissolved into water <50% w/w concentration and demonstrated to be a good potential polymer for the masking agent. PEG MW 600 remained liquid (i.e. never fully dried) for all concentrations (10%, 25%, 50%), PEG MW 4000 and 8000 were essentially a solid at 50%. PEG at 50% concentration did not completely dissolve, but PEG masking agent solutions at 45% w/w or less will likely dissolve. All PEG masking solutions cracked after the drying process. PEG samples crack similar to "desert cracks" (large, protruded cracks), whereas PVP samples crack similar to "window glass cracks" (small, micro channel cracking). The use of a plasticizer, such as glycerol may eliminate or minimize the presence of cracks.

Removing excess masking agent from the outside of the graft surface may be accomplished by subjecting the outside of the graft to a wash or mist of water or other wash solvent. The step of removing excess masking agent may include having the graft disposed over a mandrel, such as mandrel 20. As described herein, the mandrel 20 may offer a solid exterior surface for which may act as a barrier from water washing the masking agent from the interior portions of the graft. Alternatively, or in addition to, mandrel 20 may have holes or perforations through which a medium, such as air or nitrogen, may flow to act as a further barrier against water from washing the masking agent from the interior portion of the graft.

Masking Agent Application Methods: No masking agent deposition differences between pipetting masking agent directly onto the graft and graft placed on top of masking agent solution. Added weight (a nickel) dispersed the wicking of the masking agent and created an obvious gradient in the masking agent drying pattern. More masking agent was present on the graft where weight was not applied. The masking agent mass applied per unit surface area for PET samples was relatively consistent which indicates that the immersion dipping process is reasonably consistent. An even masking agent distribution and 100% penetration for all application methods: (a) Graft material placed on top of masking agent solution for wicking, (b) pipet masking agent solution on top of the graft material and (c) immersion dipping of graft.

Mask Drying Methods: Oven drying did not affect masking agent drying compared to ambient air. Covered drying at room temperature or using heat increases masking agent drying time. Warm airflow around the graft surface appeared to have a significant effect on the masking agent drying mechanism and can be used to influence the final location and conglomeration of masking agent. The application of hot airflow through the inside of the graft appeared to promote the conglomeration of masking agent on the inner surface which provides an attractive process feature in ensuring the inner graft surface is free of silicone dispersion whilst minimizing masking agent presence on the outer surface that could reduce Silicone to fabric adhesion levels. The horizontal rotation of the graft during the masking agent drying process remained a valuable process aid to provide a perfectly straight (co-axial) graft for subsequent spray coating process, otherwise the graft dries in a bow shape. The horizontal rotation during drying process may be included when considering methods to apply warm airflow.

Mask Washing Process: Blue dye added to masking agent solution provides a useful indication of both the dried masking agent location and concentration/conglomeration, however the dye may stain the PET graft permanently and is therefore may not a good tool for assessing or confirming the presence of PVP Mask in the finished sealed graft post-washing.

The PET graft edges and seam appeared to hold or absorb different amounts of Mask when compared to the main body of the graft due to the localized differences in weave structure and density.

Additional Testing on Textile Grafts:
Graft Tested: ATEX Technologies Polyester Vascular Graft; 14 mm Diameter, 28.5 crimps per inch (CPI)
Equipment and Materials:
I. 14 mm crimped polyester fabric (Atex Technologies)
II. Hothouse (HH) Spray Rig
III. Bespoke Mandrels
IV. Polyvinylpyrrolidone (PVP) Powder
V. NuSil MED-6606 RTV Silicone
VI N-Heptane
VII. Easy Composites Royal Blue Pigment
VIII. De-ionized water
IX. Magnetic Stirrer (VFT Asset ID:22)
X. Plastic Beakers
XI. Cable ties
XII. Single edge Razor Blades
XIII. Scales (VFT Asset ID:84)

Coating Variables:
The formulation of the masking agent and sealant composition are variables for consideration in controlling the effectiveness of the coating for the graft. Other factors that have been identified as being important include, but not limited to, masking agent drying method. The drying method was not varied in the below examples, and all grafts were dried in ambient air whilst being rotated.

In examples described earlier herein above, silicone was brushed on to ensure a large coverage was achieved, this was to ensure there was enough silicone on the graft to show penetration but also a good coverage to ensure delamination was demonstrated. There was also blue dye added to the silicone to help assess the penetration visually. The below examples were carried out on two sets of 26 samples. The first set had blue dye added to the silicone and the coverage was set at 14 mg/cm$^2$, these samples were used to assess penetration. The second set had silicone with no dye and the coverage was set at 20 mg/cm$^2$, these samples were used to test adhesion.

In addition to the above-described 52 samples, there was also be two control grafts C1 and C2. These were coated with silicone only with no mask application, C1 had the blue dye added to the silicone also.

Coating Variable Ranges:
The following values were used for the testing:
PVP Concentration in DI water: 1%, 2%, 4%, 6%, 8%, 10%, 12% 15%, 17%, and 20%.
Silicone dispersion concentration: 15% and 30%
Glycerol Concentrations used on each PVP concentrations: 5%, 10%, and 15%. These concentrations are percentage of Glycerol to PVP concentration.

The various samples prepared are shown in Table 30 below with target masking agent and sealant components as listed below.

TABLE 30

Test Matrix

| Sample ID Blue Dye | Sample ID No Dye | HH Sample ID Blue Dye | HH Sample ID No Dye | PVP Concentration (%) 1 | 2 | 4 | 6 | 8 | 10 | 12 | 15 | 17 | 20 | Glycerol Conc. (% of PVP) 5 | 10 | 15 | Silicone Conc. (%) 15 | 30 |
|---|---|---|---|---|---|---|---|---|---|---|---|---|---|---|---|---|---|---|
| C1 | C2 | 136A | 136B | | | | | | | | | | | | | | X | |
| 1 | 27 | 137A | 137B | X | | | | | | | | | | | | | X | |
| 2 | 28 | 138A | 138B | | X | | | | | | | | | | | | X | |
| 3 | 29 | 139A | 139B | | | X | | | | | | | | | | | X | |
| 4 | 30 | 142A | 142B | | | | X | | | | | | | | | | X | |
| 5 | 31 | 141A | 141B | | | | | X | | | | | | | | | X | |
| 6 | 32 | 140A | 140B | | | | | | X | | | | | | | | X | |
| 7 | 33 | 143A | 143B | | | | | | | X | | | | | | | X | |
| 8 | 34 | 144A | 144B | | | | | | | | X | | | | | | X | |
| 9 | 35 | 145A | 145B | | | | | | | | | X | | | | | X | |
| 10 | 36 | 146A | 146B | | | | | | | | | | X | | | | X | |
| 11 | 37 | 147A | 147B | | X | | | | | | | | | | X | | X | |
| 12 | 38 | 148A | 148B | | X | | | | | | | | | | | X | | X |

TABLE 30-continued

Test Matrix

| Sample ID | | HH Sample ID | | PVP Concentration (%) | | | | | | | | | | Glycerol Conc. (% of PVP) | | | Silicone Conc. (%) | |
|---|---|---|---|---|---|---|---|---|---|---|---|---|---|---|---|---|---|---|
| Blue Dye | No Dye | Blue Dye | No Dye | 1 | 2 | 4 | 6 | 8 | 10 | 12 | 15 | 17 | 20 | 5 | 10 | 15 | 15 | 30 |
| 13 | 39 | 149A | 149B | | | | | X | | | | | | X | | | X | |
| 14 | 40 | 150A | 150B | | | | | X | | | | | | | X | | X | |
| 15 | 41 | 151A | 151B | | | | | | | X | | | | X | | | X | |
| 16 | 42 | 152A | 152B | | | | | | | X | | | | | X | | X | |
| 17 | 43 | 153A | 153B | | | | | | | | | X | | X | | | X | |
| 18 | 44 | 154A | 154B | | | | | | | | | X | | | X | | X | |
| 19 | 45 | 155A | 155B | X | | | | | | | | | | X | | | X | |
| 20 | 46 | 156A | 156B | X | | | | | | | | | | X | | | | X |
| 21 | 47 | 157A | 157B | | | X | | | | | | | | X | | | X | |
| 22 | 48 | 158A | 158B | | | X | | | | | | | | X | | | | X |
| 23 | 49 | 159A | 159B | | | | | | X | | | | | X | | | X | |
| 24 | 50 | 160A | 160B | | | | | X | | | | | | X | | | | X |
| 25 | 51 | 161A | 161B | | | | | | | | | X | | X | | X | | |
| 26 | 52 | 162A | 162B | | | | | | | | | | X | X | | | | X |

Note:
Samples C1 and 1-26 had a coverage of about 14 mg/cm$^2$.
Samples C2 and 27-52 had a coverage of about 20 mg/cm$^2$.

Preparation Method:

Sample Preparation:

Each sample was removed from the store and assigned a HH sample ID number. Each sample was to be made up of a section of graft. Firstly, the graft was cut to length. The graft was fully stretched removing the crimp, and a section of 225 mm length was cut with a single edge razor blade, once cut the end was cauterized to prevent fraying. The sample was clean and free of any debris, if it is not then it is to be discarded or washed and allowed to dry. Weighed the cut graft and noted the weight on the test sheet. Marked each sample with the HH sample ID number using black ink.

Masking Agent Preparation:

To prepare the masking agent formulation, the quantities of the components needed were calculated. This was done by calculating the percentage of each based on the test matrix. The amount of each component was noted on the test sheet for each sample. The following steps were followed to make the masking agent formulation.

Placed the correct amount of de-ionized water into a 100 ml plastic beaker.
   Placed magnetic stirrer in the water and place the beaker on the magnetic stirrer.
   Turned the magnetic stirrer on at a speed of approximately 400 RPM at room temperature.
   Measured the correct weight of PVP and glycerol onto weighing boats.
   Added the PVP and Glycerol to the water.
   Stirred till there is no solute visible.

Masking Agent Application:

After the mask was fully prepared, the graft was coated. This was done by immersing the graft within the masking agent solution and agitating the graft by gloved hands, so it was fully coated inside and out.

Once the graft was saturated, the excess masking agent solution was removed by running the graft between a thumb and index finger. Next the graft was attached to a mandrel, this was done using cable ties. Cable tied one end of the graft to the mandrel, extended the graft to 60% of its overall extended length (135 mm), and cable tied the other end of the graft to the mandrel. The mandrel was then be placed horizontally on the rotisserie and allowed to air dry for 12 hours. Once dry, weighed the masked graft and noted the weight on the test sheet.

Sealant Preparation:

The sealant came supplied as a 30% solid content. For the samples requiring the 30% the sealant was used straight from the container. For the remainder of the samples the sealant was diluted. The correct amount of n-Heptane was added to reduce that solid content to 15%.

To allow for visualization of where the sealant is on grafts C1 and 1-26, blue dye was added to the silicone dispersion. The blue dye was to be added so that it amounted to 5% concentration with the solid content, i.e. at 15% solid content 15 g of dispersion has 2.25 g of solid content therefore you would add 0.11 g of dye.

The appropriate amount of silicone was measured out to give the target coverage of either 14 mg/cm$^2$ or 20 mg/cm$^2$ coverage, and it was loaded into one of the disposable syringe barrels. This amount accounted for a 25% loss when spraying, therefore the actual target spray levels were 17.5 mg/cm$^2$ and 25 mg/cm$^2$ respectively.

Sealant Application:

The spray head was flushed with n-Heptane to ensure correct flow. The mandrel with the graft was then mounted in the spray rig. The spray rig was set up to spray the entire length of graft. The syringe barrel with silicone was mounted onto the spray head. The graft was rotated at 150 RPM, and the rate of traverse was set to 20 mm/s. The spray head was started and traversed over the entire length of the graft, once it reached the opposite end the spray head was stopped and allowed to return to the start of the graft. The solvent was allowed to flash off before making another pass, the time taken for the solvent to flash off increased with the amount applied. After the first pass a time of 10 seconds was waited, after each additional pass another 10 seconds was added to the wait time up to a maximum of 40 seconds between each pass. This continued till there was no dispersion left in the syringe barrel or there was an insufficient amount to make another full pass. Once the graft was removed from the spray rig the spray head was flushed with n-Heptane again.

After application the graft was transferred to the rotisserie for a period of 12 hours then transferred to a stationary mount and allowed to air dry for a further 60 hours. Once dry, the sealed graft was weighed and the weight recorded.

Masking Agent Removal:

Once the graft was fully dried the mask was removed. This was done by washing the grafts in a washing machine on a "cotton cycle" at 90° C. (with no detergent). This caused the PVP to be dissolved in the water and removed, and also the high temperatures aided the curing of the silicone. When the wash was complete, the graft was hung up to air dry. Once the masking agent was removed and the graft was dry, the finished graft weight was recorded.

Testing Method:

Silicone Adherence:

Silicone adherence may be difficult to measure in that the force to peel the silicone and the force to break the very thin silicone are both extremely low. Therefore, one method to demonstrate if the graft has good adherence is to pressurize the sample and see if there are any signs of the silicone losing its bond from the graft. The pressure was to be increased slowly to a maximum pressure of 600 mmHg. The adherence was to be noted as follows:

0—Silicone is well adhered to graft and showing no signs of failure.
1—Graft reached the maximum pressure, but the leak rate has visibly increased.
2—Silicone coating has started to fail, showing jets of water coming from the graft.
3—Silicone coating has failed, and a bubble has appeared on the surface.

The adherence test was to be completed for all samples.

Penetration Depth:

The effectiveness of the masking agent was determined by how far the silicone wicked through the fabric. Ideally the silicone will sit on the outside surface of the graft and not penetrate the graft structure. If the masking agent was not effective, then the silicone may be visible within the fabric and on the inside edge. To visualize this, each graft was cut lengthways so that a cross section could be examined under high magnification. Particular attention was given to where this cut was made as the penetration may vary between the main body of the graft and at the seams. For comparative purposes a cross section was made at each position and the penetration noted at each.

As the depth cannot be measured the penetration was noted as follows:

0—Silicone only visible on the outer surface of the graft.
1—Silicone is visible between fibers of the graft but only up to 50% of the thickness.
2—Silicone is visible penetrating to the inside surface.
3—Silicone visible everywhere, the entire graft structure is blue.

The penetration depth test was completed for grafts C1 and 1-26 only.

Results & Analysis:

Table 31 below lists the measured weights of the masking agent and sealant formulations after the noted processing steps. Masking agent and sealant coverages are noted in the table.

TABLE 31

Weight Summary

| Sample No. | HH ID | Initial (mg) | After Masking and Drying (mg) | After Sealant and Curing (mg) | After Washing and Drying (mg) | Mask Coverage (mg/cm$^2$) | Sealant Coverage (mg/cm$^2$) |
|---|---|---|---|---|---|---|---|
| C1 | 136A | 1459 | 1459 | 3045 | 3041 | 0.000 | 15.2 |
| 1 | 137A | 1440 | 1451 | 2927 | 2918 | 0.107 | 14.4 |
| 2 | 138A | 1469 | 1495 | 2867 | 2839 | 0.246 | 13.0 |
| 3 | 139A | 1475 | 1532 | 2815 | 2756 | 0.540 | 12.1 |
| 4 | 142A | 1440 | 1590 | 3071 | 2915 | 1.439 | 14.2 |
| 5 | 141A | 1187 | 1307 | 2584 | 2468 | 1.428 | 15.2 |
| 6 | 140A | 1487 | 1578 | 3085 | 2993 | 0.855 | 14.1 |
| 7 | 143A | 1575 | 1799 | 3214 | 2995 | 2.005 | 12.7 |
| 8 | 144A | 1564 | 1867 | 3279 | 2973 | 2.681 | 12.5 |
| 9 | 145A | 1534 | 1862 | 3161 | 2835 | 3.044 | 12.1 |
| 10 | 146A | 1318 | 1645 | 3000 | 2677 | 3.474 | 14.4 |
| 11 | 147A | 1619 | 1690 | 3139 | 3074 | 0.621 | 12.7 |
| 12 | 148A | 1485 | 1557 | 2911 | 2841 | 0.679 | 12.8 |
| 13 | 149A | 1311 | 1422 | 2605 | 2493 | 1.190 | 12.7 |
| 14 | 150A | 1580 | 1723 | 3043 | 2899 | 1.270 | 11.7 |
| 15 | 151A | 1588 | 1810 | 2870 | 2650 | 1.979 | 9.5 |
| 16 | 152A | 1561 | 1805 | 3078 | 2834 | 2.219 | 11.6 |
| 17 | 153A | 1510 | 1901 | 3011 | 2625 | 3.599 | 10.3 |
| 18 | 154A | 1558 | 2029 | 3205 | 2745 | 4.216 | 10.6 |
| 19 | 155A | 1374 | 1426 | 2405 | 2350 | 0.537 | 10.1 |
| 20 | 156A | 1342 | 1395 | 2948 | 2901 | 0.560 | 16.5 |
| 21 | 157A | 1333 | 1452 | 2706 | 2589 | 1.247 | 13.2 |
| 22 | 158A | 1393 | 1503 | 2962 | 2852 | 1.107 | 14.7 |
| 23 | 159A | 1390 | 1600 | 2844 | 2633 | 2.132 | 12.6 |
| 24 | 160A | 1344 | 1525 | 3023 | 2842 | 1.905 | 15.8 |
| 25 | 161A | 1398 | 1776 | 3273 | 2904 | 3.737 | 14.9 |
| 26 | 162A | 1344 | 1722 | 3231 | 2857 | 3.979 | 15.9 |
| C2 | 136B | 1520 | 1520 | 3860 | 3857 | 0.000 | 21.6 |
| 27 | 137B | 1432 | 1444 | 3474 | 3470 | 0.117 | 19.8 |
| 28 | 138B | 1396 | 1428 | 3460 | 3439 | 0.321 | 20.5 |
| 29 | 139B | 1493 | 1556 | 3625 | 3573 | 0.602 | 19.9 |
| 30 | 142B | 1430 | 1582 | 3846 | 3711 | 1.509 | 22.6 |
| 31 | 141B | 1428 | 1543 | 3695 | 3604 | 1.147 | 21.7 |
| 32 | 140B | 1468 | 1570 | 3758 | 3571 | 1.004 | 20.7 |

TABLE 31-continued

Weight Summary

| Sample No. | HH ID | Initial (mg) | After Masking and Drying (mg) | After Sealant and Curing (mg) | After Washing and Drying (mg) | Mask Coverage (mg/cm$^2$) | Sealant Coverage (mg/cm$^2$) |
|---|---|---|---|---|---|---|---|
| 33 | 143B | 1533 | 1723 | 3758 | 3571 | 1.714 | 18.4 |
| 34 | 144B | 1539 | 1868 | 4044 | 3720 | 2.992 | 19.8 |
| 35 | 145B | 1523 | 1818 | 4034 | 3742 | 2.749 | 20.7 |
| 36 | 146B | 1350 | 1704 | 3743 | 3393 | 3.709 | 21.4 |
| 37 | 147B | 1459 | 1519 | 3649 | 3595 | 0.581 | 20.7 |
| 38 | 148B | 1578 | 1636 | 3618 | 3547 | 0.517 | 17.6 |
| 39 | 149B | 1266 | 1366 | 3074 | 2966 | 1.109 | 18.9 |
| 40 | 150B | 1495 | 1638 | 3172 | 3030 | 1.344 | 14.4 |
| 41 | 151B | 1556 | 1806 | 3289 | 3040 | 2.265 | 13.4 |
| 42 | 152B | 1482 | 1700 | 3108 | 2890 | 2.065 | 13.3 |
| 43 | 153B | 1560 | 2014 | 3509 | 3068 | 4.096 | 13.6 |
| 44 | 154B | 1578 | 2132 | 4480 | 3944 | 4.979 | 21.3 |
| 45 | 155B | 1263 | 1316 | 3473 | 3427 | 0.594 | 24.2 |
| 46 | 156B | 1321 | 1375 | 3489 | 3434 | 0.571 | 22.3 |
| 47 | 157B | 1324 | 1454 | 3681 | 3551 | 1.368 | 23.4 |
| 48 | 158B | 1286 | 1407 | 3524 | 3407 | 1.316 | 23.1 |
| 49 | 159B | 1287 | 1487 | 3644 | 3447 | 2.155 | 23.3 |
| 50 | 160B | 1294 | 1488 | 3508 | 3317 | 2.052 | 21.4 |
| 51 | 161B | 1270 | 1675 | 3802 | 3409 | 4.470 | 23.6 |
| 52 | 162B | 1305 | 1684 | 3781 | 3406 | 4.065 | 22.5 |

The above-described penetration grading of the sealant is listed in Table 32 below.

TABLE 32

Penetration

| Sample No. | HH ID | PVP (g) | Glycerol as % of PVP | Polymer Concentration (%) | Penetration Grading |
|---|---|---|---|---|---|
| C1 | 136A | 0 | 0 | 15 | 3 |
| 1 | 137A | 1 | 0 | 15 | 3 |
| 2 | 138A | 2 | 0 | 15 | 3 |
| 3 | 139A | 4 | 0 | 15 | 3 |
| 4 | 142A | 6 | 0 | 15 | 3 |
| 5 | 141A | 8 | 0 | 15 | 3 |
| 6 | 140A | 10 | 0 | 15 | 3 |
| 7 | 143A | 12 | 0 | 15 | 3 |
| 8 | 144A | 15 | 0 | 15 | 3 |
| 9 | 145A | 17 | 0 | 15 | 3 |
| 10 | 146A | 20 | 0 | 15 | 2 |
| 11 | 147A | 4 | 5 | 15 | 3 |
| 12 | 148A | 4 | 15 | 15 | 2 |
| 13 | 149A | 8 | 5 | 15 | 3 |
| 14 | 150A | 8 | 15 | 15 | 3 |
| 15 | 151A | 12 | 5 | 15 | 2 |
| 16 | 152A | 12 | 15 | 15 | 2 |
| 17 | 153A | 20 | 5 | 15 | 2 |
| 18 | 154A | 20 | 15 | 15 | 2 |
| 19 | 155A | 4 | 10 | 15 | 2 |
| 20 | 156A | 4 | 10 | 30 | 2 |
| 21 | 157A | 8 | 10 | 15 | 2 |
| 22 | 158A | 8 | 10 | 30 | 2 |
| 23 | 159A | 12 | 10 | 15 | 1 |
| 24 | 160A | 12 | 10 | 30 | 2 |
| 25 | 161A | 20 | 10 | 15 | 2 |
| 26 | 162A | 20 | 10 | 30 | 1 |

Permeability data at 120 mmHg and leakage data are 600 mmHg are shown below in Table 33.

TABLE 33

Adhesion

| Sample No. | HH ID | PVP (g) | Glycerol as % of PVP | Measured Leakage (ml/min) @ 120 mmHg | Measured Leakage (ml/min) @ 600 mmHg | Permeability at 120 mmHg (ml/min/cm$^2$) | Adhesion Grading Scale 0-3 |
|---|---|---|---|---|---|---|---|
| C1 | 136A | 0 | | 0 | | | |
| 1 | 137A | 1 | | 0 | | | |
| 2 | 138A | 2 | | 0 | | | |
| 3 | 139A | 4 | | 0 | | | |
| 4 | 140A | 6 | | 0 | | | |
| 5 | 141A | 8 | | 0 | | | |
| 6 | 142A | 10 | | 0 | | | |
| 7 | 143A | 12 | 0 | 0 | 4.8 | 0 | 1 |
| 8 | 144A | 15 | 0 | 2.8 | 27 | 0.05 | 1 |
| 9 | 145A | 17 | 0 | 2.8 | 21 | 0.05 | 1 |
| 10 | 146A | 20 | 0 | 7 | 43 | 0.14 | 1 |

TABLE 33-continued

Adhesion

| Sample No. | HH ID | PVP (g) | Glycerol as % of PVP | Measured Leakage (ml/min) @ 120 mmHg | Measured Leakage (ml/min) @ 600 mmHg | Permeability at 120 mmHg (ml/min/cm$^2$) | Adhesion Grading Scale 0-3 |
|---|---|---|---|---|---|---|---|
| 11 | 147A | 4 | 5 | 0 | 0 | 0 | 0 |
| 12 | 148A | 4 | 15 | 0 | 0 | 0 | 0 |
| 13 | 149A | 8 | 5 | 0 | 0 | 0 | 0 |
| 14 | 150A | 8 | 15 | 0 | 4.6 | 0 | 1 |
| 15 | 151A | 12 | 5 | 0 | 8.8 | 0 | 1 |
| 16 | 152A | 12 | 15 | 2.5 | 16 | 0.05 | 1 |
| 17 | 153A | 20 | 5 | 15 | 100 | 0.32 | 2 |
| 18 | 154A | 20 | 15 | Delaminated circumferentially | Delaminated circumferentially | 0 | 3 |
| 19 | 155A | 4 | 10 | 0 | 0 | 0 | 0 |
| 20 | 156A | 4 | 10 | 0 | 0 | 0 | 0 |
| 21 | 157A | 8 | 10 | 0 | Delaminated at the seam | 0 | 3 |
| 22 | 158A | 8 | 10 | 0 | Delaminated at the seam | 0 | 3 |
| 23 | 159A | 12 | 10 | 0 | Delaminated at the seam | 0 | |
| 24 | 160A | 12 | 10 | 0 | Delaminated at the seam | 0 | 3 |
| 25 | 161A | 20 | 10 | Delaminated | Delaminated | 0 | 3 |
| 26 | 162A | 20 | 10 | Delaminated | Delaminated | 0 | 3 |
| C2 | 136B | 0 | 0 | 0 | 0 | 0 | 0 |
| 27 | 137B | 1 | 0 | 0 | 0 | 0 | 0 |
| 28 | 138B | 2 | 0 | 0 | 0 | 0 | 0 |
| 29 | 139B | 4 | 0 | 0 | 0 | 0 | 0 |
| 30 | 142B | 6 | 0 | 0 | 0 | 0 | 0 |
| 31 | 141B | 8 | 0 | 0 | Delaminated at the seam | 0 | 3 |
| 32 | 140B | 10 | 0 | 0 | Delaminated at the seam | 0 | 3 |
| 33 | 143B | 12 | 0 | 0 | Delaminated at the seam | 0 | 3 |
| 34 | 144B | 15 | 0 | Delaminated circumferentially | Delaminated | 0 | 3 |
| 35 | 145B | 17 | 0 | 0 | Delaminated circumferentially | | 3 |
| 36 | 146B | 20 | 0 | Delaminated circumferentially | Delaminated circumferentially | 0 | 3 |
| 37 | 147B | 4 | 5 | 0 | 0 | 0 | 0 |
| 38 | 148B | 4 | 15 | 0.5 | 5.2 | 0.01 | 1 |
| 39 | 149B | 8 | 5 | 0 | 0 | 0 | 0 |
| 40 | 150B | 8 | 15 | 0 | 0 | 0 | 0 |
| 41 | 151B | 12 | 5 | 0 | Delaminated | 0 | 3 |
| 42 | 152B | 12 | 15 | 0 | Delaminated at the seam | 0 | 3 |
| 43 | 153B | 20 | 5 | Delaminated circumferentially | Delaminated | 0 | 3 |
| 44 | 154B | 20 | 15 | Delaminated | Delaminated | 0 | 3 |
| 45 | 155B | 4 | 10 | 0 | 0 | 0 | 0 |
| 46 | 156B | 4 | 10 | 0 | 0 | 0 | 0 |
| 47 | 157B | 8 | 10 | 0 | 0 | 0 | 0 |
| 48 | 158B | 8 | 10 | 0 | 0 | 0 | 0 |
| 49 | 159B | 12 | 10 | 0 | Delaminated at the seam | 0 | 3 |
| 50 | 160B | 12 | 10 | 0 | Delaminated at the seam | 0 | 3 |
| 51 | 161B | 20 | 10 | Delaminated | Delaminated | 0 | 3 |
| 52 | 162B | 20 | 10 | Delaminated | Delaminated | 0 | 3 |

Glycerol Concentration:

All samples in the above tables were considered for penetration and adhesion respectively, for each glycerol concentration and averaged. The addition of glycerol generally appeared to decrease penetration on 4-12% PVP, but had little effect in higher concentrations of 20%. With respect to adhesion the addition of glycerol appeared to have less effect at lower concentrations of PVP and tended to decrease adhesion at higher PVP concentrations.

Silicone Dispersion Concentration:

Looking at silicone concentrations showed no real significant difference between 15% or 30%. The penetration grading was so close when grading that they could be assumed to be the same for each PVP concentration. Therefore, there was no real difference in either case. One notable difference when spraying was that, the 30% silicone dispersion required much less time between coats and required less dispersion to be put on the graft, therefore the total time to coat these grafts was reduced.

Table 34 lists forces-to-extend values for the various samples tested.

TABLE 34

Handling

| HH Sample ID | PVP Mask Conc. (%) | Glycerol Conc. (% of PVP) | Polymer Conc. (%) | Silicone Coverage (mg/cm$^2$) | Force to Extend (Normalized with Circumference) (N/mm) |
|---|---|---|---|---|---|
| 136(A) | 0 | 0 | 15 | 15.24111 | 0.052 |
| 137(A) | 1 | 0 | 15 | 14.4225 | 0.046 |
| 138(A) | 2 | 0 | 15 | 12.97871 | 0.041 |
| 139(A) | 4 | 0 | 15 | 12.13556 | 0.029 |
| 140(A) | 10 | 0 | 15 | 14.1503 | 0.025 |
| 141(A) | 8 | 0 | 15 | 15.24888 | 0.031 |
| 142(A) | 6 | 0 | 15 | 14.14919 | 0.035 |
| 143(A) | 12 | 0 | 15 | 12.71091 | 0.024 |
| 144(A) | 15 | 0 | 15 | 12.46522 | 0.019 |
| 145(A) | 17 | 0 | 15 | 12.0735 | 0.020 |
| 146(A) | 20 | 0 | 15 | 14.43869 | 0.023 |
| 147(A) | 4 | 5 | 15 | 12.72365 | 0.038 |
| 148(A) | 4 | 15 | 15 | 12.79277 | 0.037 |
| 149(A) | 8 | 5 | 15 | 12.67663 | 0.029 |
| 150(A) | 8 | 15 | 15 | 11.71459 | 0.026 |
| 151(A) | 12 | 5 | 15 | 9.46905 | 0.019 |
| 152(A) | 12 | 15 | 15 | 11.57739 | 0.023 |
| 153(A) | 20 | 5 | 15 | 10.26361 | 0.015 |
| 154(A) | 20 | 15 | 15 | 10.62525 | 0.014 |
| 155(A) | 4 | 10 | 15 | 10.0867 | 0.029 |
| 156(A) | 4 | 10 | 30 | 16.48655 | 0.032 |
| 157(A) | 8 | 10 | 15 | 13.15988 | 0.029 |
| 158(A) | 8 | 10 | 30 | 14.67807 | 0.027 |
| 159(A) | 12 | 10 | 15 | 12.61668 | 0.020 |
| 160(A) | 12 | 10 | 30 | 15.76813 | 0.023 |
| 161(A) | 20 | 10 | 15 | 14.88741 | 0.020 |
| 162(A) | 20 | 10 | 30 | 15.92602 | 0.020 |

Handling was assessed using the same procedure as described herein above. The above table shows average force values against PVP concentrations. PVP concentrations of above 10% gave better handling than the reference sample describe earlier herein. This supports the conclusions that the higher PVP concentrations lower penetration into yarn bundles which results in more favorable handling characteristics.

Also, to be noted from the results was that although generally a higher silicone coverage resulted in poorer handling, it was not the only factor. For example, sample 162(A) had a high coverage of 15.9 mg/cm$^2$, but had a better handling result than the reference sample. Alternatively, sample 147(A) had a lower coverage of 12.7 mg/cm$^2$ and had worse handling than the reference sample. This suggests that it is in fact penetration that more greatly impacts handling rather than coverage as sample 162(A) had a penetration score of 1 compared to sample 147(A) that had a penetration score of 3. The increase in silicone coverage may have a smaller impact on handling than the change in PVP concentrations.

Seam Delamination:

During the adhesion testing, seam delamination was observed at higher pressures. The bubbles formed were diametrically opposed, running along the seam. The fabric was examined under microscope and the seam region was visibly more tightly weaved compared to the main body of the graft. Therefore, it was only logical to ask if the delamination at the seam is solely due to the protocol followed and should be considered a "fail", or the tight seam hinders the silicone to adhere.

In the initial analysis, any type of delamination was given an adhesion grade 3. However, after consideration, it was decided to examine the data again. The delamination at the seam was, this time, not considered a grade 3. So, this section will compare two cases: (1) seam delamination is considered as a fail criterion, (2) seam delamination is not considered as a fail criterion.

Seam delamination was observed in the 8-12% range. An improvement of adhesion is evident in case 2, which only reinforces previous conclusions that the seam can have a negative effect on silicone adhesion. Similarly, a comparison between silicone content and adhesion in the two cases in question shows there is increased adhesion in case 2, specifically for 30% silicone. In case 1, 15% silicone content yields more favorable results, while in case 2, this is true for 30% silicone content.

Conclusions

A consistent silicone coverage was achieved with a spray rig with a small standard deviation of the spraying results. The use of blue dyed silicone for penetration assessment and clear for adhesion assessment appeared to work very well. A repeatable mask coverage is achievable with standard deviation at 10% of the average value. The fabric has a large impact on the success of the coating, in particular the presence of a seam. Adhesion results of seamed grafts were not as comparable to seamless grafts, but if the grafts had not delaminated at the seams, the results would have been much closer. Both glycerol concentration and silicone dispersion concentration appeared to have less effect than previous, this may be a result of the points above. Glycerol appears to lower penetration at low PVP concentrations and has less effect at higher PVP concentrations. Glycerol has less effect on adhesion at lower PVP concentrations and at higher PVP concentrations lowers adhesion. Silicone dispersion had no clear influence on the success of the coating with respect to adhesion and penetration. Grafts coated with the 30% dispersion appeared to have a more uniform coating of silicone. Coating time was greatly reduced when using 30% dispersion compared to 15%. The reduced coating time with 30% dispersion lead to less blockages within the spray head. Handling was more sensitive to penetration rather than silicone coverage.

The use of glycerol is, however, not limited to just as an additive to the masking agent formulation. Glycerol may be applied to the graft, in particular, to select portions of the graft, prior to the application of the masking agent. Such added glycerol may act as a plasticizer to the masking agent applied at the portion of the graft having the added glycerol. Portions of grafts that have, for example, different densities, such as but not limited to seams, may benefit with the application of glycerol prior to the application of the masking agent.

Handling comparable to reference sample 64B was achievable with PVP concentrations greater than 10%. Handling is also effected by the uniformity of the silicone coating from peaks to valleys. Excluding seam delamination from the fail criteria, yields more positive results for a range of concentrations that were previously thought to be favorable.

In summary, adhesion was higher in 8-12% PVP concentration. Higher silicone content offered better adhesion.

Visual Indicators:

As described herein, the masking agent formulation and/or the sealant composition may contain a colorant or dye. The colorant or dye may be any useful and medically suitable, e.g., biocompatible, dye. The dye may be biostable or may degrade over time after implantation in the body. Any useful color, such as blue, green, red, orange, and the like may be used. Further, the masking agent and/or sealant compositions may have an inherent color or tint which is distinguishable from medical grade textile yarns.

Such a visually distinguishable masking agent and/or sealant compositions may be useful with the methods and products of the present invention. For example, visually distinguishable masking agent may be useful in ascertaining that the interior portions of a graft have sufficient masking agent coverage to inhibit sealant migration thereto. Such a visually distinguishable masking agent may also be useful in ascertaining that the exterior portions of the graft are free or substantially free of masking agent coverage so that the sealant composition may adequately cover the exterior of the graft, including securably covering the exterior of the graft to achieve substantially fluid impermeable sealing.

A visually distinguishable sealant composition may be useful in ascertaining that exterior portions of the grant have sealant coverage. For example, a practitioner could differentiate between a non-sealed graft having the color, such as white, typical of medical textiles and a sealed graft of the present invention having a non-white color, such as blue, green, etc. Thus, a practitioner could readily distinguish between a permeable non-sealed graft and a substantially impermeable sealed graft of the present invention.

If colorants or dyes are added to the masking agent and/or sealant compositions, then the levels of the colorants or dyes should not be at a level which interferes with the intended purpose of the masking agent and/or sealant compositions.

Homogeneous Sealant Application and Coverage:

Tests were performed to investigate the theory that the addition of the mask allows a thinner coating of silicone to be applied to the graft before a sufficient seal is obtained. This was done by applying silicone coatings at various target coverage levels and carrying out whole graft porosity on them to determine the level of seal. While the tests were performed with particular sealing and masking agents, any of the above-described sealing and masking agents may suitably be used.

Tests were carried out on ATEX crimped and non-crimped polyester fabric as described below:
ATEX Technologies Polyester Vascular Graft—14 mm Dia.—28.5 CPI
ATEX Technologies Polyester Vascular Graft—14 mm Dia.—Uncrimped
Equipment and Materials:
14 mm crimped polyester fabric (Atex Technologies)
14 mm non-crimped polyester fabric (ATEX Technologies)
Polyvinylpyrrolidone (PVP) Powder
De-ionised water
MED6-6606 Silicone Dispersion
n-Heptane
Easy composite royal blue pigment
Mandrels and mounts
Hothouse (HH) Rotisserie
Magnetic Stirrer
Measuring jug
Scales
Blasting Cabinet
Coating Variables:

The presence of the masking agent has been shown to limit the penetration of the silicone through the graft structure as described earlier herein. The masking agent also appears to cause the silicone left on the surface to be more homogenous, resulting in a thinner coverage required to get a complete seal than with bare or non-masked fabric. Therefore, a range of silicone coverages was tested on a control of bare fabric and on grafts prepared with an optimised mask process. This was carried out on both crimped and non-crimped fabric to determine any differences.

Control Graft Samples Preparation:

Woven graft samples were coated with a 30% silicone dispersion in heptane (no mask). The silicone coverages targeted were 4, 6, 8, 10, and 12 mg/cm$^2$.

Optimized Mask Samples Preparation:

Woven graft samples were prepared with mask (20% w/w PVP and 5% w/w Glycerol (to PVP) in water) applied using an immersion method. Once the mask was dried via rotation at room temperature, excess mask on the outer graft surface was soda blasted via sodium bicarbonate at 25-30 psig, while rotating the graft at 100 RPM. Blast particles were removed using a vacuum and heptane wash, then dried. Masked coated graft samples were sprayed coated with a 30% silicone/heptane dispersion. The silicone coverages targeted were 4, 6, 8, 10, 12 mg/cm$^2$.

Silicone Dispersion:

Flushed spray head with n-heptane. Mounted graft and silicone/heptane dispersion syringe barrel in the spray rig. Sprayed silicone onto graft during rotation at 150 RPM and traverse 20 mm/s. Sprayed whole length of graft, then allowed heptane to flash off before making another pass (about 10 seconds). Repeated until no dispersion left in the syringe barrel. Dried for 6 hours with rotation and 66 hours stationary. Graft sample were dried if there was no vinegar odour.

Removed mask via water wash at 90 degrees C. Warm water wash dissolved the PVP for removal and aided the silicone curing. Dried via ambient air.

The most desirable mask process used a 20% PVP masking agent with 5% Glycerol (to PVP). The masking agent once dried was abraded with sodium bicarbonate soda at pressure of 25 to 30 psig. Details of the abrading process are described previously herein. The grafts were also coated with a 30% silicone dispersion. The decision for this process was taken from results presented earlier herein, where a 20% PVP masking agent performed well after abrasion and that at higher PVP concentrations a lower glycerol concentration was beneficial.

Details for preparing (1) control graft samples and (2) masked graft samples for silicone coverage trials are listed below in Table 35.

TABLE 35

Test Matrix

| | Sample ID | HH Sample ID | Controls Silicone Coverage (mg/cm$^2$) | | | | | Optimised Mask Silicone Coverage (mg/cm$^2$) | | | | |
|---|---|---|---|---|---|---|---|---|---|---|---|---|
| | | | 4 | 6 | 8 | 10 | 12 | 4 | 6 | 8 | 10 | 12 |
| Crimped | 1 | 220 | X | | | | | | | | | |
| | 2 | 221 | | X | | | | | | | | |
| | 3 | 222 | | | X | | | | | | | |
| | 4 | 223 | | | | X | | | | | | |
| | 5 | 224 | | | | | X | | | | | |
| | 6 | 225 | | | | | | X | | | | |
| | 7 | 226 | | | | | | | X | | | |
| | 8 | 227 | | | | | | | | X | | |
| | 9 | 228 | | | | | | | | | X | |
| | 10 | 229 | | | | | | | | | | X |
| Un-Crimped | 11 | 230 | X | | | | | | | | | |
| | 12 | 231 | | X | | | | | | | | |
| | 13 | 232 | | | X | | | | | | | |
| | 14 | 233 | | | | X | | | | | | |
| | 15 | 234 | | | | | X | | | | | |
| | 16 | 235 | | | | | | X | | | | |
| | 17 | 236 | | | | | | | X | | | |

TABLE 35-continued

Test Matrix

| Sample ID | HH Sample ID | Controls Silicone Coverage (mg/cm²) | | | | | Optimised Mask Silicone Coverage (mg/cm²) | | | | |
|---|---|---|---|---|---|---|---|---|---|---|---|
| | | 4 | 6 | 8 | 10 | 12 | 4 | 6 | 8 | 10 | 12 |
| 18 | 237 | | | | | | | | X | | |
| 19 | 238 | | | | | | | | | X | |
| 20 | 239 | | | | | | | | | | X |

Method:

Sample Preparation:

Each sample was removed from the store and assigned a HH sample ID number. Each sample was to be made up of half a graft. Firstly, the graft was cut in half. The graft was fully stretched removing the crimp, if applicable, and cut at the midpoint with a single edge razor blade, once cut the end was cauterized to prevent fraying. The samples were clean and free of any debris. The weights of Cut graft sections were recorded. Each sample was marked with sample IDs.

The control samples were put to the side ready for mounting.

Masking Agent Preparation:

To aid the abrasion of the mask it was beneficial to have some sort of dye in the masking agent. The reason for this is that it gives a visual aid into how much is being removed.

To prepare the masking agent formulation, the following steps were followed:
  Placed 200 ml of de-ionised water into a 100 ml plastic beaker.
  Placed Magnetic stirrer in the water and place the beaker on the magnetic stirrer.
  Turned the magnetic stirrer on at a speed of approx. 400 RPM at room temperature.
  Measured 40 g of PVP and 4 g of glycerol onto weighing boats.
  Added the PVP and Glycerol to the water.
  Added 2 drops of yellow dye.
  Stirred till there was no solute visible.

Masking Agent Application and Drying:

After the mask was fully prepared, the graft was coated. This was done by immersing the graft within the masking agent solution and agitating the graft by gloved hands, so it is fully coated inside and out.

Once the graft was saturated, the excess mask solution was removed by running the graft between a thumb and index finger. Next the graft was to be attached to a mandrel, this was done using cable ties. Cable tied one end of the graft to the mandrel, in the case of the crimped grafts, extended the graft to 60% of its overall extended length, and cable tied the other end of the graft to the mandrel. The mandrel was then be placed horizontally on the rotisserie and allowed to air dry for 12 hours. Once dried, the weight of the masked graft was recorded.

The dry masked graft were then mounted on a solid mandrel and cable tied in place. The mandrel was mounted within the blasting cabinet attached to the rotating chuck and set to a speed of approximately 100 RPM. The soda blaster (or sodium bicarbonate abrader) was filled with bicarbonate of soda and set to a pressure of 25 to 30 psig. The graft was then be rotated and the soda blast gun traversed over the surface at a sufficient speed to not miss any of the surface, once one full pass was made, repeated the traverse for a second time. It should be noted that the pressure of the abrader for the present invention may be as high as 50 psig, which in some cases will affect the integrity of the underlying textile but may be acceptable depending on the remaining structural integrity, of the textile.

After the blasted grafts have been ablated, they were washed to remove any particulates of mask or bicarbonate of soda that was still on the surface. This was done by first passing a vacuum over the surface then pouring heptane over the outside of the graft.

After washing the graft, the graft was allowed to dry then be weighed again, and the weight noted on the test sheet.

Once the masked graft was dried and weighed it was mounted back onto the suspended mandrel. At this point the control samples were also mounted onto the appropriate mandrel to match the target silicone coverage as per the test matrix.

Sealant Preparation:

The sealant came supplied as a 30 wt % silicone in heptane and was used as is.

The appropriate amount of silicone was measured out to give the target coverage as per the test matrix and it was loaded into one of the disposable syringe barrels. These amounts were set to account for a 25% loss when spraying.

Sealant Application:

The spray head was flushed with n-Heptane to ensure correct flow. The mandrel with the graft was then mounted in the spray rig. The spray rig was set up to spray the entire length of graft. Mounted the syringe barrel with silicone onto the spray head. The graft was rotated at 150 RPM and the rate of traverse was set to 20 mm/s. The spray head was started and traversed over the entire length of the graft, once it reached the opposite end the spray head was stopped and allowed to return to the start of the graft. The solvent was allowed to flash off before making another pass, after each pass a delay of 10 seconds was observed. This was continued till there was no dispersion left in the syringe barrel or there was an insufficient amount to make another full pass. Once the graft was removed from the spray rig the spray head was again flushed with n-heptane.

After application the graft was transferred to the rotisserie for a period of 6 hours then transferred to a stationary mount and allowed to air dry for a further 66 hours, the graft was confirmed dry if it did not have a perceptible vinegar odour coming from it. Once dry, the sealed graft was weighed and the weight recorded.

Mask Removal:

Once the graft has been fully dried the mask was removed. This was done by washing the grafts in a washing machine on a 'cotton cycle' at 90° C. (with no detergent). This caused the PVP to be dissolved in the water and removed and also the high temperatures aided the curing of the silicone. When the wash was complete, the graft was hung up to air dry. Once the mask had been removed and the graft was dry, the finished graft was weighed and the weight recorded.

Assessment of Handling:

The handling of crimped grafts was assessed using tensile extension force testing. Mounted crimped graft samples between jaws of Lloyd Tensile Test machine. Extend jaws by 20% (16 mm) and measure maximum force.

Permeability Testing (ISO 7198—Whole Graft Leak Testing):

Permeability was assessed via a whole graft porosity test (ISO 7198). Connected the graft to the pressure rig and ensure there are no leaks. Slowly increased pressure to 120 mmHg, once at that pressure the leakage, if any, from the graft surface was measured over the period of 1 minute and recorded on the test sheet. Once the leak rate was obtained, this was divided by the test surface area to obtain the permeability reading.

Delamination Testing:

Delamination was assessed via a whole graft porosity test. Connected the graft to the pressure rig and ensured there are no leaks. Slowly increased pressure to 600 mmHg, once at that pressure the leakage, if any, from the graft surface was measured over the period of 1 minute and recorded on the test sheet. Once the leak rate was obtained, this was divided by the test surface area to obtain the permeability reading.

Results & Analysis:

The data in the table below demonstrated the ability to get a consistent mask coverage over a range of samples and obtain the target coverage levels of silicone.

Table 36 below lists the measured weights of the masking agent and sealant formulations after the noted processing steps. Masking agent and sealant coverages are noted in the table.

TABLE 36

Weight Summary

| Sample ID | HH ID | Initial (mg) | After Masking and Drying (mg) | After Sealant and Curing (mg) | After Washing and Drying (mg) | Mask Coverage (mg/cm$^2$) | Silicone Coverage (mg/cm$^2$) | Target Silicone Coverage |
|---|---|---|---|---|---|---|---|---|
| 1 | 220 | 2699 | 2699 | 3417 | 3412 | 0.00 | 3.64 | 4 |
| 2 | 221 | 2665 | 2665 | 3881 | 3878 | 0.00 | 6.23 | 6 |
| 3 | 222 | 2729 | 2729 | 4398 | 4396 | 0.00 | 8.44 | 8 |
| 4 | 223 | 2679 | 2679 | 4569 | 4564 | 0.00 | 9.81 | 10 |
| 5 | 224 | 2683 | 2683 | 4872 | 4868 | 0.00 | 11.27 | 12 |
| 6 | 225 | 2646 | 3393 | 4127 | 3374 | 3.90 | 3.81 | 4 |
| 7 | 226 | 2641 | 3382 | 4382 | 3651 | 3.86 | 5.27 | 6 |
| 8 | 227 | 2674 | 3367 | 4910 | 4205 | 3.59 | 7.93 | 8 |
| 9 | 228 | 2692 | 3385 | 5538 | 4840 | 3.56 | 11.02 | 10 |
| 10 | 229 | 2700 | 3314 | 6083 | 5454 | 3.12 | 14.01 | 12 |
| 11 | 230 | 1756 | 1756 | 2101 | 2093 | 0.00 | 2.39 | 4 |
| 12 | 231 | 1767 | 1767 | 2576 | 2574 | 0.00 | 5.73 | 6 |
| 13 | 232 | 1745 | 1745 | 2757 | 2747 | 0.00 | 7.12 | 8 |
| 14 | 233 | 1700 | 1700 | 3199 | 3200 | 0.00 | 10.66 | 10 |
| 15 | 234 | 1699 | 1699 | 3432 | 3438 | 0.00 | 12.36 | 12 |
| 16 | 235 | 1716 | 2020 | 2611 | 2294 | 2.16 | 4.11 | 4 |
| 17 | 236 | 1735 | 2027 | 2918 | 2597 | 2.07 | 6.12 | 6 |
| 18 | 237 | 1711 | 1998 | 3215 | 2892 | 2.04 | 8.39 | 8 |
| 19 | 238 | 1712 | 2005 | 3487 | 3167 | 2.08 | 10.34 | 10 |
| 20 | 239 | 1728 | 2035 | 3773 | 3437 | 2.18 | 12.14 | 12 |

Results from the table above demonstrate all woven PET graft samples had a consistent mask coverage. Crimped graft samples (samples 6-10) generally held more mass of mask compared to uncrimped graft samples (samples 17-20). This may be caused from the topography of the crimped graft. The above table demonstrated the ability to get a consistent mask coverage over a range of samples and also to be able to target the coverage levels of silicone. As the masked samples were blasted the following table shows the weight data for that also.

Additionally, all woven PET graft sample achieved actual silicone coverage levels close to the target silicone coverage levels. Crimped grafts tended to have slightly less actual silicone coverage compared to its target silicone coverage. On the other hand, uncrimped grafts tended to have slightly more actual silicone coverage compared to its target silicone coverage. This observation may be related to the mask coverage. Less mask coverage, as seen in the uncrimped samples, allowed for higher silicone attachment to the PET graft.

As the masked graft samples were soda blasted, the following table shows the weight before and after ablation.

Results for graft sample mass measurements before and after ablation are listed below in Table 37.

TABLE 37

| Sample ID | HH ID | Initial (mg) | After Masking and Drying (mg) | After Ablation (mg) | Weight difference after ablation (mg) |
|---|---|---|---|---|---|
| 6 | 225 | 2699 | 3393 | 3424 | −31 |
| 7 | 226 | 2665 | 3382 | 3407 | −25 |
| 8 | 227 | 2729 | 3367 | 3402 | −35 |
| 9 | 228 | 2679 | 3385 | 3416 | −31 |
| 10 | 229 | 2683 | 3314 | 3351 | −37 |
| 16 | 235 | 2646 | 2020 | 2054 | −34 |
| 17 | 236 | 2641 | 2027 | 2073 | −46 |
| 18 | 237 | 2674 | 1998 | 2043 | −45 |

TABLE 37-continued

| Sample ID | HH ID | Initial (mg) | After Masking and Drying (mg) | After Ablation (mg) | Weight difference after ablation (mg) |
|---|---|---|---|---|---|
| 19 | 238 | 2692 | 2005 | 2044 | −39 |
| 20 | 239 | 2700 | 2035 | 2081 | −46 |

The ablation weight data table above, shows that there was consistent weight gain for each of the 10 ablated samples. This suggested that although the mask is being ablated that there is also bicarbonate being deposited on the surface.

Handling:

The handling of the crimped grafts was assessed using the same technique as described above, although for this report the whole graft was considered and not a section of 80 mm. The same 20% extension was used; therefore, the results are comparable. The table below shows the results of this testing.

The results showed that for both sets of grafts, with increasing silicone coverages an increased in the force to extend was measured. Also evident was the increase in the force to extend between the controls and the grafts with an optimized mask. The controls required roughly double the force for the same 20% extension, strengthening the theory that higher levels of penetration result in a higher force to extend, and furthermore worse handling.

Table 38 lists forces-to-extend values for the various samples tested.

TABLE 38

| Sample ID | HH Sample ID | PVP Mask Conc. (%) | Glycerol Conc. (% of PVP) | Silicone Coverage (mg/cm$^2$) | Force to Extend (N) | Force to Extend (Normalised with Circumference) (N/mm) |
|---|---|---|---|---|---|---|
| 1 | 220 | 0 | 0 | 3.64 | 0.47739 | 0.011 |
| 2 | 221 | 0 | 0 | 6.23 | 0.66692 | 0.015 |
| 3 | 222 | 0 | 0 | 8.44 | 0.72483 | 0.016 |
| 4 | 223 | 0 | 0 | 9.81 | 0.67862 | 0.015 |
| 5 | 224 | 0 | 0 | 11.27 | 0.69653 | 0.016 |
| 6 | 225 | 20 | 5 | 3.81 | 0.17895 | 0.004 |
| 7 | 226 | 20 | 5 | 5.27 | 0.20019 | 0.005 |
| 8 | 227 | 20 | 5 | 7.93 | 0.21045 | 0.005 |
| 9 | 228 | 20 | 5 | 11.02 | 0.34497 | 0.008 |
| 10 | 229 | 20 | 5 | 14.01 | 0.39559 | 0.009 |

The force-to-extend results show that all crimped graft samples tested increase the amount of force to extend with increasing silicone coverages. Additionally, the crimped graft samples with mask (samples 1-5) decreased the amount of force to extend compared to the crimped graft samples without mask (samples 6-10). The controls (crimp grafts with no mask) require roughly double the force for the same 20% extension compared to crimp grafts with mask. This testing strengthens the theory that higher levels of silicone penetration results in a higher force to extend, and furthermore worse handling properties.

Figure 20:
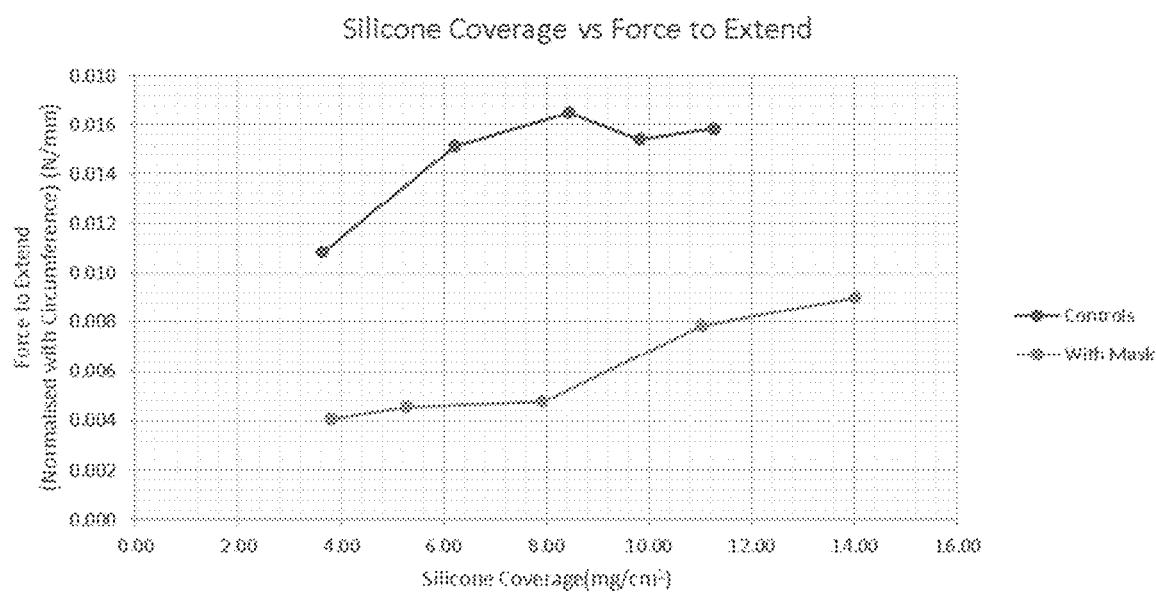
FIG. 20 is a graft showing force-to-extend test values for grafts of the present invention.

As depicted in FIG. 20, the force to extend was higher for textile grafts having the silicone applied to unmasked grafts, e.g., grafts not having applied masking agent (labelled as "Controls" in FIG. 20), as compared to grafts having applied masking agents (labelled as "With Mask" in FIG. 20). This is observed even for the same levels of silicone coverage. While not being bound by any particular theory, it is believed that the application of the masking agent permits more even application of the silicone by allowing the silicone to spread out there over. In other words, the use of the masking agent facilitates the disposition or placement of the silicone over the graft. The reduced force is also an indication of improved handling for the grafts having the masking agent applied thereto. While not being bound by any particular theory, it is believed unmasked grafts had higher levels of penetration of the silicone, thereby resulting in higher forces to extend.

Permeability Testing (ISO 7198—Whole Graft Leak Testing):

The below table shows the results of the permeability testing carried out on all 20 samples. As expected the low coverages on the unmasked grafts gave high permeability reading compared to the masked equivalents. On higher silicone coverage levels the permeability was more comparable.

Results for permeability testing (ISO 7198) are listed below in Table 39.

TABLE 39

| Sample ID | HH Sample ID | PVP Mask Concentration (%) | Glycerol Concentration (% of PVP) | Silicone Coverage (mg/cm$^2$) | Permeability (ml/min/cm$^2$) |
|---|---|---|---|---|---|
| 1 | 220 | — | — | 3.64 | 12.82 |
| 2 | 221 | — | — | 6.23 | 0.97 |
| 3 | 222 | — | — | 8.44 | 0.48 |
| 4 | 223 | — | — | 9.81 | 0.76 |
| 5 | 224 | — | — | 11.27 | 0.16 |
| 6 | 225 | 20 | 5 | 3.81 | 2.05 |
| 7 | 226 | 20 | 5 | 5.27 | 0.42 |
| 8 | 227 | 20 | 5 | 7.93 | 5.37 |
| 9 | 228 | 20 | 5 | 11.02 | 0.04 |
| 10 | 229 | 20 | 5 | 14.01 | 0.00 |
| 11 | 230 | — | — | 2.39 | 22.08 |
| 12 | 231 | — | — | 5.73 | 10.25 |
| 13 | 232 | — | — | 7.12 | 0.55 |
| 14 | 233 | — | — | 10.66 | 0.00 |
| 15 | 234 | — | — | 12.36 | 0.00 |
| 16 | 235 | 20 | 5 | 4.11 | 1.36 |
| 17 | 236 | 20 | 5 | 6.12 | 0.38 |
| 18 | 237 | 20 | 5 | 8.39 | 0.05 |
| 19 | 238 | 20 | 5 | 10.34 | 0.02 |
| 20 | 239 | 20 | 5 | 12.14 | 0.05 |

Crimped graft and uncrimped grafts with no mask and low silicone coverage (3-6 mg/cm$^2$) demonstrated high permeability reading compared to the masked graft equivalents. Therefore, it is observed that the application of masking agent lowers the amount of silicone needed to seal the graft.

Silicone coverage seals the graft with mask or without mask at about 8 mg/cm$^2$. With higher silicone coverage (>7 mg/cm$^2$), the permeability is more comparable for masked and non-masked graft samples.

Sample 8 (crimped graft with mask) gave an unexpected result. The permeability for this sample is higher than any other graft at that concentration. Sample 8 was expected to be one of the lowest permeability results. This permeability result does not follow the pattern of other grafts with similar silicone coverage (6 mg/cm$^2$ and 10 mg/cm$^2$). No obvious pattern of leakage was observed. It is suggested there was an issue with the silicone itself or the application method used. A hypothesis is that the silicone sat too long in air whilst spraying or there was a blockage during spraying that has caused the coating to fail.

Delamination Testing:

The table below shows the results of the delamination testing carried out on select crimped graft samples.

Results for delamination testing detailed below in Table 40.

TABLE 40

| Test Sample ID | Hothouse Sample ID | Mask | Soda blast | Silicone Coverage mg/cmsq | Leakage @ 600 mmHg |
|---|---|---|---|---|---|
| 2 | 221 | No | No | 6 | 395 ml |
| 5 | 224 | No | No | 12 | 43 ml |
| 7 | 226 | 20% | 30 psi | 6 | 1800 ml |
|   | 133 | 20% | 50 psi | 7 | 95 |

Conclusions

All silicone coated samples with masking agent and without masking agent did not delaminate at 600 mmHg. In other words, all samples passed the delamination test. The silicone coated samples with masking agent and without masking agent may have had very minor, for example 1 to six, fine micro-jets of leakage at 600 mmHg. Nevertheless, all samples still passed the delamination test. Masking agent application and blasting or ablating processes did not compromise the silicone attachment to the grafts. Higher blasting pressures provided an increased amount of non-masked fibres on the outer surface of the graft for a stronger silicone attachment and significantly less leakage at 600 mmHg. Soda blasting at 50 psi caused minor breakage of fibres which improved silicone attachment (decreased leakage amount) and provided better handleability of the graft.

Immersion of the textile graft into the masking agent showed a consistent method of applying PVP to crimped and uncrimped graft samples. Spray method using force air showed an accurate way of achieving target coverage levels of silicone. Decreasing silicone coverage improved handling slightly. The addition of the mask improved handling by reducing penetration of the silicone. Crimped and uncrimped fabric have similar permeability levels at corresponding silicone coverages. The addition of masking agent results in lower permeability values at lower silicone coverages. At higher silicone coverages the addition of masking agent has less effect.

In summary, the water soluble masking agent may have a viscosity from about 2,000 centipoise at room temperature to about 100,000 centipoise at room temperature, including from about 50,000 centipoise at room temperature to about 100,000 centipoise at room temperature. The water soluble masking agent may comprise from about 25% w/w of the polyvinylpyrrolidone in the glycerol to about 75% w/w of the polyvinylpyrrolidone in glycerol, including from about 30% w/w of the polyvinylpyrrolidone in the glycerol to about 70% w/w of the polyvinylpyrrolidone in the glycerol, including from about 40% w/w of the polyvinylpyrrolidone in the glycerol to about 60% w/w of the polyvinylpyrrolidone in glycerol, more desirably including from about 45% w/w of the polyvinylpyrrolidone in the glycerol to about 55% w/w of the polyvinylpyrrolidone in glycerol, in particular about 50% w/w of the polyvinylpyrrolidone in the glycerol. The polyvinylpyrrolidone may have a molecular weight of from about 2,500 g/mol to about 55,000 g/mol, including from about 3,500 g/mol to about 50,000 g/mol, from about 5,000 g/mol to about 40,000 g/mol, from about 5,000 g/mol to about 30,000 g/mol, from about 5,000 g/mol to about 20,000 g/mol, and desirably from about 8,000 g/mol to about 10,000 g/mol.

Modifications may be made to the foregoing embodiments within the scope of the present invention.

The following embodiments or aspects of the invention may be combined in any fashion and combination and be within the scope of the present invention, as follows:

Embodiment 1

A method of manufacturing a tubular graft comprising the steps of:

providing a textile comprising a tubular wall disposed between a first open end and an opposed second open end, an inner surface and an opposed outer surface defining an interior wall portion therein between, the tubular wall comprising a textile construction of one or more filaments or yarns, the textile construction by itself being permeable to liquid;

applying a substantially water-soluble material to at least a portion of the tubular wall; and applying a substantially water-insoluble sealant to at least a part of the outer surface of the tubular wall, the substantially water-insoluble sealant being configured to mitigate movement of fluid through the wall of the conduit;

wherein the water-soluble material is configured to mitigate penetration of the sealant to the inner surface of the conduit.

Embodiment 2

The method of embodiment 1, wherein the step of applying the water-soluble material to at least a portion of the tubular wall comprises applying the water-soluble material to at least a portion of the inner surface and a portion of the interior portion of the tubular wall.

Embodiment 3

The method of embodiment 1 or 2, wherein the step of applying the water-soluble material to at least a portion of the tubular wall comprises applying the water-soluble material to at least a portion of the outer surface of the tubular wall.

Embodiment 4

The method of any preceding embodiment, wherein the water-soluble material is a solution of the water-soluble material and a solvent.

Embodiment 5

The method of any preceding embodiment, wherein the solvent is selected form the group consisting of water, lower alcohols, and combinations thereof.

Embodiment 6

The method of any preceding embodiment, wherein the solvent is at least partially removed prior to applying the substantially water-insoluble sealant.

Embodiment 7

The method of any preceding embodiment, further comprising removal of at least a portion of the water-soluble material is by dissolution, abrading, peeling, degrading, and combinations thereof.

Embodiment 8

The method of any preceding embodiment, wherein the water-soluble material is selected from the group consisting of polyvinylpyrrolidone, glycerol, methyl cellulose, poly(ethylene glycol), poly(ethylene glycol) hydrogel, polyethylene oxide, and combinations thereof.

Embodiment 9

The method of any preceding embodiment, wherein the substantially water-insoluble sealant is an elastomeric material selected from the group consisting of moisture curing, light curing, thermo-curing, platinum catalyzed, anaerobic curing materials or a combination of these curing mechanisms.

Embodiment 10

The method of embodiment 9, wherein the elastomeric material is selected from the group consisting of silicones, polyurethanes, polycarbonates, thermoplastic elastomers, and combinations thereof.

Embodiment 11

The method of any preceding embodiment, wherein one of more of the substantially water-soluble coating or the substantially water-insoluble coating further comprises a component selected from the group consisting of a colorant, a therapeutic agent, a dye, and a fluorescent indicator.

Embodiment 12

The method of any preceding embodiment, wherein the water-soluble material comprises polyvinylpyrrolidone having a molecular weight of between approximately 6,000 g/mol and approximately 15,000 g/mol.

Embodiment 13

The method of any preceding embodiment, wherein applying the water-soluble material forms layer on substantially all of the inner surface of the tubular wall.

Embodiment 14

The method of any preceding embodiment, further comprising curing the substantially water-insoluble sealant.

Embodiment 15

The method of any preceding embodiment, further comprising curing the substantially water-insoluble sealant; and thereafter removing at least a portion of the water-soluble material.

Embodiment 16

The method of embodiment 14, further comprising removing substantially all of the water-soluble material from the inner surface of the tubular wall.

Embodiment 17

The method of any preceding embodiment, further comprising:
removing at least a part of the water-soluble material from at least a part of the outer surface of the tubular wall prior to the applying the substantially water-insoluble sealant.

Embodiment 18

The method of any one of embodiments 15 to 17, wherein the removing at least the portion of the water-soluble material is carried out at a temperature of between approximately 15° C. and approximately 140° C.

Embodiment 19

The method of any one of embodiments 15 to 18, wherein the removing at least the portion of the water-soluble material further comprises the step of applying a solvent thereto.

Embodiment 20

The method of embodiment 19, wherein the solvent comprises water, lower alcohols, and combinations thereof.

Embodiment 21

The method of any one of embodiments 15 to 20, wherein the tubular textile is agitated, rotated, spun, and shaken, or the like, during the removal of the water-soluble material.

Embodiment 22

The method of any one of embodiments 15 to 21, wherein the removal of the water-soluble material comprises dissolving, etching, plasma etching, ablating, abrading and combinations thereof of the water-soluble material.

Embodiment 23

The method of any preceding embodiment, wherein the step of applying the water-soluble material further comprises spraying the water-soluble material, brushing the water-soluble material, immersing at least a portion of the tubular wall into a solution of the water-soluble material, and combinations thereof.

Embodiment 24

The method of any preceding embodiment, wherein the substantially water-insoluble sealant is a polymer solution.

Embodiment 25

The method of embodiment 24, wherein the polymer solution comprises an organic solvent.

Embodiment 26

The method of embodiment 25, wherein the organic solvent comprises at least one of heptane and xylene.

Embodiment 27

The method of any preceding embodiment, wherein the substantially water-insoluble sealant is applied by brushing, spraying, roller coating the substantially water-insoluble sealant thereon.

Embodiment 28

The method of any preceding embodiment, wherein the method comprises one or more steps of selectively applying the substantially water-insoluble sealant to one or more portions of the tubular wall, such that the tubular wall comprises at least two sections having substantially different amounts of the substantially water-insoluble sealant thereon.

Embodiment 29

The method of any one of embodiments 14 to 28, wherein the tubular wall having the coating of the substantially water-insoluble sealant is, after curing thereof, substantially impermeable to liquid.

Embodiment 30

The method of any preceding embodiment, wherein, after curing of the substantially water-insoluble sealant, the tubular wall has a water permeability of about 0.16 ml/min/cm$^2$ at 120 mm Hg pressure or less than 0.16 ml/min/cm$^2$ at 120 mm Hg pressure.

Embodiment 31

A textile comprising:
a tubular wall disposed between a first open end and an opposed second open end and having an inner surface and an opposed outer surface, the tubular wall comprising a textile construction of one or more filaments or yarns, the textile construction by itself being permeable to liquid;
wherein a portion of the inner surface comprises a coating of a substantially water-soluble material thereon;
wherein the outer surface further comprises a coating of a substantially water-insoluble sealant disposed thereon; and
wherein the tubular wall having the coating of the substantially water-insoluble sealant is, after curing thereof, substantially impermeable to liquid.

Embodiment 32

The textile of embodiment 31, wherein the water-soluble material is selected from the group consisting of polyvinylpyrrolidone, glycerol, methyl cellulose, poly(ethylene glycol), poly(ethylene glycol) hydrogel, polyethylene oxide, and combinations thereof.

Embodiment 33

The textile of embodiment 31 or 32, wherein the coating of the water-soluble material comprises an oleophobic layer.

Embodiment 34

The textile of any one of embodiments 31 to 33, wherein the water-soluble material comprises polyvinylpyrrolidone having a molecular weight of between approximately 6,000 g/mol and approximately 15,000 g/mol.

Embodiment 35

The textile of any one of embodiments 31 to 34, the water-soluble material comprises polyvinylpyrrolidone and glycerol.

Embodiment 36

The textile of any one of embodiments 31 to 35, wherein the substantially water-insoluble sealant is an elastomeric material selected from the group consisting of moisture curing, light curing, thermo-curing, platinum catalyzed, anaerobic curing materials or a combination of these curing mechanisms.

Embodiment 37

The textile of embodiment 36, wherein the elastomeric material is selected from the group consisting of silicones, polyurethanes, polycarbonates, thermoplastic elastomers, and combinations thereof.

Embodiment 38

The textile of any one of embodiments 31 to 37, wherein one of more of the substantially water-soluble coating or the substantially water-insoluble coating comprises a component selected from the group consisting of a colorant, a therapeutic agent, a dye, and a fluorescent indicator.

Embodiment 39

The textile of any one of embodiments 31 to 38, wherein, after curing of the substantially water-insoluble sealant, the tubular wall has a water permeability of about 0.16 ml/min/cm$^2$ at 120 mm Hg pressure or less than 0.16 ml/min/cm$^2$ at 120 mm Hg pressure.

Embodiment 40

The textile of any one of embodiments 31 to 39, wherein the textile construction is selected from the group consisting of a weave of the one or more filaments or yarns, a knit of the one or more filaments or yarns, a braid of the one or more filaments or yarns, and a web of the one or more filaments or yarns.

Embodiment 41

The textile of any one of embodiments 31 to 40, wherein the tubular wall is a crimped wall having a series of peaks and valleys.

Embodiment 42

The textile of embodiment 41, wherein the substantially water-insoluble sealant is disposed at about 8 mg/cm$^2$ of area of the tubular wall or greater than 8 mg/cm$^2$ of area of the tubular wall.

Embodiment 43

The textile of any one of embodiments 31 to 40, wherein the tubular wall is a non-crimped wall being substantially free of peaks and valleys.

Embodiment 44

The textile of embodiment 43, wherein the substantially water-insoluble sealant is disposed at about 4 mg/cm$^2$ of area of the tubular wall or greater than 4 mg/cm$^2$ of area of the tubular wall.

Embodiment 45

The textile of any one of embodiments 31 to 44, wherein the substantially water-insoluble sealant is disposed at about 14 mg/cm$^2$ of area of the tubular wall or less than 14 mg/cm$^2$ of area of the tubular wall.

Embodiment 46

The textile of any one of embodiments 31 to 45,
wherein one portion of the tubular wall has a first level of the substantially water-insoluble sealant to provide a first soft, flexible zone;
wherein another portion of the tubular wall has a second level of the substantially water-insoluble sealant to provide a second zone having a stiffness greater than the first zone; and
wherein the second level the substantially water-insoluble sealant is greater than the first level of the substantially water-insoluble sealant.

Embodiment 47

The textile of any one of embodiments 31 to 46, wherein at least a portion of the coating of the substantially water-insoluble sealant engages at least a portion of the one or more filaments or yarns.

Embodiment 48

The textile of any one of embodiments 31 to 47, where in the textile is an implantable medical device.

Embodiment 49

The textile of embodiment 48, wherein the implantable medical device is selected from the group consisting of surgical vascular grafts, and endovascular graphs, meshes, patches, hernia plugs, vascular wraps, heart valves, filters, and the like.

Embodiment 50

The textile of any one of embodiments 31 to 49, wherein the textile is a delivery medical device.

Embodiment 51

The textile of embodiment 50, wherein the delivery medical device is a catheter.

Embodiment 52

A textile structure comprising:
a fluid permeable polymeric textile layer having opposing first and second surfaces and a length;
a cross-linkable water-insoluble elastomeric layer on the first textile surface configured to render the liquid permeable polymeric textile layer substantially impermeable to fluid when cured; and
a substantially dried water-soluble polymer layer on the second textile surface;
wherein water-soluble polymer layer substantially inhibits migration of the water-insoluble elastomeric layer onto the second surface; and wherein the water-soluble polymer layer is substantially removable by exposure to water.

Embodiment 53

The textile structure of embodiment 52, wherein the weight ratio of the cross-linkable water-insoluble elastomeric polymer to the water-soluble polymer is from about 0.1:1 to about 100:1.

Embodiment 54

The textile structure of embodiment 53, wherein the weight ratio of the cross-linkable water-insoluble elastomeric polymer to the water-soluble polymer is from about 1:1 to about 20:1.

Embodiment 55

A textile structure comprising:
a fluid permeable polymeric textile layer having opposing first and second surfaces and a length;
a crosslinked water-insoluble elastomeric polymer layer on the first textile surface forming a substantially fluid impermeable barrier, wherein the crosslinked water-insoluble elastomeric layer is adhered to the first textile surface by elastomeric shrinkage; and
a water dissolvable polymer layer dried on the second textile surface;
wherein the weight ratio of the crosslinked water-insoluble elastomeric polymer to the water dissolvable polymer is from about 0.1:1 to about 100:1.

Embodiment 56

The textile construction of embodiment 55, wherein the weight ratio of the crosslinked water-insoluble elastomeric polymer to the water dissolvable polymer is from about 1:1 to about 20:1.

Embodiment 57

A graft comprising:
a tubular wall disposed between a first open end and an opposed second open end and having an inner surface and an opposed outer surface, the tubular wall comprising a textile construction of one or more filaments or yarns;
wherein the outer surface comprises a coating of a substantially water-insoluble sealant disposed thereon;
wherein the inner surface is substantially free of the substantially water-insoluble sealant; and
wherein the tubular wall has a water permeability of about 0.16 ml/min/cm$^2$ at 120 mm Hg pressure or less than 0.16 ml/min/cm$^2$ at 120 mm Hg pressure.

Embodiment 58

The graft of embodiment 57, wherein the textile construction is selected from the group consisting of a weave of the one or more filaments or yarns, a knit of the one or more filaments or yarns, a braid of the one or more filaments or yarns, and a web of the one or more filaments or yarns.

Embodiment 59

The graft of embodiment 57 or 58, wherein the coating is disposed within an intermediate portion of the tubular wall between the inner surface and the opposed outer surface.

Embodiment 60

The graft of any one of embodiments 57 to 59, wherein the tubular wall is a crimped wall having a series of peaks and valleys.

Embodiment 61

The graft of any one of embodiments 57 to 60, wherein the substantially water-insoluble sealant is disposed at about 8 mg/cm$^2$ of area of the tubular wall or greater than 8 mg/cm$^2$ of area of the tubular wall.

Embodiment 62

The graft of any one of embodiments 57 to 59, wherein the tubular wall is a non-crimped wall being substantially free of peaks and valleys.

Embodiment 63

The graft of any one of embodiments 57 to 62, wherein the substantially water-insoluble sealant is disposed at about 4 mg/cm$^2$ of area of the tubular wall or greater than 4 mg/cm$^2$ of area of the tubular wall.

Embodiment 64

The graft of any one of embodiments 57 to 63, wherein the substantially water-insoluble sealant is disposed at about 14 mg/cm$^2$ of area of the tubular wall or less than 14 mg/cm$^2$ of area of the tubular wall.

Embodiment 65

The graft of any one of embodiments 57 to 64, wherein the substantially water-insoluble sealant is an elastomeric material selected from the group consisting of moisture curing, light curing, thermo-curing, platinum catalyzed, anaerobic curing materials or a combination of these curing mechanisms.

Embodiment 66

The graft of embodiment 65, wherein the elastomeric material is selected from the group consisting of silicones, polyurethanes, polycarbonates, thermoplastic elastomers, and combinations thereof.

Embodiment 67

The graft of any one of embodiments 57 to 66, wherein one of more of the substantially water-soluble coating or the substantially water-insoluble coating comprises a component selected from the group consisting of a colorant, a therapeutic agent, a dye, and a fluorescent indicator.

Embodiment 68

The graft of any one of embodiments 57 to 67, wherein the substantially water-insoluble sealant is selected from the group consisting of silicone, room temperature vulcanizing silicone, thermoplastic polyurethane, aliphatic polycarbonate, one or more thermoplastic elastomers, polycarbonate, and combinations thereof.

Embodiment 69

The graft of any one of embodiments 57 to 69,
wherein one portion of the tubular wall has a first level of the substantially water-insoluble sealant to provide a first soft, flexible zone;
wherein another portion of the tubular wall has a second level of the substantially water-insoluble sealant to provide a second zone having a stiffness greater than the first zone; and
wherein the second level the substantially water-insoluble sealant is greater than the first level of the substantially water-insoluble sealant.

Embodiment 70

An implantable or deliverable medical textile comprising:
a wall having a textile construction and having a first surface and an opposed second surface;
wherein the second surface comprises a coating of a substantially water-insoluble sealant disposed thereon;
wherein the first surface is substantially free of the substantially water-insoluble sealant; and
wherein the wall has a water permeability of about 0.16 ml/min/cm$^2$ at 120 mm Hg pressure or less than 0.16 ml/min/cm$^2$ at 120 mm Hg pressure.

Embodiment 71

An assembly for producing an implantable or deliverable medical textile having a selectively applied water-insoluble sealant layer, comprising:
a mandrel having a length, a hollow lumen disposed within a portion of the length, at least one open end, and a plurality of perforations through a wall of the mandrel;
a reservoir in fluid communication with the open lumen of the mandrel; and
a water-soluble polymer disposed within the reservoir.

Embodiment 72

The assembly of embodiment 71, further comprising a tubular graft securably disposed over a portion of the mandrel having the plurality of perforations.

Embodiment 73

The assembly of embodiment 71 or 72, further comprising a vacuum source in fluid communication with the hollow lumen of the mandrel.

Embodiment 74

The assembly of embodiment 73, further comprising a manifold configured to provide selective fluid communication between the hollow lumen of the mandrel and the reservoir and/or the vacuum source.

Embodiment 75

The assembly of any one of embodiments 71 to 74, further comprising a source of pressurized and/or blown air.

Embodiment 76

The assembly of embodiment 75, wherein the pressurized and/or blown air is in fluid communication with the hollow lumen of the mandrel.

Embodiment 77

The method, textile, graft, device or assembly of any preceding embodiment, further including a support member.

Embodiment 78

The method of any one of embodiments 1 to 30, wherein the support member is added to the outer surface of the wall of the conduit.

Embodiment 79

The method of embodiment 78, wherein the support member is wrapped around the outer surface of the wall of the conduit.

Embodiment 80

The method of embodiment 79, wherein the conduit comprises a plurality of crimps, and the support member is arranged to nest between the plurality of crimps.

Embodiment 81

The method of any one of embodiments 78 to 80, wherein a step of adding the support member to the conduit is carried out prior to the step of adding the sealant to the conduit.

Embodiment 82

The method of any one of embodiments 78 to 81, wherein a step of adding the sealant to the conduit is used, at least in part, to attach the support member to the conduit.

Embodiment 83

The method of any one of embodiments 78 to 82, wherein the support member is a flexible, polymer member.

Embodiment 84

The method of any one of embodiments 78 to 83, wherein the flexible support member is present on a portion of the length of the graft.

Embodiment 85

A method of manufacturing a vascular prosthesis, the method comprising the steps of:
(i) providing a conduit comprising a wall, the wall of the conduit comprising an inner surface and an outer surface, at least a section of the conduit being porous;
(ii) adding a masking agent to at least a part of the porous section of the conduit; and
(iii) adding a sealant to at least a part of the porous section of the conduit, the sealant being configured to mitigate movement of fluid through the wall of the conduit;
wherein the masking agent is configured to mitigate presence of the sealant on the inner surface of the conduit.

Embodiment 86

The method of embodiment 85, wherein the sealant forms a sealing layer on at least a part of the outer surface of the wall of the conduit.

Embodiment 87

The method of embodiment 85 or embodiment 86, wherein the sealant forms a sealing layer on substantially all of the outer surface of the wall of the conduit.

Embodiment 88

The method of any preceding embodiments 85 to 87, wherein the masking agent forms a masking agent layer on at least a part of the inner surface of the wall of the conduit.

Embodiment 89

The method of any preceding embodiments 85 to 88, wherein the masking agent forms a masking agent layer on substantially all of the inner surface of the wall of the conduit.

Embodiment 90

The method of any preceding embodiments 85 to 89, wherein substantially all of the conduit is porous.

Embodiment 91

The method of any preceding embodiments 85 to 90, wherein the method comprises one or more masking agent removal steps, the, or each, masking agent removal step comprising the step of removing at least a part of the masking agent from the conduit.

Embodiment 92

The method of embodiment 91, wherein the method comprises the step of removing at least a part of the masking agent from at least a part of the outer surface of the wall of the conduit prior to the step of adding the sealant to the porous section of the conduit.

Embodiment 93

The method of embodiment 91 or embodiment 92, wherein the method comprises the step of removing at least a part of the masking agent from the inner surface of the wall of the conduit subsequent to the step of adding the sealant to at least a part of the porous section of the conduit.

Embodiment 94

The method of any one of embodiments 91 to 93, wherein the method comprises the step of removing substantially all of the masking agent from the conduit subsequent to the step of adding the sealant to at least a part of the porous section of the conduit.

Embodiment 95

The method of any one of embodiments 91 to 94, wherein at least one of the masking agent removal steps is carried out at a temperature of between approximately 15° C. and approximately 140° C.

Embodiment 96

The method of any one of embodiments 91 to 95, wherein at least one of the masking agent removal steps comprises the step of removing at least a part of the masking agent by applying a solvent thereto.

Embodiment 97

The method of embodiment 96, wherein the solvent comprises water.

Embodiment 98

The method of any one of embodiments 91 to 97, wherein the conduit is at least one of: agitated, rotated, spun, and shaken, or the like, during at least one of the masking agent removal steps.

Embodiment 99

The method of any one of embodiments 91 to 98, wherein at least one of the masking agent removal steps is carried out by etching, plasma etching, ablating and/or abrading the masking agent.

Embodiment 100

The method of any preceding embodiments 85 to 99, wherein the inner surface of the wall of the conduit is configured to promote the growth of biological tissue thereon.

Embodiment 101

The method of any preceding embodiments 85 to 100, wherein the masking agent comprises a polymer.

Embodiment 102

The method of embodiment 101, wherein the masking agent comprises a water-soluble polymer.

Embodiment 103

The method of embodiment 101 or embodiment 102, wherein the masking agent comprises at least one of: polyvinylpyrrolidone, glycerol, methyl cellulose, poly(ethylene glycol), and poly(ethylene glycol) hydrogel.

Embodiment 104

The method of any preceding embodiments 85 to 103, wherein the masking agent is biocompatible.

Embodiment 105

The method of any preceding embodiments 85 to 104, wherein the masking agent forms a biocompatible masking agent layer when added to the conduit.

Embodiment 106

The method of any preceding embodiments 85 to 105, wherein the masking agent is added to at least a part of the porous section of the conduit from a masking agent solution.

Embodiment 107

The method of embodiment 106, wherein the masking agent solution is a polymer solution.

Embodiment 108

The method of embodiment 106 or embodiment 107, wherein the step of adding the masking agent to at least a part of the porous section of the conduit is performed by spraying the masking agent solution onto at least a part of the porous section of the conduit.

Embodiment 109

The method of embodiment 108, wherein the masking agent solution is added to the conduit by spraying the masking agent onto at least a part of the inner surface of the wall of the conduit.

Embodiment 110

The method of any one of embodiments 106 to embodiment 109, wherein the step of adding the masking agent to at least a part of the porous section of the conduit is performed by immersing at least a part of the porous section of the conduit in the masking agent solution.

Embodiment 111

The method of embodiment 110, wherein substantially all of the conduit is immersed in the masking agent solution.

Embodiment 112

The method of any one of embodiments 106 to 111, wherein the masking agent solution comprises between approximately 5% weight/volume (w/v) of polymer in solution and approximately 30% w/v of polymer in solution.

Embodiment 113

The method of any preceding embodiments 85 to 112, wherein the step of adding the sealant to at least a part of the porous section of the conduit does not result in the removal of the masking agent from the porous section of the conduit.

Embodiment 114

The method of any preceding embodiments 85 to 113, wherein the masking agent is configured to biodegrade when the vascular prosthesis is implanted inside the human or animal body.

Embodiment 115

The method of any preceding embodiments 85 to 114, wherein the conduit is a woven fibrous polymer conduit.

Embodiment 116

The method of any preceding embodiments 85 to 115, wherein the sealant comprises a polymer.

Embodiment 117

The method of embodiment 116, wherein the sealant is a water-insoluble polymer.

Embodiment 118

The method of any preceding embodiments 85 to 117, wherein the sealant forms a sealing layer when added to the conduit, the sealing layer being a polymer layer.

Embodiment 119

The method of any one of embodiments 116 to 118, wherein the sealant comprises at least one of: silicone, room temperature vulcanising silicone, thermoplastic polyurethane, aliphatic polycarbonate, one or more thermoplastic elastomers, and polycarbonate.

Embodiment 120

The method of any preceding embodiments 85 to 119, wherein the sealant is added to the conduit from a sealant solution.

Embodiment 121

The method of embodiment 120 wherein the sealant solution is a polymer solution.

Embodiment 122

The method of embodiment 120 or embodiment 121, wherein the sealant solution comprises an organic solvent.

Embodiment 123

The method of embodiment 122, wherein the sealant solution comprises at least one of heptane and xylene.

Embodiment 124

The method of any preceding embodiments 85 to 123, wherein the sealant is added to at least a part of the porous section of the conduit by brushing and/or spraying the sealant thereon.

Embodiment 125

The method of any preceding embodiments 85 to 124, wherein the sealant is configured to mitigate movement of blood through the wall of the conduit.

Embodiment 126

The method of any preceding embodiments 85 to 125, comprising the further step of sterilising the vascular prosthesis.

Embodiment 127

The method of embodiment 126, wherein the vascular prosthesis is sterilised by way of at least one of: a gamma sterilisation process, an electron beam sterilisation process, and an ethylene oxide sterilisation process.

Embodiment 128

The method of any preceding embodiments 85 to 127, wherein the conduit is moveable between a contracted state and an extended state.

Embodiment 129

The method of embodiment 128, wherein the step of adding the masking agent to at least a part of the porous section of the conduit is carried out, at least in part, while the conduit is in the contracted state, in the extended state, and/or when moved between the contracted state and the extended state.

Embodiment 130

The method of embodiment 128 or embodiment 129, wherein the step of adding the sealant to at least a part of the porous section of the conduit is carried out, at least in part, while the conduit is in the contracted state, in the extended state, and/or when moved between the contracted state and the extended state.

Embodiment 131

The method of any preceding embodiments 85 to 130, the method comprising one or more steps of weighing the conduit and/or measuring the length of the conduit, to determine, at least in part, the amount of masking agent, and/or or the amount of sealant, to add to at least a part of the porous section of the conduit.

Embodiment 132

The method of any preceding embodiments 85 to 131, wherein the step of adding the masking agent to at least a part of the porous section of the conduit comprises the step of providing gas to the conduit.

Embodiment 133

The method of embodiment 132, wherein the gas is directed towards the outer surface of the wall of the conduit.

Embodiment 134

The method of embodiment 132 or embodiment 133, wherein the gas is air.

Embodiment 135

The method of any preceding embodiments 85 to 134, wherein the method comprises the step of adding a support member to the conduit.

Embodiment 136

The method of embodiment 135, wherein the support member is added to the outer surface of the wall of the conduit.

Embodiment 137

The method of embodiment 136, wherein the support member is wrapped around the outer surface of the wall of the conduit.

Embodiment 138

The method of embodiment 137, wherein the conduit comprises a plurality of crimps, and the support member is arranged to nest between the plurality of crimps.

Embodiment 139

The method of any one of embodiments 135 to 138, wherein the step of adding the support member to the conduit is carried out prior to the step of adding the sealant to the conduit.

Embodiment 140

The method of any one of embodiments 135 to 139, wherein the step of adding the sealant to the conduit is used, at least in part, to attach the support member to the conduit.

Embodiment 141

The method of any one of embodiments 135 to 140, wherein the support member is a flexible, polymer member.

Embodiment 142

The method of any preceding embodiments 85 to 141, wherein the method comprises one or more steps of selectively adding sealant to one or more sections of the conduit, such that the conduit comprises at least two sections comprising substantially different amounts of sealant thereon.

Embodiment 143

A vascular prosthesis comprising:
a conduit comprising a wall, the wall of the conduit comprising an inner surface and an outer surface, at least a section of the conduit being porous;
wherein at least a part of the porous section comprises a sealant configured to mitigate movement of fluid through the wall of the conduit; and
wherein the inner surface of the wall of the conduit is substantially devoid of the sealant.

Embodiment 144

The vascular prosthesis of embodiment 143, wherein the sealant forms a sealing layer on at least a part of the outer surface of the wall of the conduit.

Embodiment 145

The vascular prosthesis of embodiment 143 or embodiment 144, wherein the sealant forms a sealing layer on substantially all of the outer surface of the wall of the conduit.

Embodiment 146

The vascular prosthesis of any one of embodiments 143 to 145, wherein substantially all of the conduit is porous.

Embodiment 147

The vascular prosthesis of any one of embodiments 143 to 146, wherein the inner surface of the wall of the conduit is configured to promote the ingrowth of biological tissue thereon.

Embodiment 148

The vascular prosthesis of any one of embodiments 143 to 147, wherein the conduit is a woven fibrous polymer conduit.

Embodiment 149

The vascular prosthesis of any one of embodiments 143 to 148, wherein the sealant forms a sealing layer, the sealing layer being a polymer layer.

Embodiment 150

The vascular prosthesis of any one of embodiments 143 to 149, wherein the sealant comprises at least one of: silicone, room temperature vulcanising silicone, thermoplastic polyurethane, aliphatic polycarbonate, one or more thermoplastic elastomers, and polycarbonate.

Embodiment 151

The vascular prosthesis of any one of embodiments 143 to 150, wherein the sealant is configured to mitigate movement of blood through the wall of the conduit.

Embodiment 152

The vascular prosthesis of any one of embodiments 143 to 151, wherein the vascular prosthesis is sterilised.

Embodiment 153

The vascular prosthesis of embodiment 152, wherein the vascular prosthesis is sterilised by way of at least one of the following: a gamma sterilisation process, an ethylene oxide sterilisation process, and an electron beam sterilisation process.

Embodiment 154

The vascular prosthesis of any one of embodiments 143 to 153, wherein the conduit is moveable between a contracted state and an extended state.

Embodiment 155

The vascular prosthesis of any one of embodiments 143 to 154, wherein the conduit comprises a support member.

Embodiment 156

The vascular prosthesis of embodiment 155, wherein the support member is located substantially adjacent to the outer surface of the wall of the conduit.

Embodiment 157

The vascular prosthesis of embodiment 156, wherein the support member is wrapped around the outer surface of the wall of the conduit.

Embodiment 158

The vascular prosthesis of embodiment 157, wherein the conduit comprises a plurality of crimps, the support member being arranged to nest between the plurality of crimps.

Embodiment 159

The vascular prosthesis of any one of embodiments 155 to 158, wherein the sealant is arranged to, at least in part, attach the support member to the conduit.

Embodiment 160

The vascular prosthesis of any one of embodiments 155 to 159, wherein the support member is a flexible, polymer member.

Embodiment 161

The vascular prosthesis of any one of embodiments 143 to 160, wherein the conduit is configured to have at least two sections having substantially different amounts of sealant thereon.

Embodiment 162

A kit of parts for manufacturing a vascular prosthesis, the kit of parts comprising:
(i) a conduit comprising a wall, the wall of the conduit comprising an inner surface and an outer surface, at least a section of the conduit being porous;
(ii) a masking agent; and
(iii) a sealant;
when applied to at least a part of the porous section of the conduit, the masking agent being configured to mitigate presence of the sealant on the inner surface of the conduit; and
when applied to at least a part of the porous section of the conduit, the sealant being configured to mitigate movement of fluid through the wall of the conduit.

Embodiment 163

The kit of parts of embodiment 162, wherein addition of the sealant to at least a part of the porous section of the conduit forms a sealing layer on at least a part of the outer surface of the wall of the conduit.

Embodiment 164

The kit of parts of embodiment 162 or embodiment 163, wherein addition of the masking agent to at least a part of the porous section of the conduit forms a masking agent layer on at least part of the inner surface of the wall of the conduit.

Embodiment 165

The kit of parts of any one of embodiments 162 to 164, wherein substantially all of the conduit is porous.

Embodiment 166

The kit of parts of any one of embodiments 162 to 165, the kit of parts comprising a masking agent remover, the masking agent remover being operable to remove applied masking agent from the conduit.

Embodiment 167

The kit of parts of embodiment 166, wherein the masking agent remover comprises a solvent.

Embodiment 168

The kit of parts of embodiment 167, wherein the solvent comprises water.

Embodiment 169

The kit of parts of any one of embodiments 166 to 168, wherein the masking agent remover is operable to remove applied masking agent from the conduit at a temperature of between approximately 15° C. and approximately 140° C.

Embodiment 170

The kit of parts of any one of embodiments 162 to 169, the kit of parts comprising an abrading tool, the abrading tool being operable to remove applied masking agent from the conduit.

Embodiment 171

The kit of parts of any one of embodiments 162 to 170, wherein the inner surface of the wall of the conduit is configured to promote the ingrowth of biological tissue thereon.

Embodiment 172

The kit of parts of any one of embodiments 162 to 171, wherein the masking agent comprises a polymer.

Embodiment 173

The kit of parts of embodiment 172, wherein the masking agent comprises a water-soluble polymer.

Embodiment 174

The kit of parts of any one of embodiments 162 to 173, wherein masking agent applied to the conduit forms a masking agent layer, the masking agent layer being a polymer layer.

Embodiment 175

The kit of parts of any one of embodiments 172 to 174, wherein the masking agent comprises at least one of: polyvinylpyrrolidone, glycerol, methyl cellulose, and poly(ethylene glycol) hydrogel.

Embodiment 176

The kit of parts of any one of embodiments 162 to 175, wherein the masking agent is biocompatible.

Embodiment 177

The kit of parts of any one of embodiments 162 to 176, wherein masking agent applied to the conduit forms a biocompatible masking agent layer.

Embodiment 178

The kit of parts of any one of embodiments 162 to 177, wherein the kit of parts comprises a masking agent solution, the masking agent solution being operable to apply masking agent to the conduit.

Embodiment 179

The kit of parts of embodiment 178, wherein the masking agent solution is a polymer solution.

Embodiment 180

The kit of parts of embodiment 178 or embodiment 179, wherein the conduit is immersible in the masking agent solution.

Embodiment 181

The kit of parts of any one of embodiments 178 to 180, wherein the masking agent solution comprises between approximately 5% w/v of polymer in solution and approximately 30% w/v of polymer in solution.

Embodiment 182

The kit of parts of any one of embodiments 162 to 181, wherein when the masking agent and the sealant are applied to the conduit, the sealant is configured such that addition of the sealant to the conduit does not result in the removal of the applied masking agent from the conduit.

Embodiment 183

The kit of parts of any one of embodiments 162 to 182, wherein the masking agent is configured to biodegrade when implanted inside the human or animal body.

Embodiment 184

The kit of parts of any one of embodiments 162 to 183, wherein the conduit is a woven fibrous polymer conduit.

Embodiment 185

The kit of parts of any one of embodiments 162 to 184, wherein the sealant comprises a polymer, optionally a water-insoluble polymer.

Embodiment 186

The kit of parts of any one of embodiments 162 to 185, wherein the sealant, when applied to the conduit, forms a sealing layer, the sealing layer being a polymer layer.

Embodiment 187

The kit of parts of embodiment 185 or embodiment 186, wherein the sealant comprises at least one of: silicone, room temperature vulcanising silicone, thermoplastic polyurethane, aliphatic polycarbonate, one or more thermoplastic elastomers, and polycarbonate.

Embodiment 188

The kit of parts of any one of embodiments 162 to 187, wherein the kit of parts comprises a sealant solution operable to apply sealant to the conduit.

Embodiment 189

The kit of parts of embodiment 188, wherein the sealant solution is a polymer solution.

Embodiment 190

The kit of parts of embodiment 188 or embodiment 189, wherein the sealant solution comprises an organic solvent.

Embodiment 191

The kit of parts of embodiment 190, wherein the sealant solution comprises at least one of heptane and xylene.

Embodiment 192

The kit of parts of any one of embodiments 162 to 191, the kit of parts comprising a sealant applicator operable to apply sealant to the conduit, and/or a masking agent applicator operable to apply masking agent to the conduit.

Embodiment 193

The kit of parts of embodiment 192, wherein the sealant applicator is an apparatus for spray coating the sealant, and/or a brush, or the like.

Embodiment 194

The kit of parts of embodiment 192 or embodiment 193, wherein the masking agent applicator is a brush, an apparatus for spray-coating the masking agent, an apparatus for dipping or immersing the conduit in the masking agent, and/or an apparatus for wiping the masking agent onto the conduit.

Embodiment 195

The kit of parts of any one of embodiments 162 to 194, wherein the sealant, when applied to at least a part of the porous section of the conduit, is configured to mitigate movement of blood through the wall of the conduit.

Embodiment 196

The kit of parts of any one of embodiments 162 to 195, wherein the conduit is moveable between a contracted state and an extended state.

Embodiment 197

The kit of parts of any one of embodiments 162 to 196, the kit of parts comprising a further prosthesis.

Embodiment 198

The kit of parts of embodiment 197, wherein the further prosthesis is at least one of: a biological heart valve, a synthetic heart valve, a cardiac assist device, and a ventricular assist device, or the like.

Embodiment 199

The kit of parts of any one of embodiments 162 to 198, the kit of parts comprising a weighing device and/or a device for measuring the length of the conduit.

Embodiment 200

The kit of parts of any one of embodiments 162 to 199, the kit of parts comprising a gas flow apparatus operable to provide gas flow to the conduit.

Embodiment 201

The kit of parts of embodiment 200, wherein the gas is air.

Embodiment 202

A vascular system, the vascular system comprising:
a vascular prosthesis manufactured according to any one of embodiments 85 to 142; and
a further prosthesis;
wherein the vascular prosthesis is connected to the further prosthesis, such that fluid can flow between the vascular prosthesis and the further prosthesis.

Embodiment 203

The vascular system of embodiment 202, wherein the further prosthesis is at least one of: a biological heart valve, a synthetic heart valve, a cardiac assist device, and a ventricular assist device, or the like.

Embodiment 204

A method of implanting a vascular prosthesis, the method comprising the steps of:
providing a vascular prosthesis manufactured using the method of any one of embodiments 85 to 142;
connecting an inlet of the vascular prosthesis to a first blood vessel; and
connecting an outlet of the vascular prosthesis to a second blood vessel;
such that blood can flow between the first and second blood vessels through the vascular prosthesis.

Embodiment 205

The method of embodiment 204, wherein the first and second blood vessels are formed from a blood vessel which is diseased, or has been severed, bisected, or the like.

Embodiment 206

A method of implanting a vascular prosthesis, the method comprising the steps of:
providing a vascular prosthesis according to any one of embodiments 143 to 161;
connecting the vascular prosthesis to a first blood vessel; and
connecting the vascular prosthesis to a second blood vessel;
such that blood can flow between the first and second blood vessels through the vascular prosthesis.

Embodiment 207

The method of embodiment 206, wherein the first and second blood vessels are formed from a blood vessel which is diseased, or has been severed, bisected, or the like.

Embodiment 207

A method of implanting a vascular system, the method comprising the steps of:
providing a vascular system, the vascular system comprising:
a vascular prosthesis manufactured according to any one of embodiments 85 to 142; and
a further prosthesis;
wherein the vascular prosthesis is connectable to the further prosthesis;
connecting the vascular prosthesis to the further prosthesis, such that blood can flow therebetween;
connecting an end of a blood vessel to the vascular prosthesis; and
connecting the further prosthesis to the heart;
such that blood can flow between the blood vessel and the heart through the vascular system.

Embodiment 209

The method of embodiment 208, wherein the further prosthesis is at least one of: a biological heart valve, a synthetic heart valve, a cardiac assist device, and a ventricular assist device, or the like.

Embodiment 210

A method for manufacturing a substantially impermeable textile graft comprising:
providing a textile graft having a first surface and an opposed second surface;
providing a water soluble masking agent comprising polyvinylpyrrolidone and glycerol without mixing or combining the polyvinylpyrrolidone and the glycerol with added water;
applying the water soluble masking agent to a portion of the first surface of the textile graft;
providing a water insoluble sealing agent;
maintaining the second surface of the textile graft receptive for receiving the water insoluble sealing agent; and
applying the water insoluble sealing agent to the second surface of the textile graft.

Embodiment 211

The method of embodiment 210, wherein the water soluble masking agent consists essentially of polyvinylpyrrolidone and glycerol.

Embodiment 212

The method of any previous embodiments starting with 210, wherein the water soluble masking agent comprises from about 25% w/w of the polyvinylpyrrolidone in the glycerol to about 75% w/w of the polyvinylpyrrolidone in glycerol.

Embodiment 213

The method of any previous embodiments starting with 210, wherein the water soluble masking agent is flowable.

Embodiment 214

The method of any previous embodiments starting with 210, wherein the water soluble masking agent is prepared by dissolving the polyvinylpyrrolidone in the glycerol.

Embodiment 215

The method of any previous embodiments starting with 210, wherein the polyvinylpyrrolidone is dissolved into the glycerol with one or more of stirring and application of heat.

Embodiment 216

The method of any previous embodiments starting with 210, wherein the step of maintaining the second surface of the textile graft receptive for receiving the water insoluble sealing agent comprises preventing egress of the water soluble masking agent from the first surface to the second surface.

Embodiment 217

The method of any previous embodiments starting with 210, wherein the step of preventing the egress of the water soluble masking agent from the first surface to the second surface comprises substantially prohibiting wicking of the water soluble masking agent from the first surface to the second surface.

Embodiment 218

The method of any previous embodiments starting with 210, wherein the step of maintaining the second surface of the textile graft receptive for receiving the water insoluble sealing agent comprises removal of the water soluble masking agent from the second surface.

Embodiment 219

The method of any previous embodiments starting with 210, wherein the step of removal of the water soluble masking agent from the second surface comprises dissolving the water soluble masking agent from the second surface.

Embodiment 220

The method of any previous embodiments starting with 210, wherein the step of removal of the water soluble masking agent from the second surface comprises ablating the water soluble masking agent from the second surface.

Embodiment 221

The method of any previous embodiments starting with 210, wherein the polyvinylpyrrolidone has a molecular weight of from about 2,500 g/mol to about 55,000 g/mol.

Embodiment 222

The method of any previous embodiments starting with 210, wherein the water insoluble sealing agent comprises a material selected from the group consisting of silicones, polyurethanes, polycarbonates, thermoplastic elastomers, and combinations thereof.

Embodiment 223

The method of any previous embodiments starting with 210, wherein the step of applying the water insoluble sealing agent to the second surface of the textile graft comprises spraying water insoluble sealing agent onto the second surface of the textile graft.

Embodiment 224

The method of any previous embodiments starting with 210, wherein the spraying is forced air spraying or ultrasonic spraying.

Embodiment 225

The method of any previous embodiments starting with 210, further comprising removing the water soluble masking agent after the step of applying the water insoluble sealing agent.

Embodiment 226

The method of any previous embodiments starting with 210, further comprising curing the water insoluble sealing agent.

Embodiment 227

The method of any previous embodiments starting with 210, wherein, after curing of the water insoluble sealing agent, the textile graft is substantially impermeable to liquid.

Embodiment 228

The method of any previous embodiments starting with 210, wherein, after curing of the water insoluble sealing agent, the textile graft has a water permeability of about 0.16 ml/min/cm$^2$ at 120 mm Hg pressure or less than 0.16 ml/min/cm$^2$ at 120 mm Hg pressure.

Embodiment 229

The method of any previous embodiments starting with 210, wherein the textile graft is a tubular textile graft.

Embodiment 230

The method of any previous embodiments starting with 210, wherein the water soluble masking agent has a viscosity from about 2,000 centipoise at room temperature to about 100,000 centipoise at room temperature.

Embodiment 231

The method of any previous embodiments starting with 210, wherein the water soluble masking agent has a viscosity from about 50,000 centipoise at room temperature to about 100,000 centipoise at room temperature.

Embodiment 232

A method for manufacturing a substantially impermeable textile graft comprising:

providing a textile graft having a first surface and an opposed second surface;

providing a water soluble masking agent selected from the group consisting of polyvinylpyrrolidone, glycerol, methyl cellulose, poly(ethylene glycol), poly(ethylene glycol) hydrogel, polyethylene oxide, and combinations thereof;

applying the water soluble masking agent to a portion of the first surface of the textile graft, wherein a portion of the water insoluble sealing agent is optionally disposed on the second surface of the textile graft;

ablating a portion of the water soluble masking agent from the second surface of the textile graft;

providing a water insoluble sealing agent selected from the group consisting of silicones, polyurethanes, polycarbonates, thermoplastic elastomers, and combinations thereof; and applying the water insoluble sealing agent to the second surface of the textile graft.

Embodiment 233

The method of embodiment 232, wherein the step of ablating further comprises providing a flow of solid particulates against the second surface of the textile graft.

Embodiment 234

The method of any previous embodiments starting with 232, wherein the solid particulates are a material selected from the group consisting of sodium bicarbonate, sodium chloride, sugar, magnesium sulphate, potassium chloride, and combinations thereof.

Embodiment 235

The method of any previous embodiments starting with 232, wherein the solid particulates have an average particle size across their largest dimension from about 50 microns to about 300 microns.

Embodiment 236

The method of any previous embodiments starting with 232, wherein the solid particulates have a Moh's hardness from about 1 to about 4.

Embodiment 237

The method of any previous embodiments starting with 232, wherein the solid particulates are sprayed at a pressure from about 10 psig to about 50 psig.

Embodiment 238

The method of any previous embodiments starting with 232, further comprising curing the water insoluble sealing agent.

Embodiment 239

The method of any previous embodiments starting with 232, wherein, after curing of the water insoluble sealing agent, the textile graft is substantially impermeable to liquid.

Embodiment 240

The method of any previous embodiments starting with 232, wherein, after curing of the water insoluble sealing agent, the textile graft has a water permeability of about 0.16 ml/min/cm$^2$ at 120 mm Hg pressure or less than 0.16 ml/min/cm$^2$ at 120 mm Hg pressure.

Embodiment 241

The method of any previous embodiments starting with 232, further comprising removing the water soluble masking agent after the step of applying the water insoluble sealing agent.

Embodiment 240

The method of any previous embodiments starting with 232, further comprising adding a dye to the water insoluble sealing agent.

Embodiment 241

The method of any previous embodiments starting with 232, further comprising adding a dye to the water soluble masking agent.

Embodiment 242

A textile graft made by the method of any of the embodiments 210-231.

Embodiment 243

A textile graft made by the method of any of the embodiments 232-241.

Embodiment 244

A method of providing a sealant to a textile graft comprising:

providing a textile graft having a first surface and an opposed second surface and having a textile pattern of yarns inter-engaging yarns and interstices between or in the yarns;

providing a water soluble masking agent selected from the group consisting of polyvinylpyrrolidone, glycerol, methyl cellulose, poly(ethylene glycol), poly(ethylene glycol) hydrogel, polyethylene oxide, and combinations thereof;

applying the water soluble masking agent to at least a portion of the first surface of the textile graft, wherein a portion of the water soluble masking agent is further disposed at a plurality of the interstices;

providing a water insoluble sealing agent selected from the group consisting of silicones, polyurethanes, polycarbonates, thermoplastic elastomers, and combinations thereof; and applying the water insoluble sealing agent to the second surface of the textile graft and over the portion of the water soluble masking agent being disposed at a plurality of the interstices;

whereby the water insoluble sealing agent spreads over the water soluble masking agent to provide one or more of the following: a substantially homogenous layer of the water insoluble sealing agent; a substantially uniform and uninterrupted coating of the water insoluble sealing agent; a layer of water insoluble sealing agent having a substantially uniform weight per given area of application; a substantially liquid impermeable barrier to the underlying textile graft surface; a substantially lower force to extend a graft coated with the water insoluble sealing agent as compared to comparable grafts which have not used a masking agent; a substantially less amount of water insoluble sealing agent to provide a substantially liquid impermeable barrier to the underlying textile graft surface as compared to comparable grafts which have not used a masking agent; and combinations thereof.

Embodiment 245

The method of embodiment 244, further comprising removing the water soluble masking agent after the step of applying the water insoluble sealing agent.

Embodiment 246

The method of any previous embodiments starting with 244, further comprising curing the water insoluble sealing agent.

Embodiment 247

The method of any previous embodiments starting with 244, wherein, after curing of the water insoluble sealing agent, the water insoluble sealing agent is disposed over the interstices between and in the yarns.

Embodiment 248

The method of any previous embodiments starting with 244, wherein, the textile graft is substantially impermeable to liquid.

Embodiment 249

The method of any previous embodiments starting with 244, wherein, after curing of the water insoluble sealing agent, the textile graft has a water permeability of about 0.16 ml/min/cm$^2$ at 120 mm Hg pressure or less than 0.16 ml/min/cm$^2$ at 120 mm Hg pressure.

Embodiment 250

A textile graft made by the method of any of the embodiments 244-249.

Embodiment 251

A method of sealing a textile graft comprising:
applying a coating of a substantially water soluble masking agent, having a viscosity of from about 2,000 centipoise at room temperature to about 100,000 centipoise at room temperature, to at least a portion of a luminal surface of the textile graft, wherein a portion of the water soluble masking agent is further disposed at a plurality of interstices in the graft; and
applying a water insoluble sealing agent to an outer graft surface opposing the luminal surface of the graft;
wherein the water soluble masking agent causes one or more of the following to occur:
a substantially homogenous layer of the water insoluble sealing agent is formed; a substantially uniform and uninterrupted coating of the water insoluble sealing agent is formed; a layer of water insoluble sealing agent having a substantially uniform weight per given area of application; a substantially liquid impermeable barrier to the underlying textile graft surface; a substantially lower force to extend a graft coated with the water insoluble sealing agent as compared to comparable grafts which have not used a masking agent; a substantially less amount of water insoluble sealing agent to provide a substantially liquid impermeable barrier to the underlying textile graft surface as compared to comparable grafts which have not used a masking agent; and combinations thereof.

Embodiment 252

The method of any of the embodiments claims 210 to 231, wherein the steps of applying the water soluble masking agent and applying the water insoluble sealing agent are performed substantially concurrently.

Embodiment 253

The method of embodiment 252, wherein the step of applying the water soluble masking agent further comprises applying heat, directly or indirectly, to the water soluble masking agent.

Embodiment 254

The method of embodiment 253, wherein the step of applying water insoluble sealing agent further comprises applying cooling, directly or indirectly, to the second surface of the textile graft.

Embodiment 255

The method of any of the embodiments claims 210 to 231, further comprising:
controlling temperature of the water soluble masking agent while apply the water soluble masking agent to the first surface of the textile graft to control flow of the water soluble masking agent at the first surface of the textile graft; and
controlling temperature at or near the second surface of the textile graft while apply the water soluble masking agent to the first surface of the textile graft to control the flow of the water soluble masking agent towards the second surface of the textile graft.

Embodiment 256

The method of claim 255, wherein the step of controlling the temperature at or near the second textile surface is performed prior to the step of applying the water insoluble sealing agent to the second surface of the textile graft.

Embodiment 257

The method of claim 255, wherein the step of controlling the temperature at or near the second textile surface is performed during the step of applying the water insoluble sealing agent to the second surface of the textile graft.

Embodiment 258

The method of claim 255, wherein the step of controlling the temperature at or near the second textile surface is performed prior the step of applying the water insoluble sealing agent to the second surface of the textile graft and during the step of applying the water insoluble sealing agent to the second surface of the textile graft.

The invention claimed is:
1. A method for manufacturing a substantially impermeable textile graft comprising:

providing a textile graft having a first surface and an opposed second surface;

providing a water soluble masking agent comprising polyvinylpyrrolidone and glycerol without mixing or combining the polyvinylpyrrolidone and the glycerol with added water;

applying the water soluble masking agent to a portion of the first surface of the textile graft;

providing a water insoluble sealing agent;

maintaining the second surface of the textile graft receptive for receiving the water insoluble sealing agent; and applying the water insoluble sealing agent to the second surface of the textile graft.

2. The method of claim 1, wherein the water soluble masking agent consists essentially of polyvinylpyrrolidone and glycerol.

3. The method of claim 1, wherein the water soluble masking agent comprises from about 25% w/w of the polyvinylpyrrolidone in the glycerol to about 75% w/w of the polyvinylpyrrolidone in glycerol.

4. The method of claim 1, wherein the water soluble masking agent is flowable.

5. The method of claim 1, wherein the water soluble masking agent is prepared by dissolving the polyvinylpyrrolidone in the glycerol.

6. The method of claim 5, wherein the polyvinylpyrrolidone is dissolved into the glycerol with one or more of stirring and application of heat.

7. The method of claim 1, wherein the step of maintaining the second surface of the textile graft receptive for receiving the water insoluble sealing agent comprises preventing egress of the water soluble masking agent from the first surface to the second surface.

8. The method of claim 7, wherein the step of preventing the egress of the water soluble masking agent from the first surface to the second surface comprises substantially prohibiting wicking of the water soluble masking agent from the first surface to the second surface.

9. The method of claim 1, wherein the step of maintaining the second surface of the textile graft receptive for receiving the water insoluble sealing agent comprises removal of the water soluble masking agent from the second surface.

10. The method of claim 9, wherein the step of removal of the water soluble masking agent from the second surface comprises dissolving the water soluble masking agent from the second surface.

11. The method of claim 9, wherein the step of removal of the water soluble masking agent from the second surface comprises ablating the water soluble masking agent from the second surface.

12. The method of claim 1, wherein the polyvinylpyrrolidone has a molecular weight of from about 2,500 g/mol to about 55,000 g/mol.

13. The method of claim 1, wherein the water insoluble sealing agent comprises a material selected from the group consisting of silicones, polyurethanes, polycarbonates, thermoplastic elastomers, and combinations thereof.

14. The method of claim 1, wherein the step of applying the water insoluble sealing agent to the second surface of the textile graft comprises spraying water insoluble sealing agent onto the second surface of the textile graft.

15. The method of claim 14, wherein the spraying is forced air spraying or ultrasonic spraying.

16. The method of claim 1, further comprising removing the water soluble masking agent after the step of applying the water insoluble sealing agent.

17. The method of claim 16, further comprising curing the water insoluble sealing agent.

18. The method of claim 17, wherein, after curing of the water insoluble sealing agent, the textile graft is substantially impermeable to liquid.

19. The method of claim 17, wherein, after curing of the water insoluble sealing agent, the textile graft has a water permeability of about 0.16 ml/min/cm$^2$ at 120 mm Hg pressure or less than 0.16 ml/min/cm$^2$ at 120 mm Hg pressure.

20. The method of claim 1, wherein the textile graft is a tubular textile graft.

21. The method of claim 1, wherein the water soluble masking agent has a viscosity from about 2,000 centipoise at room temperature to about 100,000 centipoise at room temperature.

22. The method of claim 21, wherein the water soluble masking agent has a viscosity from about 50,000 centipoise at room temperature to about 100,000 centipoise at room temperature.

23. A method for manufacturing a substantially impermeable textile graft comprising:

providing a textile graft having a first surface and an opposed second surface;

providing a water soluble masking agent selected from the group consisting of polyvinylpyrrolidone, glycerol, methyl cellulose, poly(ethylene glycol), poly(ethylene glycol) hydrogel, polyethylene oxide, and combinations thereof;

applying the water soluble masking agent to a portion of the first surface of the textile graft;

ablating a portion of the water soluble masking agent from the second surface of the textile graft;

providing a water insoluble sealing agent selected from the group consisting of silicones, polyurethanes, polycarbonates, thermoplastic elastomers, and combinations thereof; and applying the water insoluble sealing agent to the second surface of the textile graft.

24. The method of claim 23, wherein the step of ablating further comprises providing a flow of solid particulates against the second surface of the textile graft.

25. The method of claim 24, wherein the solid particulates are a material selected from the group consisting of sodium bicarbonate, sodium chloride, sugar, magnesium sulphate, potassium chloride, and combinations thereof.

26. The method of claim 24, wherein the solid particulates have an average particle size across their largest dimension from about 50 microns to about 300 microns.

27. The method of claim 24, wherein the solid particulates have a Moh's hardness from about 1 to about 4.

28. The method of claim 24, wherein the solid particulates are sprayed at a pressure from about 10 psig to about 50 psig.

29. The method of claim 23, further comprising curing the water insoluble sealing agent.

30. The method of claim 29, wherein, after curing of the water insoluble sealing agent, the textile graft is substantially impermeable to liquid.

31. The method of claim 30, wherein, after curing of the water insoluble sealing agent, the textile graft has a water permeability of about 0.16 ml/min/cm$^2$ at 120 mm Hg pressure or less than 0.16 ml/min/cm$^2$ at 120 mm Hg pressure.

32. The method of claim 23, further comprising removing the water soluble masking agent after the step of applying the water insoluble sealing agent.

33. The method of claim 23, further comprising adding a dye to the water insoluble sealing agent.

34. The method of claim 23, further comprising adding a dye to the water soluble masking agent.

35. A textile graft made by the method of claim 1.

36. A textile graft made by the method of claim 23.

37. A method of providing a sealant to a textile graft comprising:
providing a textile graft having a first surface and an opposed second surface and having a textile pattern of inter-engaging yarns and interstices between or in the yarns;
providing a water soluble masking agent selected from the group consisting of polyvinylpyrrolidone, glycerol, methyl cellulose, poly(ethylene glycol), poly(ethylene glycol) hydrogel, polyethylene oxide, and combinations thereof;
applying the water soluble masking agent to at least a portion of the first surface of the textile graft, wherein a portion of the water soluble masking agent is further disposed at a plurality of the interstices;
providing a water insoluble sealing agent selected from the group consisting of silicones, polyurethanes, polycarbonates, thermoplastic elastomers, and combinations thereof;
applying the water insoluble sealing agent to the second surface of the textile graft and over the portion of the water soluble masking agent being disposed at a plurality of the interstices; and
removing the water soluble masking agent after the step of applying the water insoluble sealing agent;
whereby the water insoluble sealing agent spreads over the water soluble masking agent to provide one or more of the following: a substantially homogenous layer of the water insoluble sealing agent; a substantially uniform and uninterrupted coating of the water insoluble sealing agent; a layer of water insoluble sealing agent having a substantially uniform weight per given area of application; a substantially liquid impermeable barrier to the underlying textile graft surface; a substantially lower force to extend a graft coated with the water insoluble sealing agent as compared to comparable grafts which have not used a masking agent; a substantially less amount of water insoluble sealing agent to provide a substantially liquid impermeable barrier to the underlying textile graft surface as compared to comparable grafts which have not used a masking agent; and combinations thereof.

38. The method of claim 37, further comprising curing the water insoluble sealing agent.

39. The method of claim 38, wherein, after curing of the water insoluble sealing agent, the water insoluble sealing agent is disposed over the interstices between and in the yarns.

40. The method of claim 39, wherein, the textile graft is substantially impermeable to liquid.

41. The method of claim 40, wherein, after curing of the water insoluble sealing agent, the textile graft has a water permeability of about 0.16 ml/min/cm$^2$ at 120 mm Hg pressure or less than 0.16 ml/min/cm$^2$ at 120 mm Hg pressure.

42. A textile graft made by the method of claim 37.

43. A method of sealing a textile graft comprising:
applying a coating of a substantially water soluble masking agent, having a viscosity of from about 2,000 centipoise at room temperature to about 100,000 centipoise at room temperature, to at least a portion of a luminal surface of the textile graft, wherein a portion of the water soluble masking agent is further disposed at a plurality of interstices in the graft; and
applying a water insoluble sealing agent to an outer graft surface opposing the luminal surface of the graft;
wherein the water soluble masking agent causes one or more of the following to occur:
a substantially homogenous layer of the water insoluble sealing agent is formed; a substantially uniform and uninterrupted coating of the water insoluble sealing agent is formed; a layer of water insoluble sealing agent having a substantially uniform weight per given area of application; a substantially liquid impermeable barrier to the underlying textile graft surface; a substantially lower force to extend a graft coated with the water insoluble sealing agent as compared to comparable grafts which have not used a masking agent; a substantially less amount of water insoluble sealing agent to provide a substantially liquid impermeable barrier to the underlying textile graft surface as compared to comparable grafts which have not used a masking agent; and combinations thereof.

44. The method of claim 1, wherein the steps of applying the water soluble masking agent and applying the water insoluble sealing agent are performed substantially concurrently.

45. The method of claim 44, wherein the step of applying the water soluble masking agent further comprises applying heat, directly or indirectly, to the water soluble masking agent.

46. The method of claim 44, wherein the step of applying water insoluble sealing agent further comprises applying cooling, directly or indirectly, to the second surface of the textile graft.

47. The method of claim 1, further comprising:
controlling temperature of the water soluble masking agent while applying the water soluble masking agent to the first surface of the textile graft to control flow of the water soluble masking agent at the first surface of the textile graft; and
controlling temperature at or near the second surface of the textile graft while apply the water soluble masking agent to the first surface of the textile graft to control the flow of the water soluble masking agent towards the second surface of the textile graft.

48. The method of claim 47, wherein the step of controlling the temperature at or near the second textile surface is performed prior to the step of applying the water insoluble sealing agent to the second surface of the textile graft.

49. The method of claim 47, wherein the step of controlling the temperature at or near the second textile surface is performed during the step of applying the water insoluble sealing agent to the second surface of the textile graft.

50. The method of claim 47, wherein the step of controlling the temperature at or near the second textile surface is performed prior the step of applying the water insoluble sealing agent to the second surface of the textile graft and during the step of applying the water insoluble sealing agent to the second surface of the textile graft.

* * * * *